US009573956B2

(12) United States Patent
Cuadrado Tejedor et al.

(10) Patent No.: US 9,573,956 B2
(45) Date of Patent: Feb. 21, 2017

(54) COMPOUNDS AS DUAL INHIBITORS OF PHOSPHODIESTERASES AND HISTONE DEACETYLASES

(71) Applicant: FUNDACIÓN PARA LA INVESTIGACIÓN MÉDICA APLICADA, Pamplona (ES)

(72) Inventors: María Del Mar Cuadrado Tejedor, Pamplona (ES); Rafael Franco Fernández, Pamplona (ES); Ana María García Osta, Pamplona (ES); Julen Oyarzabal Santamarina, Pamplona (ES); Maria Obdulia Rabal Gracia, Pamplona (ES)

(73) Assignee: FUNDACIÓN PARA LA INVESTIGACIÓN MÉDICA APLICADA, Pamplona (ES)

( * ) Notice: Subject to any disclaimer, the term of this patent is extended or adjusted under 35 U.S.C. 154(b) by 0 days.

(21) Appl. No.: 14/770,065

(22) PCT Filed: Feb. 27, 2014

(86) PCT No.: PCT/EP2014/053877
§ 371 (c)(1),
(2) Date: Aug. 24, 2015

(87) PCT Pub. No.: WO2014/131855
PCT Pub. Date: Sep. 4, 2014

(65) Prior Publication Data
US 2016/0002246 A1  Jan. 7, 2016

(30) Foreign Application Priority Data

Mar. 1, 2013 (EP) .................................... 13382065

(51) Int. Cl.
*A01N 43/90* (2006.01)
*A61K 31/519* (2006.01)
(Continued)

(52) U.S. Cl.
CPC .......... *C07D 487/04* (2013.01); *A61K 31/519* (2013.01); *C07D 213/81* (2013.01);
(Continued)

(58) Field of Classification Search
None
See application file for complete search history.

(56) References Cited

FOREIGN PATENT DOCUMENTS

EP         2 535 049       12/2012
WO     WO 2004/101567      11/2004
(Continued)

OTHER PUBLICATIONS

International Search Report and Written Opinion for PCT/EP2014/053877, mailed Mar. 27, 2014, 15 pgs.
(Continued)

Primary Examiner — Jeffrey H Murray
(74) Attorney, Agent, or Firm — Squire Patton Boggs (US) LLP

(57) ABSTRACT

It relates to certain compounds having a polycyclic structure and a hydroxamic acid moiety, wherein the polycyclic structure comprises at least three ring systems, wherein one ring system is a polycyclic ring system comprising from 2 to 4 rings; at least one ring is an aromatic ring; and wherein the structure comprises at least 3 nitrogen atoms and 1 oxygen atom. It also relates to a process for their preparation, as well as to pharmaceutical compositions containing them, and to their use in medicine, in particular in the treatment and/or prevention of neurological disorders coursing with a cognition deficit or impairment, or neurodegenerative diseases. wherein $B_1$ is a radical selected from the group consisting of formula (A"), formula (B"), formula (C"), and formula (D"):

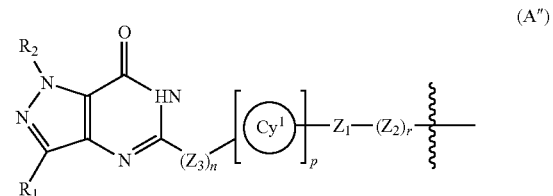

(A")

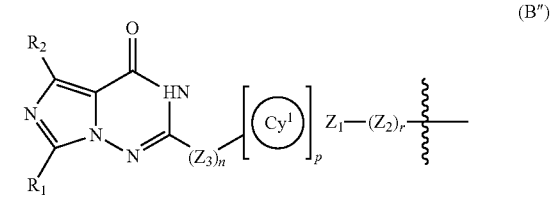

(B")

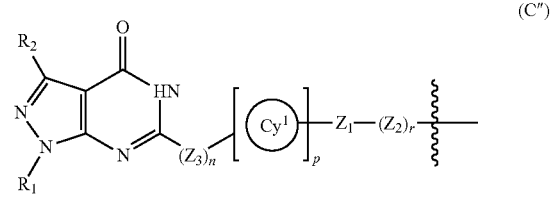

(C")

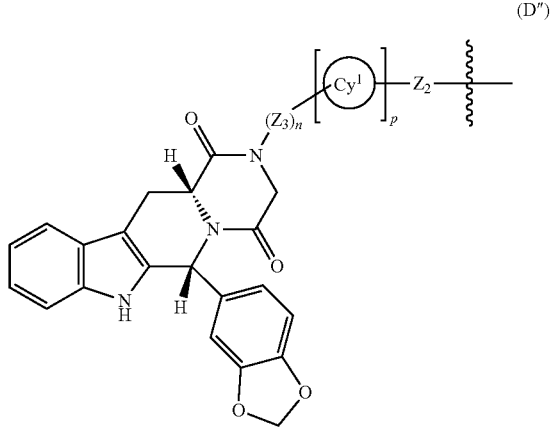

(D")

(Continued)

-continued

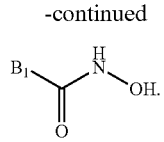
(I)

17 Claims, No Drawings

(51) Int. Cl.
C07D 487/00 (2006.01)
C07D 487/04 (2006.01)
C07D 401/14 (2006.01)
C07D 213/81 (2006.01)
C07D 401/12 (2006.01)
C07D 471/04 (2006.01)
C07D 487/14 (2006.01)

(52) U.S. Cl.
CPC ......... *C07D 401/12* (2013.01); *C07D 401/14* (2013.01); *C07D 471/04* (2013.01); *C07D 487/14* (2013.01)

(56) References Cited

FOREIGN PATENT DOCUMENTS

| WO | WO 2008/024494 | 2/2008 |
|---|---|---|
| WO | WO 2012/020022 | 2/2012 |

OTHER PUBLICATIONS

Chen et al., "Suberoylanilide hydroxamic acid, a histone deacetylase inhibitor, protects dopaminergic neurons from neurotoxin-induced damage", British J. of Pharmacology vol. 165, No. 2, pp. 494-505 (2012).

Cuadrado-Tejedor et al., "Sildenafil restores cognitive function without affecting [beta]-amyloid burden in a mouse model of Alzheimer's disease", British J. of Pharmacology vol. 164, No. 8, pp. 2029-2041 (2011).

Green et al., Protective Groups in Organic Chemistry, Wiley, $3^{rd}$ et. Chapter 2, pp. 17-200 (1999).

COMPOUNDS AS DUAL INHIBITORS OF PHOSPHODIESTERASES AND HISTONE DEACETYLASES

The present invention relates to compounds, which are dual inhibitors of PDEs and HDACs; and to processes for their preparation. It also relates to pharmaceutical compositions containing them, and to their use in medicine, in particular in the treatment and/or prevention of neurological disorders coursing with a cognition deficit or impairment, or neurodegenerative diseases.

BACKGROUND ART

Mild cognitive impairment is characterized by deficits in memory, language and/or other essential cognitive functions that do not interfere with an individual's daily life. The condition often evolves towards dementia, which is characterized by a global deterioration of cognitive abilities to an extent that does interfere with daily life. Alzheimer's disease (AD) is the most common form of dementia among older people and refers to dementia that does not have an antecedent cause, such as stroke, brain trauma, or alcohol; it is characterized by the presence in the brain of extracellular amyloid plaques and intracellular neurofibrillary tangles that provoke neuronal dysfunction and cell death. The increasing number of AD patients associated with the aging of the population makes the development of new disease management/treatment strategies critical.

The search for effective AD management has been largely based on the amyloid (A$\beta$) hypothesis, mainly focusing on reducing the number of senile plaques, although with little success to date. Focus is placed now on other hallmarks of the disease such as hyperphosphorylation of the cytoskeletal protein tau, which is the main component of neurofibrillary tangles.

Gene transcription and protein synthesis plays an important role in the formation of new memories. An increase in histone (H3 and/or H4) acetylation using histone deacetylase (HDAC) inhibitors induces chromatin re-structuring, which is associated with gene transcription activation. HDAC proteins are classified in four families: class I (HDAC 1-3, HDAC8), class IIa (HDAC 4, 5, 7 and 9), class IIb (HDAC 6 and 10), and class IV (HDAC 11). The expression pattern of each HDACs in the central nervous system (CNS) and its contribution in memory function varies among each subtype.

4-phenylbutyrate (PBA), a HDAC inhibitor, is an effective cognitive-enhancer in the Tg2576 transgenic mouse model of AD, which overexpresses a mutant form of the amyloid precursor protein (APP). Additionally, PBA reversed the pathological hallmarks of the disease and restored dendritic spine loss in this animal model. Taking into account that PBA inhibits HDACs class I and IIb, all these data strongly suggest the potential for therapeutic benefits of HDAC inhibitors in AD, especially for class I HDACs and HDAC6. Class I HDAC inhibitors enhance memory function by increasing histone acetylation levels, which facilitates gene transcription in the brain. Moreover, HDAC6 inhibitors induce tubuline acetylation (AcTub) that may help cytoskeleton stability and protein traffic. This could play an important role in misfolding protein disorders, such as AD, in which HDAC6 inhibitors have been shown to reduce amyloid precursor protein processing (APP) by reducing its amyloid precursor (C99) production.

Moreover, aging is associated with an increase in phosphodiesterase (PDE) expression and activity. Thus, phosdiesterases (PDEs) are good candidates for non-amyloid targets in cognition deficits in general and in AD in particular. Rolipram, which is a specific PDE4 inhibitor, was the first that proved useful in restoring cognition deficits in animal models of AD.

Specific phosphodiesterase (PDE) inhibitors (e.g. PDE5 inhibitors: Sildenafil, or Tadalafil; and, PDE9 inhibitor: PF-4447943 (6-[(3S,4S)-4-methyl-1-(pyrimidin-2-ylmethyl)pyrrolidin-3-yl]-1-(tetrahydro-2H-pyran-4-yl)-1H-pyrazolo[3,4-d]pyrimidin-4(5H)-one)) have been shown to improve memory performance or/and enhance synaptic plasticity and cognitive function in different animal models of AD. PDE inhibitors regulate signalling pathways by elevating levels of cAMP and/or cGMP, which may ultimately promote gene transcription by directly and/or indirectly activating the cAMP response element-binding (CREB). CREB-dependent gene expression underlies long-term memory formation and persistent long-term potentiation (LTP), which are indicators of synaptic plasticity and strength. In the hippocampus, this probably occurs through the formation of new synaptic connections, which are needed to restore cognitive deficits. Thus, by activating the CREB signalling pathway, PDE inhibitors may ameliorate AD symptoms. Moreover, other CREB-independent mechanisms seem to act in synergy to restore cognitive impairment in AD via increase of cAMP and/or cGMP levels. Cognitive performance may be also improved indirectly by means of PDE-inhibitor-mediated increase of cerebral blood flow and/or of brain glucose consumption.

Besides amyloid burden, Tau phosphorylation is another histopathological marker of AD progression. Importantly, it has been shown that the PDE5 inhibitors Sildenafil and Tadalafil, reduce Tau phosphorylation (pTau levels) in different animal models of AD.

Therefore, there is still a need of developing compounds which show improved activity in the treatment and/or prevention of neurological disorders coursing with a cognition deficit or impairment, or neurodegenerative diseases.

Document WO 2008/024494 discloses compounds having an imidazo[5,1-f][1,2,4]triazin-4-one core, which are PDE5 inhibitors. In particular, it discloses compound 14 (page 70), which has an imidazo[5,1-f][1,2,4]triazin-4-one core and a hydroxamic acid ester. This compound, hereby referred as comparative example 2-01, was synthethized by the present inventors and as shown in the examples below, it was inactive against HDAC1, HDAC2 and HDAC6; IC50>20 µM.

Document WO 2012/020022 discloses 6-cycloalkyl-1,5-dihydro-pyrazolo[3,4-d]pyrimidin-4-one derivatives and their use as PDE9A inhibitors. In particular, it discloses in example 8B (page 77) a compound with a 1,5-dihydro-pyrazolo[3,4-d]pyrimidin-4-one core and a hydroxamic acid ester. This compound, hereby referred as comparative example 3-01, was synthethized by the present inventors and as shown in the examples below, it was inactive against HDAC1, HDAC2 and HDAC6; IC50>20 µM.

SUMMARY OF THE INVENTION

Inventors have found new compounds having a polycyclic structure and a hydroxamic acid moiety which are capable to inhibit one or more phosphodiesterases (PDE) and simultaneously one or more histone deacetylases (HDACs). These compounds are therefore dual inhibitors of PDEs and HDACs and could be useful to improve cognition. The compounds of the invention have the advantage that are addressed to two different pathways of those that, in animal models, have proved useful to prevent the progression of neurodegenerative diseases and/or to increase cognition deficits associated to neurodegenerative diseases. Considering that the major drawback of the treatments for AD in clinical phases is their lack of efficacy when targeting a single pathophysiological event; the compounds of the present invention, which have an impact on two pathophysiological events, may lead to a more efficacious treatment.

Therefore, a first aspect of the invention relates to a compound of formula (I), or a pharmaceutically acceptable salt thereof, or any stereoisomer or mixtures thereof, either of the compound of formula (I) or of any of its pharmaceutically acceptable salts,

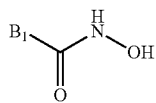

(I)

wherein
$B_1$ is a radical selected from the group consisting of formula (A"), formula (B"), formula (C"), and formula (D"):

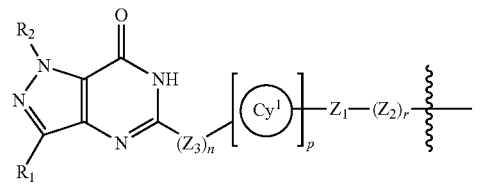

(A")

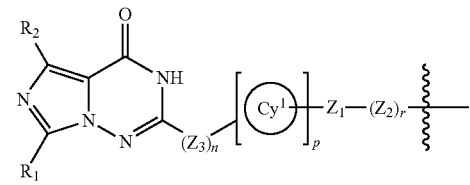

(B")

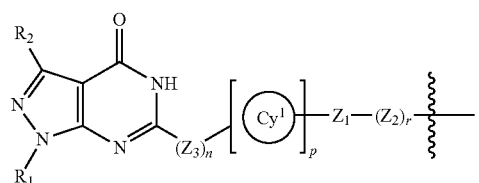

(C")

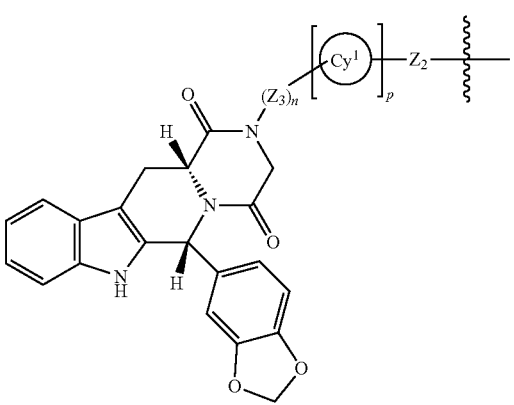

(D")

p, n and r are independently 0 or 1;
$R_1$ and $R_2$ are independently selected from the group consisting of H; saturated or unsaturated $(C_1-C_7)$alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from halogen and $(C_1-C_3)$alkyl;
$Z_1$ is a biradical selected from the group consisting of a formula (E), formula (F"), formula (G'), formula (H'), formula (J') and formula (K):

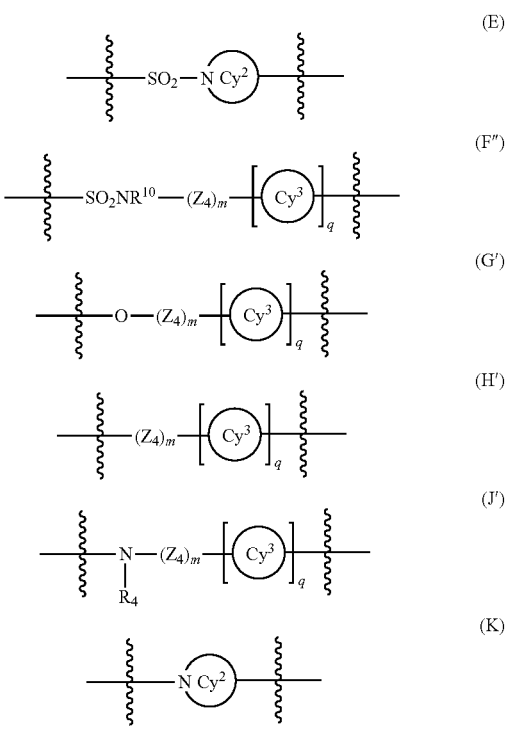

$Z_2$ is selected from the group consisting of $-Z_5-$; $-Z_5-Cy^4-$; $-Z_5-Cy^4-Z_5-$; and $-Cy^4-$;
$Z_3$ and each $Z_5$ are independently a biradical of a saturated or unsaturated $(C_1-C_6)$alkyl optionally substituted with one or more halogen atoms;
$Z_4$ is a biradical of a saturated or unsaturated $(C_1-C_6)$alkyl optionally substituted with one or more substituents selected from halogen, OH, and $-O(C_1-C_3)$alkyl optionally substituted with one or more halogen atoms; or alternatively $Z_4$ is $-CR^{11}R^{12}-$, wherein $R^{11}$ and $R^{12}$ taken together with the carbon they are attached to form C=O or a 3- to 7-membered carbocyclic or heterocyclic monocyclic ring, which is saturated or partially unsaturated, and which is optionally substituted with one or more halogen atoms or $(C_1-C_3)$alkyl optionally substituted with one or more halogen atoms;
q and m are independently 0 or 1;
$Cy^1$, $Cy^3$ and $Cy^4$ are independently phenyl or a 3- to 7-membered carbocyclic or heterocyclic monocyclic ring, which is saturated or partially unsaturated or aromatic, and which is optionally substituted with one or more $R_3$ groups; or alternatively
$Cy^1$ is a 3- to 7-membered saturated or partially unsaturated heterocyclic monocyclic ring, which is fused, bridged-fused or spiro-fused to a 3- to 7-membered saturated or partially unsaturated carbocyclic or heterocyclic monocyclic ring, wherein $Cy^1$ is optionally substituted with one or more $R_3$ groups;
$Cy^2$ is a N-attached 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein $Cy^2$ is optionally substituted with one or more $R_3$ groups;
$R_3$ is selected from halogen; saturated or unsaturated ($C_1$-$C_7$)alkyl optionally substituted with one or more halogen atoms; saturated or unsaturated —O($C_1$-$C_7$)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and ($C_1$-$C_6$)alkyl optionally substituted with one or more halogen atoms;
$R_4$ and $R^{10}$ are independently H or ($C_1$-$C_6$)alkyl optionally substituted with one or more halogen atoms; and
wherein in any heterocyclic ring one or more of the ring members are selected from NH, N, O, and S;
wherein in all saturated or partially unsaturated rings one or two members of the rings are optionally C(=O) and/or C(=NH) and/or C[=N($C_1$-$C_4$)alkyl],
wherein saturated alkyl refers to a linear or branched hydrocarbon chain which contains only single bonds; and unsaturated alkyl refers to a linear or branched hydrocarbon chain which contains one or two double bonds and/or one or two triple bonds;
wherein in any alkyl group one or two chain members selected from $CH_2$ or CH are optionally replaced by chain members independently selected from N, $NR_4$, O, C(=O), C(=O)$NR_4$, $NR_4$C(=O) and S;
with the condition that the moiety ($L_1$) of the formula (A"), formula (B"), and formula (C"), and the moiety ($L_2$) of the formula (D")

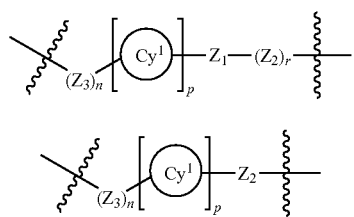

have a chain length comprised from 1 to 20 atoms.

The present invention also relates to processes for the preparation of compounds of formula (I). Accordingly, another aspect of the invention relates to the preparation of compounds of formula (I) as defined above by reacting a compound of formula $B_1$—COOR' (IV) with a hydroxylamine of formula RO—$NH_2$ (V), wherein $B_1$ is as previously defined; R' is H and R is a hydroxamic acid protective group, to give a compound of formula (III)

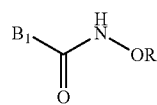

and subsequently removing the protective group of the hydroxamic acid to give a compound of formula (I).

Another aspect of the invention relates to a pharmaceutical composition which comprises a therapeutically effective amount of a compound of formula (I) as defined above, together with one or more pharmaceutically acceptable excipients or carriers.

As previously described, the compounds of the invention are dual inhibitors of PDEs and HDACs and can be useful to improve cognition. Therefore, another aspect of the invention relates to a compound of formula (I) or a pharmaceutical composition comprising the compound of formula (I) as defined above, for use as a medicament.

Another aspect of the present invention relates to a compound of formula (I) or a pharmaceutical composition comprising the compound of formula (I) as defined above, for use in the treatment and/or prevention of diseases mediated by the dual inhibition of PDE and HDAC. Thus, this aspect relates to the use of a compound of formula (I) as defined above, for the preparation of a medicament for the treatment and/or prevention of diseases mediated by the dual inhibition of PDE and HDAC; and may also be formulated as a method for the treatment and/or prevention of diseases mediated by the dual inhibition of PDE and HDAC, which comprises administering a therapeutically effective amount of the previously defined compound of formula (I), and one or more pharmaceutical acceptable excipients or carriers, in a subject in need thereof, including a human.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "carbocyclic" ring system refers to a known ring system wherein all the ring members contain carbon atoms. The term "heterocyclic" ring system refers to a known ring system wherein one or more of the ring members, preferably 1, 2, 3, or 4 ring members, are selected from NH, N, O, and S, where chemically possible. The remaining ring members of the heterocyclic ring are independently selected from C, CH, $CH_2$, O, N, NH, and S. Unless otherwise specified, the "heterocyclic" ring system may be attached to the rest of the molecule through a C or a N atom of the ring system. Both the carbocyclic and heterocyclic rings can be saturated or partially unsaturated, and may be unsubstituted or substituted as described herein, being the substituents placed on any available position.

According to the present invention, the term "polycyclic" ring refers to a ring system which is formed by two, three or four rings which can be fused, bridged-fused, spiro-fused or can contain different types of fusion. For the purposes of the present invention, in "fused" rings the fusion occurs through one bond which is common to two adjoining rings; in "bridged-fused" rings the fusion occurs through a sequence of atoms (bridgehead) which is common to two rings; and in "spiro-fused" rings, the fusion occurs through only one atom (spiro atom), preferably a carbon atom, which is common to two adjoining rings (including bridged rings).

The term "heteroaromatic" ring refers to a known aromatic ring system, wherein one or more of the ring members, preferably 1, 2, 3, or 4 ring members, are selected from NH, N, O, and S, where chemically possible. The remaining ring members of the heteroaromatic ring are independently selected from C, CH, O, N, NH, and S. The heteroaromatic ring may be unsubstituted or substituted as described herein, being the substituents placed on any available position.

The term "known ring system" as used herein refers to a ring system which is chemically feasible and is known in the art and so intends to exclude those ring systems that are not chemically possible.

For the purposes of the present invention, in all saturated or partially unsaturated rings, one or two members of the rings are optionally C(=O) and/or C(=NH) and/or C[=N(C$_1$-C$_4$)alkyl].

The term linear or branched, saturated or unsaturated (C$_1$-C$_n$)alkyl refers to a linear or branched hydrocarbon chain which contains from 1 to n carbon atoms. When the (C$_1$-C$_n$)alkyl is saturated it contains only single bonds. When the (C$_1$-C$_n$)alkyl is unsaturated it contains one or two double bonds and/or one or two triple bonds. The saturated or unsaturated (C$_1$-C$_n$)alkyl may be substituted or unsubstituted as described herein. Moreover, in any alkyl group one or two chain members selected from CH$_2$ or CH are optionally replaced by chain members independently selected from N, NR, O, C(=O), C(=O)NR, NRC(=O) and S; wherein R is as described herein. When in the present invention it is not specified whether the term (C$_1$-C$_n$)alkyl is saturated or unsaturated, the term (C$_1$-C$_n$)alkyl has to be understood as a saturated linear or branched hydrocarbon chain which contains from 1 to n carbon atoms. The above definitions apply also for O(C$_1$-C$_n$)alkyl.

A halogen substituent means fluoro, chloro, bromo or iodo.

In the embodiments of the invention referring to the compounds of formula (I), where the substitution or unsubstitution of a certain group is not specified, e.g. either by indicating a certain substitution for that group or by indicating that the group is unsubstituted, it has to be understood that the possible substitution of this group is the one as in the definition of the formula (I).

"Protective group" (PG) refers to a grouping of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

As mentioned above, a first aspect of the invention relates to compounds of formula (I) or a pharmaceutically acceptable salts thereof. There is no limitation on the type of salt that can be used, provided that these are pharmaceutically acceptable when they are used for therapeutic purposes. The term "pharmaceutically acceptable salts", embraces salts commonly used to form alkali metal salts and to form addition salts of free acids or free bases.

The preparation of pharmaceutically acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically acceptable base or acid in water or in an organic solvent or in a mixture of them. The compounds of formula (I) and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically acceptable solvents such as water, ethanol and the like are equivalent to the unsolvated form for the purposes of the invention.

Some compounds of formula of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

In all embodiments of the invention referring to the compounds of formula (I), the pharmaceutically acceptable salts thereof and the stereoisomers either of any of the compounds of formula (I) or of any of their pharmaceutically acceptable salts are always contemplated even if they are not specifically mentioned.

The compounds of formula (I) of the invention are characterized in that they have a polycyclic ring system selected from the group consisting of formula (A'), formula (B'), formula (C'), and formula (D'):

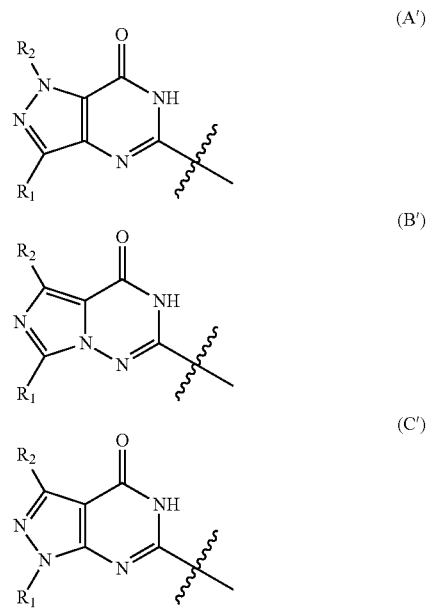

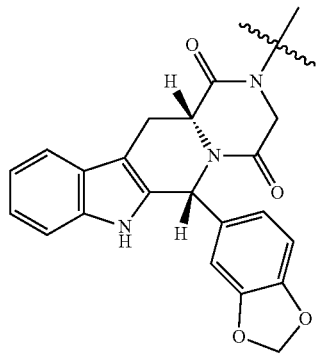

(D')

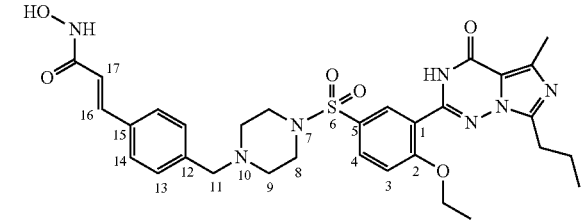 [SMILES: CCCc1nc(C)c2c(=O)[nH]c(-c3cc(S(=O)(=O)N4CCN(Cc5ccc(/C=C/C(=O)NO)cc5)CC4)ccc3OCC)nn12]

and a hydroxamic acid moiety. This polycyclic ring system comprises from 2 to 4 rings; being at least one ring an aromatic ring; and comprises at least 3 nitrogen atoms and 1 oxygen atom. The linker between the polycyclic ring system defined above and the hydroxamic acid moiety, i.e. a structure of formula ($L_1$) or ($L_2$),

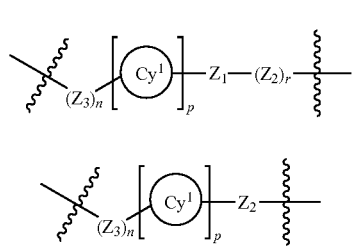

has a chain length comprised from 1 to 20 atoms and comprises a hydrocarbon chain, wherein one or more carbon atoms are optionally replaced by nitrogen, sulphur and/or oxygen atoms, which optionally contains one or more aromatic, heteroaromatic, carbocyclic and/or heterocyclic rings.

In a particular embodiment, the linker between the polycyclic ring system and the hydroxamic acid moiety is a structure of formula ($L_1'$) or ($L_2'$)

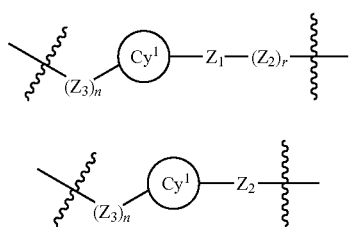

having a chain length comprised from 3 to 20 atoms. For the purposes of the invention, if there is more than one possibility for counting the chain length, the chain length corresponds to the highest number of atoms. As an example, in the compound 2-01 below the linker has a chain length of 17 atoms:

In another embodiment, the invention relates to a compound of formula (I), or a pharmaceutically acceptable salt thereof, or any stereoisomer or mixtures thereof, either of the compound of formula (I) or of any of its pharmaceutically acceptable salts,

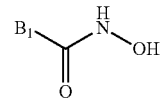

(I)

wherein $B_1$ is a radical selected from the group consisting of formula (A"), formula (B"), formula (C"), and formula (D"):

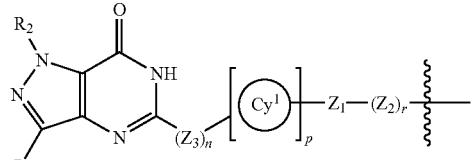

(A")

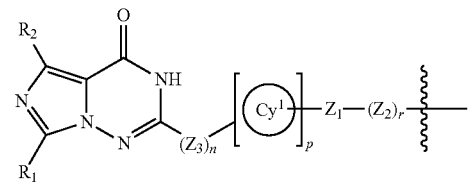

(B")

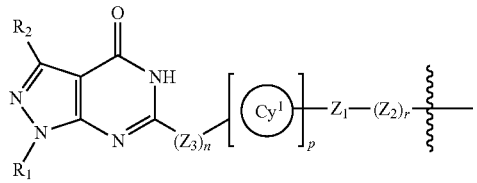

(C")

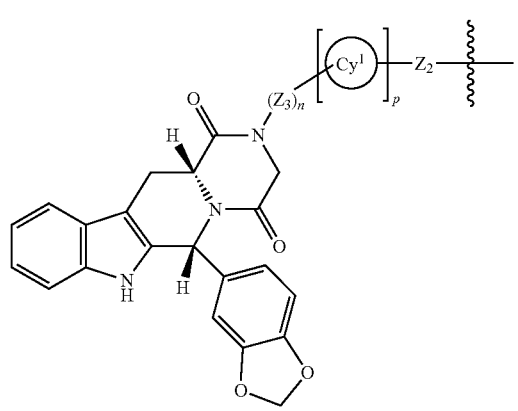

(D")

p, n and r are independently 0 or 1;

$R_1$ and $R_2$ are independently selected from the group consisting of H; saturated or unsaturated $(C_1-C_7)$alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from halogen and $(C_1-C_3)$alkyl;

$Z_1$ is a biradical selected from the group consisting of a formula (E), formula (F'), formula (G'), formula (H'), formula (J') and formula (K):

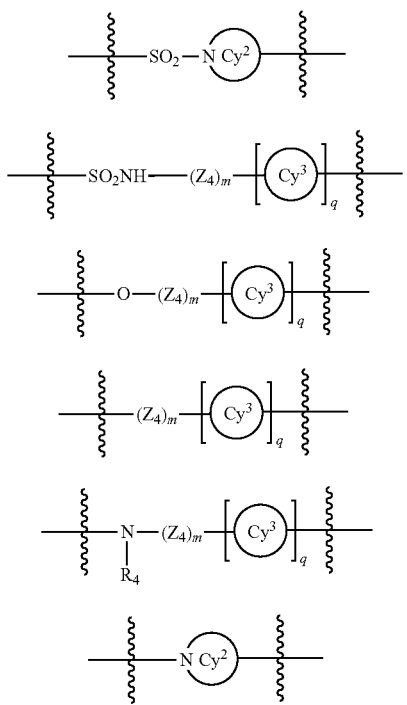

$Z_2$ is selected from the group consisting of —$Z_5$—; —$Z_5$-$Cy^4$-; —$Z_5$-$Cy^4$-$Z_5$—; and -$Cy^4$-;

$Z_3$, $Z_4$ and each $Z_5$ are independently a biradical of a saturated or unsaturated $(C_1-C_6)$alkyl optionally substituted with one or more halogen atoms;

q and m are independently 0 or 1;

$Cy^1$, $Cy^3$ and $Cy^4$ are independently phenyl or a 3- to 7-membered carbocyclic or heterocyclic monocyclic ring, which is saturated or partially unsaturated or aromatic, and which is optionally substituted with one or more $R_3$ groups;

$Cy^2$ is a N-attached 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein $Cy^2$ is optionally substituted with one or more $R_3$ groups;

$R_3$ is selected from halogen; saturated or unsaturated $(C_1-C_7)$alkyl optionally substituted with one or more halogen atoms; saturated or unsaturated —$O(C_1-C_7)$alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and $(C_1-C_6)$ alkyl optionally substituted with one or more halogen atoms;

$R_4$ is H or $(C_1-C_6)$alkyl optionally substituted with one or more halogen atoms; and wherein in any heterocyclic ring one or more of the ring members are selected from NH, N, O, and S;

wherein in all saturated or partially unsaturated rings one or two members of the rings are optionally C(=O) and/or C(=NH) and/or C[=N($C_1$-$C_4$)alkyl], wherein saturated alkyl refers to a linear or branched hydrocarbon chain which contains only single bonds; and unsaturated alkyl refers to a linear or branched hydrocarbon chain which contains one or two double bonds and/or one or two triple bonds;

wherein in any alkyl group one or two chain members selected from $CH_2$ or CH are optionally replaced by chain members independently selected from N, $NR_4$, O, C(=O), C(=O)$NR_4$, $NR_4$C(=O), and S; and with the condition that the moiety ($L_1$) of the formula (A"), formula (B"), and formula (C"), and the moiety ($L_2$) of the formula (D")

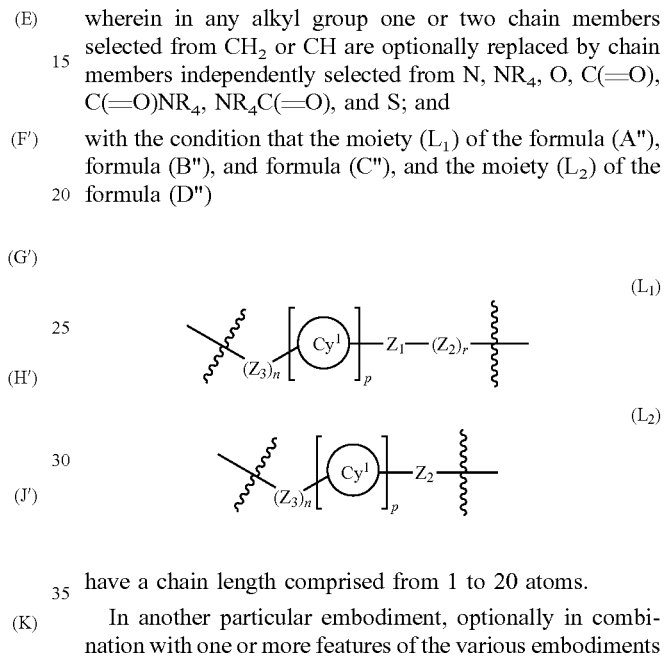

have a chain length comprised from 1 to 20 atoms.

In another particular embodiment, optionally in combination with one or more features of the various embodiments described above or below, in a compound of formula (I), $B_1$ is a radical selected from the group consisting of

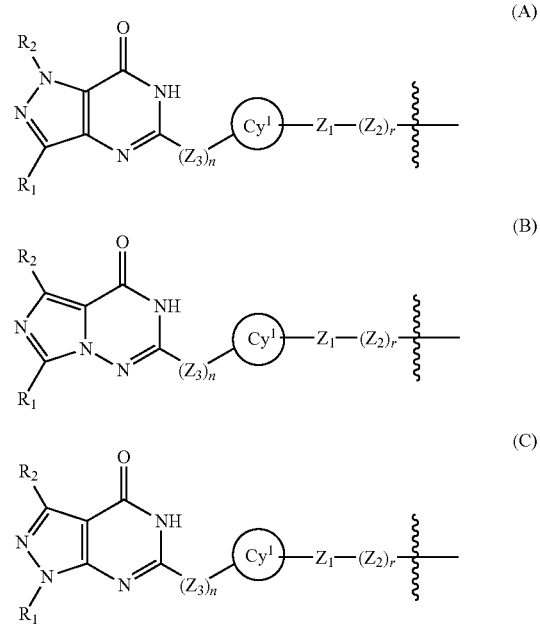

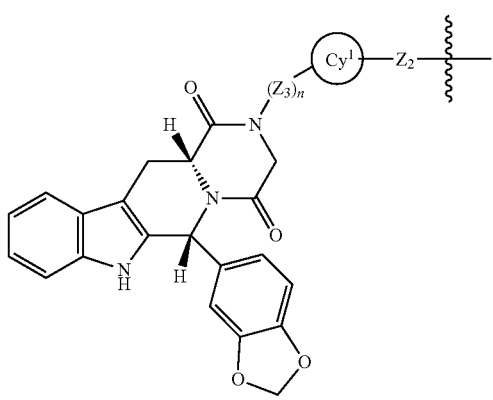

(D)

formula (A), formula (B), formula (C), and formula (D): $R_2$ is H or saturated or unsaturated $(C_1\text{-}C_4)$alkyl optionally substituted with one or more halogen atoms; $Z_1$ is a biradical selected from the group consisting of a formula (E), formula (F), formula (G), formula (H), formula (J), and formula (K):

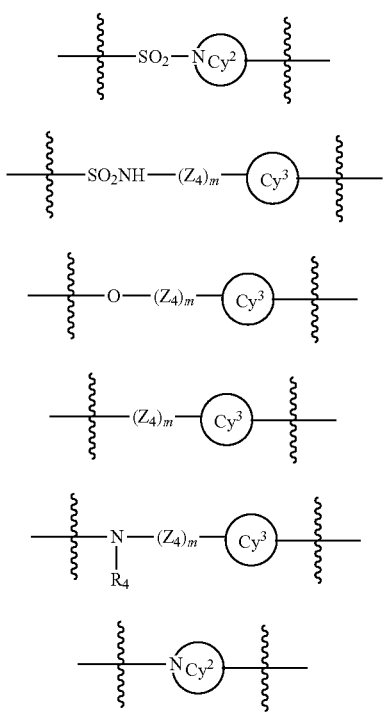

and $R_3$ is selected from halogen, saturated or unsaturated $(C_1\text{-}C_4)$alkyl optionally substituted with one or more halogen atoms; and saturated or unsaturated $—O(C_1\text{-}C_4)$alkyl optionally substituted with one or more halogen atoms. More particularly, $Cy^2$ is a N-attached 5- to 7-membered heterocyclic monocyclic ring, which is saturated or partially unsaturated, and which is optionally substituted with one or more $R_3$ groups.

In a more particular embodiment, optionally in combination with one or more features of the various embodiments described above or below, in a compound of formula (I), n is 0 and $Cy^1$ is selected from the group consisting of phenyl, 5- to 6-membered heteroaromatic ring, 3- to 6-membered carbocyclic ring, and 3- to 7-membered heterocyclic ring, wherein $Cy^1$ is optionally substituted with one or more $R_3$ groups. In a more particular embodiment, n is 0 and $Cy^1$ is phenyl optionally substituted with $R_3$, more particularly phenyl substituted with $—O(C_1\text{-}C_4)$alkyl or $Cy^1$ is pyrrolidine optionally substituted with $R_3$, more particularly pyrrolidine substituted with $—(C_1\text{-}C_4)$alkyl.

In another more particular embodiment, optionally in combination with one or more features of the various embodiments described above or below, in a compound of formula (I), n is 1; $Z_3$ is $—CH(R_5)—$, wherein $R_5$ is H or $(C_1\text{-}C_4)$alkyl optionally substituted with one or more halogen atoms; and $Cy^1$ is a 3- to 6-membered carbocyclic ring or 3- to 7-membered heterocyclic ring, wherein $Cy^1$ is optionally substituted with one or more $R_3$ groups. In a more particular embodiment, n is 1; $Z_3$ is $—CH(R_5)—$; $R_5$ is H or methyl and $Cy^1$ is piperidine or azetidine.

In another particular embodiment, optionally in combination with one or more features of the various embodiments described above or below, in the compound of formula (I), $R_1$ is selected from the group consisting of $(C_1\text{-}C_7)$alkyl optionally substituted with one or more halogen atoms, 3- to 6-membered carbocyclic ring optionally substituted with one or more substituents selected from halogen and $(C_1\text{-}C_3)$alkyl, and 3- to 7-membered heterocyclic ring optionally substituted with one or more substituents selected from halogen and $(C_1\text{-}C_3)$alkyl. In a more particular embodiment, $R_1$ is propyl, cyclopentane or tetrahydropyran.

In another particular embodiment, optionally in combination with one or more features of the various embodiments described above or below, in the compound of formula (I), $R_2$ is H or optionally substituted $(C_1\text{-}C_4)$alkyl. In a more particular embodiment, $R_2$ is H or methyl.

In another particular embodiment, optionally in combination with one or more features of the various embodiments described above or below, in a compound of formula (I), $Cy^2$ is optionally substituted saturated 5- to 7-membered heterocyclic ring. More particularly, $Cy^2$ is piperidine or piperazine.

In another particular embodiment, optionally in combination with one or more features of the various embodiments described above or below, in a compound of formula (I), $Cy^2$ is a N-attached 3- to 7-membered heterocyclic monocyclic ring, which is spiro-fused to a 3- to 7-membered carbocyclic or heterocyclic monocyclic ring, wherein $Cy^2$ is optionally substituted with one or more $R_3$ groups.

In another particular embodiment, in a compound of formula (I), optionally in combination with one or more features of the various embodiments described above or below, $Cy^3$ is selected from the group consisting of phenyl, 5- to 6-membered heteroaromatic ring, 5- to 6-membered carbocyclic ring, 3- to 7-membered carbocyclic ring, 4- to 6-membered heterocyclic ring, and 5- to 7-membered heterocyclic ring, wherein $Cy^3$ is optionally substituted with one or more $R_3$ groups. More particularly, $Cy^3$ is phenyl, azetidine, piperidine, piperazine, pyrimidine, thiophene, furan, pyridine, cyclobutane, cyclopentane, cyclohexane, cyclohexene, or cycloheptane.

In another particular embodiment, in a compound of formula (I), optionally in combination with one or more features of the various embodiments described above or below, $Cy^4$ is selected from the group consisting of phenyl, and 5- to 6-membered heteroaromatic ring, wherein $Cy^4$ is optionally substituted with one or more $R_3$ groups. More particularly, $Cy^4$ is phenyl, pyridine or pyrimidine.

In another particular embodiment, in a compound of formula (I), optionally in combination with one or more features of the various embodiments described above or below, $Z_1$ is a biradical of formula (H), wherein m is 0 and q is 0 ($Z_1$ is absent).

In another particular embodiment, in a compound of formula (I), optionally in combination with one or more features of the various embodiments described above or below, Z, is selected from the group consisting of:

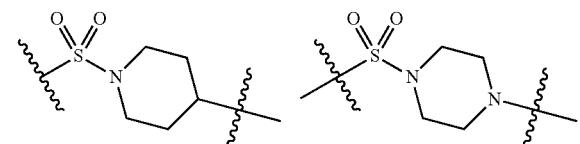
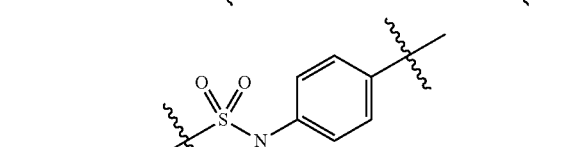
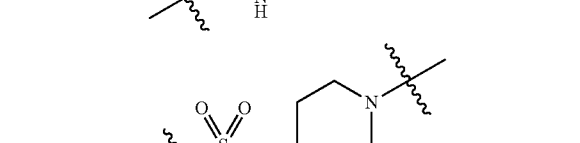
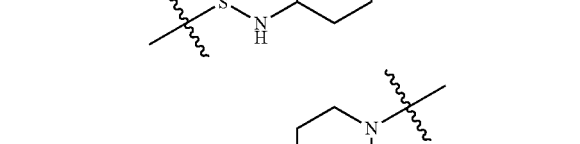
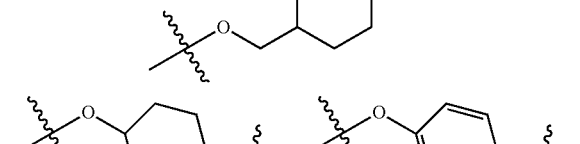
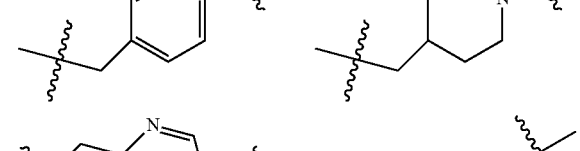
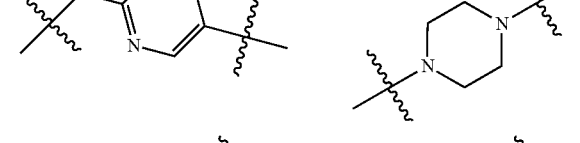
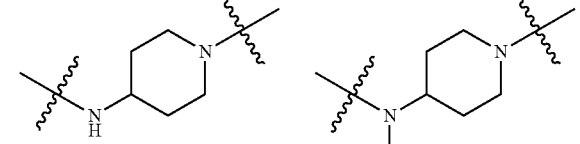
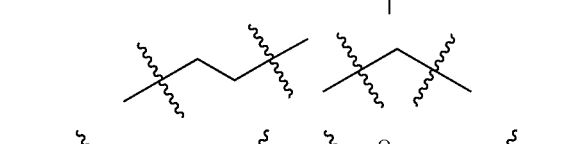
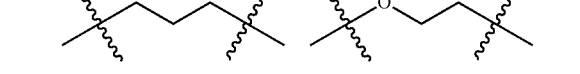
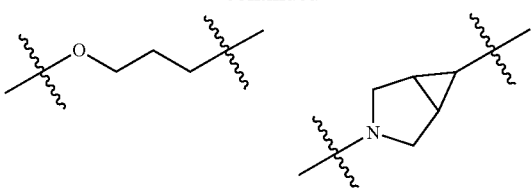
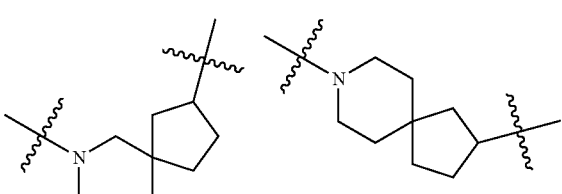
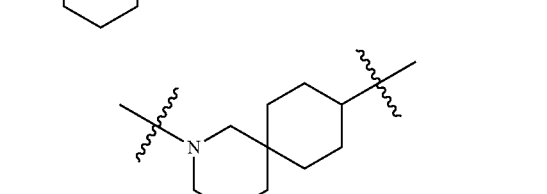
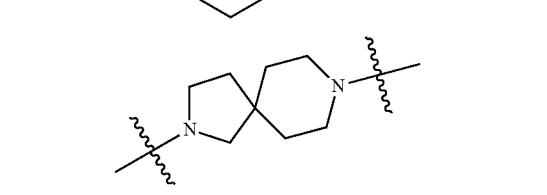
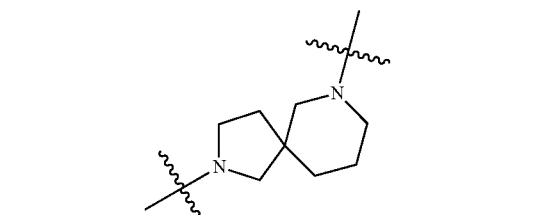

In another particular embodiment, in a compound of formula (I), optionally in combination with one or more features of the various embodiments described above or below, $Z_1$ is selected from the group consisting of:

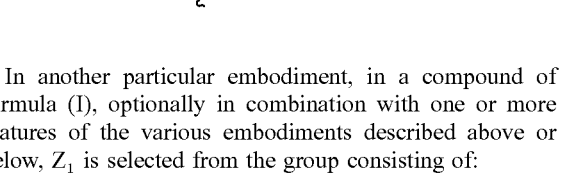
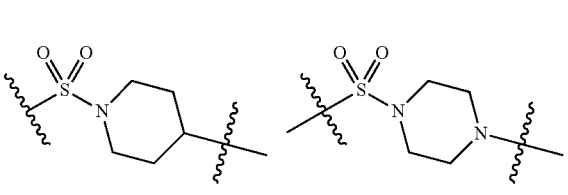
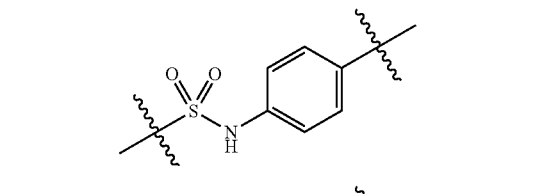
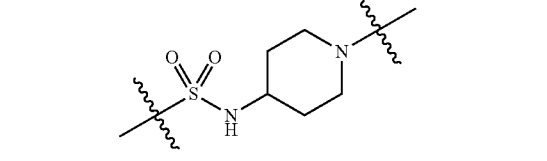

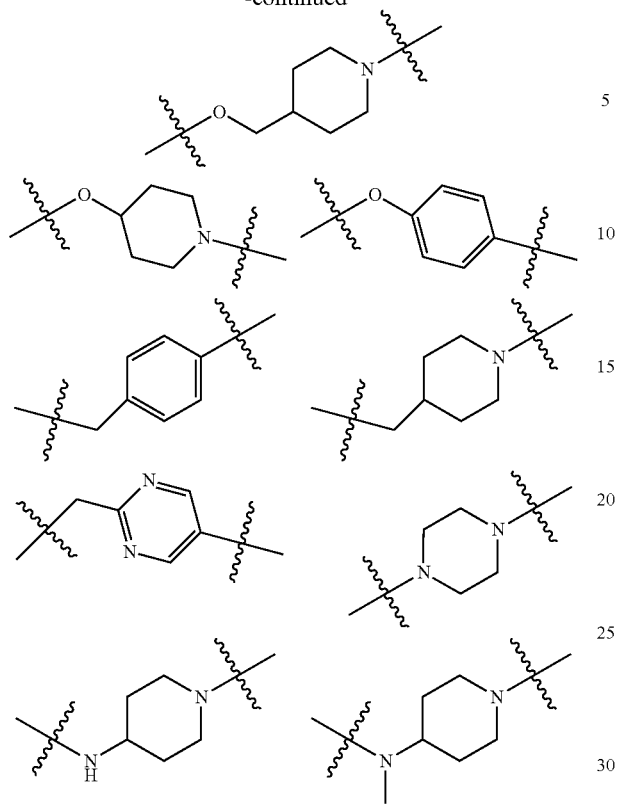

In another particular embodiment, in a compound of formula (I), optionally in combination with one or more features of the various embodiments described above or below, r is 1 and $Z_2$ is selected from the group consisting of:

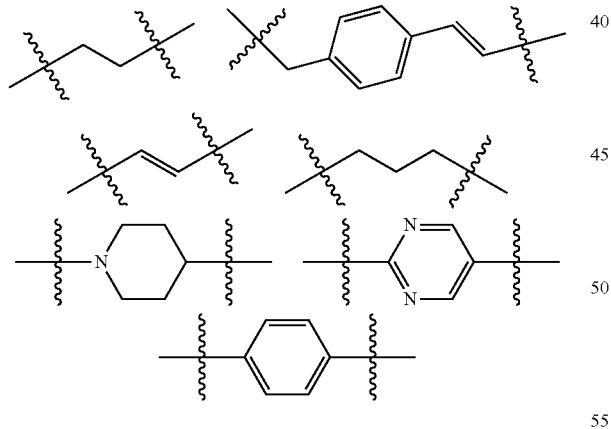

In another particular embodiment, in a compound of formula (I), optionally in combination with one or more features of the various embodiments described above or below, m is 0.

In another particular embodiment, in a compound of formula (I), optionally in combination with one or more features of the various embodiments described above or below, m is 1, and $Z_4$ is —$(CH_2)_t$—, wherein t is 1-3.

In another particular embodiment, in a compound of formula (I), optionally in combination with one or more features of the various embodiments described above or below, $Z_5$ is selected from the group consisting of: —$(CH_2)_t$—, wherein t is 1-3, and —CH=CH—.

In another particular embodiment, in a compound of formula (I), optionally in combination with one or more features of the various embodiments described above or below, r is 1 and the group —$Z_1$—$Z_2$— is selected from the group consisting of:

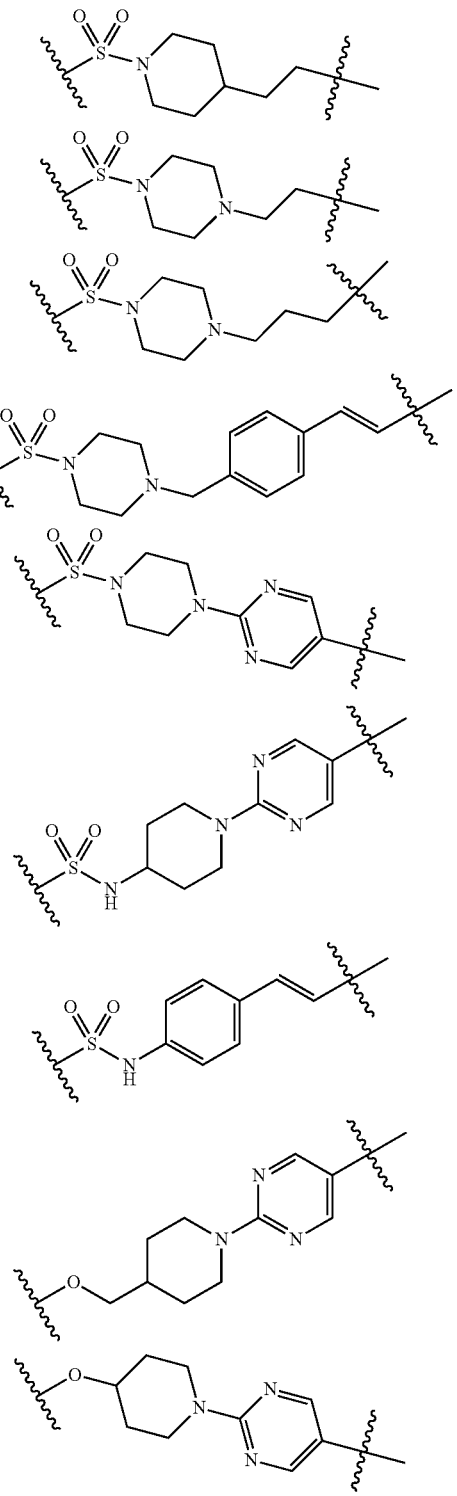

-continued
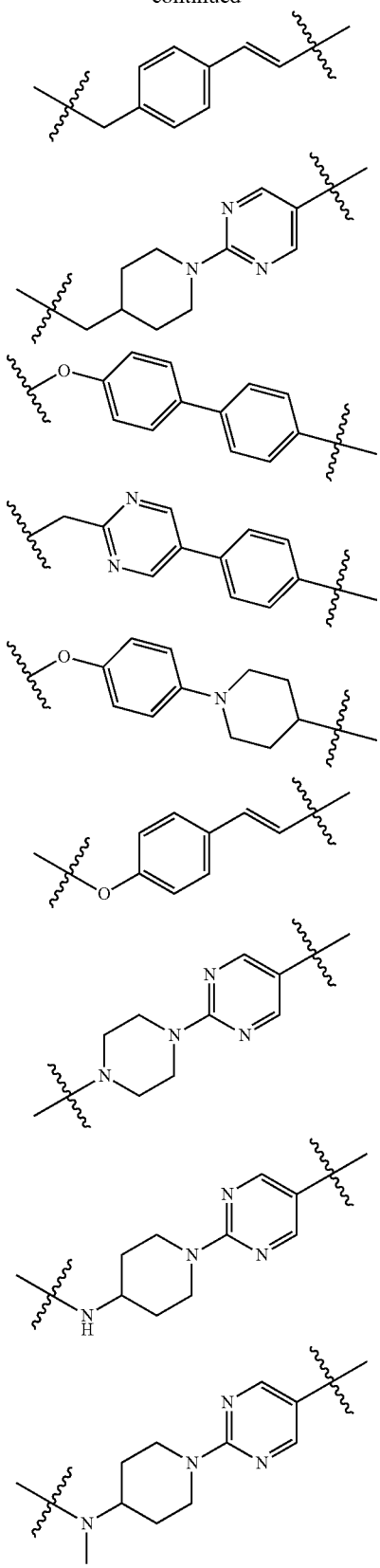
In another particular embodiment, in a compound of formula (I), optionally in combination with one or more features of the various embodiments described above or below, r is 1 and the group —$Z_1$—$Z_2$— is selected from the group consisting of:
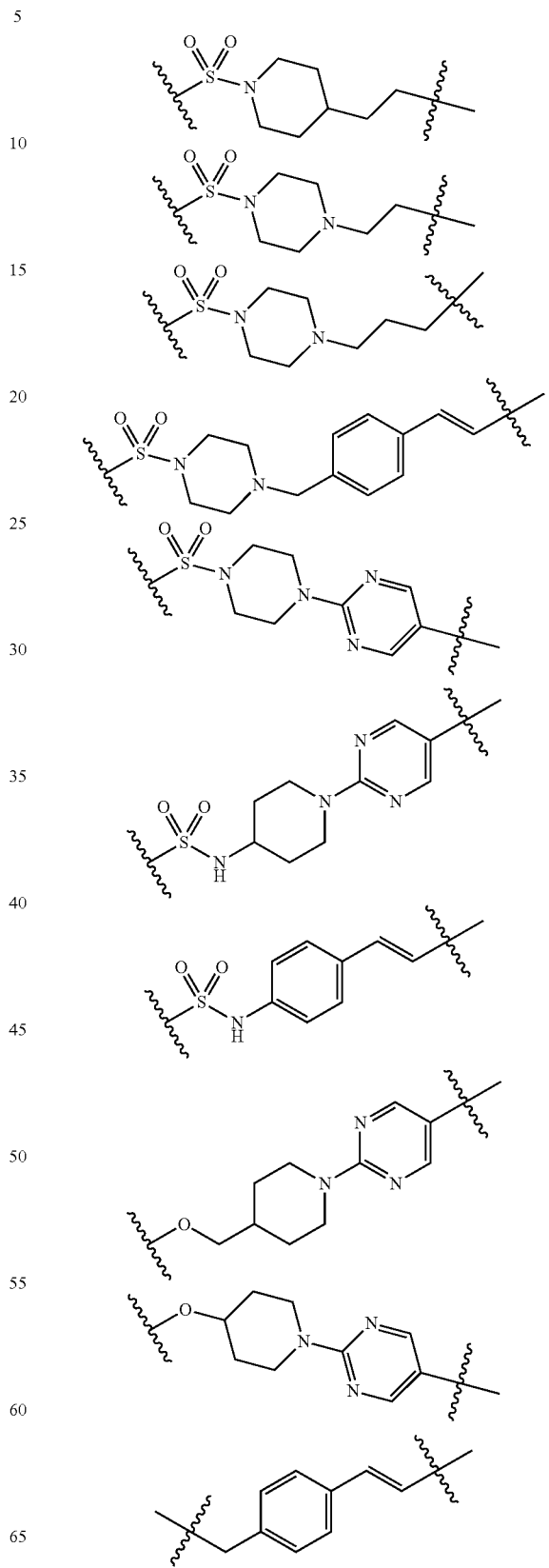

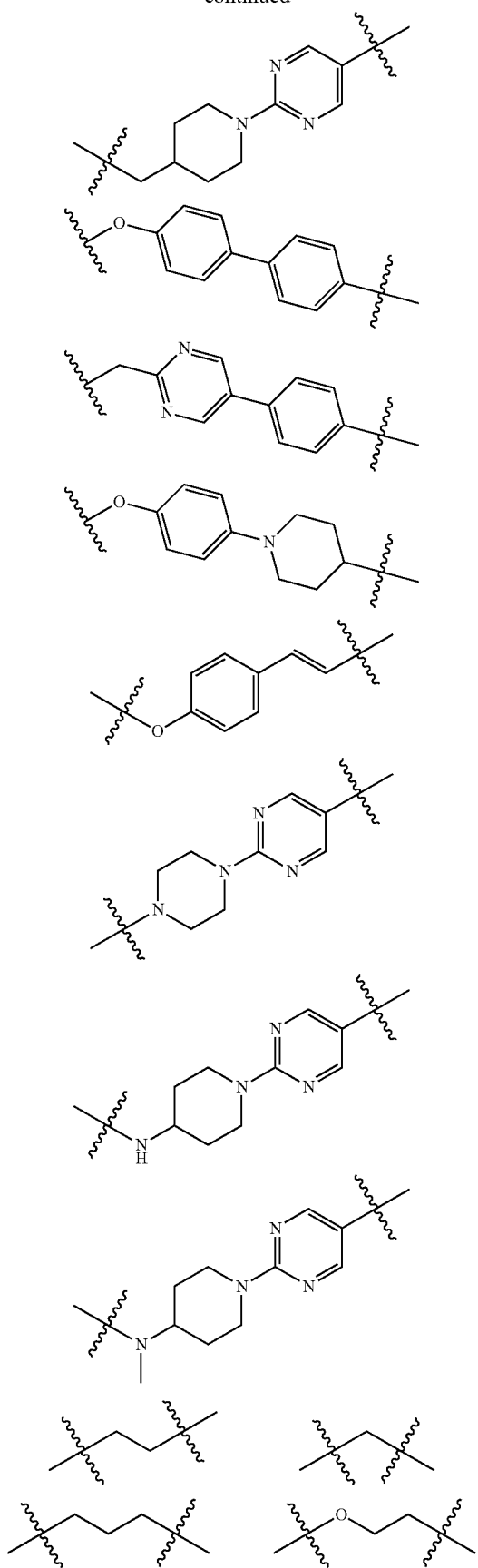
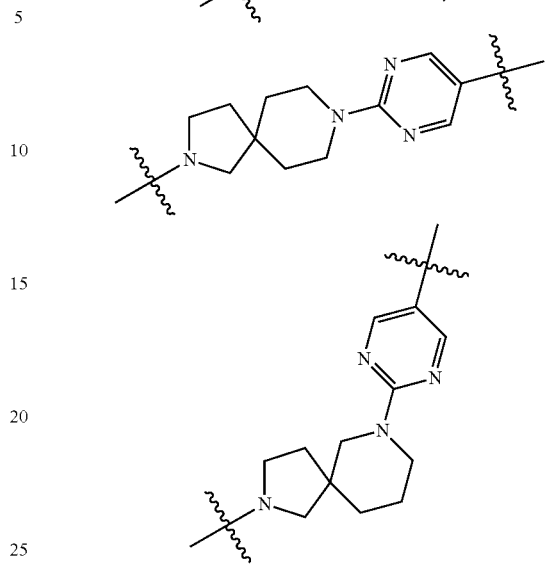
In another particular embodiment, the compound of formula (I) has the formula (I'),
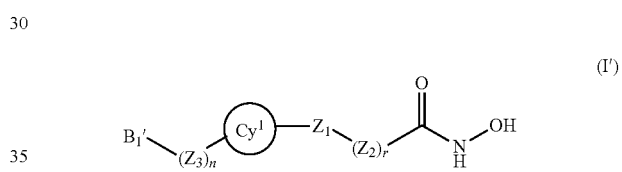
wherein $B_1'$ is selected from the group consisting of formula (A'), formula (B'), and formula (C')
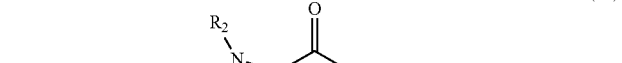
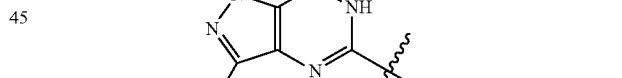
wherein $Z_3$, n, $Cy^1$, r, $Z_1$, $Z_2$, $R_1$ and $R_2$ are as previously defined.

The particular embodiments mentioned above for compounds of formula (I) are also particular embodiments of the compounds of formula (I').

In another embodiment, the compound of formula (I') is a compound of formula (IA) or formula (IB):

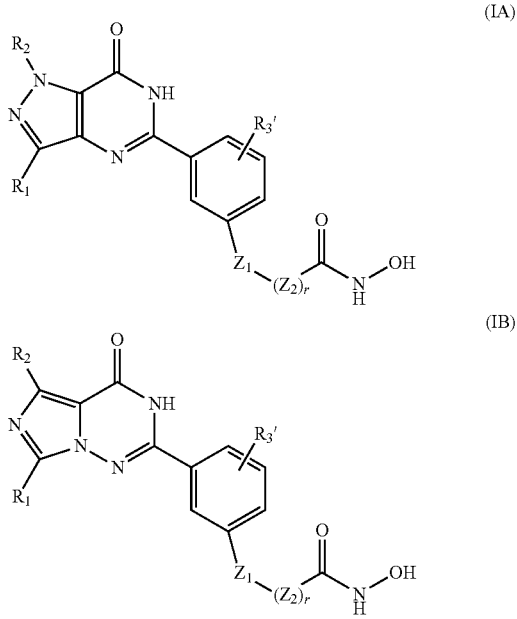

(IA)

(IB)

wherein r, $Z_1$, $Z_2$, $R_1$ and $R_2$ are as previously defined; and $R_3'$ is selected from H; halogen; saturated or unsaturated $(C_1$-$C_4)$alkyl optionally substituted with one or more halogen atoms; saturated or unsaturated —O($C_1$-$C_4$)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and $(C_1$-$C_6)$alkyl optionally substituted with one or more halogen atoms.

In a particular embodiment, in the compounds of formula (IA) or formula (IB), $R_3'$ is selected from H; halogen; saturated or unsaturated $(C_1$-$C_4)$alkyl optionally substituted with one or more halogen atoms; and saturated or unsaturated —O($C_1$-$C_4$)alkyl optionally substituted with one or more halogen atoms.

The particular embodiments mentioned above for compounds of formula (I) are also particular embodiments of the compounds of formula (IA) and of formula (IB).

In a particular embodiment, optionally in combination with one or more features of the various embodiments described above or below, in the compound of formula (IA) or formula (IB), $R_1$ is optionally substituted $(C_1$-$C_7)$alkyl, more particularly, propyl.

In another particular embodiment, optionally in combination with one or more features of the various embodiments described above or below, in the compound of formula (IA) or formula (IB), $R_2$ is optionally substituted $(C_1$-$C_4)$alkyl, more particularly, methyl.

In another particular embodiment, optionally in combination with one or more features of the various embodiments described above or below, in the compound of formula (IA) or formula (IB), $R_3'$ is optionally substituted —O($C_1$-$C_4$)alkyl, more particularly, ethoxy, even more particularly ethoxy placed at the ortho position with respect to the carbon attached to the bicyclic ring.

In another particular embodiment, optionally in combination with one or more features of the various embodiments described above or below, in the compound of formula (IA) or formula (IB), $Z_1$ is a biradical selected from the group consisting of formula (E), formula (F) and formula (G) as defined above.

In another embodiment, the invention relates to a compound of formula (I), which is a compound of formula (IC):

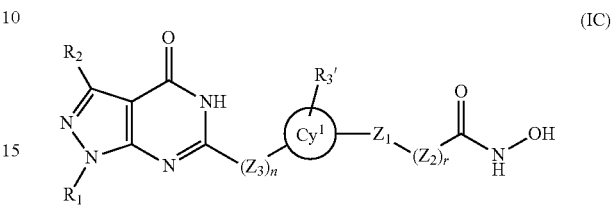

(IC)

wherein $R_1$-$R_2$, r, $Z_1$-$Z_3$, and n are as previously defined, $Cy^1$ is 4- to 6-membered heterocyclic ring, and $R_3'$ is selected from H; saturated or unsaturated $(C_1$-$C_4)$alkyl optionally substituted with one or more halogen atoms; and 3- to 7-membered carbocyclic or heterocyclic monocyclic ring, which is saturated or partially unsaturated or aromatic, and which is optionally substituted with one or more substituents selected from the group consisting of halogen and $(C_1$-$C_6)$alkyl optionally substituted with one or more halogen atoms.

In a particular embodiment, in the compounds of formula (IC), $R_3'$ is selected from H, and saturated or unsaturated $(C_1$-$C_4)$alkyl optionally substituted with one or more halogen atoms.

The particular embodiments mentioned above for compounds of formula (I) are also particular embodiments of the compounds of formula (IC).

In a particular embodiment, optionally in combination with one or more features of the various embodiments described above or below, in the compound of formula (IC), n is O.

In another particular embodiment, optionally in combination with one or more features of the various embodiments described above or below, in the compound of formula (IC), n is 1, and $Z_3$ is —CH($R_5$)—, wherein $R_5$ is H or $(C_1$-$C_4)$ alkyl optionally substituted with one or more halogen atoms, more particularly, $R_5$ is H or methyl.

In another particular embodiment, optionally in combination with one or more features of the various embodiments described above or below, in the compound of formula (IC), $Cy^1$ is pyrrolidine, piperidine, piperazine or azetidine.

In a particular embodiment, optionally in combination with one or more features of the various embodiments described above or below, in the compound of formula (IC), $R_1$ is saturated 3- to 7-membered carbocyclic or heterocyclic ring, more particularly, tetrahydropyran or cyclopentane.

In another particular embodiment, optionally in combination with one or more features of the various embodiments described above or below, in the compound of formula (IC), $R_2$ is H.

In another particular embodiment, optionally in combination with one or more features of the various embodiments described above or below, in the compound of formula (IC), and $R_3'$ is H or $(C_1$-$C_6)$alkyl optionally substituted with one or more halogen atoms, more particularly, H or methyl.

In another particular embodiment, optionally in combination with one or more features of the various embodiments described above or below, in the compound of formula (IC), $Z_1$ is a biradical selected from the group consisting of formula (G) and formula (H) as defined above.

In another embodiment, the compound of formula (I) is a compound of formula (ID):

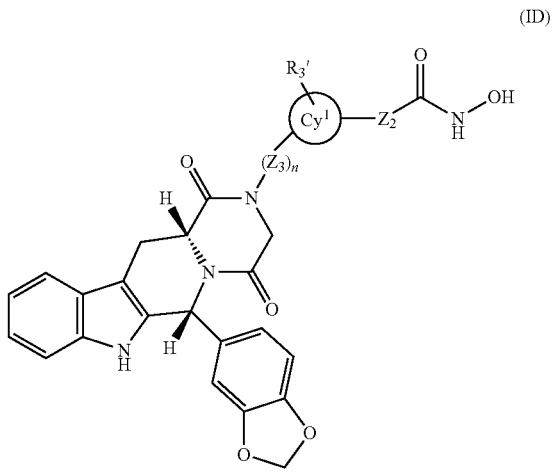

wherein $Z_2$, $Z_3$, n and $Cy^1$ are as previously defined, and $R_3'$ is selected from H; halogen; saturated or unsaturated $(C_1-C_4)$alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and $(C_1-C_6)$alkyl optionally substituted with one or more halogen atoms.

In a particular embodiment, in the compounds of formula (ID), $R_3'$ is selected from H, halogen, and saturated or unsaturated $(C_1-C_4)$alkyl optionally substituted with one or more halogen atoms.

The particular embodiments mentioned above for compounds of formula (I) are also particular embodiments of the compounds of formula (ID).

In a particular embodiment, in a compound of formula (ID), n is 0 and $Cy^1$ is selected from the group consisting of phenyl, 5- to 6-membered heteroaromatic ring, 5- to 6-membered carbocyclic ring, and 5- to 7-membered heterocyclic ring, wherein $Cy^1$ is optionally substituted with one or more $R_3$ groups. In a more particular embodiment, n is 0 and $Cy^1$ is optionally substituted phenyl, more particularly, unsubstituted phenyl.

In another particular embodiment, in a compound of formula (ID), n is 1; $Z_3$ is —CH($R_5$)—, wherein $R_5$ is H or $(C_1-C_4)$alkyl optionally substituted with one or more halogen atoms; and $Cy^1$ is 3- to 6-membered carbocyclic ring or 3- to 7-membered heterocyclic ring wherein $Cy^1$ is optionally substituted with one or more $R_3$ groups. In a more particular embodiment, n is 1, $Z_3$ is —CH($R_5$)—, $R_5$ is H, and $Cy^1$ is piperidine.

In another embodiment, in a compound of formula (ID), —$Z_2$— is selected from the group consisting of:

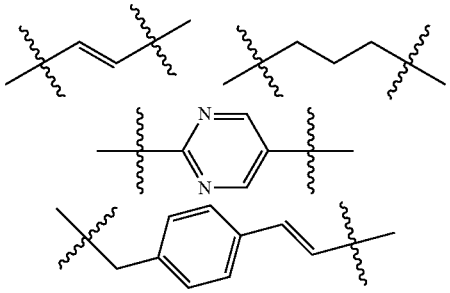

In another particular embodiment, optionally in combination with one or more features of the various embodiments described above or below, the invention relates to a compound of formula (I), wherein $B_1$ is a radical of formula (A").

In another particular embodiment, optionally in combination with one or more features of the various embodiments described above or below, the invention relates to a compound of formula (I), wherein $B_1$ is a radical of formula (B").

In another particular embodiment, optionally in combination with one or more features of the various embodiments described above or below, the invention relates to a compound of formula (I), wherein $B_1$ is a radical of formula (C").

In another particular embodiment, optionally in combination with one or more features of the various embodiments described above or below, the invention relates to a compound of formula (I), wherein $R_1$ is selected from the group consisting of saturated or unsaturated $(C_1-C_4)$alkyl optionally substituted with one or more halogen atoms, 5- to 6-membered saturated carbocyclic ring optionally substituted with one or more substituents selected from halogen and $(C_1-C_3)$alkyl, and 5- to 6-membered saturated heterocyclic ring optionally substituted with one or more substituents selected from halogen and $(C_1-C_3)$alkyl.

In another particular embodiment, optionally in combination with one or more features of the various embodiments described above or below, the invention relates to a compound of formula (I), wherein $R_2$ is H or saturated or unsaturated $(C_1-C_4)$alkyl optionally substituted with one or more halogen atoms.

In another particular embodiment, optionally in combination with one or more features of the various embodiments described above or below, the invention relates to a compound of formula (I), wherein $Z_1$ is a biradical selected from the group consisting of a formula (E), formula (G'), and formula (H'), more particularly, wherein q is 1, and even more particularly, wherein $Z_1$ is a biradical of formula (G) or formula (H).

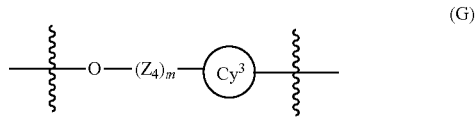

(G)

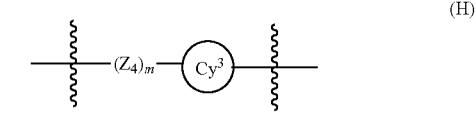

(H)

In another particular embodiment, optionally in combination with one or more features of the various embodiments described above or below, the invention relates to a compound of formula (I), wherein r is 0, or alternatively r is 1 and $Z_2$ is -$Cy^4$-; more particularly, wherein r is 0.

In another particular embodiment, optionally in combination with one or more features of the various embodiments described above or below, the invention relates to a compound of formula (I), wherein $B_1$ is a radical of formula (D").

In another particular embodiment, optionally in combination with one or more features of the various embodiments described above or below, the invention relates to a compound of formula (I), wherein p is 1; more particularly, wherein
Cy$^1$ is selected from the group consisting of: phenyl, 5- to 6-membered heteroaromatic ring, and 4- to 6-membered saturated heterocyclic ring, wherein Cy$^1$ is optionally substituted with one or more R$_3$ groups.

In another particular embodiment, optionally in combination with one or more features of the various embodiments described above or below, the invention relates to a compound of formula (I), which is a compound of formula (IA):

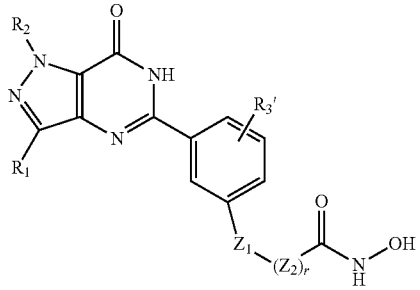

(IA)

wherein R$_3$' is H or R$_3$.

In another particular embodiment, optionally in combination with one or more features of the various embodiments described above or below, the invention relates to a compound of formula (I), which is a compound of formula (IB):

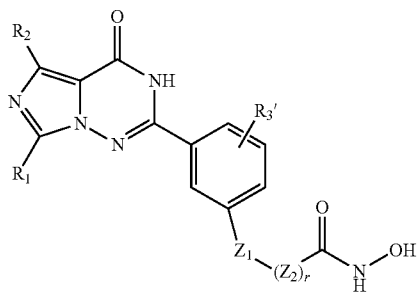

(IB)

wherein R$_3$' is H or R$_3$.

In another particular embodiment, optionally in combination with one or more features of the various embodiments described above or below, the invention relates to a compound of formula (I), in particular a compound of formula (IA) or a compound of formula (IB), wherein R$_3$' is selected from H, halogen, saturated or unsaturated (C$_1$-C$_4$)alkyl optionally substituted with one or more halogen atoms; and saturated or unsaturated —O(C$_1$-C$_4$)alkyl optionally substituted with one or more halogen atoms.

In another particular embodiment, optionally in combination with one or more features of the various embodiments described above or below, the invention relates to a compound of formula (I), which is a compound of formula (IC):

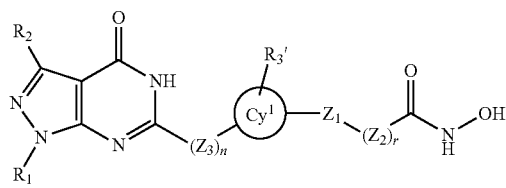

(IC)

wherein R$_3$' is H or R$_3$.

In another particular embodiment, optionally in combination with one or more features of the various embodiments described above or below, the invention relates to a compound of formula (I), which is a compound of formula (IC$^{III}$) or a compound of formula (IC$^{IV}$):

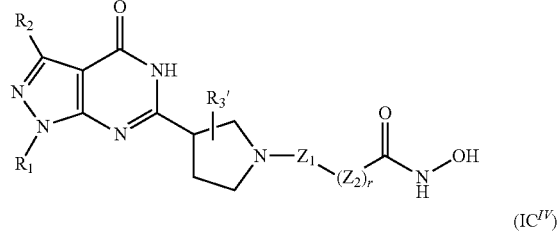

(IC$^{III}$)

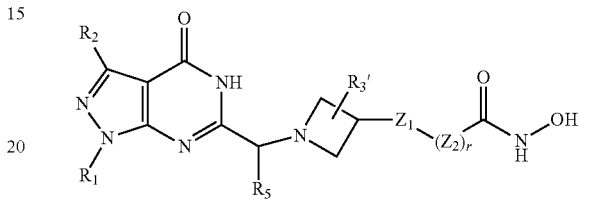

(IC$^{IV}$)

wherein R$_5$ is selected from the group consisting of: H, halogen, and (C$_1$-C$_4$)alkyl optionally substituted with one or more halogen atoms.

In another particular embodiment, optionally in combination with one or more features of the various embodiments described above or below, the invention relates to a compound of formula (I), in particular a compound of formula (IC), a compound of formula (IC$^{III}$) or a compound of formula (IC$^{IV}$), wherein R$_3$' is selected from H and saturated or unsaturated (C$_1$-C$_4$)alkyl optionally substituted with one or more halogen atoms.

In another particular embodiment, optionally in combination with one or more features of the various embodiments described above or below, the invention relates to a compound of formula (I), which is a compound of formula (ID):

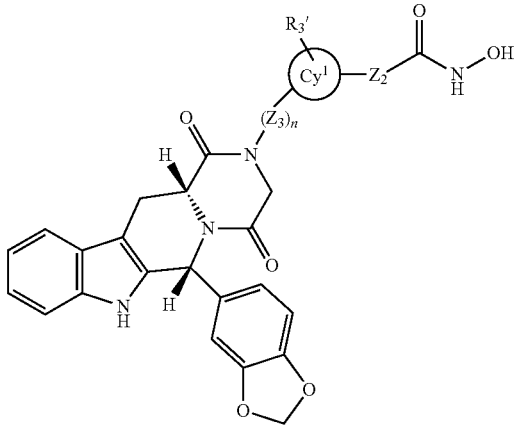

(ID)

wherein R$_3$' is H or R$_3$.

In another particular embodiment, optionally in combination with one or more features of the various embodiments described above or below, the invention relates to a compound of formula (I), in particular a compound of formula (ID), wherein R$_3$' is selected from H, halogen, and saturated or unsaturated (C$_1$-C$_4$)alkyl optionally substituted with one or more halogen atoms.

The inventors have found that compounds of formula (II) also comprising several ring systems and a hydroxamic acid moiety are also dual inhibitors of PDEs and HDACs. Thus, the present invention also relates to compounds of formula (II), including any stereoisomer or mixtures thereof, or pharmaceutically acceptable salts thereof,

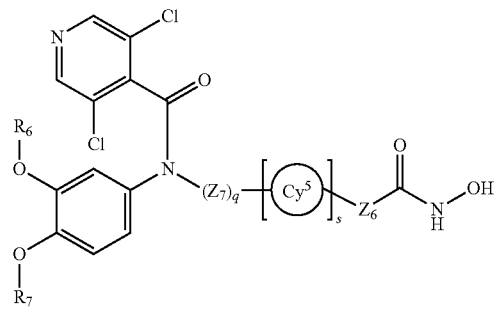
(II)

wherein
q and s are independently 0 or 1;
$R_6$ and $R_7$ are independently selected from the group consisting of H; saturated or unsaturated $(C_1-C_6)$alkyl optionally substituted with one or more halogen atoms; and 3- to 6-membered carbocyclic or heterocyclic monocyclic ring containing from 1 to 3 ring members selected from NH, N, O, and S, which is saturated or partially unsaturated or aromatic, and which is optionally substituted with one or more $R_8$ groups;
$Z_6$ is selected from the group consisting of —$Z_8$—; —$Z_8$-$Cy^6$-; —$Z_8$-$Cy^6$-$Z_8$—; and -$Cy^7$-;
$Z_7$ and $Z_8$ are independently a biradical of a saturated or unsaturated $(C_1-C_6)$alkyl optionally substituted with one or more halogen atoms;
$Cy^5$ and $Cy^6$ are independently phenyl or a 4- to 6-membered carbocylic or heterocyclic monocyclic ring; which is saturated or partially unsaturated or aromatic; and which is optionally substituted with one or more $R_8$ groups;
$R_8$ is selected from halogen, saturated or unsaturated $(C_1-C_4)$alkyl optionally substituted with one or more halogen atoms; and saturated or unsaturated —$O(C_1-C_4)$alkyl optionally substituted with one or more halogen atoms;
wherein in any heterocyclic ring one or more of the ring members are selected from NH, N, O, and S;
wherein in all saturated or partially unsaturated rings one or two members of the rings are optionally C(=O) and/or C(=NH) and/or C[=N($C_1-C_4$)alkyl]; and
wherein in any alkyl group one or two chain members selected from $CH_2$ or CH are optionally replaced by chain members independently selected from N, $NR_9$, O, C(=O), C(=O)$NR_9$, $NR_9$C(=O) and S; and $R_9$ is H or $(C_1-C_6)$alkyl optionally substituted with one or more halogen atoms;
with the condition that the moiety ($L_3$) of the formula (II)

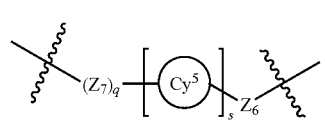
($L_3$)

has a chain length comprised from 1 to 20 atoms.
In a particular embodiment, in a compound of formula (II), q is 0, s is 1, and $Cy^5$ is 3- to 6-membered carbocyclic ring or 3- to 6-membered heterocyclic ring, wherein $Cy^5$ is optionally substituted with one or more $R_8$ groups. In a more particular embodiment, q is 0, r is 1 and $Cy^5$ is piperidine.

In another embodiment, in a compound of formula (II), q is 0 and s is 0.
In another embodiment, in a compound of formula (II), —$Z_6$— is selected from the group consisting of:

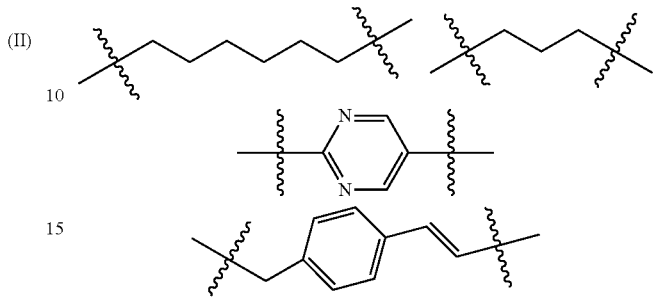

In another embodiment of the invention, the compound of formula (I) is selected from the group consisting of:

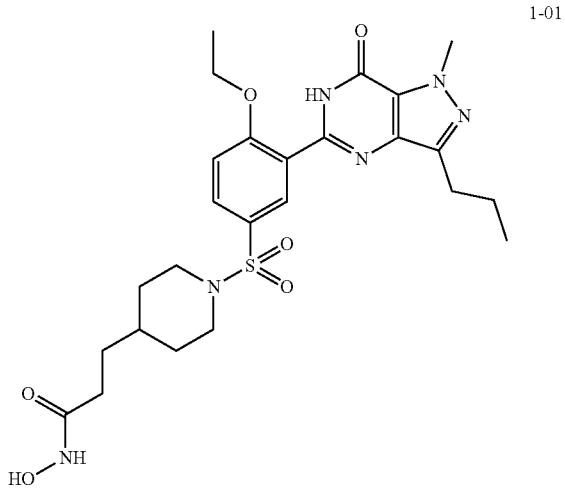
1-01

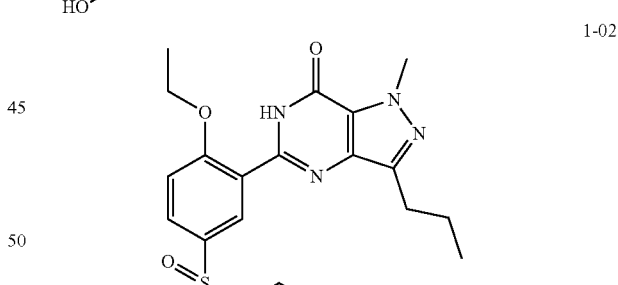
1-02

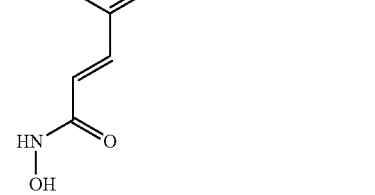

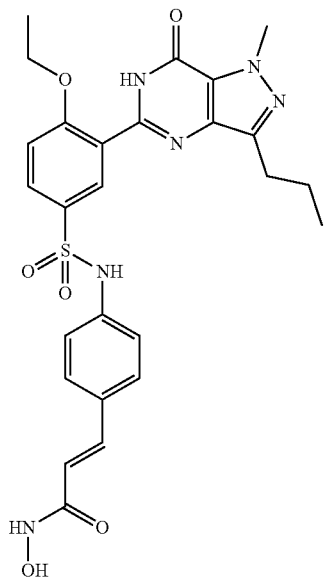
1-03
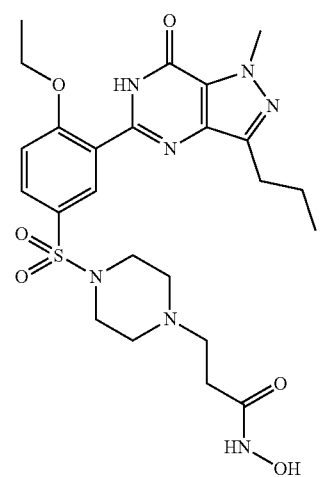
1-04
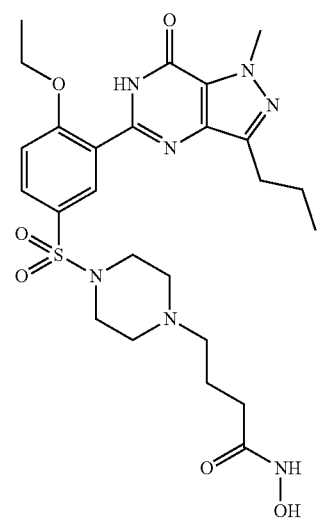
1-05
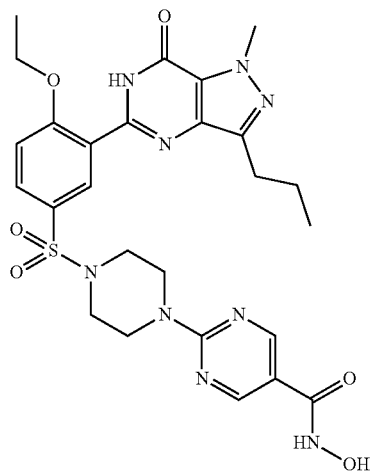
1-06
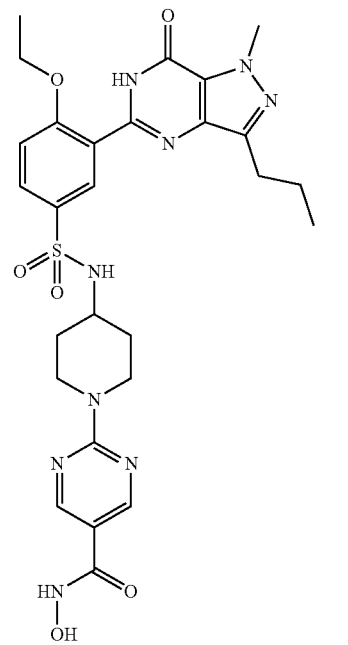
1-07
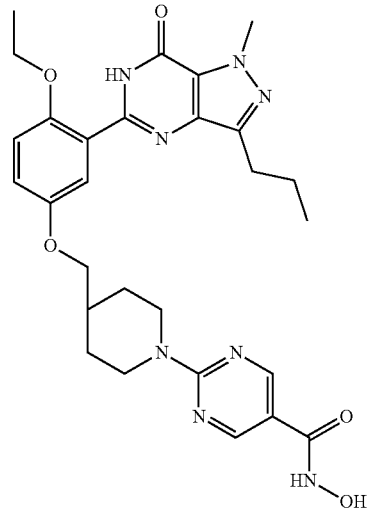
1-11

-continued
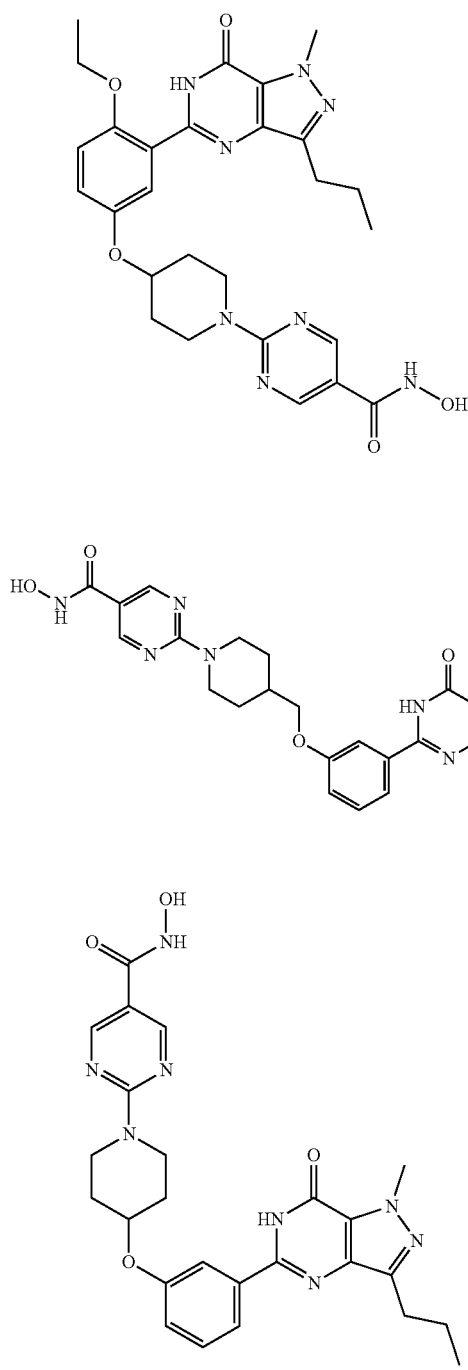
1-12
1-13
1-14
1-15
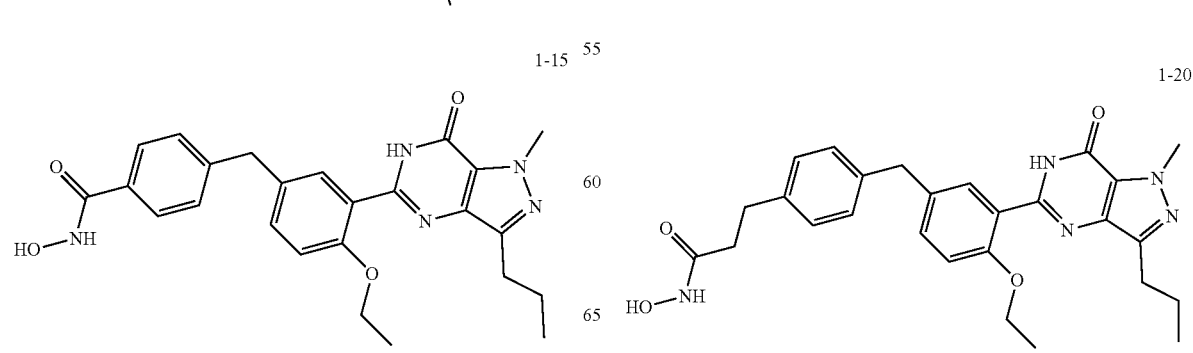
1-16
1-17
1-18
1-19
1-20

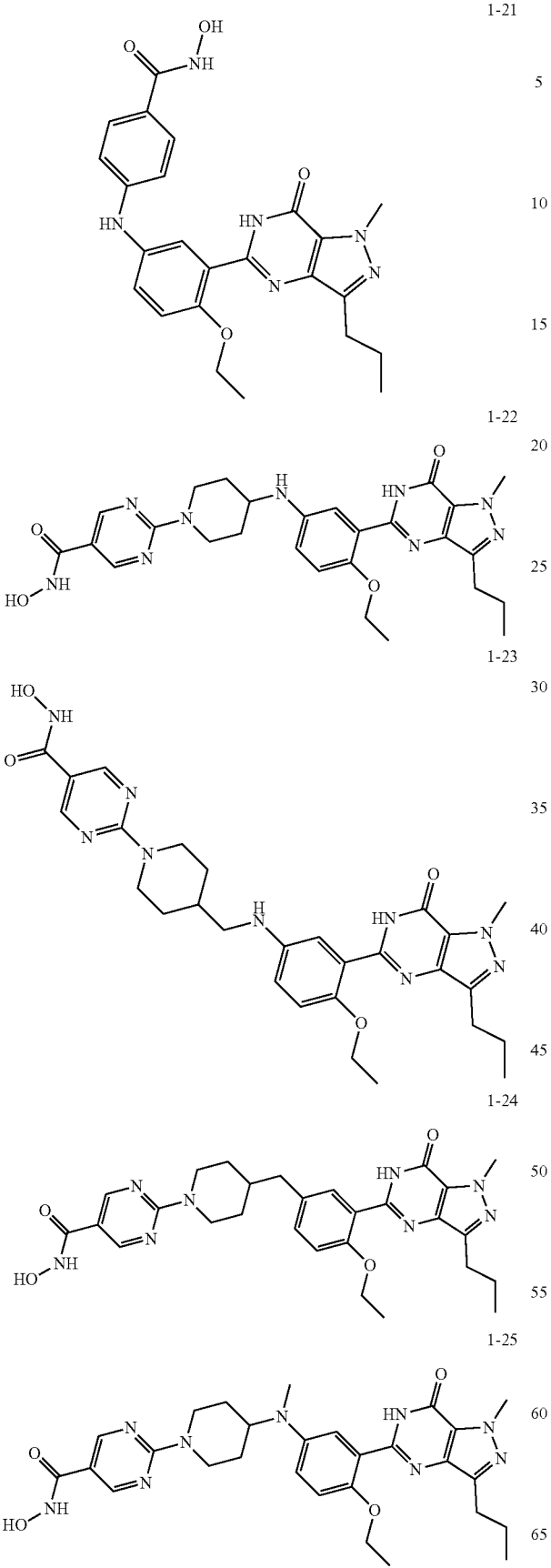
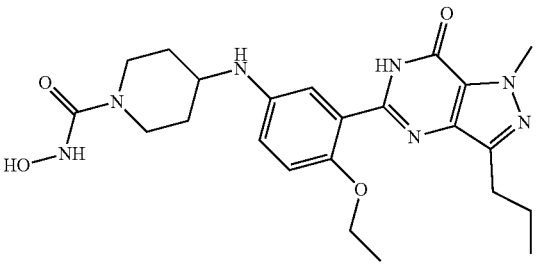
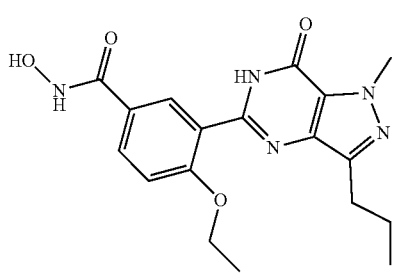
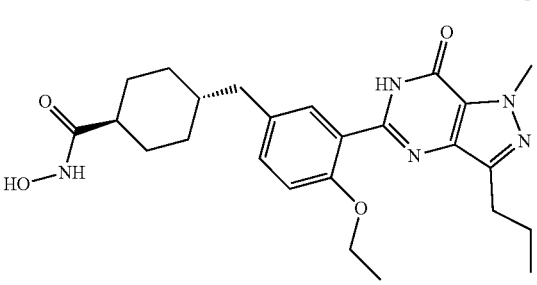
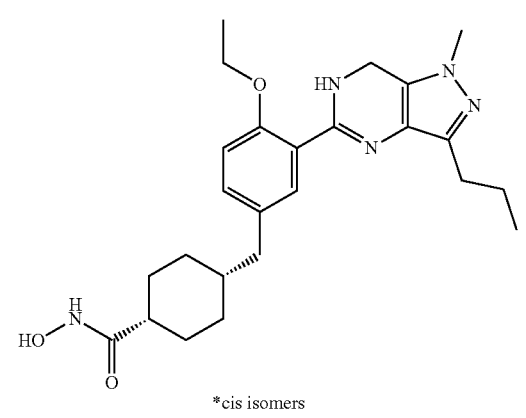
* trans isomers
*cis isomers 37
-continued
1-30
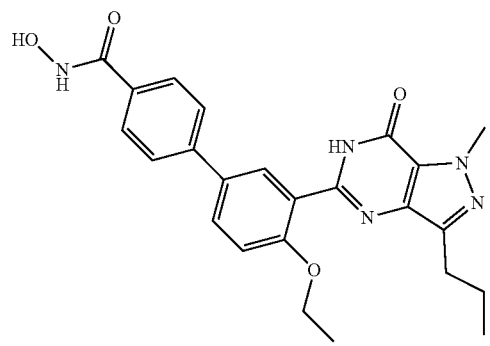
1-31
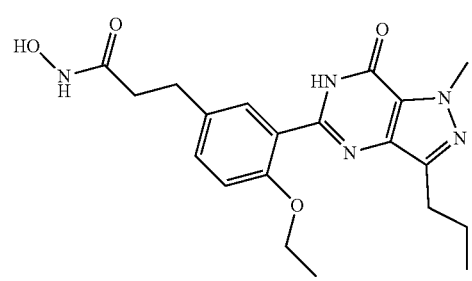
1-32
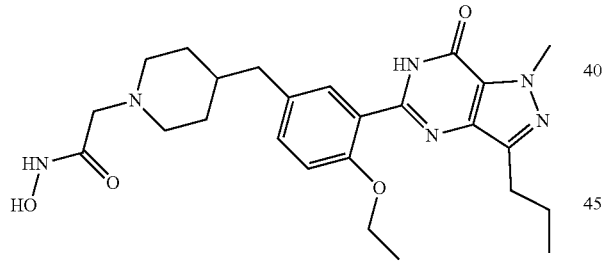
1-33
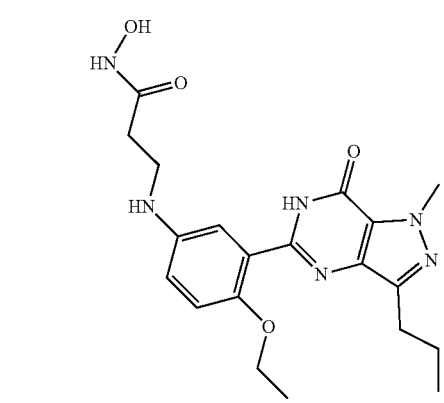
38
-continued
1-34
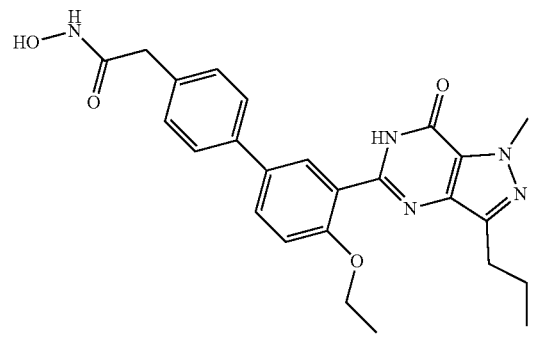
1-35
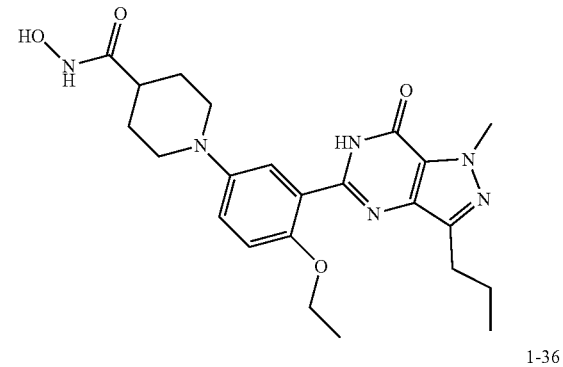
1-36
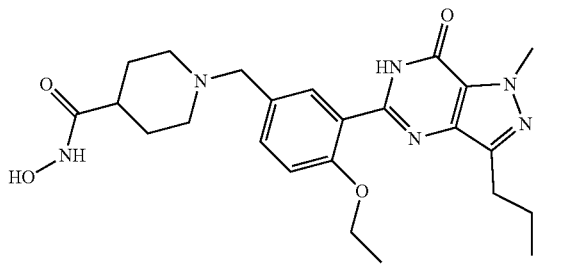
1-37
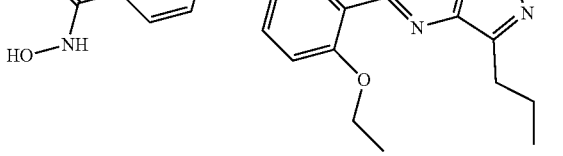
1-38
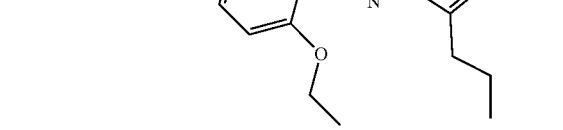

-continued
1-39
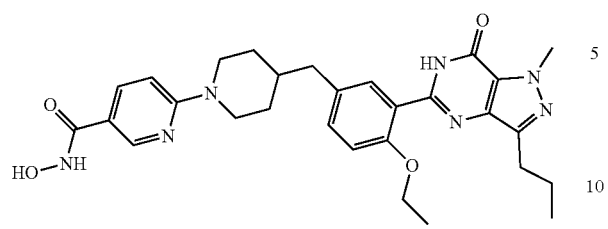
1-40
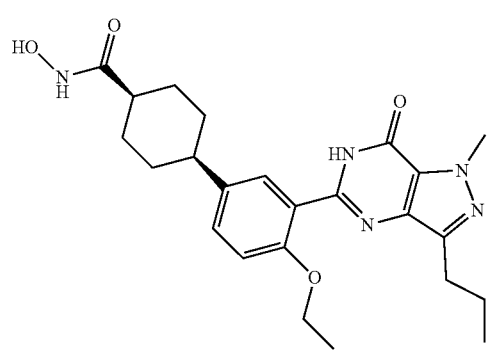
*cis isomers
1-41
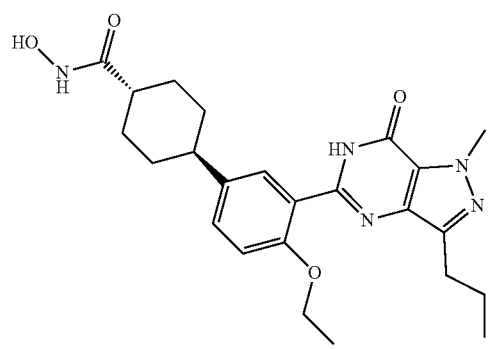
*trans isomers
1-42
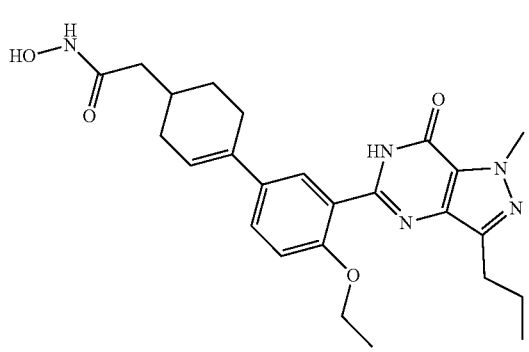
-continued
1-43
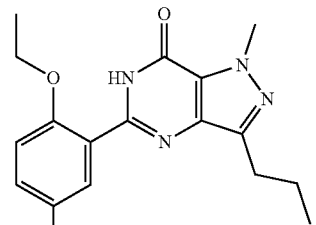
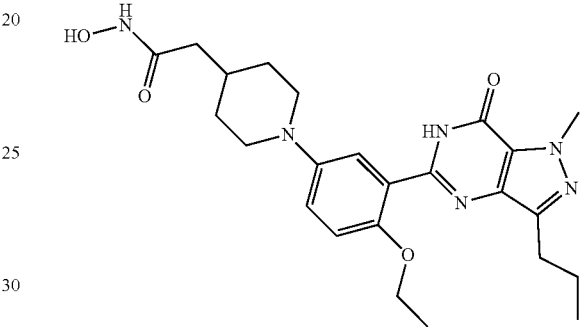
1-44
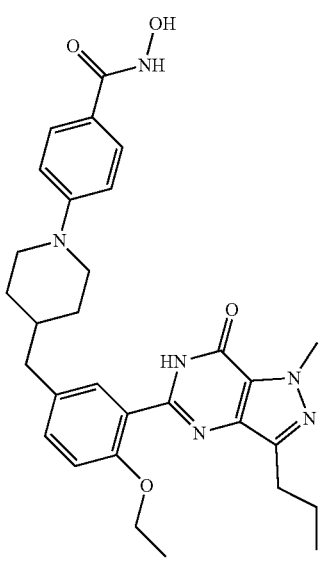
1-45
1-46
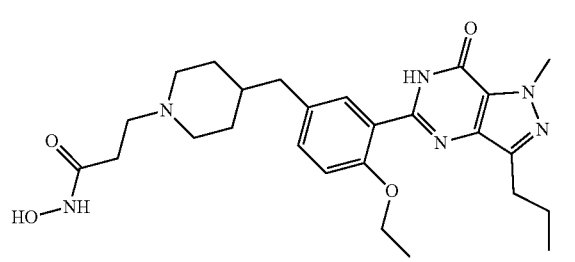

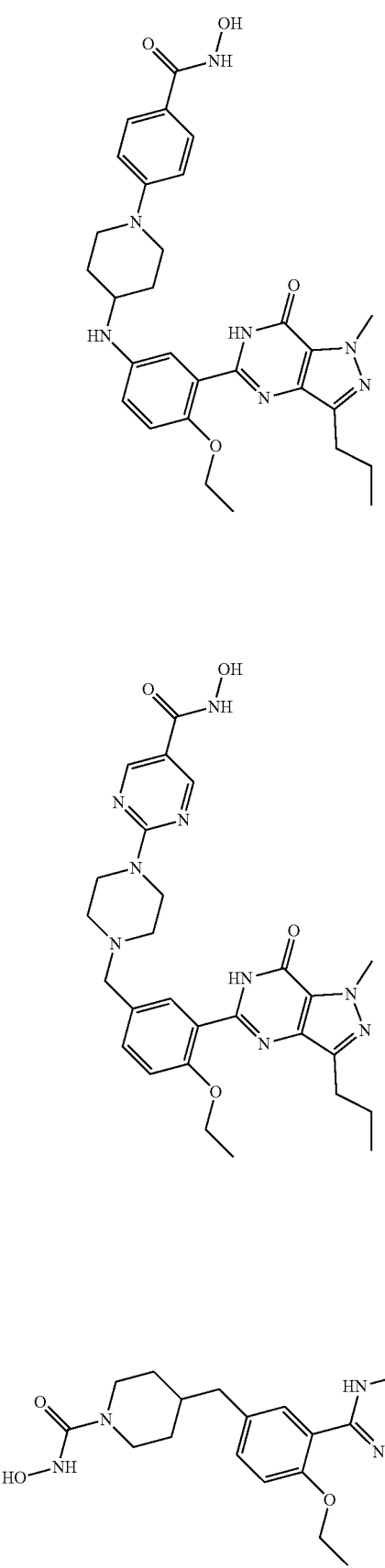
1-47
1-48
1-49
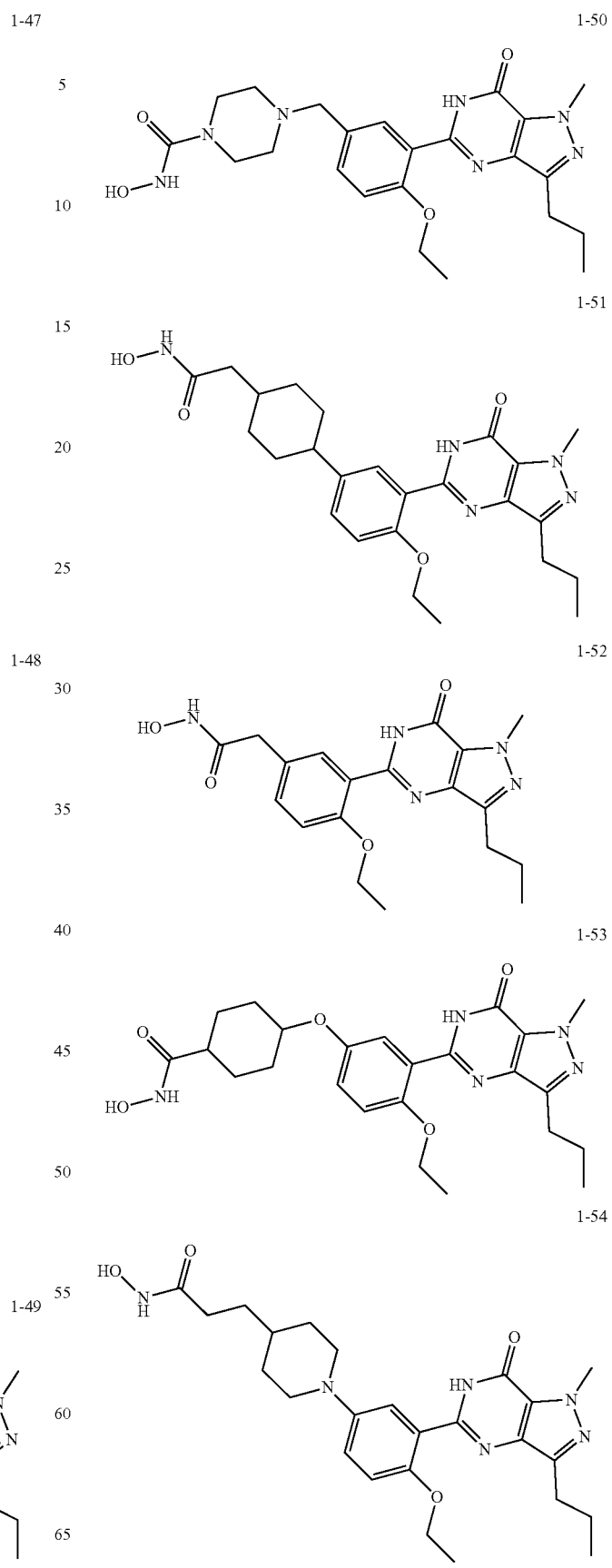
1-50
1-51
1-52
1-53
1-54

1-55
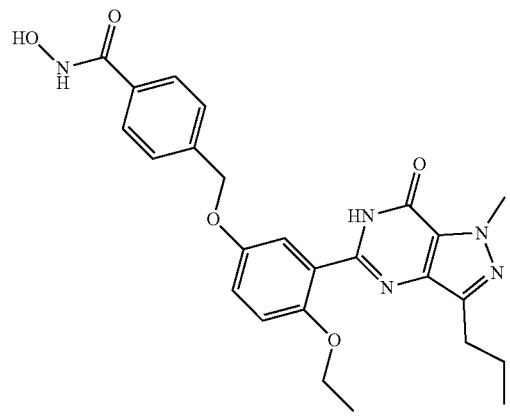
1-56
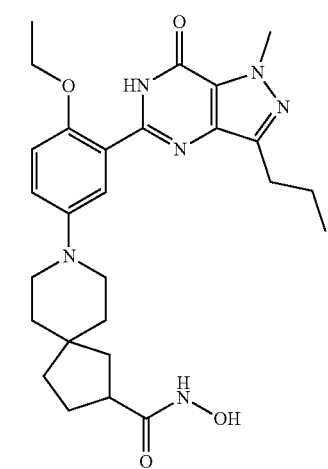
1-57
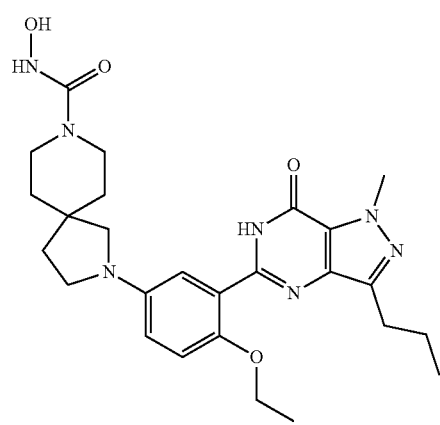
1-58
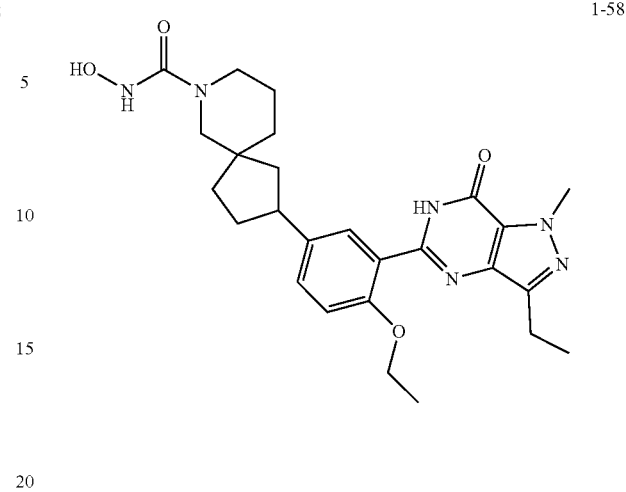
1-59
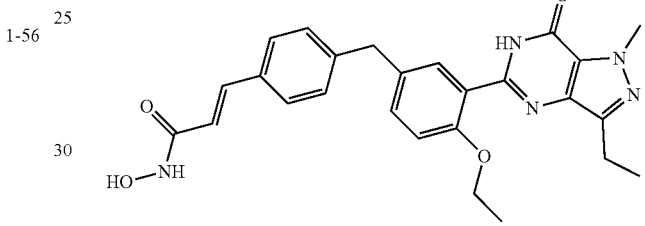
1-60
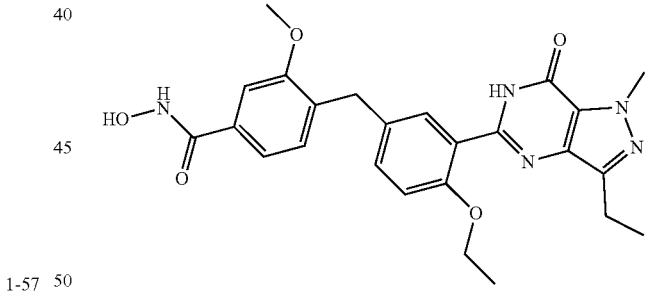
1-61
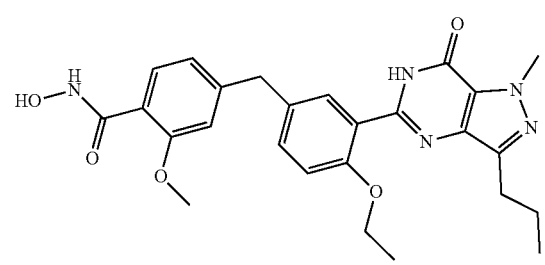

1-62
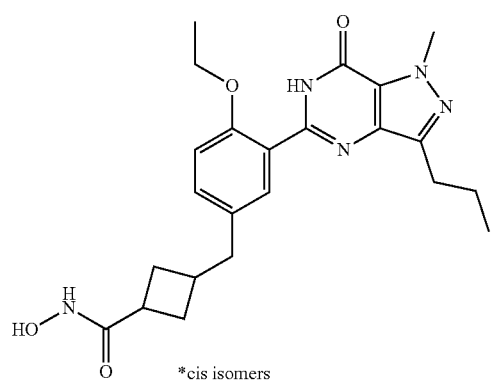
*cis isomers
1-63
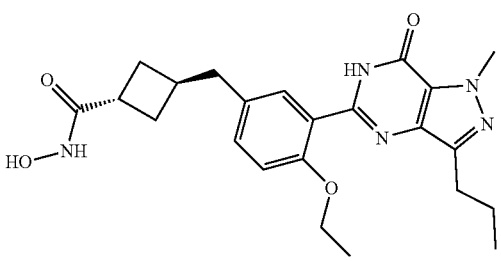
*trans isomers
1-64
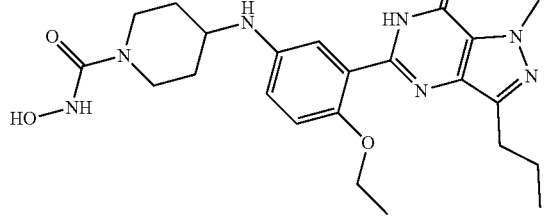
1-65
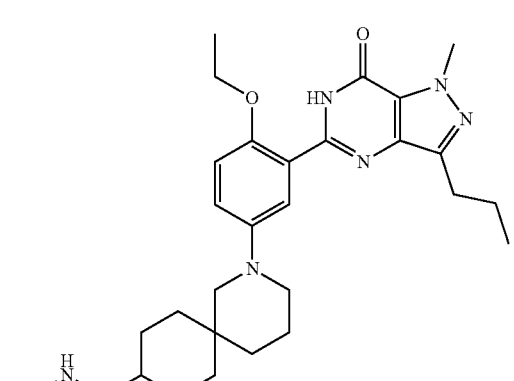
1-66
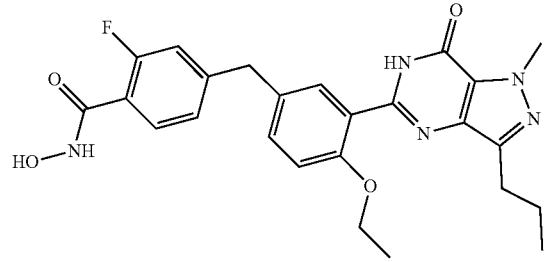
1-67
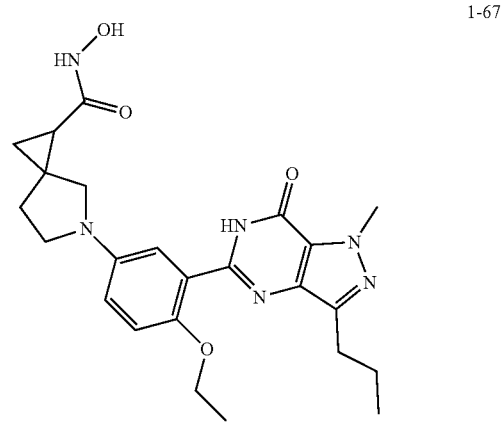
1-68
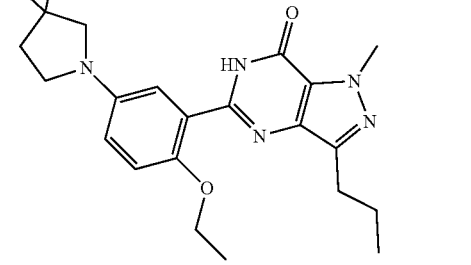
1-69
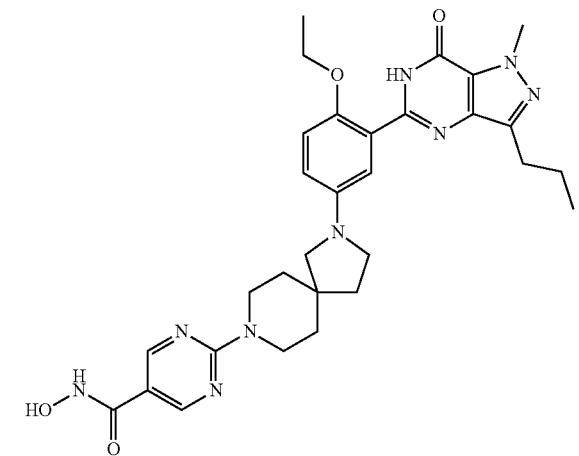

-continued
1-70
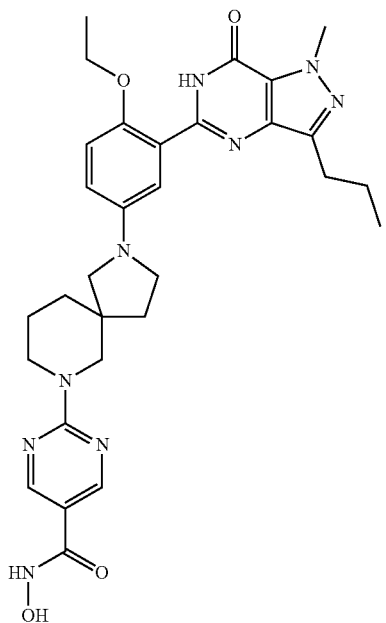
1-71
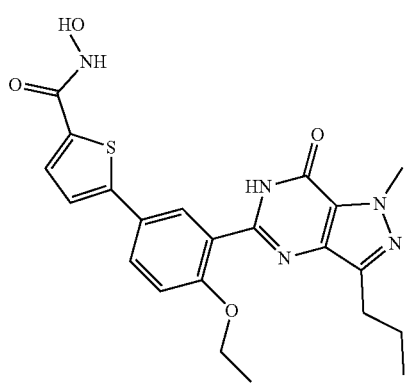
1-72
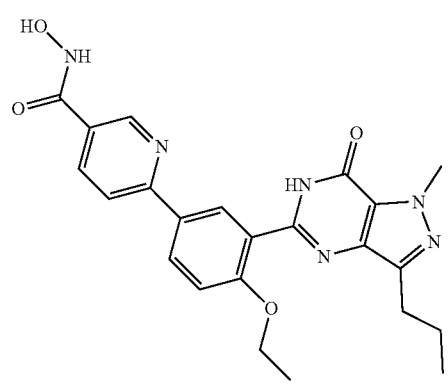
-continued
1-73
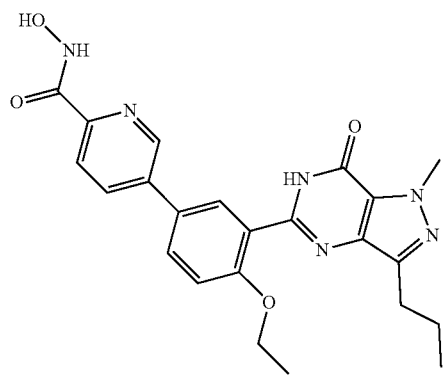
1-74
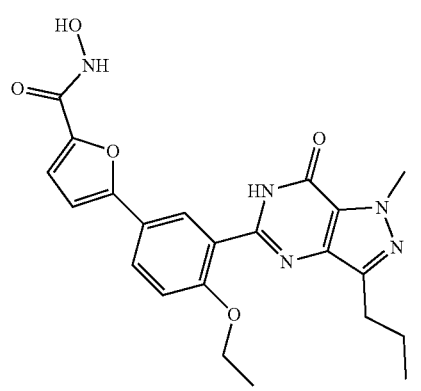
1-75
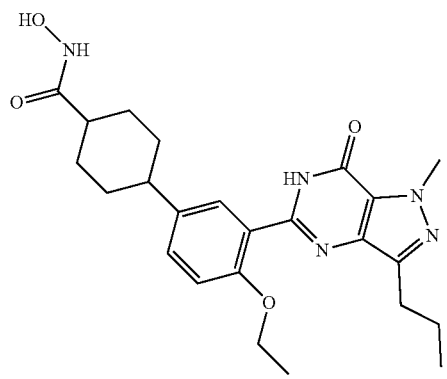
1-76
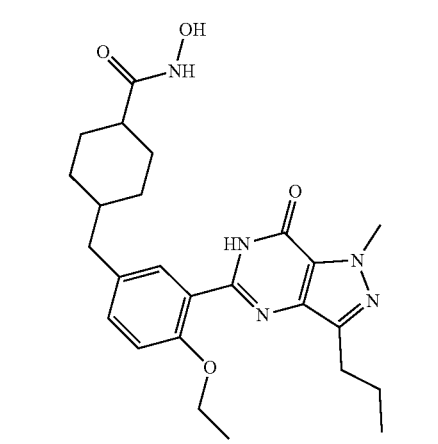

-continued
1-77
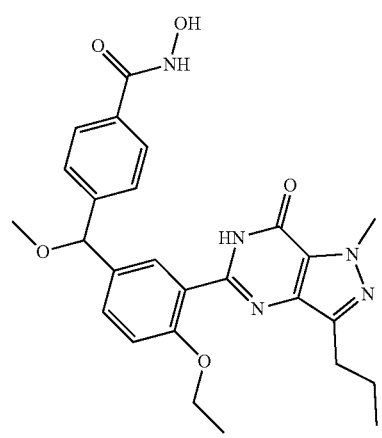
1-78
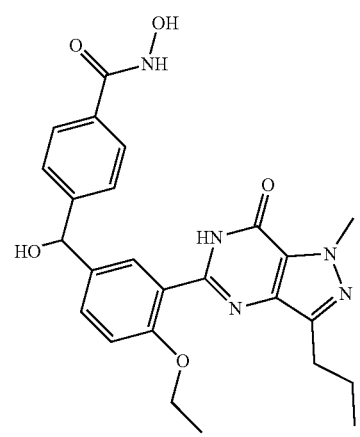
1-79
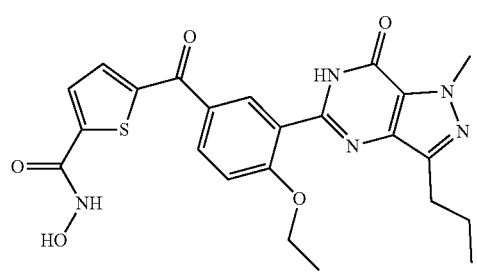
1-80
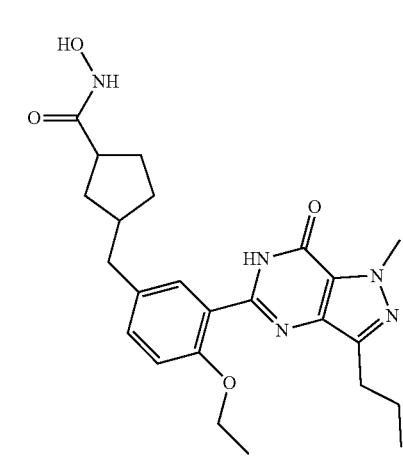
-continued
1-81
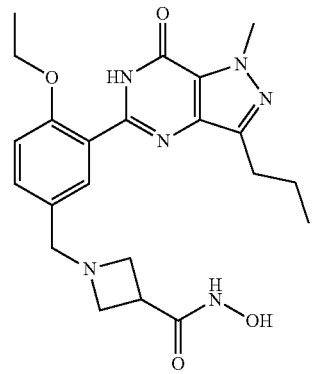
1-82
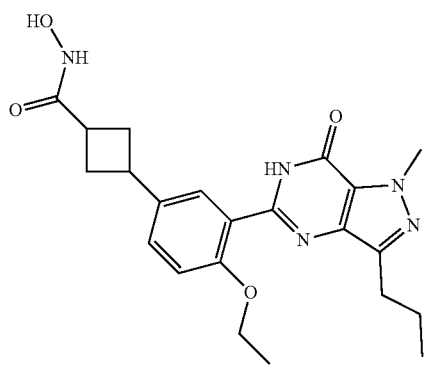
1-83
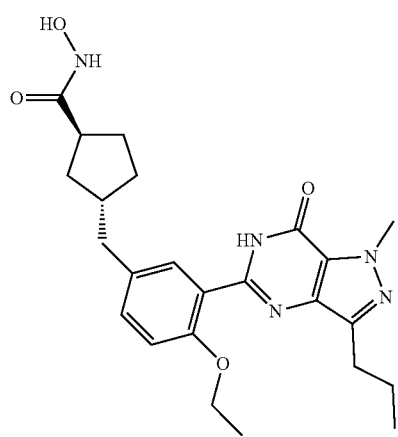
* trans isomers
1-84
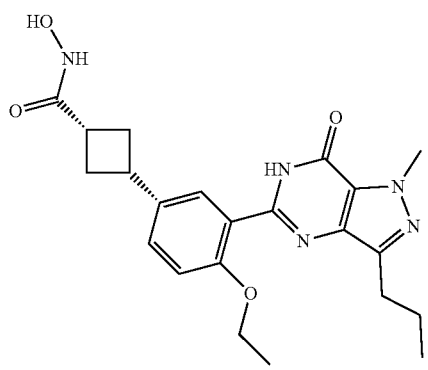
* cis isomers 1-85

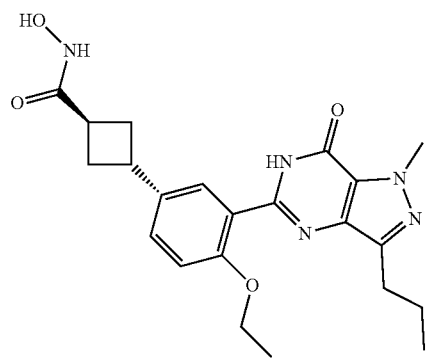

* trans isomers 1-86

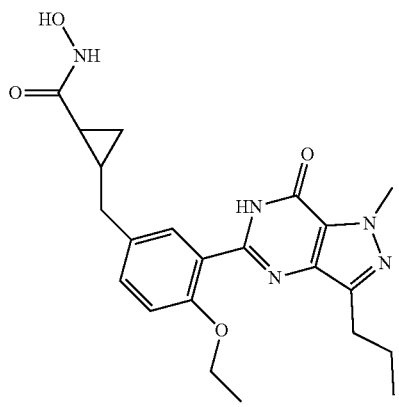

*Regarding these compounds, an aleatory absolute configuration of the cis and trans isomers is shown. In the examples it is clearly indicated which of the isomers is concerned in relative terms by differentiating unambiguously between cis and trans isomers by their physical and/or spectroscopic properties.

In another embodiment of the invention, the compound of formula (I) is selected from the group consisting of:

2-01

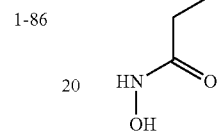
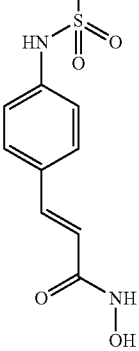
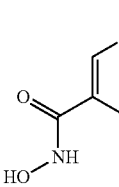

2-02

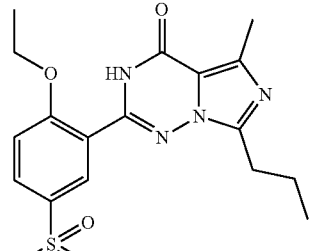

2-03

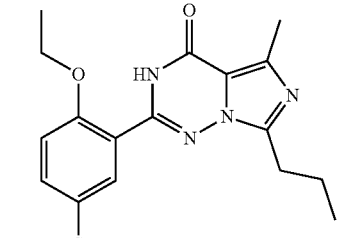

2-05

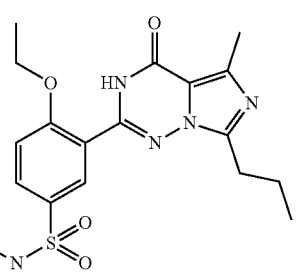

2-06
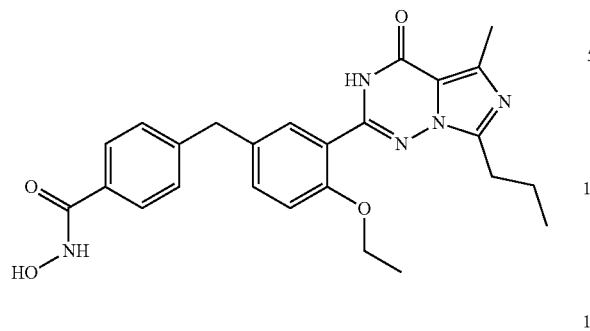
2-10
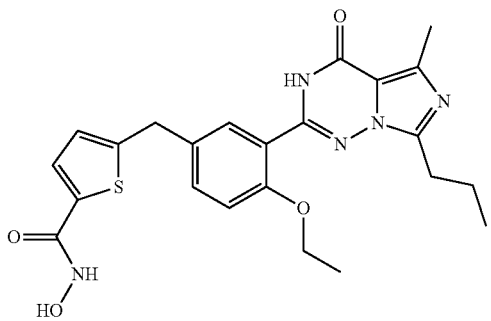
2-07
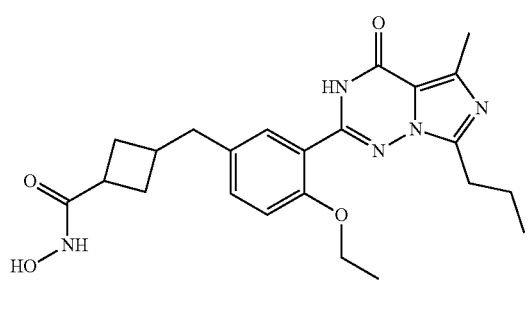
2-11
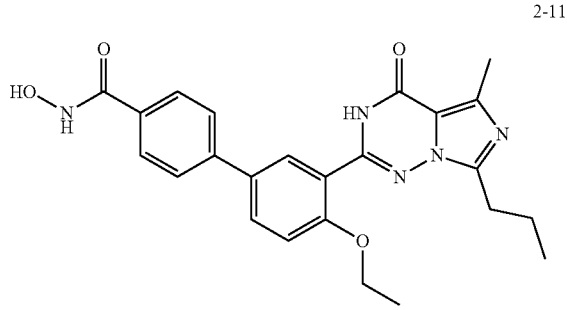
2-08
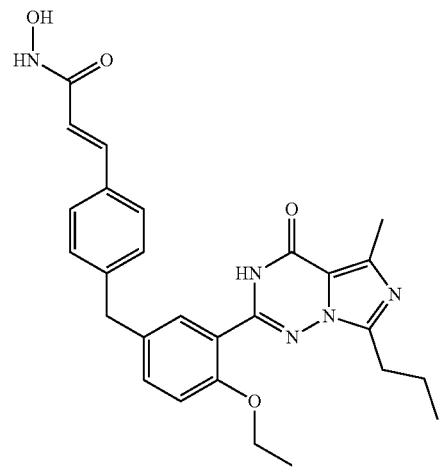
2-12
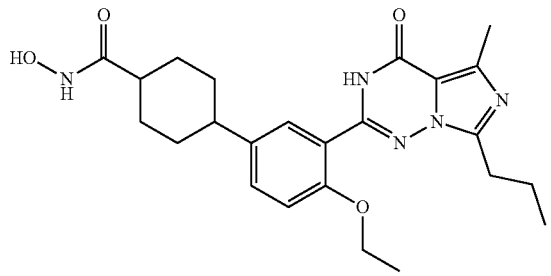
2-09
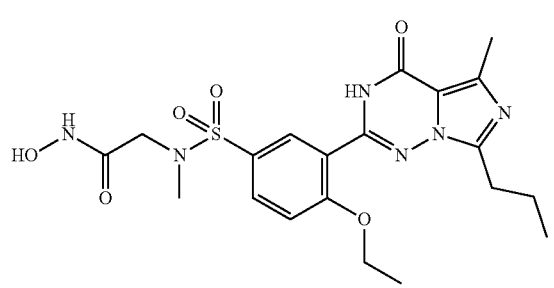
2-13
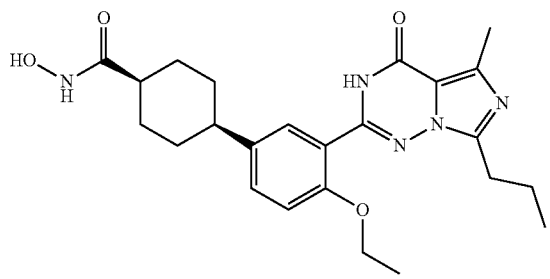
*cis isomers 2-14

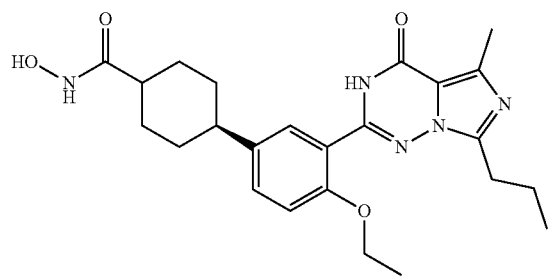

*trans isomers

*Regarding these compounds, an aleatory absolute configuration of the cis and trans isomers is shown. In the examples it is clearly indicated which of the isomers is concerned in relative terms by differentiating unambiguously between cis and trans isomers by their physical and/or spectroscopic properties.

In another embodiment of the invention, the compound of formula (I) is selected from the group consisting of:

3-01

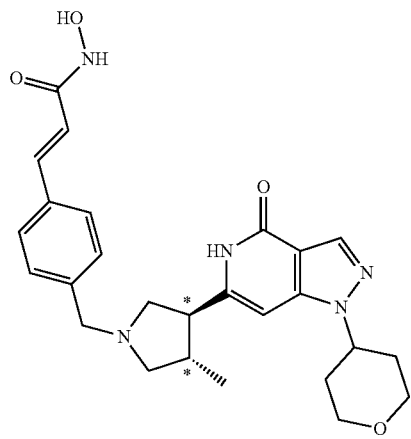

* trans racemic 3-02

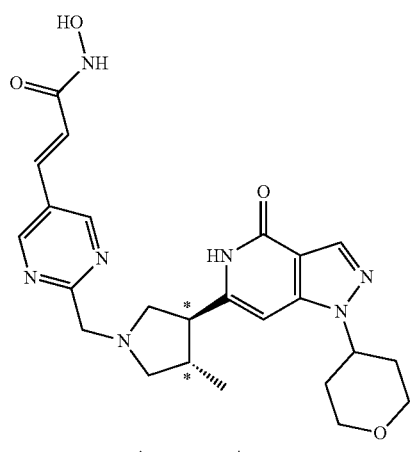

* trans racemic 3-03

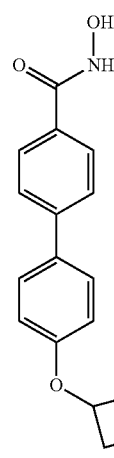

3-04

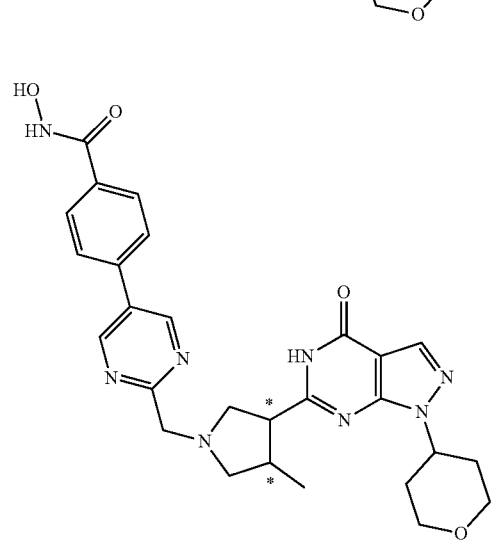

* trans racemic 3-05

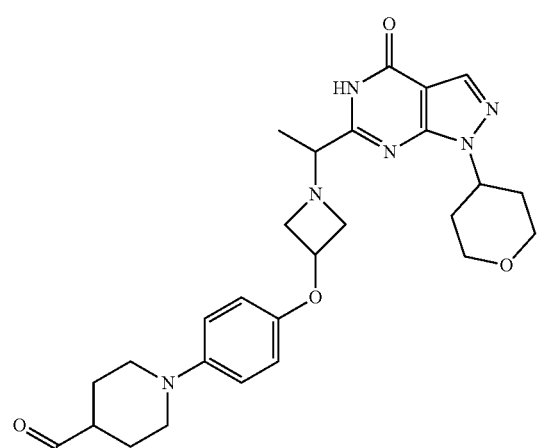

3-06
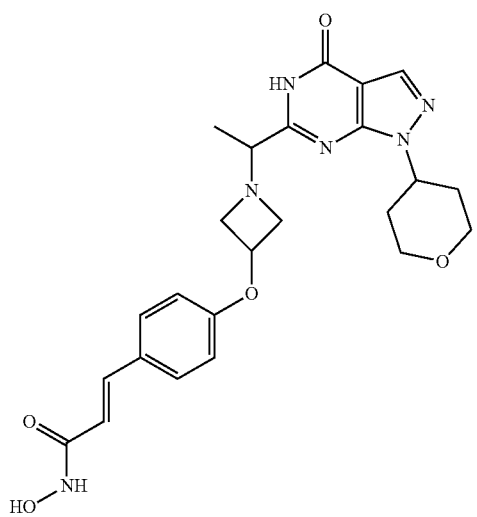
3-07
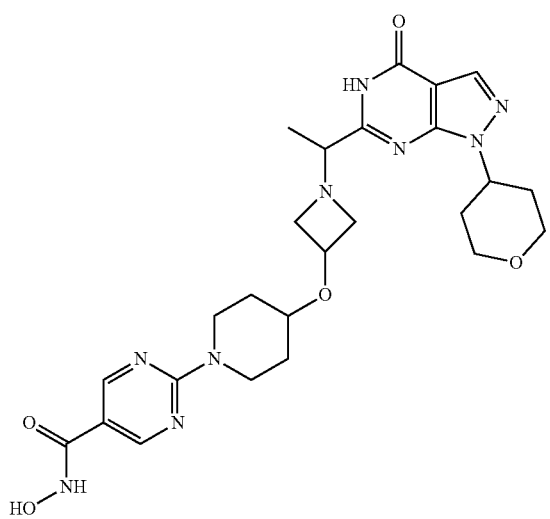
3-08
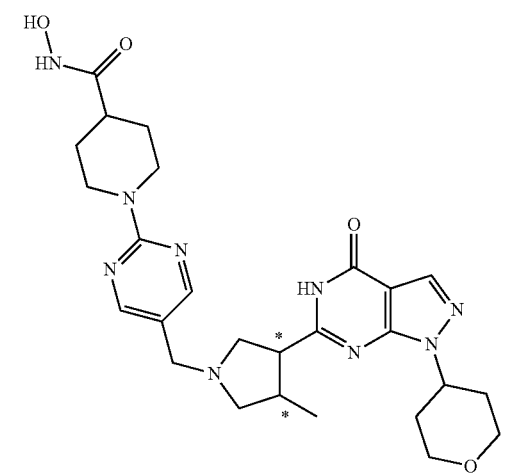
* trans racemic
3-09
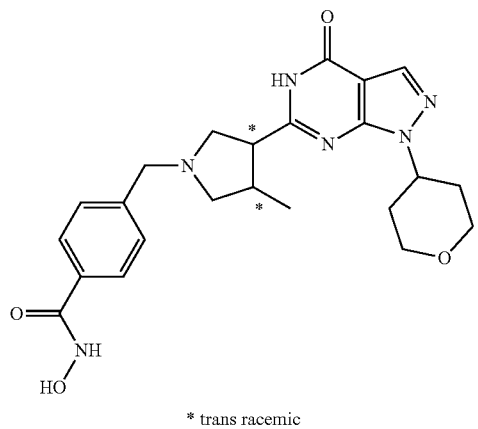
* trans racemic
3-10
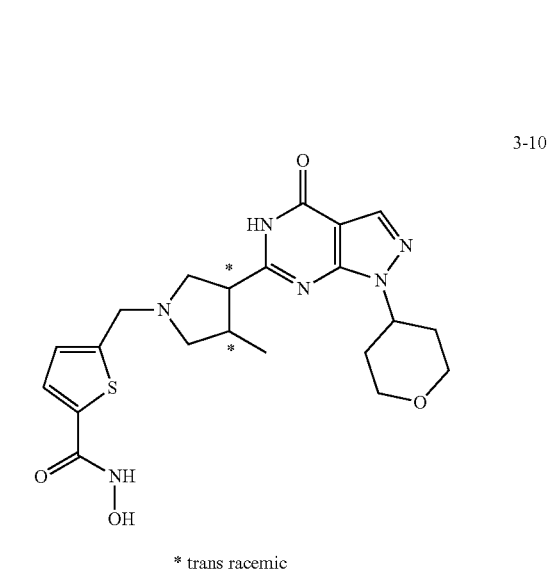
* trans racemic
3-11
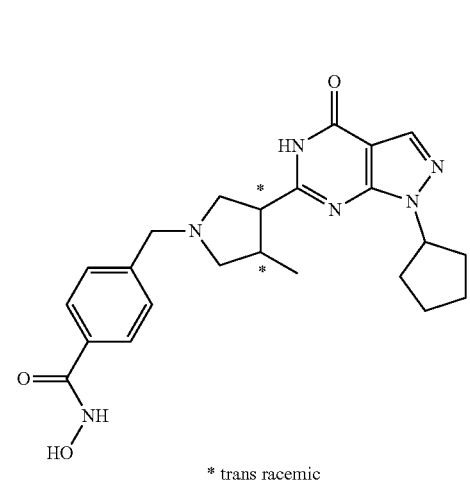
* trans racemic 3-12
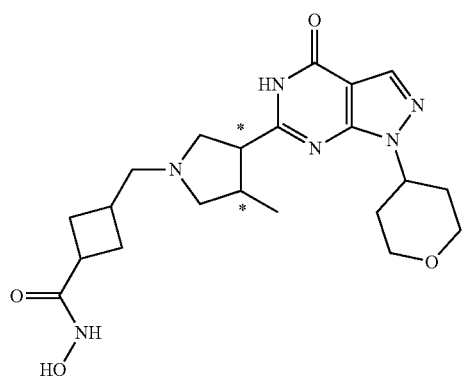
* trans racemic
3-13
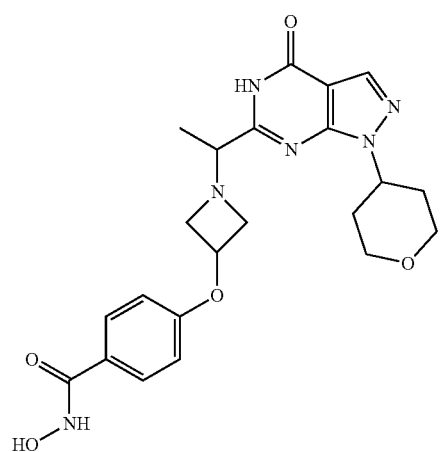
3-14
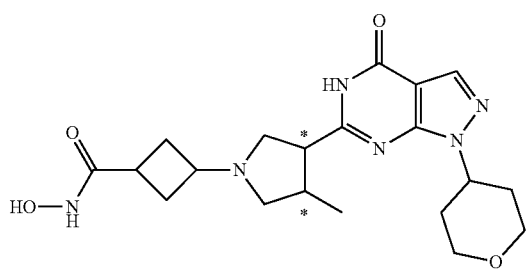
* trans racemic
3-15
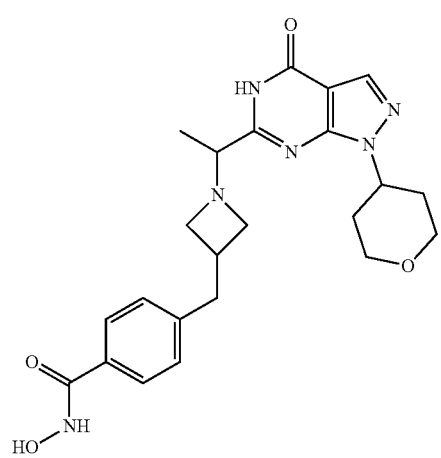
3-16
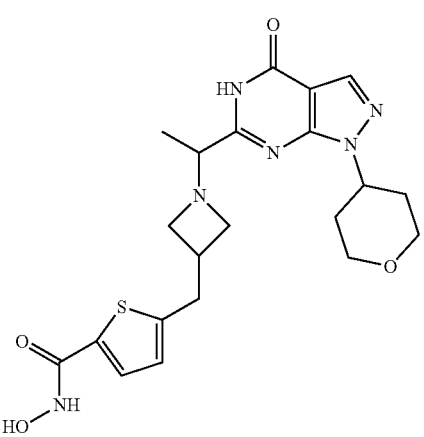
3-17
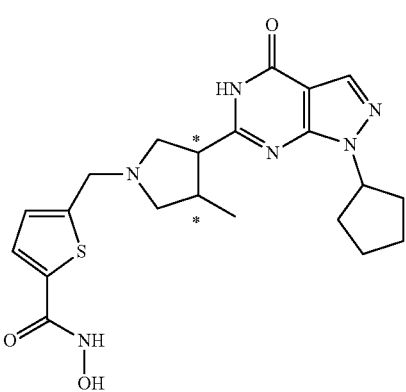
* trans racemic
In another embodiment of the invention, the compound of formula (I) is selected from the group consisting of:
4-01
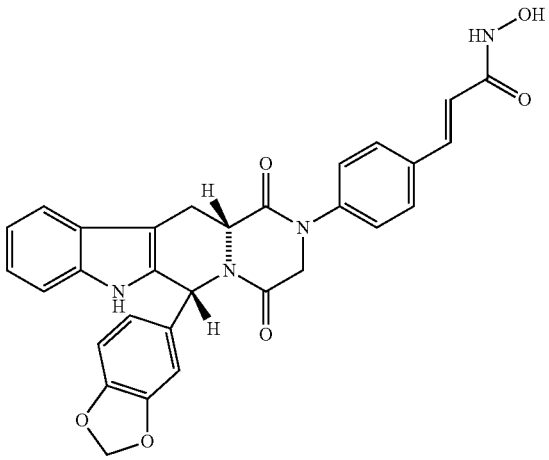

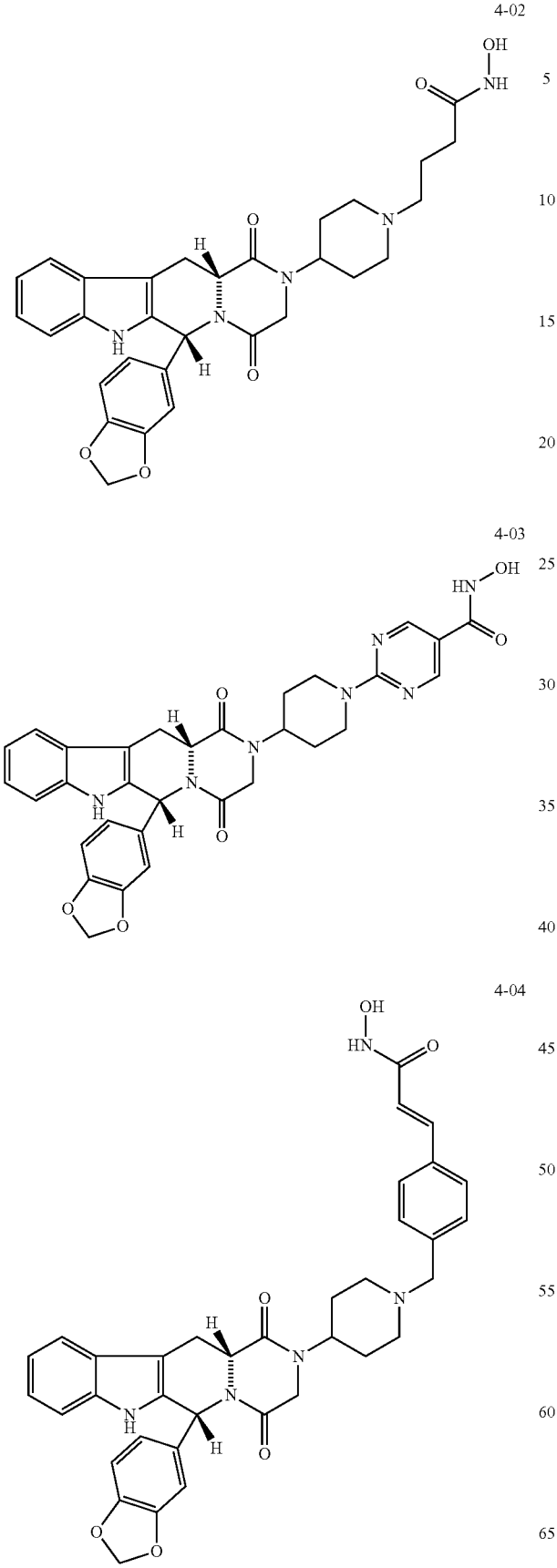
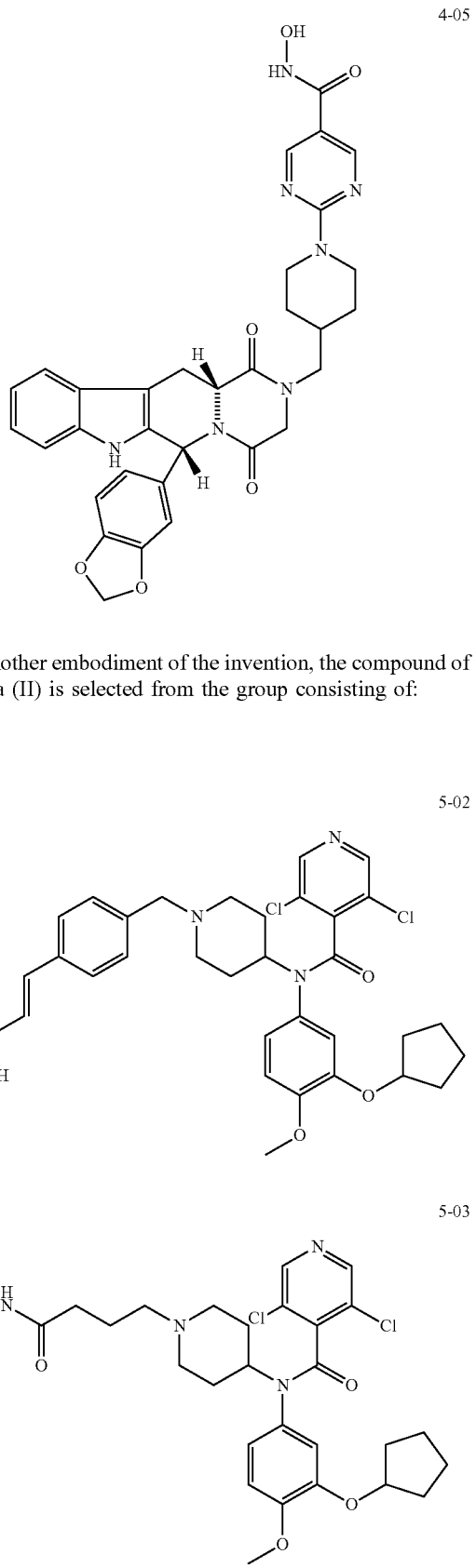
In another embodiment of the invention, the compound of formula (II) is selected from the group consisting of:

5-04

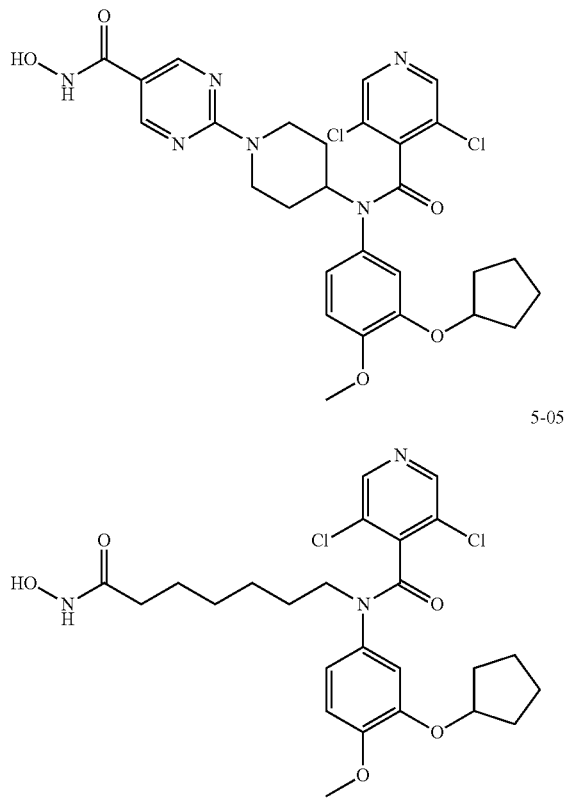

5-05

Generally, compounds of formula (I) as defined above may be obtained by reacting a compound of formula $B_1$—COOR' (IV) with a hydroxylamine of formula RO—$NH_2$ (V), wherein $B_1$ is as previously defined; R' is H and R is a hydroxamic acid protective group, to give a compound of formula (III)

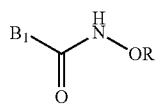
(III)

and subsequently removing the protective group of the hydroxamic acid to give a compound of formula (I).

The first conversion can be carried out in the presence of an activating agent such as 1-ethyl-3-(3-dimethylaminopropyl)carbodiimide hydrochloride (EDC.HCl) and hydroxybenzotriazole (HOBt), preferably in the presence of a base, such as N-methylmorpholine (NMM), in a suitable solvent, such as dichloromethane, chloroform or dimethylformamide, at a temperature comprised from room temperature to the temperature of the boiling point of the solvent, preferably at room temperature.

The removal of the protective group of the hydroxamic acid is carried out by standard methods well-known in the art as described for example in T. W. Green and P. G. M. Wuts, Protective Groups in Organic Chemistry (Wiley, 3rd ed. 1999, Chapter 2, pp. 17-200). Representative hydroxy protective groups include those where the hydroxy group is either acylated or alkylated such as benzyl, and trityl ethers as well as alkyl ethers, tetrahydropyranyl ethers, trialkylsilyl ethers and allyl ethers. For example, the hydroxamic acid protective group is tetrahydro-2H-pyran-2-yloxy (THP), benzyl, 1-naphthylmethyl or dimethyloxybenzyl (DMB). When the hydroxamic acid protective group is THP, the deprotection is carried out in acidic medium, for example with HCl, in a suitable solvent such as dioxane.

Compounds of formula (IV) wherein R' is H can be obtained by removing the protective group of a compound of formula (IV) wherein R' is a carboxy protective group by standard methods well-known in the art as described for example in T. W. Green and P. G. M. Wuts, Protective Groups in Organic Chemistry (Wiley, 3rd ed. 1999, Chapter 5, pp. 369-451). Representative carboxy protective groups include alkyl, aryl or benzyl esters, sylil esters, amides or hydrazides. For example, the carboxy protective group is $(C_1-C_6)$alkyl, benzyl, p-methoxyphenyl, trimethylsilyl, or [2-(Trimethylsilyl)-ethoxy]methyl (SEM). When the carboxy protective group is $(C_1-C_6)$alkyl, the deprotection is carried out in basic medium, for example with LiOH in a suitable solvent such as tetrahydrofuran-methanol.

Compounds of formula (IV) having the formula (IVa) or the formula (IVb):

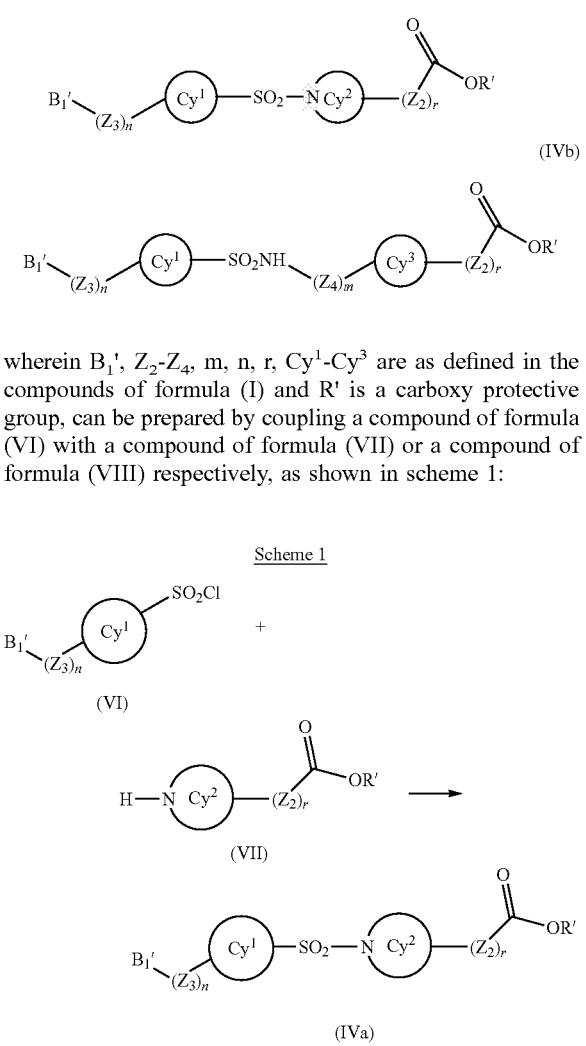

wherein $B_1'$, $Z_2$-$Z_4$, m, n, r, $Cy^1$-$Cy^3$ are as defined in the compounds of formula (I) and R' is a carboxy protective group, can be prepared by coupling a compound of formula (VI) with a compound of formula (VII) or a compound of formula (VIII) respectively, as shown in scheme 1:

-continued

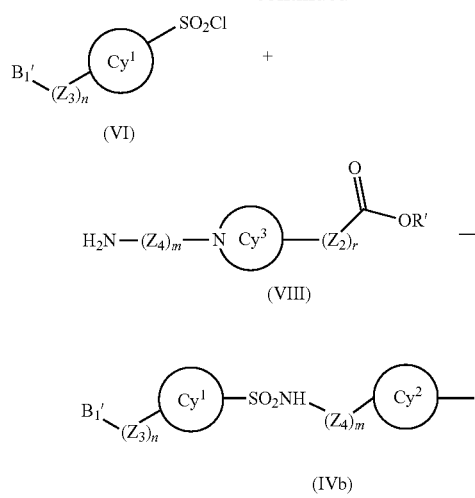

(VI)

(VIII)

(IVb)

This conversion can be carried out in the presence of a base such as triethylamine, in a suitable solvent such as ethanol, and at a suitable temperature, preferably heating.

Compounds of formula (IV) having the formula (IVc) or the formula (IVd):

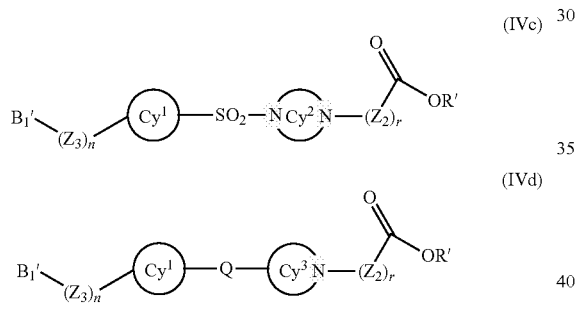

(IVc)

(IVd)

wherein Q is selected from the group consisting of $-SO_2NH-(Z_4)_m-$; $-O-(Z_4)_m-$; and $-(Z_4)_m-$; $B_1'$, $Z_2$-$Z_4$, m, n, r, $Cy^1$-$Cy^3$ are as defined in the compounds of formula (I); and R' is a carboxy protective group, can be prepared by coupling a compound of formula (IX) or formula (X) respectively with a compound of formula (XI), wherein X is a leaving group, such as halogen or methanesulfonate, as shown in scheme 2:

Scheme 2

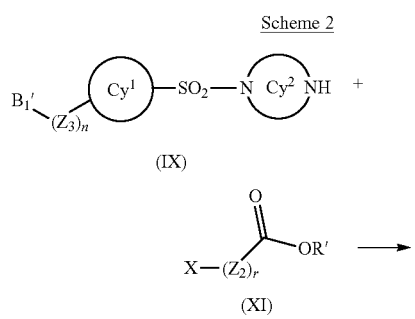

(IX)

(XI)

-continued

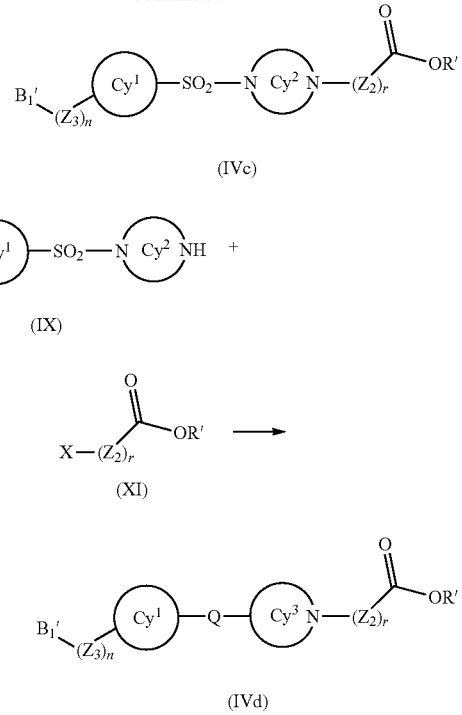

(IVc)

(IX)

(XI)

(IVd)

This conversion can be carried out in the presence of a base such as potassium carbonate, in a suitable solvent, such as acetonitrile, and at a suitable temperature, preferably heating.

Compounds of formula (IV) having the formula (IVe):

(IVe)

wherein $B_1'$, $Z_1$-$Z_2$, n, $Cy^1$-$Cy^3$ are as defined in the compounds of formula (I) and R' is a carboxy protective group, can be prepared by coupling a compound of formula (XII) with a compound of formula (XIII), wherein X is a leaving group, such as halogen or methanesulfonate, as shown in scheme 3:

Scheme 3

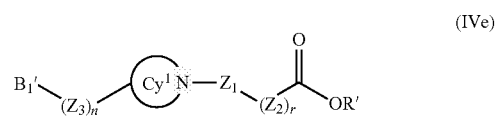

(VI)              (XIII)

(IVe)

Compounds of formula (IV) having the formula (IVf):

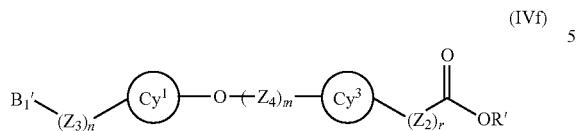

(IVf)

wherein $B_1'$, $Z_1$-$Z_2$, n, $Cy^1$-$Cy^3$ are as defined in the compounds of formula (I) and R' is as defined above, can be prepared by coupling a compound of formula (XIV) with a compound of formula (XV), as shown in scheme 4:

Scheme 4

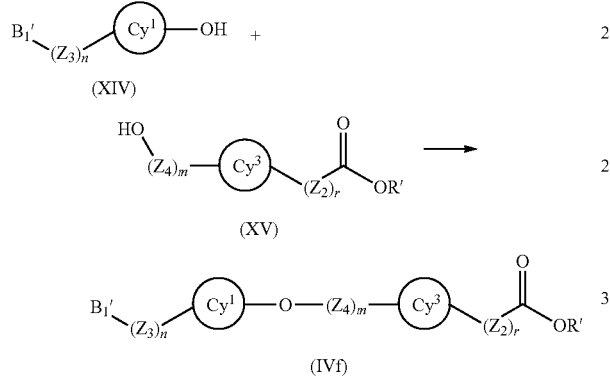

This conversion can be carried out in the presence of $Ph_3P$ and diisopropyl azodicarboxylate (DIAD) in a suitable solvent, such as toluene, and at a suitable temperature, preferably heating.

Compounds of formula (IV) having the formula (IVg):

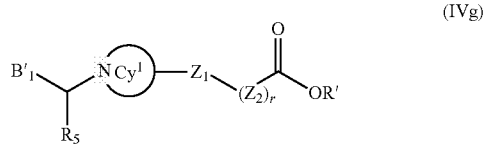

(IVg)

wherein $B_1'$, $Z_1$-$Z_2$, n, $Cy^1$-$Cy^3$ are as defined in the compounds of formula (I) and R' is as defined above, can be prepared by coupling a compound of formula (XVI) with a compound of formula (XVII), wherein X is a leaving group, such as halogen or methanesulfonate, and $R_5$ is H or optionally substituted $(C_1$-$C_4)$alkyl as shown in scheme 5:

Scheme 5

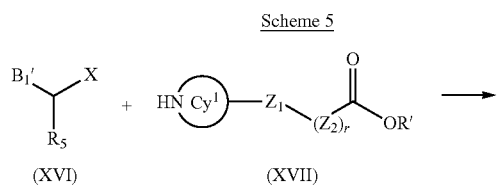

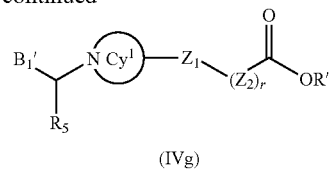

(IVg)

The compounds (IVe) and (IVg) can be prepared as defined above using analogous reaction conditions to those described for the preparation of compounds of formula (IVc) or (IVd).

Compounds of formula (IV) having the formula (IVh):

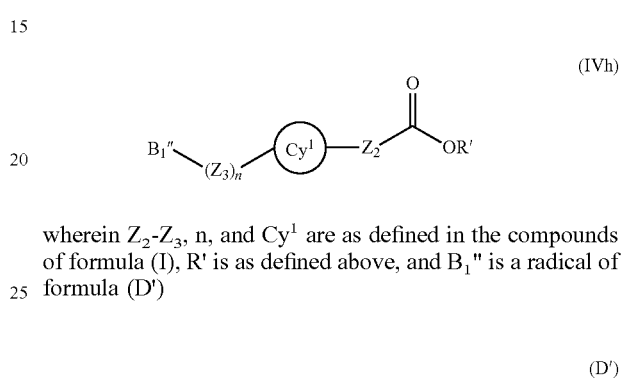

(IVh)

wherein $Z_2$-$Z_3$, n, and $Cy^1$ are as defined in the compounds of formula (I), R' is as defined above, and $B_1''$ is a radical of formula (D')

(D')

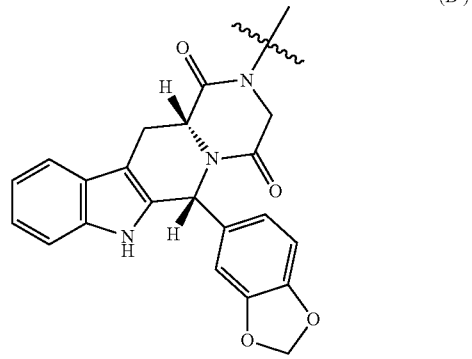

can be prepared by coupling a compound of formula (XVIII) with a compound of formula (XIX), wherein X is a leaving group, such as halogen or methanesulfonate, as shown in scheme 6:

Scheme 6

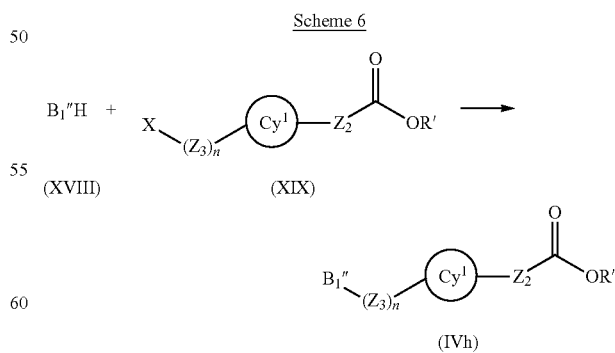

This conversion can be carried out in the presence of CuI, $K_3PO_4$ and (±)-1,2-transdiaminocyclohexane, in a suitable solvent, such as dioxane, and at a suitable temperature, preferably room temperature.

Alternatively, compounds of formula (IVh) can be prepared by coupling a compound of formula (XX) with a compound of formula (XXI), as shown in scheme 7:

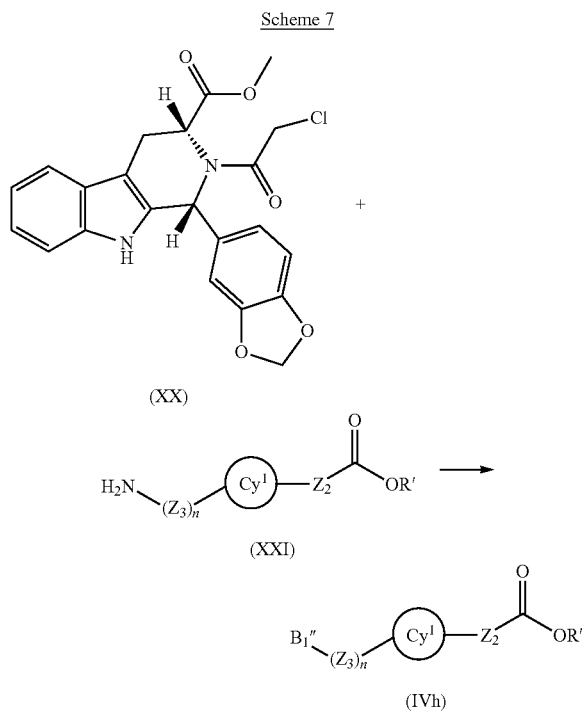

Scheme 7

This conversion can be carried out in a suitable solvent, such as methanol, and at a suitable temperature, preferably heating.

Compounds of formula (II) can be prepared by an analogous manner to compounds of formula (I) as described above. The compounds of formulas (V) to (XXI) are commercially available or can be obtained by conventional synthetic processes as shown in the examples below.

The present invention also relates to a pharmaceutical composition comprising a therapeutically effective amount of a compound of formula (I) or a compound of formula (II) as defined above together with pharmaceutically acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration. For example, a dose of from about 0.01 to about 300 mg/kg may be used.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

The election of the pharmaceutical formulation will depend upon the nature of the active compound and its route of administration. Any route of administration may be used, for example oral, parenteral and topical administration.

For example, the pharmaceutical composition may be formulated for oral administration and may contain one or more physiologically compatible carriers or excipients, in solid or liquid form. These preparations may contain conventional ingredients such as binding agents, fillers, lubricants, and acceptable wetting agents.

The pharmaceutical composition may be formulated for parenteral administration in combination with conventional injectable liquid carriers, such as water or suitable alcohols. Conventional pharmaceutical excipients for injection, such as stabilizing agents, solubilizing agents, and buffers, may be included in such compositions. These pharmaceutical compositions may be injected intramuscularly, intraperitoneally, or intravenously.

The pharmaceutical composition may be formulated for topical administration. Formulations include creams, lotions, gels, powders, solutions and patches wherein the compound is dispersed or dissolved in suitable excipients.

The pharmaceutical compositions may be in any form, including, among others, tablets, pellets, capsules, aqueous or oily solutions, suspensions, emulsions, or dry powdered forms suitable for reconstitution with water or other suitable liquid medium before use, for immediate or retarded release.

The appropriate excipients and/or carriers, and their amounts, can readily be determined by those skilled in the art according to the type of formulation being prepared.

As demonstrated in the examples, the compounds of the invention are dual inhibitors of PDEs and HDACs, and therefore, may be used in the treatment and/or prevention of diseases mediated by the dual inhibition of PDE and HDAC.

In a particular embodiment, the invention refers to compounds of formula (I) as previously described, wherein $B_1$ is a radical of formula (A"), (B") or (D"), which are dual inhibitors of PDE5 and at least one HDAC selected from the group consisting of HDAC1, HDAC2, HDAC3 y HDAC6.

In another particular embodiment, the invention refers to compounds of formula (I) as previously described, wherein $B_1$ is a radical of formula (C") which are dual inhibitors of PDE9 and at least one HDAC selected from the group consisting of HDAC1, HDAC2, HDAC3 y HDAC6.

Thus, the invention relates to a compound of formula (I) or a compound of formula (II) or a pharmaceutical composition comprising the compound of formula (I) or formula (II) as defined above, for use as a medicament.

Moreover, the invention relates to a compound of formula (I) or a compound of formula (II) or a pharmaceutical composition comprising the compound of formula (I) or formula (II) as defined above, for use in the treatment and/or prevention of diseases mediated by the dual inhibition of PDE and HDAC. Thus, this aspect relates to the use of a compound of formula (I) or a compound of formula (II) as defined above, for the preparation of a medicament for the treatment and/or prevention of diseases mediated by the dual inhibition of PDE and HDAC; and may also be formulated as a method for the treatment and/or prevention of diseases mediated by the dual inhibition of PDE and HDAC, which comprises administering a therapeutically effective amount of the previously defined compound of formula (I) or a compound of formula (II) and one or more pharmaceutical acceptable excipients or carriers, in a subject in need thereof, including a human.

Examples of diseases mediated by the dual inhibition of PDE and HDAC include neurological disorders coursing with a cognition deficit or impairment, and neurodegenerative diseases. Thus, the compounds of the present invention may be useful in the treatment and/or prevention of neurological disorders coursing with a cognition deficit or impairment, or neurodegenerative diseases.

Therefore, the invention also relates to a compound of formula (I) or a compound of formula (II) or a pharmaceutical composition comprising the compound of formula (I) or formula (II) as defined above, for use in the treatment and/or prevention of neurological disorders coursing with a cognition deficit or impairment, or neurodegenerative diseases. Thus, this aspect relates to the use of a compound of formula (I) or a compound of formula (II) as defined above, for the preparation of a medicament for the treatment and/or prevention of neurological disorders coursing with a cognition deficit or impairment, or neurodegenerative diseases; and may also be formulated as a method for the treatment and/or prevention of neurological disorders coursing with a cognition deficit or impairment, or neurodegenerative diseases comprising administering a therapeutically effective amount of the previously defined compound of formula (I) or a compound of formula (II), and one or more pharmaceutical acceptable excipients or carriers, in a subject in need thereof, including a human.

In a particular embodiment, the neurodegenerative diseases are neurodegenerative diseases coursing with a cognition deficit or impairment. More particularly, the neurodegenerative disease or neurological disorder coursing with a cognition deficit or impairment is selected from Alzheimer's disease, Parkinson's disease, Huntington's disease, vascular dementia (uncomplicated, with delirium, with delusions or with depressed mood), mild cognitive impairment and age-associated cognition impairment. More preferably, the disease is Alzheimer's disease.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention.

EXAMPLES

General Procedure for Preparative HPLC Purification Method

The HPLC measurement was performed using Gilson 281 from 233 pump (binary), an autosampler, and a UV detector. The fractions was detected by LC-MS. The MS detector was configured with an electrospray ionization source. The source temperature was maintained at 300-350° C.
HPLC Methods (Purification Methods):
Method 1:
Reversed phase HPLC was carried out on luna (100×30 mm; 4 um-5 um). Solvent A: water with 0.075% TFA; Solvent B: acetonitrile with 0.075% TFA. Gradient: At 25° C., from 10-36% of B to 40-63% of B within 6-16 min; then 40-63% B over 1-4 min, PDA
Method 2:
Reversed phase HPLC was carried out on luna C18 (100×30 mm; 4 um). Solvent A: water with 0.075% TFA; Solvent B: acetonitrile with 0.075% TFA. Gradient: At 25° C., from 20% of B to 40% of B within 6 min; then 40% B over 2 min, PDA
Method 3:
Compound was purified by column chromatography (EA: PE=1:30-1:3) and recrystallization (EA)

The following abbreviations have been used in the examples:
AcOH: acetic acid; Boc: tert-butoxycarbonyl; calc.: calculated; conc.: concentrated; DMAP: 4-Dimethylaminopyridine; DCM: dichloromethane; DIAD: Diisopropyl azodicarboxylate; DMF: dimethylformamide; DMSO: dimethylsulfoxide; EA: ethyl acetate; EDC.HCl: 1-ethyl-3-(3-dimethylamino-propyl)carbodiimide hydrochloride; eq: equivalent; ESI-MS: electrospray ionization mass spectrometry; Et$_3$N: triethylamine; HOBt: Hydroxybenzotriazole; HPLC: High-performance liquid chromatography; LDA: Lithium diisopropylamide; MW: microwaves; NMM: N-methyl morpholine; PE: petrol ether; r.t.: room temperature; TFA: trifluoroacetic acid; THF: tetrahydrofuran; THP: tetrahydropyran; TLC: thin layer chromatography Preparation of Reagents Preparation of reagent KR-1: 3,5-Dichloropyridine-4-carboxylic acid To a solution of the commercially available 3,5-dichloropyridine (10 g, 0.067 mol) in THF (20 mL) was added LDA (60 mL, 0.074 mol), the reaction was stirred at −78° C. for 1 hour. Then dry ice (5.9 g, 0.134 mol) was added to the solution. After 0.5 h, the mixture was quenched by adding water and adjusted the pH to 3-4. The solution was partitioned with EA and water. The combined organic layers were washed with brine, dried over anhydrous Na$_2$SO$_4$ and concentrated to give the crude product KR-1 (7 g, 55% yield) as a pale white solid. ESI-MS (M+1): 192 calc. for C$_6$H$_3$Cl$_2$NO$_2$: 190.95.

Preparation of reagent KR-2: (E)-Ethyl 3-(pyridin-4-yl)prop-2-enoate

To a solution of the commercially available p-formylpyridine (5.16 g, 48.22 mmol) in anhydrous THF (50 mL) was added (triphenyl-15-phosphanylidene)-acetic acid ethyl ester (20.13 g, 57.82 mmol), the reaction mixture was stirred at r.t. overnight. Then the reaction mixture was concentrated under vacuo and purified by column to give KR-2 (3 g, 36.3% yield). ESI-MS (M+1): 178 calc. for C$_{10}$H$_{11}$NO$_2$: 177.1.

Preparation of reagent KR-3: (E)-Ethyl 3-(4-formylphenyl)prop-2-enoate

KR-3 was obtained starting from commercially available terephthalaldehyde in an analogous manner to KR-2.22.3% yield. ESI-MS (M+1): 205 calc. for C$_{12}$H$_{12}$O$_3$: 204.1.

Preparation of reagent KR-4: 3,5-Dichloroisonicotinoyl chloride

To a solution of KR-1 (1.50 g, 7.85 mmol) in DCM (20 mL), containing two drops of DMF, was added thionyl chloride (1.40 g, 0.85 mL, 1.5 eq). The reaction was refluxed for 3 hours resulting a clear solution. The solution was evaporated in vacuum providing the crude product KR-4 (1.35 g, 82.3% yield) as a yellow oil. ESI-MS (M+1): 210 calc. for $C_6H_2Cl_3NO$: 208.9.

Preparation of reagent KR-5: (E)-ethyl 3-(4-(hydroxymethyl)phenyl)prop-2-enoate To a solution of KR-3 (2.04 g, 10 mmol) in MeOH (30 mL) was added $NaBH_4$ (1.9 g, 50 mmol), the reaction mixture was stirred at r.t. overnight. The mixture was diluted with EA and washed with water, brine, dried over anhydrous $Na_2SO_4$ and concentrated to give KR-5 (1.6 g, 77.7%) as a yellow solid. ESI-MS (M+1): 207 calc. for $C_{12}H_{14}O_3$: 206.1.

Preparation of reagent KR-6: (E)-Ethyl 3-(4-nitrophenyl)prop-2-enoate

To a solution of commercially available 4-nitrobenzaldehyde (30 g, 0.19 mol) in THF (300 mL) was added ethyl 2-(triphenylphosphoranylidene)-acetate (138 g, 0.39 mol, 2 eq), the reaction was stirred at 60° C. for overnight. Then mixture was concentrated and extracted with EA. The combined organic layers were washed with brine, dried over anhydrous $Na_2SO_4$ and concentrated to give the crude product which was purified by column chromatography (EA:PE=1:100-1:7) to give KR-6 (30 g, 69% yield) as a pale white solid. ESI-MS (M+1): 222 calc. for $C_{11}H_{11}NO_4$: 221.1.

Preparation of reagent KR-7: 1-tert-Butoxycarbonyl-4-(5-bromopyrimidin-2-yl)piperazine To a solution of commercially available 5-bromo-2-chloropyrimidin (9.75 g, 50 mmol) in $CH_3CN$ (100 mL) was added compound 1-Boc-piperazine (9.25 g, 50 mmol) and $K_2CO_3$ (13.8 g, 100 mmol). The reaction mixture was stirred at 80° C. overnight. Then, the reaction mixture was concentrated under vacuo and extracted with EA and washed with water, dried by $Na_2SO_4$ and concentrated under vacuo to give the KR-7 (15 g 87.7% yield). ESI-MS (M+1): 343, 345 calc. for $C_{13}H_{19}BrN_4O_2$: 342.1.

Preparation of reagent KR-8: Ethyl 2-(4-(tert-butoxycarbonyl)piperazin-1-yl)pyrimidine-5-carboxylate To a solution of KR-7 (6.00 g, 17.49 mmol) in ethanol (100 mL) was added $Et_3N$ (1.77 g, 2.43 ml) and $Pd(dppf)_2Cl_2$ (5 g), then the reaction mixture was stirred at 100° C. at 1.5 MPa under CO atmosphere for overnight. The reaction mixture was filtrated and the filtrate was concentrated under vacuo to give KR-8 (5 g, 85.2% yield). ESI-MS (M+1): 337 calc. for $C_{16}H_{24}N_4O_4$: 336.2.

Preparation of reagent KR-9: 5-bromo-2-[4-(N-tert-butoxycarbonyl-amino)piperidin-1-yl]pyrimidine KR-9 was obtained starting from 5-bromo-2-chloropyrimidin in an analogous manner to KR-7, but using tert-butylpiperidin-4-ylcarbamate instead of 1-Boc-piperazine. 84.3% yield. ESI-MS (M+1): 357, 359 calc. for $C_{14}H_{21}BrN_4O_2$: 356.1.

Preparation of reagent KR-10: Ethyl 2-[4-(N-tert-butoxycarbonyl-amino)piperidin-1-yl]pyrimidine-5-carboxylate KR-10 was obtained starting from KR-9 in an analogous manner to KR-8. 61.22% yield. ESI-MS (M+1): 350.2 calc. for $C_{17}H_{26}N_4O_4$: 350.2.

Preparation of reagent KR-11: (1-(5-Bromopyrimidin-2-yl)piperidin-4-yl)methanol KR-11 was obtained starting from 5-bromo-2-chloropyrimidin in an analogous manner to KR-7, but using 4-piperidinemethanol instead of 1-Boc-piperazine. 81.5% yield. ESI-MS (M+1): 272 calc. for $C_{10}H_{14}BrN_3O$: 271.0.

Preparation of reagent KR-12: 1-(5-Bromopyrimidin-2-yl)piperidin-4-ol

KR-12 was obtained starting from 5-bromo-2-chloropyrimidin in an analogous manner to KR-7, but using 4-piperidinol instead of 1-Boc-piperazine. 47.9% yield. ESI-MS (M+1): 258 calc. for $C_9H_{12}BrN_3O$ 257.1.

Preparation of reagent KR-13: 5-bromo-2-methyl-pyrimidine-4-carboxylic acid

To a solution of the commercially available ethanimidamide 11, as hydrochloride, (6.0 g, 63.83 mmol) in anhydrous EtOH (20 mL) was added sodium ethoxide (20 mL of a 21% solution in ethanol) and the reaction mixture was stirred at 50° C. and the commercially available (2E)-2,3-dibromo-4-oxobut-2-enoic acid 12 (6.82 g, 26.74 mmol) in EtOH (10 mL) was added into the mixture. After stirring at 50° C. for 1 hour, a further portion of sodium ethoxide (10 mL of a 21% solution in ethanol) was added and the mixture was stirred at r.t. for 16 h. The reaction mixture was filtrated and the filtrate reduced in vacuo. The residue was then treated with 2 M aqueous hydrochloric acid (30 mL) and stirred vigorously for 30 min. The resulting solid was filtrated, washed with water and air dried to give KR-13 (1.46 g, 25.2%) as a pale yellow solid. ESI-MS (M+1): 217 calc. for $C_6H_5BrN_2O_2$: 216.0.

Preparation of reagent KR-14: 5-Bromo-2-methyl-pyrimidine

A solution of KR-13 (1.46 g, 6.76 mmol) in xylene (20 mL) was heated 150° C. for 16 h. After cooling to r.t., the mixture was purified by column to give the desired product KR-14 (0.3 g, 27.3%) as a pale yellow solid. ESI-MS (M+1): 173 calc. for $C_5H_5BrN_2$: 172.0.

Preparation of reagent KR-15: Methyl 4-(2-methylpyrimidin-5-yl)benzoate

To a solution of KR-14 (637 mg, 3.7 mmol) in 1,4-dixoane was added (4-(methoxycarbonyl)phenyl)boronic acid, R-22, (718 mg, 3.7 mmol) and $(PPh_3)_4Pd$ (46 mg, 0.037 mmol), $Na_2CO_3$ (1.17 g, 11.1 mmol). The reaction was stirred at 110° C. for 1 h by MW, After TLC (PE/AE 1:1) showed the starting material was consumed, the mixture was filtrated and concentrated under vacuo, and extracted with DCM, the organic layer was washed with brine, dried over anhydrous $Na_2SO_4$, The mixture was concentrated to give the reagent KR-15 (720 mg, 85.4%) as a pale yellow solid. ESI-MS (M+1): 229.1 calc. for $C_{13}H_{12}N_2O_2$: 228.0.

Preparation of reagent KR-16: Methyl 4-(2-formylpyrimidin-5-yl)benzoate

The $SeO_2$ (308 mg, 2.77 mmol) in 1,4-dixoane was heated at 120° C. The reagent KR-15 (105 mg, 0.46 mmol) in 1,4-dixoane was added slowly. The reaction was stirred at 120° C. for 18 h. After TLC (PE/AE 1:1) showed the starting material was consumed, the mixture was filtrated and concentrated under vacuo, and extracted with DCM, the organic layer was washed with brine, dried over anhydrous $Na_2SO_4$, concentrated to give the crude product which was purified by prep-TLC (PE: EA=1:1) to give KR-16 (62 mg, 55.9%) as a pale yellow solid. ESI-MS (M+1): 243.2. calc. for $C_{13}H_{10}N_2O_3$:242.1.

Preparation of reagent KR-17: Methyl 4-[2-(hydroxymethyl)pyrimidin-5-yl]benzoate To a solution of KR-16 (40 mg, 0.16 mmol) in MeOH was added $NaBH_4$ (25 mg, 0.66 mmol). The reaction was stirred at r.t. for 10 h. After TLC (PE/AE 1:1) showed the starting material was consumed, the mixture was poured into water and concentrated under vacuo, and extracted with DCM, the organic layer was washed with brine, dried over anhydrous $Na_2SO_4$, concentrated to give the crude product which was purified by prep-TLC (PE:EA=1:1) to give the reagent KR-17 (24 mg, 61.5%) as a pale yellow solid. ESI-MS (M+1): 245.1 calc. for $C_{13}H_{12}N_2O_3$: 244.0.

Preparation of reagent KR-18: (4-Chloro-2-methylsulfanyl-pyrimidin-5-yl)methanol To a solution of the commercially available ethyl 4-chloro-2-methylthio-pyrimidine-5-carboxylate, 13, (15 g, 64 mmol) in $CH_2Cl_2$ (250 mL) at −78° C. was added Dibal-H (diisobutylaluminium hydride) (1.0 M in toluene, 128 mL, 128 mmol) slowly. The reaction mixture was stirred at 0° C. for 2 h. The reaction mixture was added $Na_2SO_4.10H_2O$ (144 g, 640 mmol) and stirred for 30 min. The organics were sequestered and the aqueous was extracted further with $CH_2Cl_2$, the organic layer was washed with water, brine, dried with anhydrous $Na_2SO_4$, concentrated to give the crude KR-18 (9.8 g, 80.9%) as a yellow solid which was used directly in the next step. ESI-MS (M+1): 191.0 calc. for $C_6H_7ClN_2OS$: 190.0.

Preparation of reagent KR-19: tert-Butyl-[(4-chloro-2-methylsulfanyl-pyrimidin-5-yl)methoxy]-dimethyl-silane To a solution of KR-18 (1.7 g, 9 mmol) in $CH_2Cl_2$ (20 mL) was added TBSCl (tert-Butyldimethylsilyl chloride) (2.0 g, 13.3 mmol), imidazole (1.2 g, 18 mmol). The reaction mixture was stirred at r.t. for 10 h. The reaction mixture was quenched into water, extracted with $CH_2Cl_2$, dried with anhydrous $Na_2SO_4$, concentrated to give the crude product which was purified by column chromatography (eluting with PE/EA=100:1 to 5:1) to give the pure reagent KR-19 (2.1 g, 77.8%) as a yellow solid. ESI-MS (M+1): 305.1 calc. for $C_{12}H_{21}ClN_2OSSi$: 304.0.

Preparation of reagent KR-20: tert-Butyl-dimethyl-[(2-methylsulfanylpyrimidin-5-yl)methoxy]silane To a solution of KR-19 (5.7 g, 18.7 mmol) in MeOH (50 mL) was added Pd/C (10 g), $Na_2CO_3$ (2.6 g, 18.7 mmol), then the reaction mixture was stirred at 50° C. at hydrogen 50 psi (345 kPa) for 18 h. After TLC (PE/EA=5:1) showed the starting material was consumed, the mixture was filtrated and concentrated, water was added and extracted with $CH_2Cl_2$, the organic layer was washed with brine, dried over anhydrous $Na_2SO_4$, concentrated to give the crude product which was purified by column chromatography (eluting with PE/EA=100:1 to 10:1) to give the reagent KR-20 (2.3 g, 46.0%) as a yellow solid. ESI-MS (M+1): 271.1 calc. for $C_{12}H_{22}N_2OSSi$: 270.1.

Preparation of reagent KR-21: tert-Butyl-dimethyl-[(2-methylsulfonylpyrimidin-5-yl)methoxy]silane To a solution of KR-20 (2.24 g, 8 mmol) in $CH_2Cl_2$ (25 mL) was added m-CPBA (meta-chloroperbenzoic acid) (4.2 g, 21 mmol). The reaction mixture was stirred at r.t for 10 h. The resulting mixture was added aqueous $Na_2SO_3$ stirred for 30 min. The organic layer was separated and the aqueous layer was extracted 3 times with $CH_2Cl_2$. The combined organic layers were washed with aqueous $NaHCO_3$ and brine, dried over sodium sulfate and concentrated under reduced pressure to afford the desired crude product which was purified by column chromatography (eluting with PE/EA=100:1 to 10:1) to give KR-21 (1.8 g, 75.1%) as a yellow solid. ESI-MS (M+1): 303.1 calc. for $C_{12}H_{22}N_2O_3SSi$: 302.1.

Preparation of reagent KR-22: Ethyl 1-[5-[[tert-butyl(dimethyl)silyl]oxymethyl]-pyrimidin-2-yl]piperidine-4-carboxylate To a solution of KR-21 (2.9 g, 9.6 mmol) in 1,4-dixoane was added ethyl piperidine-4-carboxylate, R-23, (12.0 g, 76.8 mmol), DIEA (N,N-Diisopropylethylamine) (3.7 g, 29 mmol). The reaction was stirred at 100° C. for 18 h. After TLC (PE/EA=3:1) showed the starting material was consumed, the mixture was poured into water and extracted with $CH_2Cl_2$, the organic layer was washed with brine, dried over anhydrous $Na_2SO_4$, concentrated to give the crude product which was purified by column chromatography (eluting with PE/EA=100:1 to 10:1) to give pure reagent KR-22 (2.8 g, 77.8%) as a pale yellow solid. ESI-MS (M+1): 380.1 calc. for $C_{19}H_{33}N_3O_3Si$: 379.2.

Preparation of reagent KR-23: Ethyl 1-[5-(hydroxymethyl)pyrimidin-2-yl]piperidine-4-carboxylate A solution of KR-22 (2.7 g, 7.1 mmol) in $AcOH/H_2O/THF$ (13/7/3) was stirred at 30° C. for 5 h. After TLC (PE/EA=3:1) showed the starting material was consumed, the mixture was poured into water and extracted with $CH_2Cl_2$, the organic layer was washed with brine, dried over anhydrous $Na_2SO_4$, concentrated to give the crude product which was purified by column chromatography (eluting with PE/EA=100:1 to 10:1) to give the pure reagent KR-23 (1.6 g, 85.1%) as a pale yellow solid. ESI-MS (M+1): 266.1 calc. for $C_{13}H_{19}N_3O_3$: 265.1.

Preparation of reagent KR-24: Methyl 4-(4-hydroxyphenyl)benzoate

A solution of the commercially available 4'-hydroxy biphenyl-4-carboxylic acid, 14, (5 g, 23.4 mmol) in MeOH (30 mL) was added $H_2SO_4$ (3 mL), then the mixture was stirred at 80° C. for 5 h. The resulting mixture was cooled to room temperature and concentrated under vacuo. The mixture was quenched into water, extracted with EA, dried with anhydrous $Na_2SO_4$, concentrated to give the crude reagent KR-24 (4.5 g, 84.4%) as a pale yellow solid. ESI-MS (M+1): 229.1 calc. for $C_{14}H_{12}O_3$: 228.1.

Preparation of reagent KR-25: tert-Butyl 3-[4-(4-methoxycarbonylphenyl) phenoxy]azetidine-1-carboxylate To a solution of KR-24 (400 mg, 1.76 mmol) in anhydrous toluene (15 mL) was added tert-butyl 3-hydroxyazetidine-1-carboxylate, R-24, (304 mg, 1.76 mmol), $Ph_3P$ (694 mg, 2.64 mmol) and DIAD (538 mg, 2.64 mmol). The sealed vial was irradiated in the microwave on a Biotage Smith Synthesis at 110° C. for 1 h. The resulting mixture was cooled to room temperature and concentrated under vacuo. The mixture was quenched into water, extracted with DCM, dried with anhydrous $Na_2SO_4$, concentrated to give the crude product which was purified by prep-TLC (PE:EA=1:0 to 3:1) to give KR-25 (470 mg, 69.6%) as a pale yellow solid. ESI-MS (M+1): 384.2 calc. for $C_{22}H_{25}NO_5$: 383.2.

Preparation of reagent KR-26: tert-Butyl 3-(4-bromophenoxyl)azetidine-1-carboxylate To a solution of 4-bromophenol, 15, (130 mg, 0.76 mmol) in toluene (10 mL) was added tert-butyl 3-hydroxyazetidine-1-carboxylate, R-24, (130 mg, 0.76 mmol), $PPh_3$ (240 mg, 0.91 mmol), DIAD (186 mg, 0.91 mmol). The sealed vial was irradiated in the microwave on a Biotage Smith Synthesis at 110° C. for 1 h. The reaction mixture was quenched into water, extracted with DCM, dried with anhydrous $Na_2SO_4$, concentrated to give the crude product which was purified by prep-TLC to give the reagent KR-26 (180 mg, 72.6%) as a pale yellow solid. ESI-MS (M+1): 328.1 calc. for $C_{14}H_{18}BrNO_3$: 327.0.

Preparation of reagent KR-27: Ethyl 1-[4-(1-tert-butoxycarbonylazetidin-3-yl)oxyphenyl]piperidine-4-carboxylate To a suspension of KR-26 (94 mg, 0.29 mmol) and compound ethyl piperidine-4 carboxylate, R-23, (50 mg, 0.32 mmol) in 1,4-dioxane (10 mL) was added $Cs_2CO_3$ (284 mg, 0.87 mmol), $Pd(^tBu)_3P$ (45 mg, 0.087 mmol). The mixture was stirred at 120° C. under $N_2$ for 6 h. The resulting mixture was cooled to room temperature and concentrated under vacuo. The mixture was quenched into water, extracted with DCM, dried with anhydrous $Na_2SO_4$, concentrated to give the crude product which was purified by prep-TLC (PE:EA=1:0 to 3:1) to give KR-27 (75 mg, 64.1%) as a pale yellow solid. ESI-MS (M+1): 405.2 calc. for $C_{22}H_{32}N_2O_5$: 404.2.

Preparation of reagent KR-28: Methyl (E)-3-(4-hydroxyphenyl)prop-2-enoate

A solution of the commercially available trans-4-hydroxycinnamic acid, 16, (5 g, 30.5 mmol) in MeOH (30 mL) was added $H_2SO_4$ (3 mL), then the mixture was stirred at 80° C. for 5 h. The resulting mixture was cooled to room temperature and concentrated under vacuo. The mixture was quenched into water, extracted with EA, dried with anhydrous $Na_2SO_4$, concentrated to give the product KR-28 (4.2 g, 77.8%) as a pale yellow solid. ESI-MS (M+1): 179.1 calc. for $C_{10}H_{10}O_3$: 178.0.

Preparation of reagent KR-29: tert-Butyl 3-[4-[(E)-3-methoxy-3-oxo-prop-1-enyl]phenoxy]azetidine-1-carboxylate To a solution of KR-28 (200 mg, 1.12 mmol) in anhydrous toluene (15 mL) was added tert-butyl 3-hydroxyazetidine-1-carboxylate, R-24, (194 mg, 1.12 mmol), $Ph_3P$ (353 mg, 1.13 mmol) and DIAD (230 mg, 1.13 mmol), the sealed vial was irradiated in the microwave on a Biotage Smith Synthesis at 110° C. for 1 h. The resulting mixture was cooled to room temperature and concentrated under vacuo. The mixture was quenched into water, extracted with DCM, dried with anhydrous $Na_2SO_4$, concentrated to give the crude product which was purified by prep-TLC (PE:EA=1:0 to 3:1) to give KR-29 (260 mg, 69.9%) as a pale yellow solid. ESI-MS (M+1): 334.2 calc. for $C_{18}H_{23}NO_5$: 333.1.

Preparation of reagent KR-30: tert-Butyl 3-(4-pyridyloxy)azetidine-1-carboxylate To a solution of the commercially available 4-pyridinol, 17, (500 mg, 5.26 mmol) in anhydrous toluene (15 mL) was added tert-butyl 3-hydroxyazetidine-1-carboxylate, R-24, (910 mg, 5.26 mmol), $Ph_3P$ (1.67 g, 6.2 mmol) and DIAD (1.27 g, 6.3 mmol), the sealed vial was irradiated in the microwave on a Biotage Smith Synthesis at 150° C. for 3 h. The resulting mixture was cooled to room temperature and concentrated under vacuo. The mixture was quenched into water, extracted with DCM, dried with anhydrous $Na_2SO_4$, concentrated to give the crude product which was purified by prep-TLC to give KR-30 (60 mg, 57.1%) as a pale yellow solid. ESI-MS (M+1): 251.1 calc. for $C_{13}H_{18}N_2O_3$: 250.1.

Preparation of reagent KR-31: tert-Butyl 3-(4-piperidyloxy)azetidine-1-carboxylate A solution of KR-30 (530 mg, 2.21 mmol) in anhydrous EtOH (10 mL) was added $PtO_2$ (360 mg, 1.59 mmol), 4-methylbenzenesulfonic acid (407 mg, 2.12 mmol), then the reaction mixture was stirred at 50° C. for 5 h under hydrogen 50 psi (345 kPa). The mixture was filtrated and concentrated, water was added and extracted with DCM, the organic layer was washed with brine, dried over anhydrous $Na_2SO_4$, concentrated to give the crude product which was purified by pre-TLC to give pure product KR-31 (410 mg, 72.6%) as a pale yellow solid. ESI-MS (M+1): 257.1 calc. for $C_{13}H_{24}N_2O_3$: 256.2.

Preparation of reagent KR-32: Ethyl 5-[4-(1-tert-butoxycarbonylazetidin-3-yl)oxy-1-piperidyl]pyrimidine-2-carboxylate To a solution of KR-31 (600 mg, 2.36 mmol) in $CH_3CN$ was added ethyl 2-chloropyrimidine-5-carboxylate, R-25, (366 mg, 1.97 mmol) and $K_2CO_3$ (814 mg, 5.9 mmol). The reaction was stirred at r.t for 18 h. The mixture was concentrated under vacuo, and extracted with DCM, the organic layer was washed with brine, dried over anhydrous $Na_2SO_4$, concentrated to give the crude product which was purified by column chromatography (eluting with PE/EA=1:1) to give pure product KR-32 (520 mg, 54.3%) as a pale yellow solid. ESI-MS (M+1): 407.2 calc. for $C_{20}H_{30}N_4O_5$: 406.2

Preparation of reagent KR-33: tert-butyl 4-(methylsulfonyloxymethyl)-piperidine-1-carboxylate To a solution of commercially available tert-butyl 4-(hydroxymethyl)piperidine-1-carboxylate (4.3 g, 20 mmol) was dissolved in DCM (50 mL) and triethylamine (3.03 g, 30 mmol) was added into the reaction mixture, then MsCl (2.51 g, 22 mmol) was added into reaction mixture slowly at 0° C. The reaction mixture was stirred at r.t for 3 hours. The reaction mixture was quenched by water and extracted with DCM, dried over Na2SO4 and concentrated under vacuo to give KR-33 (4 g, 68.3%). ESI-MS (M+1): 294 calc. for C12H23NO5S: 293.13.

Preparation of reagent KR-34: tert-butyl 4-[(3-methoxycarbonylphenoxy)-methyl]piperidine-1-carboxylate To KR-33 (2.93 g, 10 mmol) dissolved in CH3CN (30 mL) was added into K2CO3 (2.76 mg, 20 mmol) and commercially available methyl 3-hydroxybenzoate (1.52 mg, 10 mmol), then stirred at 80° C. overnight. The reaction mixture was concentrated under vacuo, then extracted with ethyl acetate and washed with water, dried over Na2SO4 and concentrated under vacuo to give KR-34 (3.15 g, 90%). ESI-MS (M+1): 350 calc. for C19H27NO5: 349.19.

Preparation of reagent KR-35: 3-[(1-tert-butoxycarbonyl-4-piperidyl)methoxy]-benzoic acid To a solution of reagent KR-34 (2.0 g, 5.71 mmol) in THF/MeOH/H2O (20/2/10 mL) was added LiOH.H2O (982 mg, 22.84 mmol). The resulting mixture was stirred at r.t overnight, after TLC showed that most of the starting materials were consumed completely, the mixture was diluted with water and adjusted pH to 2-3. The mixture was extracted with EtOAc and washed with brine, dried over anhydrous Na2SO4 and concentrated to give KR-35 (1.5 g, 78.08%). ESI-MS (M+1): 336 calc. for C18H25NO5: 335.17.

Preparation of reagent KR-36: tert-butyl 4-methylsulfonyloxypiperidine-1-carboxylate To a solution of commercially available tert-butyl 4-hydroxypiperidine-1-carboxylate (4.02 g, 20 mmol) was dissolved in DCM (50 mL) and triethylamine (3.03 g, 30 mmol) was added into the reaction mixture, then MsCl (2.51 g, 22 mmol) was added into the reaction mixture slowly at 0° C. The reaction mixture was stirred at r.t for 3 hours. The reaction mixture was quenched with water and extracted with DCM, dried over Na2SO4 and concentrated under vacuo to give KR-36 (4 g, 71.2%). ESI-MS (M+1): 294 calc. for C12H23NO5S: 293.13.

Preparation of reagent KR-37: tert-butyl 4-(3-methoxycarbonylphenoxy)-piperidine-1-carboxylate The reagent KR-36 (2.79 g, 10 mmol) dissolved in CH3CN (30 mL) was added into K2CO3 (2.76 mg, 20 mmol) and commercially available methyl 3-hydroxybenzoate (1.52 mg, 10 mmol), then stirred at 80° C. overnight. The reaction mixture was concentrated under vacuo, then extracted with ethyl acetate and washed with water, dried over Na2SO4 and concentrated under vacuo to give KR-37 (3.05 g, 91.4%). ESI-MS (M+1): 336 calc. for C18H25NO5: 335.17.

Preparation of reagent KR-38: 3-[(1-tert-butoxycarbonyl-4-piperidyl)oxy]-benzoic acid To a solution of reagent KR-37 (1.91 g, 5.71 mmol) in THF/MeOH/H2O (20/2/10 mL) was added LiOH.H2O (982 mg, 22.84 mmol). The resulting mixture was stirred at r.t for overnight, after TLC showed that most of the starting materials were consumed completely, the mixture was diluted with water and adjusted pH to 2-3. The mixture was extracted with EtOAc and washed with brine, dried over anhydrous Na2SO4 and concentrated to give KR-38 (1.44 g, 79.00%). ESI-MS (M+1): 322 calc. for C17H23NO5: 321.16.

Preparation of reagent KR-39: ethyl 5-methylthiophene-2-carboxylate

To a solution of commercially available 5-methylthiophene-2-carboxylic acid (9.2 g, 0.065 mol) in DMF (80 mL) was added K2CO3 (17.9 g, 0.13 mol), then compound CH3CH2I (15.2 g, 0.98 mol) was added slowly. The reaction mixture was stirred at room temperature overnight. After TLC (PE/EtOAc=2:1) showed the starting material was consumed completely, the mixture was quenched with water and extracted with EtOAc, the organic layer was washed with brine, dried over anhydrous Na2SO4, concentrated to give the crude reagent KR-39 (9.5 g, 86.3%) as a pale yellow oil which was used for the next step without further purification. ESI-MS (M+1): 171.0 calc. for C8H10O2S: 170.0.

Preparation of reagent KR-40: ethyl 3-(4-formylphenyl)propanoate

To a solution of commercially available 4-bromobenzaldehyde (6.0 g, 0.032 mol) in DMF (30 mL) was added 3,3-diethoxyprop-1-ene (12.65 g, 0.096 mol), TBACl (1.51 g, 0.032 mol), n-Bu3N (11.84 g, 0.064 mol), Pd(AcO)2 (215 mg, 0.96 mmol), then the reaction mixture was stirred at 90° C. for 1 hr until TLC showed the starting material was consumed completely, then the mixture was diluted with 2N HCl and extracted with EtOAc, the organic layer was washed with brine, dried over anhydrous Na2SO4, concentrated to give a crude which was purified by column chromatography to give pure reagent KR-40 (3.78 g, 56.59% yield) as a yellow oil. ESI-MS (M+1): 207 calc. for C12H14O3: 206.1.

Preparation of reagent KR-41: ethyl 3-[4-(hydroxymethyl)phenyl]propanoate

To a solution of reagent KR-40 (2.2 g, 10.68 mmol) in THF/MeOH (30 mL/10 mL) was added NaBH4 (619 mg, 16.29 mmol) in portions at 0° C., then the reaction mixture was stirred at 0° C. for 1 hr until TLC showed the starting material was consumed completely, then the mixture was extracted with DCM, the organic layer was washed with brine, dried over anhydrous Na2SO4, concentrated to give reagent KR-41 (1.93 g, 85.59%) as a pale yellow oil which was used for next step directly. ESI-MS (M+1): 209 calc. for C12H16O3: 208.1.

Preparation of reagent KR-42: 5-bromo-2-ethoxy-benzoic acid

To a solution of commercially available 2-ethoxybenzoic acid (50 g, 0.3 mol) in AcOH (500 mL) was added Br2 (72 g, 0.45 mol) slowly at room temperature. Then the mixture was stirred at room temperature overnight. After LC-MS showed the starting material was consumed completely, aqueous Na2SO3 was added, concentrated, the mixture was extracted with EtOAc, the organic layer was washed with aqueous NaHCO3, brine, dried over anhydrous Na2SO4, concentrated to give the crude reagent KR-42 (65.41 g, 89.4%) as a white solid. ESI-MS (M+1): 245.0 calc. for C9H9BrO3: 243.9.

Preparation of reagent KR-43: benzyl 5-bromo-2-ethoxy-benzoate

To a solution of reagent KR-42 (65.41 g, 0.27 mol) in DMF (240 mL) was added BnBr (51.3 g, 0.3 mol) and K2CO3 (82.8 g, 0.6 mol), then the mixture was stirred at r.t. overnight. The mixture was diluted with DCM and washed with brine, dried over anhydrous Na2SO4, concentrated to give the crude reagent KR-43 (65 g, 73%) as a white solid. ESI-MS (M+1): 335.1 calc. for C16H15BrO3: 334.0.

Preparation of reagent KR-44: benzyl 2-ethoxy-5-(4-methoxycarbonylanilino)-benzoate To a solution of compound reagent KR-43 (2.0 g, 6.0 mmol) in 1,4-dioxane (80 mL) was added commercially available methyl 4-aminobenzoate (1.06 g, 7.0 mmol), Pd2(dba)3 (550 mg, 0.6 mmol), X-Phos (695 mg, 1.2 mmol), and Cs2CO3 (4.9 g, 15 mmol). The resulting mixture was stirred at 90° C. overnight until TLC showed the starting material was consumed completely, then filtered and the mixture was extracted with EtOAc, the organic layer was washed with brine, dried over anhydrous Na2SO4, concentrated to give the crude compound which was purified by column chromatography to give pure reagent KR-44 (1.82 g, 75% yield) as a pale yellow oil.
ESI-MS (M+1): 406.2 calc. for C24H23NO5: 405.1.

Preparation of reagent KR-45: benzyl 5-(N-tert-butoxycarbonyl-4-methoxycarbonyl-anilino)-2-ethoxy-benzoate To a solution of compound reagent KR-44 (1.82 g, 4.5 mmol) in CH2Cl2 (40 mL) was added Boc2O (3.05 g, 14 mmol) and DMAP (1.1 g, 9 mmol), then the mixture was stirred at reflux overnight. The mixture was extracted with CH2Cl2, the organic layer was washed with aqueous NH4Cl, brine, dried over anhydrous Na2SO4, concentrated to give the crude product which was purified by column chromatography to give pure reagent KR-45 (1.5 g, 66% yield) as a yellow solid. ESI-MS (M-55): 450.2 calc. for C29H31NO7: 505.21.

Preparation of reagent KR-46: ethyl 2-(1,4-dioxaspiro[4.5]decan-8-ylidene)acetate To a solution of commercially available ethyl 2-diethoxyphosphorylacetate (9.5 g, 42.3 mmol) in THF (20 mL) was added NaH (1.7 g, 42.3 mmol) at 0° C. The mixture solution was stirred at 0° C. for 1 h. Then a solution of commercially available 1,4-dioxaspiro[4.5]decan-8-one (6 g, 38.5 mmol) in THF (5 mL) was added at 0° C. The solution was stirred at r.t overnight. The mixture was quenched with aqueous NH4Cl and extracted with EtOAc, the organic layer was washed with brine, dried over anhydrous Na2SO4, concentrated to give the crude product which was purified by column to give reagent KR-46 (6.6 g, 69% yield) as a white solid. ESI-MS (M+1): 227.2; calc. for C12H18O4: 226.1.

Preparation of reagent KR-47: ethyl 2-(1,4-dioxaspiro[4.5]decan-8-yl)acetate

To a solution of reagent KR-46 (6 g, 26.5 mmol) in MeOH (40 mL) was added Pd/C (3 g). The solution was stirred at r.t for 3 hrs under H2 atmosphere. The solution was filtered and the filtrate was concentrated to give reagent KR-47 (5 g, 83%) as a white solid. ESI-MS (M+1): 229.2 calc. for C12H20O4: 228.1.

Preparation of reagent KR-48: ethyl 2-(4-oxocyclohexyl)acetate

A solution of reagent KR-47 (5 g, 21.9 mmol) in HCl (6N, 10 mL) was stirred at 70° C. overnight, then concentrated to give the crude product which was purified by the column to obtained pure reagent KR-48 (3 g, 75%) as white solid. ESI-MS (M+1): 185.2 calc. for C10H16O3: 184.1.

Preparation of reagent KR-49: methyl 4-(1,4-dioxa-8-azaspiro[4.5]decan-8-yl)benzoate To a solution of commercially available reagents 1,4-dioxa-8-azaspiro[4.5]decane (1.43 g, 10 mmol) and (4-methoxycarbonylphenyl)-boronic acid (3.6 g, 20 mmol)) in DCM (20 mL), Cu(OAc)2 (1.82 g, 10 mmol) and Et3N (2 g, 20 mmol) were added and the mixture was stirred overnight. The mixture was quenched with aqueous water and extracted with DCM, the organic layer was washed with brine, dried over anhydrous Na2SO4, concentrated to give the crude product which was purified by the column to give the compound reagent KR-49 (1.2 g, 44%) as a pale yellow solid. ESI-MS (M+1): 278.2; calc. for C15H19NO4: 277.1.

Preparation of reagent KR-50: O5-tert-butyl O2-ethyl 5-azaspiro[2.4]heptane-2,5-dicarboxylate To a solution of commercially available 5-tert-butoxycarbonyl-5-azaspiro[2.4]heptane-2-carboxylic acid (400 mg, 1.66 mmol) in DMF (30 mL) was added compound CH3CH2I (343 mg, 2.2 mmol) and K2CO3 (410 mg, 3.0 mmol), then the reaction mixture was stirred at room temperature for 4 hrs.
After TLC (PE/EtOAc=5:1) showed the starting material was consumed completely, the mixture was quenched with water and extracted with EtOAc, the organic layer was washed with brine, dried over anhydrous Na2SO4, concentrated to give the crude reagent KR-50 (450 mg, ~100%) as a yellow oil which was used for the next step without further purification. ESI-MS (M-55): 214.0 calc. for C14H23NO4: 269.1.

Preparation of reagent KR-51: benzyl 3-oxocyclobutanecarboxylate

To a mixture of commercially available 3-oxocyclobutanecarboxylic acid (13.50 g, 118.32 mmol) and Cs2CO3 (46.26 g, 141.98 mmol) in CH3CN (120 mL), was added bromomethylbenzene (21.25 g, 124.24 mmol) in one portion at r.t. under N2. The mixture was stirred at r.t. for 20 hours. LCMS and TLC showed the reaction was completed. The residue was poured into water and stirred for 20 min. The aqueous phase was extracted with EtOAc (120 mL). The combined organic phase was washed with saturated brine (140 mL), dried with anhydrous Na2SO4, filtered and concentrated in vacuum. The residue was purified by silica gel chromatography to afford reagent KR-51 (8.86 g, 36.7%).

Preparation of reagent KR-52: tert-butyl 3-[(4-ethoxycarbonylphenyl)methyl]-azetidine-1-carboxylate Commercially available tert-butyl 3-methyleneazetidine-1-carboxylate (500 mg, 3 mmol) was treated with a 0.5 M solution of 9-BBN in THF (10 mL), and the mixture was heated at reflux for 4 hrs. The resulting mixture was transferred into a stirred mixture of ethyl 4-iodobenzoate (1.7 g, 6 mmol), Pd2(dba)3 (270 mg, 0.3 mmol), X-Phos (450 mg, 0.9 mmol), and Na2CO3 (1 g, 9 mmol) in 1,4-dioxane (40 mL) and H$_2$O (4 mL). The resulting mixture was stirred at reflux overnight. Then filtered, the mixture was extracted with EtOAc, the organic layer was washed with brine, dried over anhydrous Na2SO4, concentrated to give the crude compound which was purified by column chromatography (eluting with PE/EtOAc=50:1 to 5:1) to give pure reagent KR-52 (200 mg, 20% yield) as a pale yellow oil. ESI-MS (M+1): 320 calc. for C18H25NO4: 319.1.

Preparation of reagent KR-53: tert-butyl 3-[(5-ethoxycarbonyl-2-thienyl)methyl]azetidine-1-carboxylate Commercially available tert-butyl 3-methyleneazetidine-1-carboxylate (500 mg, 3 mmol) was treated with a 0.5 M solution of 9-BBN in THF (10 mL), and the mixture was heated at reflux for 4 hrs. The resulting mixture was transferred into a stirred mixture of ethyl 5-bromothiophene-2-carboxylate (1.4 g, 6 mmol), Pd2(dba)3 (270 mg, 0.3 mmol), X-Phos (450 mg, 0.9 mmol), and Na2CO3 (1 g, 9 mmol) in 1,4-dioxane (40 mL) and H$_2$O (4 mL). The resulting mixture was stirred at reflux overnight, then filtered, the mixture was extracted with EtOAc, the organic layer was washed with brine, dried over anhydrous Na2SO4, concentrated to give the crude compound which was purified by column chromatography (eluting with PE/EtOAc=50:1 to 5:1) to give pure reagent KR-53 (200 mg, 20%) as a pale yellow oil. ESI-MS (M+1): 326 calc. for C16H23NO4S: 325.1.

Preparation of reagent R-09a: Ethyl 2-(piperazin-1-yl)pyrimidine-5-carboxylate

To a solution of KR-8 (2.50 g, 7.44 mmol) was added 4 mol/L DCM/HCl (30 mL). The reaction mixture was stirred at r.t. overnight, and then concentrated to give R-09a (320 mg, 96.7% yield). ESI-MS (M+1): 237 calc. for C$_{11}$H$_{16}$N$_4$O$_2$: 236.1.

Preparation of reagent R-09b: Ethyl 3-(piperidin-4-yl)propanoate

A mixture of KR-2 (3 g, 16.95 mmol) and Pd/C (0.5 g) in MeOH (30 mL) was stirred at 40° C. at 40 Psi (276 kPa) overnight. The mixture was filtered, the filtrate was concentrated under vacuo to give R-09b (3 g, 95.8% yield). ESI-MS (M+1): 186 calc. for C$_{10}$H$_{19}$NO$_2$: 185.2.

Preparation of reagent R-09c: (E)-Ethyl 3-(4-((piperazin-1-yl)methyl)phenyl)-prop-2-enoate To a solution of KR-3 (0.204 g, 1 mmol) in MeOH (10 mL) was added AcOH (0.1 mL) and piperazine (0.164 g, 2 mmol), the reaction mixture was stirred at r.t. overnight, then NaBH$_3$CN (0.0189 g, 3 mmol) was added into the reaction mixture, stirred at r.t. for 2 hours. Then the reaction mixture was concentrated under vacuo to give R-09c (250 mg, 91.2% yield) which used for the next step directly. ESI-MS (M+1): 275 calc. for C$_{16}$H$_{22}$N$_2$O$_2$: 274.3.

Preparation of reagent R-09d: (E)-Ethyl 3-(4-aminophenyl)prop-2-enoate

To a solution of KR-6 (30 g, 0.136 mol) in AcOH (20 mL) was added Fe (41.4 g, 0.74 mol), the reaction was stirred at r.t for 5 hours. Then the mixture was filtered, the filtrate was concentrated to give the crude product which was purified by column chromatography (EA:PE=1:20-1:2) to give R-09d (17 g, 65% yield) as a yellow solid. ESI-MS (M+1): 192 calc. for C$_{11}$H$_{13}$NO$_2$: 191.1.

Preparation of reagent R-09e: Ethyl 2-(4-aminopiperidin-1-yl)pyrimidine-5-carboxylate R-09e was obtained starting from KR-10 in an analogous manner to R-09a. 93.5% yield. ESI-MS (M+1): 251 calc. for C$_{12}$H$_{18}$N$_4$O$_2$: 250.1.

Preparation of reagent R-09f: Methyl 4-[4-(azetidin-3-yloxy)phenyl]benzoate

A solution of KR-25 (500 mg, 1.3 mmol) in HCl/dioxane (4M, 5 mL) was stirred at r.t. for 1 h, the reaction mixture was concentrated to give the desired reagent R-09f (325 mg, 88.3%) as a pale yellow solid. ESI-MS (M+1): 284.2 calc. for C$_{17}$H$_{17}$NO$_3$: 283.1.

Preparation of reagent R-09g: Ethyl 1-[4-(azetidin-3-yloxy)phenyl]piperidine-4-carboxylate R-09g was obtained starting from KR-27 in an analogous manner to R-09f. 87.6% yield, as a yellow solid. ESI-MS (M+1): 305.1 calc. for C$_{17}$H$_{24}$N$_2$O$_3$: 304.2.

Preparation of reagent R-09h: Methyl (E)-3-[4-(azetidin-3-yloxy)phenyl]prop-2-enoate R-09h was obtained starting from KR-29 in an analogous manner to R-09f. 75.0% yield. ESI-MS (M+1): 234.1 calc. for C$_{13}$H$_{15}$NO$_3$: 233.1.

Preparation of reagent R-09i: Ethyl 5-[4-(azetidin-3-yloxy)-1-piperidyl]pyrimidine-2-carboxylate R-09i was obtained starting from KR-32 in an analogous manner to R-09f. 89.2% yield. ESI-MS (M+1): 307.1 calc. for C$_{15}$H$_{22}$N$_4$O$_3$: 306.2.

Preparation of reagent R-09l: methyl 2-azaspiro[5.5]undecane-9-carboxylate; hydrochloride A solution of commercially available O2-tert-butyl O9-methyl 2-azaspiro[5.5]undecane-2,9-dicarboxylate (200 mg, 0.64 mmol) in HCl/EtOAc (1.0 N, 15 mL) was stirred at room temperature for 1 hr, then concentrated to give the crude reagent R-09l (120 mg, 89%) as yellow solid which was used for the next step without further purification. ESI-MS (M-35): 212.1 calc. for C12H22ClNO2: 247.1.

Preparation of reagent R-09m: ethyl 5-azaspiro[2.4]heptane-2-carboxylate

A solution of reagent KR-50 (450 mg, 1.66 mmol) in HCl/EtOAc (1.0 N, 20 mL) was stirred at room temperature for 2 hrs, then concentrated to give the crude reagent R-09m (340 mg, ~100%) as a yellow solid which was used for the next step without further purification. ESI-MS (M+1): 170.1 calc. for C9H15NO2: 169.1.

Preparation of reagent R-09o: ethyl 4-(azetidin-3-yloxy)benzoate

To a solution of ethyl 4-hydroxybenzoate (520 mg, 3 mmol) in toluene (15 mL) was added tert-butyl 3-hydroxyazetidine-1-carboxylate (456.77 mg, 3 mmol), PPh3 (1 g, 3.81 mmol), DIAD (771 mg, 3.81 mmol). The sealed vial was irradiated in the microwave on a Biotage Smith Synthesis at 110° C. for 6 hrs. The reaction mixture was quenched with water, extracted with DCM, dried with anhydrous Na2SO4, concentrated to give the crude product which was purified by column to give R-09o (480 mg, 49% yield) as a pale yellow solid. ESI-MS (M+1): 222.1 calc. for C12H15NO3: 221.1.

Preparation of reagent R-09p: ethyl 4-(azetidin-3-ylmethyl)benzoate

A solution of reagent KR-52 (200 mg, 0.63 mmol) in HCl/EtOAc (10 mL) was stirred at r.t for 1 h, then concentrated to give the crude reagent R-09p (150 mg, quant.) as a white solid. ESI-MS (M+1): 220; calc. for C13H17NO2: 219.1.

Preparation of reagent R-09q: ethyl 5-(azetidin-3-ylmethyl)thiophene-2-carboxylate A solution of reagent KR-53 (200 mg, 0.63 mmol) in HCl/EtOAc (10 mL) was stirred at r.t for 1 h, then concentrated to give the crude reagent R-09q (150 mg, quant.) as a white solid. ESI-MS (M+1): 226; calc. for C11H15NO2: 225.0.

Preparation of reagent R-10a: Ethyl 2-(4-(hydroxymethyl)piperidin-1-yl)pyrimidine-5-carboxylate R-10a was obtained starting from KR-11 in an analogous manner to KR-8. 76.5% yield. ESI-MS (M+1): 266 calc. for $C_{13}H_{19}N_3O_3$: 265.1.

Preparation of reagent R-10b: Ethyl 2-(4-hydroxy-1-piperidyl)pyrimidine-5-carboxylate R-10b was obtained starting from KR-12 in an analogous manner to KR-8. 81.1% yield. ESI-MS (M+1): 252 calc. for $C_{12}H_{17}N_3O_3$ 251.1.

Preparation of reagent R-10d: ethyl 4-hydroxycyclohexanecarboxylate

To a solution of commercially available ethyl 4-oxocyclohexanecarboxylate (5.0 g, 0.029 mol) in MeOH (50 mL) was added NaBH4 (2.24 g, 0.058 mol) at 0° C. in portions, then the mixture was stirred at room temperature for 1 hr until TLC showed the starting material was consumed completely, quenched with water and the mixture was extracted with EtOAc, the organic layer was washed with brine, dried over anhydrous Na2SO4, concentrated to give the crude reagent R-10d (4.95 g, 97.83%) as a pale yellow oil which was used for the next step directly. ESI-MS (M+1): 173 calc. for C9H16O3: 172.1.

Preparation of reagent R-11c: (1-(5-(Ethoxycarbonyl)pyrimidin-2-yl)piperidin-4-yl)methyl methanesulfonate To a solution of R-10a (2.65 g, 10 mmol) in DCM (25 mL) was added Et₃N (3.5 g, 35 mmol), then mesyl chloride (1.99 mg, 17.5 mmol) was added into the reaction mixture slowly at 0° C. The reaction mixture was stirred at r.t. overnight. The mixture was diluted with DCM and washed with water, brine, dried over anhydrous $Na_2SO_4$ and concentrated to give the crude R-11c (2.55 g, 74.3% yield) as a yellow solid. ESI-MS (M+1): 344 calc. for $C_{14}H_{21}N_3O_5S$: 343.1.

Preparation of reagent R-11d: 4-((E)-2-(Ethoxycarbonyl)vinyl)benzyl methanesulfonate To a solution of KR-5 (206 mg, 1 mmol) in DCM (20 mL) was added Et₃N (202 mg, 2 mmol), then MsCl (140 mg, 1.2 mmol) was added into the reaction mixture slowly at 0° C. The reaction mixture was stirred at r.t. overnight. The mixture was diluted with DCM and washed with water, brine, dried over anhydrous $Na_2SO_4$ and concentrated to give the starting material R-11d (150 mg, 53.0%) as a yellow liquid. ESI-MS (M+1): 285 calc. for $C_{13}H_{16}O_5S$: 284.3.

Preparation of reagent R-11f: (E)-Ethyl 3-(4-iodophenyl)prop-2-enoate

To a solution of R-09d (17 g, 0.089 mol) in CH₃CN (200 mL) was added ᵗBuONO (18.3 g, 0.178 mol), I₂ (22.6 g, 0.089 mol), the reaction was stirred at r.t. for overnight. Then the mixture was concentrated to give the crude product which was purified by column chromatography (EA:PE=1:50-1:10) to give R-11f (8 g, 31% yield) as a yellow solid. ESI-MS (M+1): 303 calc. for $C_{11}H_{11}IO_2$: 302.1.

Preparation of reagent R-11 h: Methyl 4-[2-(methylsulfonyloxymethyl)pyrimidin-5-yl]benzoate To a solution of reagent KR-17 (100 mg, 0.41 mmol) in DCM was added MsCl (mesyl chloride) (70.4 mg, 0.62 mmol), Et3N (82.8 mg, 0.82 mmol) at 0° C. The reaction was stirred at 0° C. for 1 h. After TLC (PE/AE 1:1) showed the starting material was consumed, the mixture poured into water and extracted with DCM, the organic layer was washed with brine, dried over anhydrous Na₂SO₄, concentrated to give the crude product which was purified by prep-TLC to give the reagent R-11h (95 mg, 72.0%) as a pale yellow solid. ESI-MS (M+1): 323.1 calc. for $C_{14}H_{14}N_2O_5S$: 322.0.

Preparation of reagent R-11i: Ethyl 1-[5-(methylsulfonyloxymethyl)pyrimidin-2-yl]piperidine-4-carboxylate To a solution of KR-23 (911 mg, 3.4 mmol) in $CH_2Cl_2$ was added MsCl (mesyl chloride) (590 mg, 5.15 mmol), Et₃N (687 mg, 6.8 mmol) at 0° C. The reaction was stirred at 0° C. for 18 h. After TLC (PE/EA=1:1) showed the starting material was consumed, the mixture was poured into water and extracted with $CH_2Cl_2$, the organic layer was washed with brine, dried over anhydrous $Na_2SO_4$, concentrated to give the crude product which was purified by prep-TLC to give the reagent R-11i (420 mg, 36.2%) as a pale yellow solid. ESI-MS (M+1): 344.1 calc. for $C_{14}H_{21}N_3O_5S$: 343.1.

Preparation of reagent R-11 k: ethyl 5-(bromomethyl)thiophene-2-carboxylate

To a solution of reagent KR-39 (1.9 g, 0.011 mol) in CCl4 (30 mL) was added BPO (212 mg, 0.001 mmol) and NBS (2.85 g, 0.016 mmol), then the reaction mixture was stirred at reflux for 2 hrs until TLC (PE/EtOAc=5:1) showed the starting material was consumed completely, the mixture was extracted with DCM, the organic layer was washed with aqueous NaHCO3, brine, dried over anhydrous Na2SO4, concentrated to give the crude compound which was purified by silica gel chromatography (PE/EtOAc=5:1) to give pure reagent R-11k (1.3 g, 48.1%) as a yellow oil. ESI-MS (M+1): 249.1 calc. for $C_8H_9BrO_2S$: 247.9.

Preparation of reagent R-11l: methyl 5-(bromomethyl)furan-2-carboxylate

To a solution of commercially available methyl 5-methylfuran-2-carboxylate (1.0 g, 7.14 mmol) in 0014 (20 mL) was added BPO (173 mg, 0.714 mmol) and NBS (1.91 g, 10.71 mmol), then the reaction mixture was stirred at reflux for 4 hrs until TLC (PE/EtOAc=3:1) showed the starting material was consumed completely, the mixture was extracted with DCM, the organic layer was washed with aqueous NaHCO3, brine, dried over anhydrous Na2SO4, concentrated to give a crude which was purified by Prep-TLC (PE/EtOAc=3:1) to give pure reagent R-11l (920 mg, 58.97%) as a yellow oil. ESI-MS (M+1): 219 calc. for C7H7BrO3: 217.9.

Preparation of reagent R-11m: ethyl 2-[4-(bromomethyl)phenyl]acetate

To a solution of commercially available ethyl 2-(p-tolyl)acetate (2.0 g, 11.24 mmol) in CCl4 (30 mL) was added BPO (272 mg, 1.124 mmol) and NBS (3.00 g, 16.86 mmol), then the reaction mixture was stirred at reflux for 2 hrs until TLC (PE/EtOAc=5:1) showed the starting material was consumed completely, the mixture was extracted with DCM, the organic layer was washed with aqueous NaHCO3, brine, dried over anhydrous Na2SO4, concentrated to give a crude which was purified by column chromatography to give pure reagent R-11m (1.90 g, 66%) as a yellow oil. ESI-MS (M+1): 257 calc. for C11H13BrO2: 256.0.

Preparation of reagent R-11n: ethyl 3-[4-(bromomethyl)phenyl]propanoate

To a solution of reagent KR-41 (1.93 g, 9.28 mmol) in anhydrous DCM (30 mL) was added PPh3 (1.19 g, 3.71 mmol), then the mixture was cooled to 0° C., NBS (1.96 g, 11.14 mmol) was added at 0° C., then the mixture was stirred at room temperature overnight. After LC-MS showed the starting material was consumed completely, the mixture was extracted with DCM, the organic layer was washed with brine, dried over anhydrous Na2SO4, concentrated to give a crude which was purified by column chromatography to give pure reagent R-11n (680 mg, 27% yield) as a pale yellow oil. ESI-MS (M+1): 271 calc. for C12H15BrO2: 270.0.

Preparation of reagent R-15a: Ethyl 1-benzyl-4-methylpyrrolidine-3-carboxylate (trans racemic)

To a solution of the commercially available (E)-methyl but-2-enoate (32 g, 0.28 mol) was added toluene (500 mL), N-(methoxymethyl)(phenyl)-N-((trimethylsilyl)methyl)methanamine (74 g, 0.31 mol) and CF3COOH (30 g, 0.28 mol). The reaction mixture was heated at 50° C. for 18 h. The reaction mixture was concentrated, quenched with saturated sodium bicarbonate, extracted with DCM, dried over anhydrous $Na_2SO_4$, filtered and concentrated to give crude R-15a (40 g, 57.97% yield) as a pale yellow oil. ESI-MS (M+1): 248 calc. for $C_{15}H_{21}NO_2$: 247.1.

Preparation of reagent R-22a: tert-butyl 4-[(3 chlorocarbonylphenoxy)-methyl]piperidine-1-carboxylate To a solution of reagent KR-35 (1 g, 2.86 mmol) in DCM (30 mL) was added 1-chloro-N, N, 2-trimethylprop-1-en-1-amine (571 mg, 4.29 mmol). The mixture was stirred at room temperature overnight. The mixture was concentrated under vacuo to give the reagent R-22a (1 g, 75.8%) used directly in next step. ESI-MS (M-55): 298 calc. for C18H24ClNO4: 353.14.

Preparation of reagent R-22b: tert-butyl 4-(3-chlorocarbonylphenoxy)-piperidine-1-carboxylate To a solution of reagent KR-38 (1 g, 3.11 mmol) in DCM (30 mL) was added 1-chloro-N, N, 2-trimethylprop-1-en-1-amine (621 mg, 4.67 mmol). The mixture was stirred at room temperature overnight. The mixture was concentrated under vacuo to give the reagent R-22b (0.98 g, 93.3%) used directly in next step. ESI-MS (M-55): 284 calc. for C17H22ClNO4: 339.12.

Preparation of reagent R-23a: ethyl 3-methylenecyclobutanecarboxylate

To a solution of commercially available 3-methylenecyclobutanecarbonitrile (10.7 g, 115 mmol) in EtOH (70 mL) was added KOH (25.2 g, 450 mmol), then the mixture was stirred at reflux overnight. The resulting mixture was stirred at reflux overnight until TLC showed the starting material was consumed completely, the solvent was evaporated and water was added. 1 N HCl was added to bring pH to ~3 and extracted with EtOAc, the organic layer was washed with brine, dried over anhydrous Na2SO4, concentrated to give the crude product (12.3 g, ~95%). The crude product (12.3 g, 110 mmol) was dissolved in DMF (120 mL). Then EtI (21.5 g, 138 mmol) and K2CO3 (31.7 g, 230 mmol) were added to this solution. The mixture was stirred at r.t. for 8 hrs. Then water was added and extracted with EtOAc, the organic layer was washed with brine, dried over anhydrous Na2SO4, concentrated to give a crude which was purified by column to give the reagent R-23a (13.6 g, 88% yield) as a pale yellow oil. GC-MS (M): 140 calc. for C8H12O2: 140.08.

Preparation of reagent R-23b: ethyl 4-oxocyclohexanecarboxylate

To a solution of methyl triphenyl phosphonium bromide (16 g, 45 mmol) in THF was added n-BuLi (18 mL, 2.5 M, 45 mmol) at −70° C. The mixture solution was stirred at 0° C. for 2 hrs. To this mixture, a solution of commercially available ethyl 4-oxocyclohexanecarboxylate (5 g, 30 mmol) in THF was added at −70° C. The reaction mixture was stirred at r.t overnight. The mixture was quenched with aqueous NH4Cl and extracted with EtOAc, the organic layer was washed with brine, dried over anhydrous Na2SO4, concentrated to give the crude product which was purified by the column to give reagent R-23b (3 g, 60%) as a white solid. calc. for C10H16O2: 168.1

Preparation of reagent R-23c: ethyl 2-(4-methylenecyclohexyl)acetate

To a solution of methyl triphenyl phosphonium bromide (2.74 g, 8.2 mmol) in THF was added n-BuLi (3.4 mL, 2.5

M, 8.2 mmol) at −70° C. The mixture solution was stirred at 0° C. for 2 hrs. Then a solution of reagent KR-48 (1 g, 30 mmol) in THF was added to the solution at −70° C. The mixture solution was stirred at r.t overnight. The mixture was quenched with aqueous NH4Cl and extracted with EtOAc, the organic layer was washed with brine, dried over anhydrous Na2SO4, concentrated to give the crude product which was purified by the column to give the reagent R-23c (0.5 g, 60% yield) as a white solid. calc. for C11H18O2: 182.1.

Preparation of reagent R-23d: methyl 3-methylenecyclopentanecarboxylate

To a solution of methyl triphenyl phosphonium bromide (14 g, 30 mmol) in THF was added n-BuLi (12 mL, 2.5 M, 30 mmol) at −70° C. The mixture solution was stirred at 0° C. for 2 hrs. After to a solution of commercially available methyl 3-oxocyclopentanecarboxylate (3 g, 21 mmol) in THF was added to the solution at −70° C. The mixture solution was stirred at r.t overnight. The mixture was quenched with aqueous NH4Cl and extracted with EtOAc, the organic layer was washed with brine, dried over anhydrous Na2SO4, concentrated to give the crude product which was purified by the column to give reagent R-23d (0.7 g, 24% yield) as a white solid. calc. for C8H12O2: 140.0.

Preparation of reagent R-24a: 5-(N-tert-butoxycarbonyl-4-methoxycarbonyl-anilino)-2-ethoxy-benzoic acid To a solution of reagent KR-45 (1.5 g, 3.0 mmol) in MeOH (40 mL) was added Pd/C (1.0 g). Then the reaction mixture was stirred at r.t. at hydrogen 40 psi for 2 hrs. After TLC showed the starting material was consumed, the mixture was filtrated and concentrated, water was added and extracted with CH2Cl2, the organic layer was washed with brine, dried over anhydrous Na2SO4, concentrated to give the crude product which was purified by column chromatography to give the pure reagent R-24a (1.1 g, 88.4% yield) as a yellow solid. ESI-MS (M-55): 360.1 calc. for C22H25NO7: 415.1.

Preparation of reagent R-25: tert-butyl 4-methylenepiperidine-1-carboxylate

To a solution of methyl triphenyl phosphonium bromide (59.03 g, 0.166 mol) in THF (300 mL) was added n-BuLi (66 mL, 1.1 eq) at −78° C., then the mixture was stirred at −78° C. for 1 hrs, commercially available tert-butyl 4-oxopiperidine-1-carboxylate (R-21) (30 g, 0.151 mol) was added dropwise in THF (30 mL) at −78° C. After addition, the mixture was stirred at room temperature overnight, then quenched with aqueous NH4Cl, extracted with EtOAc, the organic layer was washed with brine, dried over anhydrous Na2SO4, concentrated to give the crude compound which was purified by column chromatography (eluting with PE/EtOAc=200:1 to 20:1) to give pure reagent R-25 (18 g, 61% yield) as a pale yellow oil. ESI-MS (M+1): 198 calc. for C11H19NO2: 197.1.

Preparation of reagent R-27a: ethyl 4-(trifluoromethylsulfonyloxy)-cyclohex-3-ene-1-carboxylate To a solution of commercially available ethyl 4-oxocyclohexanecarboxylate (3.0 g, 17.65 mmol) in anhydrous THF (30 mL) was added LHMDS (18.53 mL, 1.0 M in THF, 18.53 mmol) at −78° C., then the mixture was stirred at the same temperature for 1 hr, compound PhN(SO2CF3)2 (6.62 g, 18.53 mmol) in THF (20 mL) was added under N2 protection. After addition, the mixture was stirred at room temperature overnight until TLC showed the starting material was consumed completely, the mixture was quenched with aqueous KHSO4, extracted with MTBE, the organic layer was washed with 1.0 M aqueous NaOH, aqueous NH4Cl, brine, dried over anhydrous Na2SO4, concentrated to give the crude reagent R-27a (5.0 g, 93%) as a yellow oil. ESI-MS (M+1): 303 calc. for C10H13F3O5S: 302.0.

Preparation of reagent R-27b: ethyl 2-[4-(trifluoromethylsulfonyloxy)-cyclohex-3-en-1-yl]acetate To a solution of commercially available ethyl 2-(4-oxocyclohexyl)acetate (1.0 g, 5.43 mmol) in anhydrous THF (30 mL) was added LHMDS (5.7 mL, 1.0 M in THF, 5.70 mmol) at −78° C., then the mixture was stirred at the same temperature for 1 hr, compound PhN(SO2CF3)2 (2.04 g, 5.70 mmol) in THF (20 mL) was added under N2 protection. After addition, the mixture was stirred at room temperature overnight until TLC showed the starting material was consumed completely, the mixture was quenched with aqueous KHSO4, extracted with MTBE, the organic layer was washed with 1.0 M aqueous NaOH, aqueous NH4Cl, brine, dried over anhydrous Na2SO4, concentrated to give the crude reagent R-27b (1.50 g, 87%) as a yellow oil. ESI-MS (M+1): 317 calc. for C11H15F3O5S: 316.0.

Preparation of reagent R-28a: methyl 4-(4-oxo-1-piperidyl)benzoate

A solution of reagent KR-49 (0.8 g, 2.9 mmol) in HCl (6N, 10 mL) was stirred at 70° C. overnight, then concentrated to give the crude product which was purified by the column to obtained pure reagent R-28a (0.3 g, 46% yield) as white solid. ESI-MS (M+1): 234.2 calc. for C13H15NO3: 233.1.

Preparation of reagent R-28b: tert-butyl 3-oxocyclobutanecarboxylate

To a solution of commercially available 3-oxocyclobutanecarboxylic acid (11.4 g, 100 mmol) in anhydrous DCM (100 mL) was added DCC (31 g, 150 mmol) and 2 methylpropan-2-ol (8.9 g, 120 mmol), then the mixture was stirred at room temperature overnight. The mixture was quenched with aqueous H2O, extracted with DCM, the organic layer was washed with brine, dried over anhydrous Na2SO4, filtered and concentrated in vacuo. The residue was purified by column to give reagent R-28b (15.1 g, 89% yield).

Preparation of reagent R-31a: bromo-(2-ethoxy-2-oxo-ethyl)zinc

Zn powder (5.2 g, 80 mmol) was put into a 250 mL of three-neck flask under N2 protection, and then TMSCl (0.5 mL) being dissolved in dry THF (20 mL) was injected into the flask. The suspension mixture was stirred at room temperature for 20 min, then compound ethyl 2-bromoacetate (6.5 mL) dissolved in dry THF (50 mL) was dropped into the flask for about 30 min at room temperature. After the addition was completed, the reaction mixture was stirred at 40° C. for another 30 mins and then used for the next step directly.

Preparation of reagent R-32a: benzyl 3-(methoxymethylene)cyclobutanecarboxylate LiHMDS (53 mL, 1.0 N, 53 mmol) was added to a stirred suspension of KR-51 (7.20 g, 35 mmol) in THF (120 mL) at −20° C. over a period of 20 min under nitrogen. The resulting solution was stirred at −10° C. for 1 hr, and then methoxymethyl(triphenyl)phosphonium; chloride (18.13 g, 53 mmol) in THF (10 mL) was added over a period of 15 min under nitrogen. The resulting solution was stirred at room temperature for 15 hrs. The reaction was quenched aq. NH4Cl and then extracted with EtOAc (200 mL). The combined organic phase was washed with saturated brine (100 mL), dried over anhydrous Na2SO4, filtered and concentrated in vacuo. The residue was purified by column to give the pure reagent R-32a (4.61 g, 56% yield).

Synthetic Route 1a

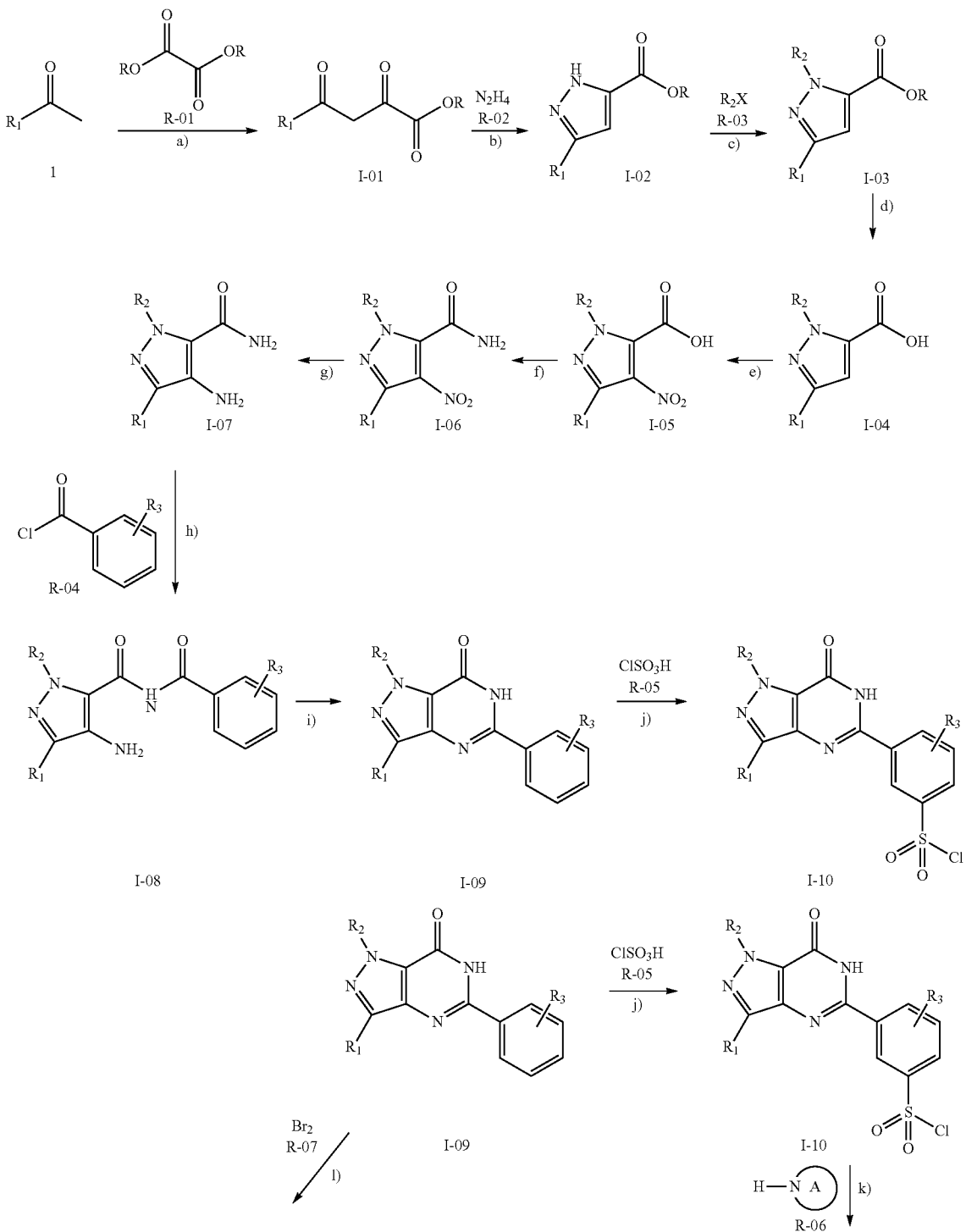

-continued

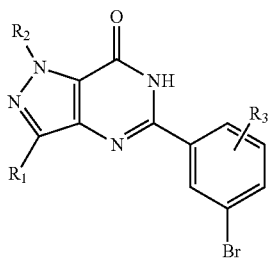

I-12

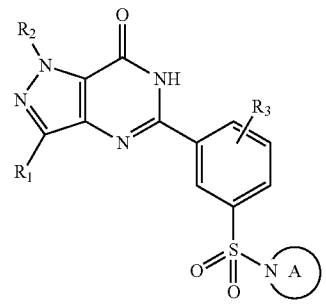

I-11

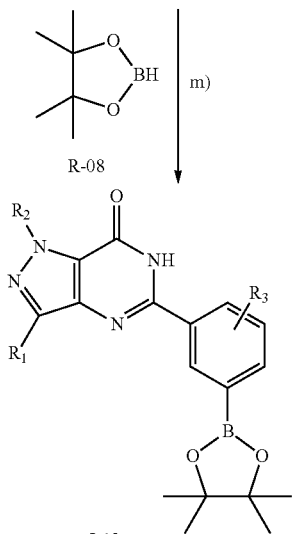

I-13

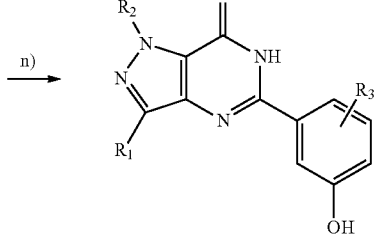

I-14

Conditions: a) Na (1 eq), 1 hour at r.t. in ethanol; then, R-01 (2 eq) overnight at r.t.; b) R-02 (2 eq) in 2-methoxyethanol/CH$_3$COOH overnight at 100° C.; c) Cs$_2$CO$_3$ (2 eq), R-03 (1.25 eq) in DMF, r.t.; d) HCl (6 M) overnight at 100° C.; e) H$_2$SO$_4$ (conc)/HNO$_3$ (1:2) added to H$_2$SO$_4$ (conc.) solution; then, overnight at 50° C.; f) refluxed overnight in SOCl$_2$; then, in THF, added into NH$_3$•H$_2$O at 0° C. for 2 hours; g) Pd/C in methanol at 30° C. under 50 Psi at H$_2$ atmosphere overnight; h) R-04 (1 eq), Et$_3$N (2 eq) in DCM, r.t. for 12 hours; i) NaOH (2 eq) in ethanol/H$_2$O/H$_2$O$_2$ (3:1:0.1) overnight at 100° C; j) ClSO$_3$H, r.t. for 2 hours; k) R-06 (2 eq) in methanol, MW at 100° C. for 1 hour; l) Br$_2$ (1.2 eq) in AcOH overnight at r.t.; m) AcOK (2 eq), R-08 (1.2 eq) and (dppf)$_2$Cl$_2$Pd (0.1 eq), in dioxane, overnight at 90° C.; n) NaOH/H$_2$O (4M) and H$_2$O$_2$ (1.3 eq) in water overnight at r.t.

In the scheme above R is (C$_1$-C$_6$)alkyl, X is a leaving group, such as halogen, A is an optionally substituted 3- to 7-membered heterocyclic monocyclic ring.

Preparation of intermediate I-01a: Ethyl 2,4-dioxoheptanoate

To a solution of methyl propyl ketone (1, 43.06 g, 0.5 mol) in ethanol (200 mL) was added Na (41.5 g, 0.5 mol), stirred at r.t. for 1 hours, then diethyl oxalate (R-01a, 73.03 g, 68 mL) was added into the reaction mixture and stirred at r.t. overnight. The reaction mixture was quenched by NH$_4$Cl solution and concentrated under vacuo to give the crude product, then extracted with EA and washed with water, concentrated under vacuo to give I-01a (60 g, 64.5% yield). ESI-MS (M+1): 187 calc. for C$_9$H$_{14}$O$_4$: 186.1.

Preparation of intermediate I-02a: Ethyl 3-propyl-1H-pyrazole-5-carboxylate

To a solution of I-01a (42 g, 0.225 mol) in 2-Methoxyethanol:CH$_3$COOH (335 mL: 335 mL) was added NH$_2$NH$_2$.H$_2$O (22.52 g, 0.45 mmol). The reaction mixture was heated to 100° C. overnight. The reaction mixture was concentrated under vacuo and extracted with EA, washed with water and the organic layer was concentrated under vacuo to give I-02a (35 g, 85% yield). ESI-MS (M+1): 183 calc. for C$_9$H$_{14}$N$_2$O$_2$: 182.1.

Preparation of intermediate I-03a: Ethyl 1-methyl-3-propyl-1H-pyrazole-5-carboxylate To a solution of I-02a (40 g, 0.22 mol) in DMF (500 mL) was added Cs$_2$CO$_3$ (0.44 mol, 2 eq), then compound CH$_3$I (0.28 mol, 1.25 eq) was added. The reaction mixture was stirred at r.t. overnight. The reaction mixture was concentrated under vacuo and extracted with DCM, washed with water. The organic layer was concentrated under vacuo to give I-03a (30 g, 70% yield). ESI-MS (M+1): 197 calc. for C$_{10}$H$_{16}$N$_2$O$_2$: 196.1.

Preparation of intermediate I-04a: 1-Methyl-3-propyl-1H-pyrazole-5-carboxylic acid The solution of I-03a (11 g, 56.12 mmol) in HCl (121 mL, 6 M) was heated to 100° C. overnight. The reaction mixture was concentrated under vacuo and extracted with EA, washed with water and the organic layer was concentrated under vacuo to give I-04a (9.4 g, 98% yield). ESI-MS (M+1): 169 calc. for C$_8$H$_{12}$N$_2$O$_2$: 168.1.

Preparation of intermediate I-05a: 1-Methyl-4-nitro-3-propyl-1H-pyrazole-5-carboxylic acid To a solution of I-04a (9.5 g, 56.54 mmol) was dissolved in conc. H$_2$SO$_4$ (40 mL). Then conc. H$_2$SO$_4$:HNO$_3$ (3.6 mL:8 mL) was added into the reaction mixture slowly, and stirred at 50° C. overnight. The reaction mixture was poured into ice-water and filtered, the filtrate cake was collected and concentrated under vacuo to give I-05a (8 g, 71.11% yield). ESI-MS (M+1): 214 calc. for $C_9H_{11}N_3O_4$: 213.1

Preparation of intermediate I-06a: 1-Methyl-4-nitro-3-propyl-1H-pyrazole-5-carboxamide To a solution of I-05a (8 g, 40.20 mmol) was dissolved in $SOCl_2$ (20 mL), then refluxed overnight. The reaction mixture was concentrated under vacuo to give 1-methyl-4-nitro-3-propyl-1H-pyrazole-5-carbonyl chloride. Then, this compound was dissolved in THF (100 mL), and then was added into $NH_3H_2O$ (100 mL) at ice-water bath. After additional 2 hours, the reaction mixture was concentrated under vacuo to give I-06a (8 g). ESI-MS (M+1): 213 calc. for $C_8H_{12}N_4O_3$: 212.1.

Preparation of intermediate I-07a: 4-Amino-1-methyl-3-propyl-1H-pyrazole-5-carboxamide To a solution of I-06a (10 g, 47.17 mmol) was dissolved in methanol (100 mL), then Pd/C (5 g) was added into the reaction mixture, and stirred at 30° C. under 50 Psi (345 kPa) at $H_2$ atmosphere overnight. The reaction mixture was filtrated and the filtrate was concentrated under vacuo to give I-07a (8.5 g, 98.83% yield). ESI-MS (M+1): 183 calc. for $C_8H_{14}N_4O$: 182.1.

Preparation of intermediate I-08a: 5-(2-Ethoxyphenylcarbonylaminocarbonyl)-1-methyl-3-propyl-1H-pyrazol-4-amine To a solution of I-07a (6 g, 32.97 mmol) in DCM (100 mL) was added $Et_3N$ (6.6 g, 65.34 mmol), 2-ethoxybenzoyl chloride (R-04a, 6.1 g, 32.97 mmol). The reaction mixture was stirred at r.t. overnight. The reaction mixture was washed quenched by adding water and extracted with DCM. The organic phase was collected, dried over $Na_2SO_4$ and concentrated under vacuo to give I-08a (10.85 g, 98% yield). ESI-MS (M+1): 331 calc. for $C_{17}H_{22}N_4O_3$: 330.2.

Preparation of intermediate I-09a: 6,7-Dihydro-5-(2-ethoxyphenyl)-1-methyl-7-oxo-3-propyl-1H-pyrazolo[4,3-d]pyrimidine To a solution of I-08a (8 g, 24.24 mmol) was dissolved in ethanol (273 mL), water (78 mL), NaOH (2.11 g, 52.75 mmol) and $H_2O_2$ (8.75 mL). The reaction mixture was stirred at 100° C. overnight. Then, the reaction mixture was concentrated under vacuo, washed with water and extracted with DCM. The organic phase was collected, dried over $Na_2SO_4$ and concentrated to give I-09a (4 g, 53.3% yield). ESI-MS (M+1): 313 calc. for $C_{17}H_{20}N_4O_2$: 312.2.

Preparation of intermediate I-10a: 4-Ethoxy-3-(6,7-dihydro-1-methyl-7-oxo-3-propyl-1H-pyrazolo[4,3-d]pyrimidin-5-yl)benzene-1-sulfonyl chloride I-09a (2.5 g, 8.0 mmol) was added into $ClSO_3H$ (R-05, 10 mL) at ice-water and stirred at r.t. for 2 hours. The reaction mixture was quenched by adding water, and then filtrated. The filtrate cake was collected and dried under vacuo to give I-10a (2.0 g) ESI-MS (M+1): 411 calc. for $C_{17}H_{19}ClN_4O_4S$: 410.1.

Preparation of intermediate I-11a: N-([3-(6,7-dihydro-1-methyl-7-oxo-3-propyl-1H-pyrazolo[4,3-d]pyrimidin-5-yl)-4-ethoxy]benzene-1-sulfonyl)piperazine To a solution of I-10a (0.41 g, 1 mmol) in ethanol (273 ml) was added piperazine (R-06a, 0.256 g, 2 mmol) and the mixture was stirred at 100° C. under microwave (MW) for 1 hour. The reaction mixture was concentrated under vacuo to give I-11a (0.4 g, 86.8% yield). ESI-MS (M+1): 461 calc. for $C_{21}H_{28}N_6O_4S$: 460.2.

Preparation of intermediate I-12a: 5-(5-Bromo-2-ethoxyphenyl)-1-methyl-3-propyl-1H-pyrazolo[4,3-d]pyrimidin-7(6H)-one To a solution of intermediate I-09a (2 g, 6.41 mmol) in AcOH (30 mL) was added $Br_2$ (1.25 g, 7.69 mmol) slowly, the reaction mixture was stirred at room temperature overnight, then $Na_2SO_3$ (0.0189 g, 3 mmol) and water was added into the reaction mixture, stirred at r.t for 2 hours. Then the reaction mixture was concentrated under vacuo and extracted by EA and washed with water and dried by $Na_2SO_4$, then concentrated under vacuo to give I-12a (2 g, 79.7%). ESI-MS (M+1): 391 calc. for $C_{17}H_{19}BrN_4O_2$: 390.2.

Preparation of intermediate I-13a: 5-(2-Ethoxy-5-(4,4,5,5-tetramethyl-1,3,2-dioxaborolan-2-yl)phenyl)-1-methyl-3-propyl-1H-pyrazolo[4,3-d]pyrimidin-7(6H)-one To a solution of compound I-12a (3.9 g, 10.0 mmol) in 1,4-dioxane (200 mL) was added AcOK (1.96 g, 20 mmol), 4,4,4',4',5,5,5',5'-octamethyl-2,2'-bi(1,3,2-dioxaborolane) (3.05 g, 12 mmol) and $(dppf)_2Cl_2Pd$ (816 mg, 1 mmol). The reaction mixture was stirred at 90° C. overnight, and then filtered and the filtrate was concentrated to give I-13a (320 mg, 96.7%). ESI-MS (M+1): 439 calc. for $C_{23}H_{31}BN_4O_4$: 438.3.

Preparation of intermediate I-14a: [3-(6,7-Dihydro-1-methyl-7-oxo-3-propyl-1H-pyrazolo[4,3-d]pyrimidin-5-yl)]-4-ethoxyphenol To a solution of compound I-13a (4.39 g, 10 mmol) in water (50 mL) was added $NaOH/H_2O$ (4 M, 13 mmol) and hydrogen peroxide (494 mg, 13 mmol). The reaction mixture was stirred at room temperature overnight. $Na_2SO_3$ solution was added and stirred for 2 hours. Then extracted by EA and dried by $Na_2SO_4$ and the organic phase was concentrated to give the intermediate I-14a (2.0 mg, 61%). ESI-MS (M+1): 329 calc. for $C_{17}H_{20}N_4O_3$: 328.4.

Synthetic Route 1b

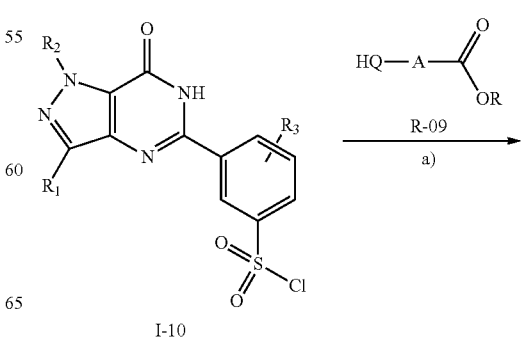

I-10

-continued

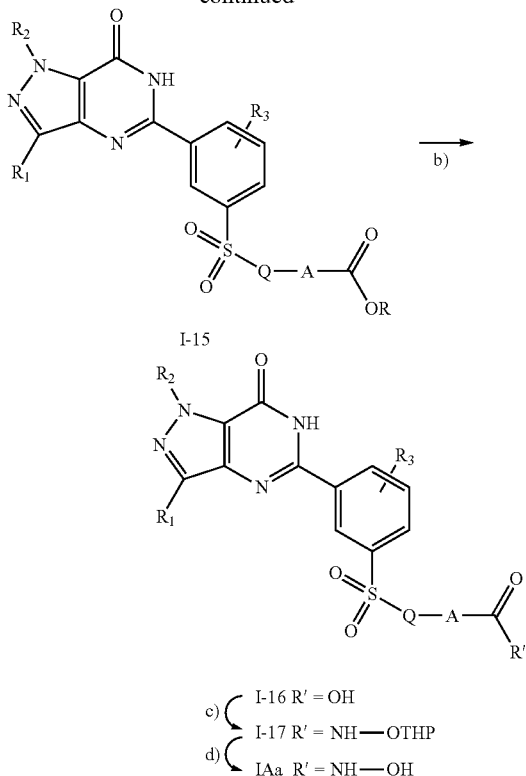

Conditions: a) Et₃N and R-09 in ethanol, MW at 100° C. for 2 hours;
b) LiOH•H₂O (5 eq) in THF/methanol/H₂O, overnight at r.t.; c) EDC•HCl (1.2 eq), HOBt (1.2 eq), THP—O—NH₂ (1.5 eq), NMM (3 eq) in DMF, overnight at r.t.;
d) HCl/dioxane (4M) at r.t for 3 hours.

In the scheme above R is $(C_1\text{-}C_6)$alkyl, Q is NH or

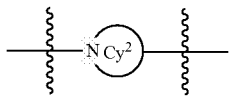

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-15a: Ethyl 2-(4-[3-(6,7-dihydro-1-methyl-7-oxo-3-propyl-1H-pyrazolo[4,3-d]pyrimidin-5-yl)-4-ethoxyphenylsulfonyl]piperazin-1-yl)pyrimidine-5-carboxylate To a solution of I-10a (0.41 g, 1 mmol) in ethanol (273 mL) was added ethyl 2-(piperazin-1-yl)pyrimidine-5-carboxylate (R-09a, 0.236 g, 2 mmol), Et₃N (303 mg, 3 mmol). The mixture was stirred at 100° C. under MW for 2 hours. The reaction mixture was concentrated under vacuo to give I-15a (0.4 g, 65.5% yield). ESI-MS (M+1): 611 calc. for $C_{28}H_{34}N_8O_6S$: 610.2.

Preparation of intermediate I-16a: 2-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)pyrimidine-5-carboxylic acid To a solution of I-15a (500 mg, 0.82 mmol) in THF/methanol/H₂O (10/1/5 mL) was added LiOH.H₂O (168 mg, 4.1 mmol). The resulting mixture was stirred at r.t. for overnight. After TLC showed that most of the starting materials were consumed completely, the mixture was diluted with water and adjusted pH to 2-3. The mixture was extract with EA and washed with brine, dried over anhydrous Na₂SO₄ and concentrated to give crude I-16a (300 mg, 63.8% yield). ESI-MS (M+1): 583 calc. for $C_{26}H_{30}N_8O_6S$: 582.2.

Preparation of intermediate I-17a: 2-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)-N-(tetrahydro-2H-pyran-2-yloxy)pyrimidine-5-carboxamide To a solution of I-16a (500 mg, 1 mmol) in DMF (10 mL) was added EDC.HCl (230 mg, 1.2 mmol), HOBt (162 mg, 1.2 mmol), THP-O—NH₂ (229 mg, 1.5 mmol), NMM (303 mg, 3 mmol). The mixture was stirred at r.t. overnight. The mixture was diluted with EA and washed with brine, dried over anhydrous Na₂SO₄ and concentrated to give the crude product which was purified by column chromatography to give I-17a (300 mg, 44.0% yield). ESI-MS (M+1): 682 calc. for $O_{31}H_{39}N_9O_7S$: 681.3.

Preparation of compound 1-06: 2-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)-N-hydroxypyrimidine-5-carboxamide To a solution of I-17a (200 mg, 0.293 mmol) in dioxane (10 mL) was added HCl/dioxane (4 M, 10 mL) and the mixture was stirred at r.t. for 3 h. The reaction mixture was concentrated to give the crude which was purified by preparative HPLC (method 1) to obtain pure compound 1-06 as TFA salt (62.5 mg, 88.0% yield). ESI-MS (M+1): 598.1 (HPLC Method: 1) calc. for $C_{26}H_{31}N_9O_6S$: 597.2.

Following the same synthetic route for compound 1-06 and using the same reagents unless otherwise indicated in the table below, the following compounds were obtained:

| Example | $R_t$ (min) | $[M + 1]^+$ | HPLC Method | Starting Materials |
|---|---|---|---|---|
| 1-01 | 3.20 | 547.1 | 1 | Ethyl 3-(piperidin-4-yl)propanoate (R-09b) |
| 1-02 | 2.94 | 636.1 | 1 | (E)-Ethyl 3-(4-((piperazin-1-yl)methyl)phenyl)prop-2-enoate (R-09c) |
| 1-03 | 3.29 | 553.0 | 1 | (E)-Ethyl 3-(4-aminophenyl)prop-2-enoate (R-09d) |
| 1-07 | 3.22 | 612.1 | 1 | Ethyl 2-(4-aminopiperidin-1-yl)pyrimidine-5-carboxylate (R-09e) |

Synthetic Route 1c

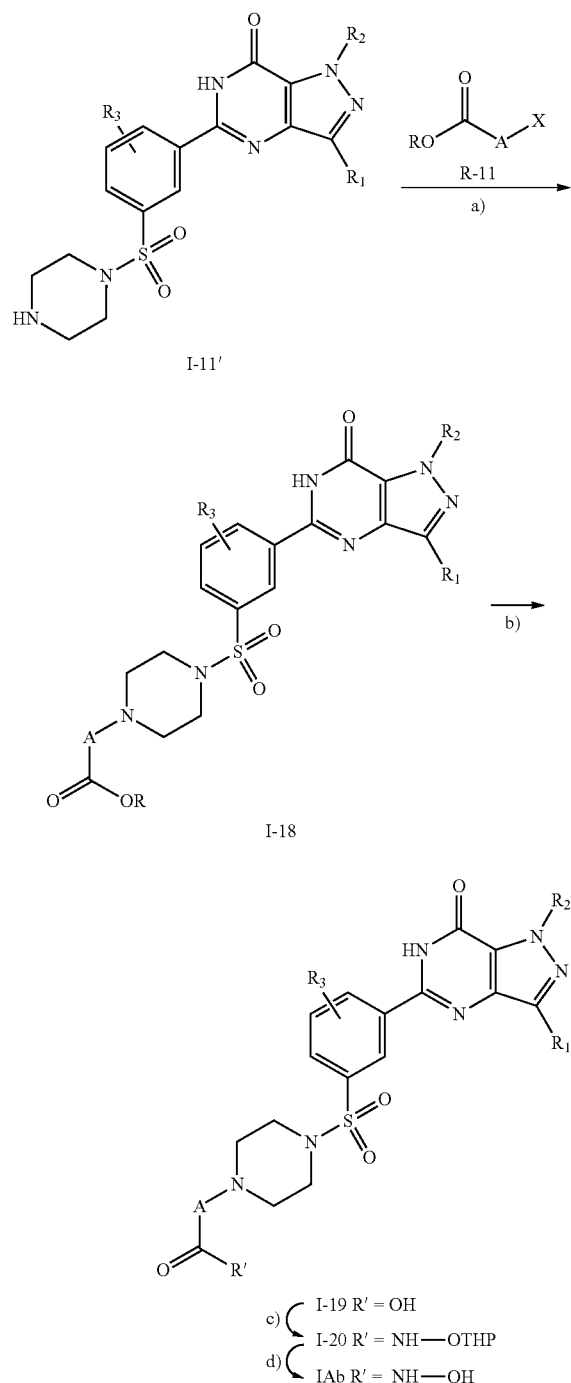

Conditions: a) K₂CO₃ (3 eq) and R-11 (1.5 eq) in CH₃CN, MW at 100° C. for 2 hours; b) LiOH·H₂O (5 eq) in THF/methanol/H₂O, overnight at r.t.; c) EDC·HCl (1.2 eq), HOBt (1.2 eq), THP—O—NH₂ (1.5 eq), NMM (3 eq) in DMF, overnight at r.t.; d) HCl/dioxane (4M) at r.t for 3 hours.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-18a: Ethyl 3-(4-[3-(6,7-dihydro-1-methyl-7-oxo-3-propyl-1H-pyrazolo[4,3-d]pyrimidin-5-yl)-4-ethoxyphenylsulfonyl]piperazin-1-yl)propanoate To a solution of I-11a (300 mg, 0.651 mmol) in CH₃CN (10 mL) was added K₂CO₃ (271 mg, 1.95 mmol) and ethyl 3-bromopropionate (R-11a, 177 mg, 0.976 mmol), and then the mixture was stirred at 100° C. for 2 hours under MW. The reaction mixture was concentrated under vacuo to give crude I-18a (260 mg, 71.23% yield). ESI-MS (M+1): 561 calc. for $C_{26}H_{36}N_6O_6S$: 560.2.

Preparation of intermediate I-19a: 3-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)propanoic acid I-19a was obtained starting from I-18a in an analogous manner to I-16a. 60.1% yield. ESI-MS (M+1): 533 calc. for $C_{24}H_{32}N_6O_6S$: 532.2.

Preparation of intermediate I-20a: 3-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)-N-(tetrahydro-2H-pyran-2-yloxy)propanamide I-20a was obtained starting from I-19a in an analogous manner to I-17a. 75.8% yield. ESI-MS (M+1): 632 calc. for $C_{29}H_{41}N_7O_7S$: 631.3.

Preparation of compound 1-04: 3-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)-N-hydroxypropanamide Compound 1-04 was obtained starting from I-20a in an analogous manner to compound 1-06. 88.0% yield. ESI-MS (M+1): 548.3 (HPLC Method: 1) calc. for $C_{24}H_{33}N_7O_6S$: 547.2; Rt is 2.20

Following the same synthetic route for compound 1-04 and using the same reagents unless otherwise indicated in the table below, the following compounds were obtained:

| Example | $R_t$ (min) | $[M + 1]^+$ | HPLC Method | Starting Materials |
|---|---|---|---|---|
| 1-05 | 2.78 | 562.1 | 1 | Ethyl 4-bromobutanoate (R-11b) |

Synthetic Route 1d

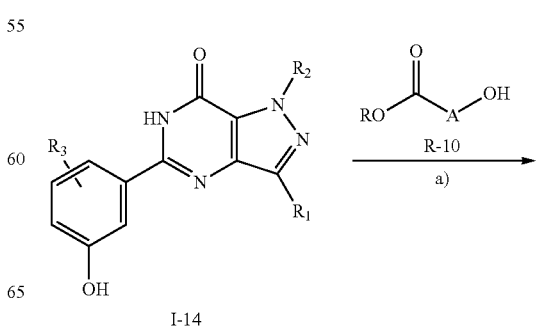

101
-continued

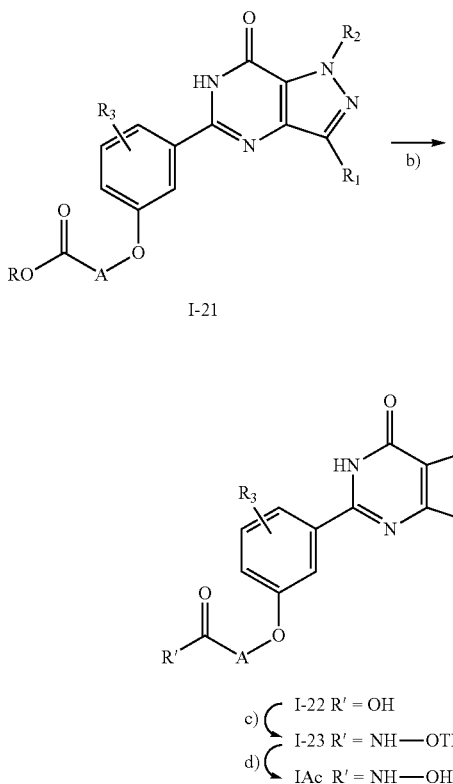

Conditions: a) Ph₃P (1 eq), DIAD (2 eq) and R-10 (1 eq) in toluene, at 110° C. for 1 hour; b) LiOH·H₂O (5 eq) in THF/methanol/H₂O, overnight at r.t.; c) EDC·HCl (1.2 eq), HOBt (1.2 eq), THP—O—NH₂ (1.5 eq), NMM (3 eq) in DMF, overnight at r.t.; d) HCl/dioxane (4M) at r.t. for 3 hours.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-21a: Ethyl 2-(4-[3-(6,7-dihydro-1-methyl-7-oxo-3-propyl-1H-pyrazolo[4,3-d]pyrimidin-5-yl)-4-ethoxyphenoxymethyl]-piperidin-1-yl)pyrimidine-5-carboxylate To a solution of I-14a (66 mg, 0.2 mmol) in anhydrous toluene (10 mL) was added ethyl 2-[4-(hydroxymethyl)-1-piperidyl]pyrimidine-5-carboxylate (R-10a) (54 mg, 0.2 mmol), Ph₃P (105 mg, 0.4 mmol) and DIAD (81 mg, 0.4 mmol), the reaction mixture was stirred at 110° C. for 1 h. Then the reaction mixture was concentrated under vacuo and purified by column (PE: EA=0:1 to 1:1) to give I-21a (100 mg, 87.0% yield) ESI-MS (M+1): 576 calc. for $C_{30}H_{37}N_7O_5$: 575.3.

102

Preparation of intermediate I-22a: 2-(4-[3-(6,7-Dihydro-1-methyl-7-oxo-3-propyl-1H-pyrazolo[4,3-d]pyrimidin-5-yl)-4-ethoxyphenoxymethyl]-piperidin-1-yl)pyrimidine-5-carboxylic acid To a solution of I-21a (57.5 mg, 0.1 mmol) in THF/MeOH/H₂O (10/1/3 mL) was added LiOH·H₂O (21.5 mg, 0.5 mmol). The resulting mixture was stirred at r.t. overnight. After TLC showed that most of the starting material was consumed completely, the mixture was diluted with water and adjusted pH to 2-3 and the extracted with EA, the organic phase was washed with brine, dried over anhydrous Na₂SO₄ and concentrated to give I-22a (46 mg, 84.0% yield). ESI-MS (M+1): 548 calc. for $C_{28}H_{33}N_7O_5$: 547.2.

Preparation of intermediate I-23a: N-(Tetrahydro-2H-pyran-2-yloxy)-2-(4-[3-(6,7-dihydro-1-methyl-7-oxo-3-propyl-1H-pyrazolo[4,3-d]pyrimidin-5-yl)-4-ethoxyphenoxymethyl]-piperidin-1-yl)pyrimidine-5-carboxamide To a solution of I-22a (273 mg, 0.5 mmol) in DMF (15 mL) was added EDC.HCl (314 mg, 2.0 mmol), HOBt (270 mg, 2.0 mmol), THP-O—NH₂ (115 mg, 1.0 mmol), NMM (202 mg, 2.0 mmol). The mixture was stirred at room temperature overnight and then diluted with EA, washed with brine, dried over anhydrous Na₂SO₄. The residue was concentrated to give crude product which was purified by column chromatography (DCM: MeOH=1:0 to 20:1) to give I-23a (150 mg, 46.4% yield). ESI-MS (M+1): 647 calc. for $C_{33}H_{42}N_8O_6$: 646.3.

Preparation of compound 1-11: N-Hydroxy-2-(4-[3-(6,7-dihydro-1-methyl-7-oxo-3-propyl-1H-pyrazolo[4,3-d]pyrimidin-5-yl)-4-ethoxyphenoxymethyl]-piperidin-1-yl)pyrimidine-5-carboxamide A solution of I-23a (100 mg, 0.15 mmol) in HCl/dioxane (4M, 10 mL) was stirred at r.t. for 3 h. The reaction mixture was concentrated to give crude compound 1-11 which was purified through Prep-HPLC to get desired (62.5 mg, 73.8%) as TFA salt. Rt is 2.59 min (HPLC Method: 1). ESI-MS (M+1): 563 calc. for $C_{28}H_{34}N_8O_5$: 562.4.

Following the same synthetic route for compound 1-11 and using the same reagents unless otherwise indicated in the table below, the following compounds were obtained:

| Example | R_t (min) | [M + 1]⁺ | HPLC Method | Starting Materials |
|---|---|---|---|---|
| 1-12 | 3.07 | 549.2 | 1 | Ethyl 2-(4-hydroxy-1-piperidyl)pyrimidine-5-carboxylate(R-10b) |

Synthetic Route 1e

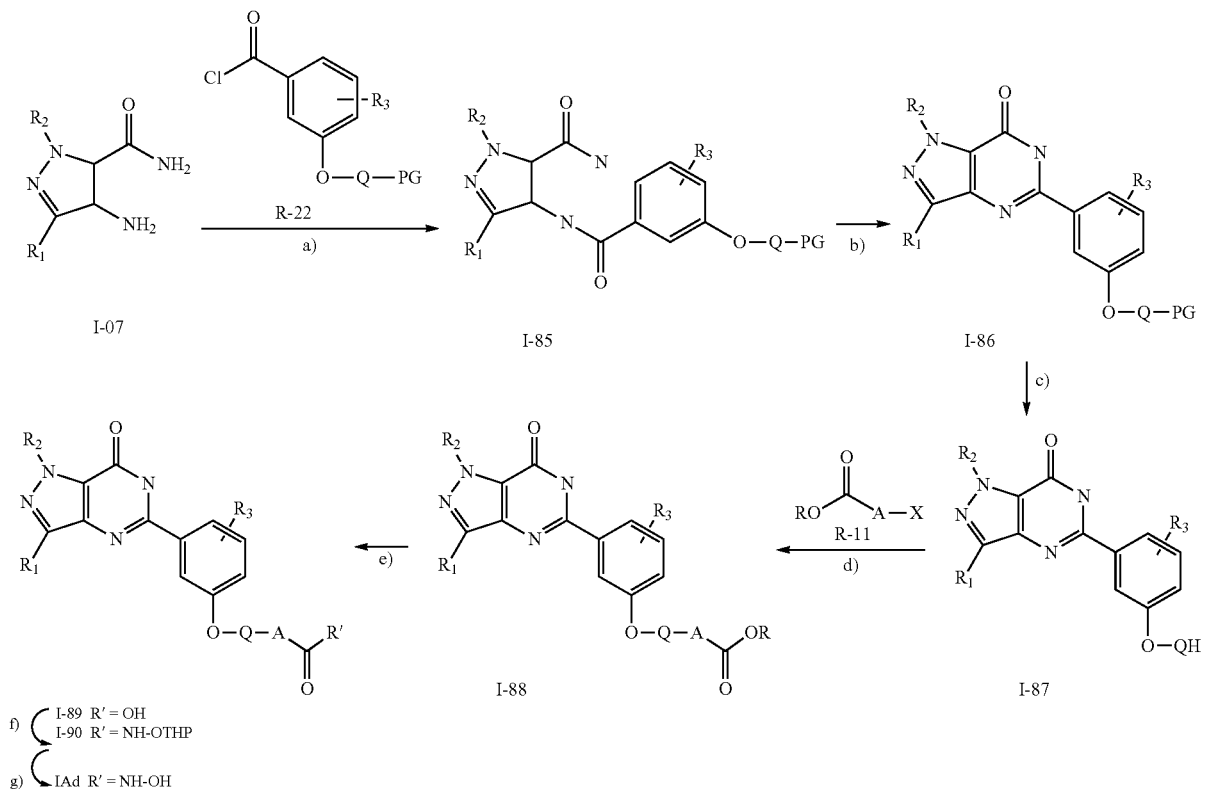

Conditions: a) Et₃N (2 eq) and R22 (1 eq) in DCM, overnight at r.t.; b) NaOH (5.5 eq) in ethanol/H₂O/H₂O₂ (10:1:1) overnight at 100° C.; c) HCl/dioxane (4M) at r.t. for 5 hours; d) K₂CO₃ (3 eq) and R-11 (1.1 eq) in CH₃CN, overnight at 80° C.; e) LiOH·H₂O (5 eq) in THF/methanol/H₂O, overnight at r.t.; f) EDC·HCl (1.1 eq), HOBt (1.1 eq), THP—O—NH₂ (1.1 eq), NMM (2 eq) in DMF, overnight at r.t.; g) HCl/dioxane (4M) at r.t. for 3 hours.

In the scheme above R is $(C_1-C_6)$alkyl, PG is a protecting group, such as boc, Q is NH or

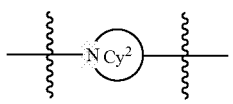

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-85a: tert-butyl 4-[[3-[(5-carbamoyl-1-methyl-3-propylpyrazol-4-yl)carbamoyl]phenoxy]methyl]piperidine-1-carboxylate Intermediate I-07a (1 g, 2.87 mmol) was dissolved in DCM (30 mL), then Et3N (0.8 mL, 5.74 mmol) and R-22a (1 g, 2.87 mmol) was added into the reaction mixture, stirred at r.t overnight. The reaction mixture was washed by water and extracted by DCM, dried by Na2SO4 and concentrated under vacuo to give the desired product I-85a (1.0 g, 70.4% yield). ESI-MS (M+1): 500 calc. for $C_{26}H_{37}N_5O_5$: 499.28.

Preparation of intermediate I-86a: tert-butyl 4-[[3-(1-methyl-7-oxo-3-propyl-6H-pyrazolo[4,3-d]pyrimidin-5-yl)phenoxy]methyl]piperidine-1-carboxylate Intermediate I-85a (499 mg, 1 mmol) was dissolved in EtOH (10 mL) and water (1 mL), then NaOH (220 mg, 5.5 mmol) and H2O2 (1 mL) was added into the reaction mixture, stirred at 100° C. overnight. The reaction mixture was quenched by Na2SO3 and concentrated under vacuo, washed by water and extracted by DCM, dried by Na2SO4 and concentrated to give the desired product I-86a (400 mg, 83.2% yield). ESI-MS (M+1): 482 calc. for C26H35N5O4: 481.27.

Preparation of intermediate I-87a 1-methyl-5-[3-(4-piperidylmethoxy)phenyl]-3-propyl-6H-pyrazolo[4,3-d]pyrimidin-7-one To a solution of intermediate I-86a (400 mg, 0.832 mmol) in DCM (10 mL) was added HCl/1,4-dioxane (10 mL, 4M/L). The reaction mixture was stirred at room temperature for 5 h, and then concentrated to give the desired product compound I-87a (310 mg, 97.8% yield). ESI-MS (M+1): 382 calc. for C21H27N5O2: 381.22.

Preparation of intermediate I-88a: ethyl 2-[4-[[3-(1-methyl-7-oxo-3-propyl-6H-pyrazolo[4,3-d]pyrimidin-5-yl)phenoxy]methyl]-1-piperidyl]pyrimidine-5-carboxylate The intermediate I-87a (310 mg, 0.842 mmol) dissolved in CH3CN (10 mL) was added into K2CO3 (350 mg, 2.527 mmol) and R-11e (ethyl 2-chloropyrimidine-5-carboxylate) (174 mg, 0.926 mmol), then stirred at 80° C. overnight. The reaction mixture was concentrated under vacuo and extracted with EtOAc, washed with water and dried over Na2SO4, concentrated to give the desired product I-88a (300 mg, 67.3% yield). ESI-MS (M+1): 532 calc. for C28H33N7O4: 531.26.

Preparation of intermediate I-89a: 2-[4-[[3-(1-methyl-7-oxo-3-propyl-6H-pyrazolo[4,3-d]pyrimidin-5-yl)phenoxy]methyl]-1-piperidyl]pyrimidine-5-carboxylic acid To a solution of intermediate I-88a ((0.3 g, 0.596 mmol) in THF/MeOH/H2O (10/1/5 mL) was added LiOH.H2O (128.2 mg, 2.982 mmol). The resulting mixture was restirred at r.t overnight, after TLC showed that most of the starting materials were consumed completely, the mixture was diluted with water and adjusted pH to 2-3. The mixture was extract with EtOAc and washed with brine, dried over anhydrous Na2SO4 and concentrated to give the product I-89a (200 mg, 66.7% yield). ESI-MS (M+1): 504 calc. for C26H29N7O4: 503.23.

Preparation of intermediate I-90a: 2-[4-[[3-(1-methyl-7-oxo-3-propyl-6H-pyrazolo[4,3-d]pyrimidin-5-yl)phenoxy]methyl]-1-piperidyl]-N-tetrahydropyran-2-yloxy-pyrimidine-5-carboxamide To a solution of intermediate I-89a (200 mg, 0.4 mmol) in DMF (20 mL) was added EDC.HCl (75.7 mg, 0.44 mmol), HOBt (59.4 mg, 0.44 mmol), THPO—NH2 (50.4 mg, 0.44 mmol), NMM (80.8 mg, 0.80 mmol). The mixture was stirred at room temperature overnight. The mixture was diluted with EtOAc and washed with brine, dried over anhydrous Na2SO4 and concentrated to give the crude product which was purified by column chromatography to give the compound I-90a (100 mg, 41.2%). Reversed phase HPLC was carried out on Gilson 281 semi-preparative HPLC systems (100×30 mm; 5 um). Solvent A: water with 0.075% 2,2,2-trifluoroacetic acid; Solvent B: acetonitrile. Gradient: At 25° C., 40% of B to 58% of B within 8.5 min; then 58% B over 4 min, PDA. ESI-MS (M+1): 603 calc. for C31H38N8O5: 602.30.

Preparation of compound 1-13: 2-[4-[[3-(1-methyl-7-oxo-3-propyl-6H-pyrazolo[4,3-d]pyrimidin-5-yl)phenoxy]methyl]-1-piperidyl]pyrimidine-5-carbohydroxamic acid A solution of intermediate I-90a (100 mg, 0.166 mmol) in HCl/dioxane (4M, 10 mL) was stirred at r.t. for 3 hrs, the reaction mixture was concentrated. The reaction crude was washed with DCM and filtrated to give the desired compound 1-13 (20 mg, 24.5% yield). ESI-MS (M+1): 519 calc. for C26H30N8O4: 518.24; Rt is 2.84.

Following the same synthetic route for compound 1-13 and using the same reagents unless otherwise indicated in the table below, the following compounds were obtained:

| Example | R$_t$ (min) | [M + 1]$^+$ | HPLC Method | Starting Materials |
|---|---|---|---|---|
| 1-14 | 2.8 | 505.0 | 1 | tert-butyl 4-(3-chlorocarbonylphenoxy)-piperidine-1-carboxylate (R-22b) |

Synthetic Route 1f

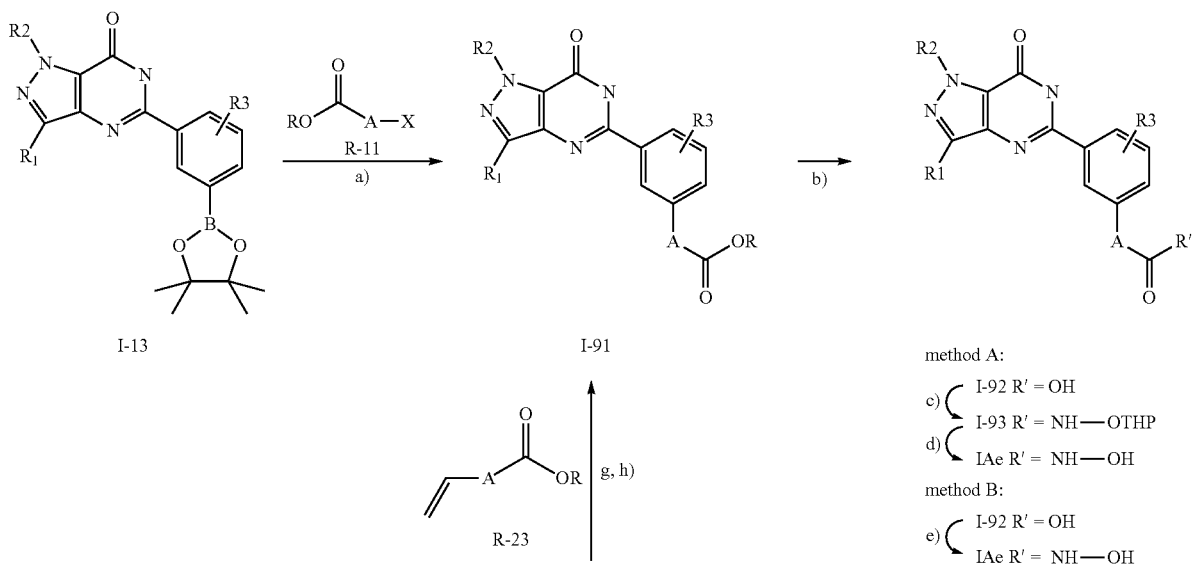

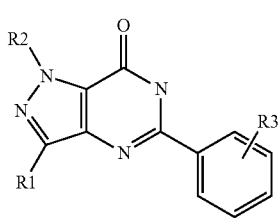

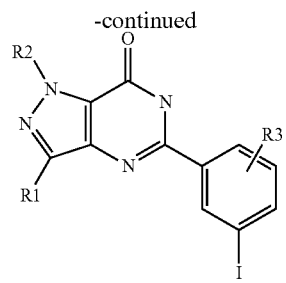

I-09     I-94

Conditions: a) K$_2$CO$_3$ (3 eq) in water, Pd(PPh3)4 (0.1 eq) and R-11 (1.1 eq) in 1,4-dioxane, overnight at 80° C.; b) LiOH•H$_2$O (5 eq) in THF/methanol/H$_2$O, overnight at 40° C.; c) EDC•HCl (2 eq), HOBt (2 eq), THP—O—NH$_2$ (2 eq), NMM (3 eq) in DMF, overnight at r.t.; d) HCl/dioxane (4M) at r.t for 1 hour; e) NH2OH HCl (1 eq), BOP (2.5 eq), DIEA, DMF, overnight at 80° C.; f) NIS (1.2 eq), TFA, overnight at r.t.; g) R-23, 9-BBN (0.5M solution) in THF, reflux for 4 hrs.; h) I-94, Pd2(dba)3 (0.05 eq), X-Phos (0.12 eq), Na2CO3 (2.5 eq), 1, 4-dioxane and H2O, reflux overnight.

In the scheme above R is (C$_1$-C$_6$)alkyl, X is an halogen and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-91a: methyl 4-[[4-ethoxy-3-(1-methyl-7-oxo-3-propyl-6H-pyrazolo[4,3-d]pyrimidin-5-yl)phenyl]methyl]benzoate To a solution of intermediate I-13a (300 mg, 0.685 mmol) in 1,4-dioxane (20 mL) was added R-11j: methyl 4-(bromomethyl)benzoate (142 mg, 0.623 mmol), K2CO3 (284 mg, 2.06 mmol in 1 mL water), Pd(PPh3)4 (722 mg, 0.0623 mmol), then the mixture was stirred at 80° C. overnight under N2 protection. After LC-MS showed the starting material was consumed completely, the mixture was extracted with EtOAc, the organic layer was washed with brine, dried over anhydrous Na2SO4, concentrated to give the crude compound which was purified by Prep-TLC (PE/EtOAc=1:1) to give pure intermediate I-91a (148 mg, 51.93% yield) as a yellow solid. ESI-MS (M+1): 461 calc. for C26H28N4O4: 460.2.

Preparation of intermediate I-92a: 4-[[4-ethoxy-3-(1-methyl-7-oxo-3-propyl-6H-pyrazolo[4,3-d]pyrimidin-5-yl)phenyl]methyl]benzoic acid To a solution of intermediate I-91a (148 mg, 0.32 mmol) in MeOH/THF/H2O (3/9/3, 15 mL) was added LiOH.H2O (135 mg, 3.2 mmol), the reaction mixture was stirred at 40° C. overnight until LC-MS showed the starting material was consumed completely. Then concentrated, the mixture was diluted with H$_2$O and adjusted pH to 1-2 with 1N HCl, then concentrated to give the crude intermediate I-92a (140 mg, 97.22%) as a yellow solid. ESI-MS (M+1): 447 calc. for C25H26N4O4: 446.1.

Preparation of intermediate I-93a: 4-[[4-ethoxy-3-(1-methyl-7-oxo-3-propyl-6H-pyrazolo[4,3-d]pyrimidin-5-yl)phenyl]methyl]-N-tetrahydropyran-2-yloxy-benzamide To a solution of intermediate I-92a (140 mg, 0.314 mmol) in DMF (10 mL) was added EDC.HCl (121 mg, 0.628 mmol), HOBt (135 mg, 0.628 mmol), THPO—NH2 (117 mg, 0.628 mmol), NMM (95 mg, 0.942 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-93a (120 mg, 70.18% yield) as a white solid. ESI-MS (M+1): 546 calc. for C30H35N5O5: 545.2.

Preparation of compound 1-15: 4-[[4-ethoxy-3-(1-methyl-7-oxo-3-propyl-6H-pyrazolo[4,3-d]pyrimidin-5-yl)phenyl]methyl]benzenecarbohydroxamic acid A solution of intermediate I-93a (120 mg, 0.22 mmol) in HCl/dioxane (4M, 5 mL) was stirred at room temperature for 1 h, then concentrated to give the crude compound which was purified by prep-HPLC (General procedure, Method 1) to obtained pure compound 1-15 (49 mg, 48.51% yield) as a white solid. ESI-MS (M+1): 462 calc. for C25H27N5O4: 461.2; Rt is 2.96.

Following the same synthetic route for compound 1-15 and using the same reagents unless otherwise indicated in the table below, the following compounds were obtained:

| Example | R$_t$ (min) | [M + 1]$^+$ | HPLC Method | Starting Materials |
|---|---|---|---|---|
| 1-16 | 2.96 | 468.1 | 1 | ethyl 5-(bromomethyl)thiophene-2-carboxylate (R-11k) |
| 1-17 | 2.77 | 452 | 1 | methyl 5-(bromomethyl)furan-2-carboxylate (R-11l) |
| 1-18 | 3.09 | 476 | 1 | ethyl 2-[4-(bromomethyl)phenyl]acetate (R-11m) |
| 1-20 | 3.11 | 490 | 1 | ethyl 3-[4-(bromomethyl)phenyl]propanoate (R-11n) |
| 1-30 | 2.87 | 448.1 | 1 | ethyl 4-iodobenzoate (R-11o) |
| 1-34 | 2.94 | 462 | 1 | ethyl 2-(4-bromophenyl)acetate (R-11p) |
| 1-59 | 3.15 | 488.2 | 1 | methyl (E)-3-[4-(bromomethyl)phenyl]prop-2-enoate (R-11r) |
| 1-60 | 3.05 | 492.2 | 1 | methyl 4-(bromomethyl)-3-methoxy-benzoate (R-11s) |
| 1-61 | 3.07 | 492.2 | 1 | methyl 4-(bromomethyl)-2-methoxy-benzoate (R-11t) |
| 1-66 | 2.84 | 480.1 | 1 | methyl 4-(bromomethyl)-2-fluoro-benzoate (R-11u) |
| 1-68 | 3.01 | 480.1 | 1 | methyl 4-(bromomethyl)-3-fluoro-benzoate (R-11v) |
| 1-71 | 2.88 | 454.1 | 1 | ethyl 5-bromothiophene-2-carboxylate (R-11w) |

| Example | R$_t$ (min) | [M + 1]$^+$ | HPLC Method | Starting Materials |
|---|---|---|---|---|
| 1-72 | 2.55 | 449.2 | 1 | methyl 6-chloropyridine-3-carboxylate (R-11q) |
| 1-73 | 2.75 | 449.2 | 1 | methyl 5-bromopyridine-2-carboxylate (R-11x) |
| 1-74 | 2.74 | 438.2 | 1 | ethyl 5-bromofuran-2-carboxylate (R-11y) |

Preparation of intermediate I-94a: 5-(2-ethoxy-5-iodo-phenyl)-1-methyl-3-propyl-6H-pyrazolo[4,3-d]pyrimidin-7-one To a solution of intermediate I-09a (10 g, 32 mmol) in TFA (50 mL) was added NIS (8.6 g, 38.4 mmol) at 0° C. The mixture solution was stirred at r.t overnight. The mixture was quenched with aqueous water and extracted with EtOAc, the organic layer was washed with brine, dried over anhydrous Na2SO4, concentrated to give the crude product which was purified by the column to give the intermediate I-94a (11 g, 79%) as a white solid. ESI-MS (M+1): 439.1; calc. for C17H19IN4O2: 438.0.

Preparation of intermediate 1-91 b: ethyl 3-[[4-ethoxy-3-(1-methyl-7-oxo-3-propyl-6H-pyrazolo[4,3-d]pyrimidin-5-yl)phenyl]methyl]cyclobutanecarboxylate Reagent R-23a (700 mg, 5 mmol) was treated with a 0.5 M solution of 9-BBN in THF (12 mL), and the mixture was heated at reflux for 3 hrs. The resulting mixture was transferred into a stirred mixture of Intermediate I-94a (1.66 g, 3.8 mmol), Pd2(dba)3 (138 mg, 0.15 mmol), X-Phos (143 mg, 0.3 mmol), and Na2CO3 (850 mg, 8 mmol) in 1,4-dioxane (35 mL) and H$_2$O (6 mL). The resulting mixture was stirred at reflux overnight until TLC showed the starting material was consumed completely, then filtered, the mixture was extracted with EtOAc, the organic layer was washed with brine, dried over anhydrous Na2SO4, concentrated to give the crude compound which was purified by column chromatography (eluting with PE/EtOAc=50:1 to 5:1) to give pure compound intermediate 1-91 b (1.38 g, 80.3% yield) as a pale yellow solid. ESI-MS (M+1): 453.2 calc. for C25H32N4O4: 452.2.

Preparation of intermediate I-92b: 3-[[4-ethoxy-3-(1-methyl-7-oxo-3-propyl-6H-pyrazolo[4,3-d]pyrimidin-5-yl)phenyl]methyl]cyclobutanecarboxylic acid To a solution of intermediate 1-91 b (1.38 g, 3.05 mmol) in THF/MeOH/H2O (3/3/2, 32 mL) was added LiOH.H2O (1.34 g, 10 eq). The resulting mixture was stirred at r.t. for 8 hrs, after TLC showed the starting materials were consumed completely, then the mixture was diluted with water and adjusted pH to 3~4 with 1N HCl and the mixture was extracted with EtOAc, washed with brine, dried over anhydrous Na2SO4, concentrated and purified by prep-TLC to afford the desired intermediate I-92b (1.30 g, ~100%). ESI-MS (M+1): 425.2; calc. for C23H28N4O4: 424.2.

Preparation of compound 1-19: (racemic) 3-[[4-ethoxy-3-(1-methyl-7-oxo-3-propyl-6H-pyrazolo[4,3-d]pyrimidin-5-yl)phenyl]methyl]cyclobutanecarbohydroxamic acid To a solution of intermediate I-92b (1.30 g, 3.05 mmol) in DMF (60 mL) was added BOP (3.39 g, 7.63 mmol), DIEA (5.51 g, 42.7 mmol) and NH2OH HCl (2.15 g, 30.5 mmol). The mixture was stirred at 80° C. overnight until LC-MS showed the starting material was consumed completely, then quenched with water and extracted with EtOAc, the organic layer was washed with brine, dried over anhydrous Na2SO4, concentrated to give the crude product which was purified by prep-HPLC (General procedure, Method 1) to obtained pure compound 1-19 (560.9 mg, 42% yield) as a yellow solid, as a racemic mixture. ESI-MS (M+1): 440.3 calc. for C23H29N5O4: 439.2; Rt is 2.86.

Following the same synthetic route for compound 1-19 and using the same reagents unless otherwise indicated in the table below, the following compounds were obtained. The method used for conversion of the carboxylic acid into the hydroxamic acid is also indicated:

| Example | R$_t$ (min) | [M + 1]$^+$ | HPLC Method | Starting Materials/Method for hydroxamic acid formation |
|---|---|---|---|---|
| I-76 racemic | 3.14 | 468.2 | 1 | ethyl 4-methylenecyclohexane-carboxylate (R-23b)/Method A |
| 1-43 racemic | 3.3 | 482.2 | 1 | ethyl 2-(4-methylenecyclo-hexyl)acetate (R-23c)/Method A |
| 1-80 racemic | 2.94 | 454.2 | 1 | methyl 3-methylenecyclopentane-carboxylate (R-23d)/Method A |

Preparation of compounds 1-62 & 1-63: cis & trans 3-[[4-ethoxy-3-(1-methyl-7-oxo-3-propyl-6H-pyrazolo[4,3-d]pyrimidin-5 yl)phenyl]methyl]cyclobutanecarbohydroxamic acid The cis and trans corresponding isomers were separated from the racemic mixture 1-19 (530 mg) by SFC to obtain cis isomers 1-62 (9.8 mg, 2%) ESI-MS (M+1): 440.2 calc. for C23H29N5O4: 439.2 (Rt is 2.80) and trans isomers 1-63 (113 mg, 21%) ESI-MS (M+1): 440.2 calc. for C23H29N5O4: 439.2 (Rt is 2.63).

Preparation of compounds 1-28 & 1-29: trans & cis 4-[[4-ethoxy-3-(1-methyl-7-oxo-3-propyl-6H-pyrazolo[4,3-d]pyrimidin-5-yl)phenyl]methyl]cyclohexanecarbohydroxamic acid The cis and trans corresponding isomers were separated from the crude racemic mixture 1-76 (100 mg) by prep-HPLC (General procedure, Method 1) to obtained trans isomers 1-28 (5.1 mg, 6.2%) as a white solid ESI-MS (M+1): 468.2 calc. for C25H33N5O4: 467.2 (Rt is 3.07) and cis isomers 1-29 (10.2 mg, 12%) as a white solid. ESI-MS (M+1): 468.2 calc. for C25H33N5O4: 467.2 (Rt is 3.11).

Preparation of compound 1-83: trans 3-[[4-ethoxy-3-(1-methyl-7-oxo-3-propyl-6H-pyrazolo[4,3-d]pyrimidin-5-yl)phenyl]methyl]cyclopentanecarbohydroxamic acid The racemic mixture 1-80 was separated by SFC (General procedure, SFC method) to obtain trans isomers 1-83 (21.4 mg, 23%): ESI-MS (M+1): 454.2 calc. for C24H31 N5O4: 453.2. Rt is 2.99.

Synthetic Route 1g

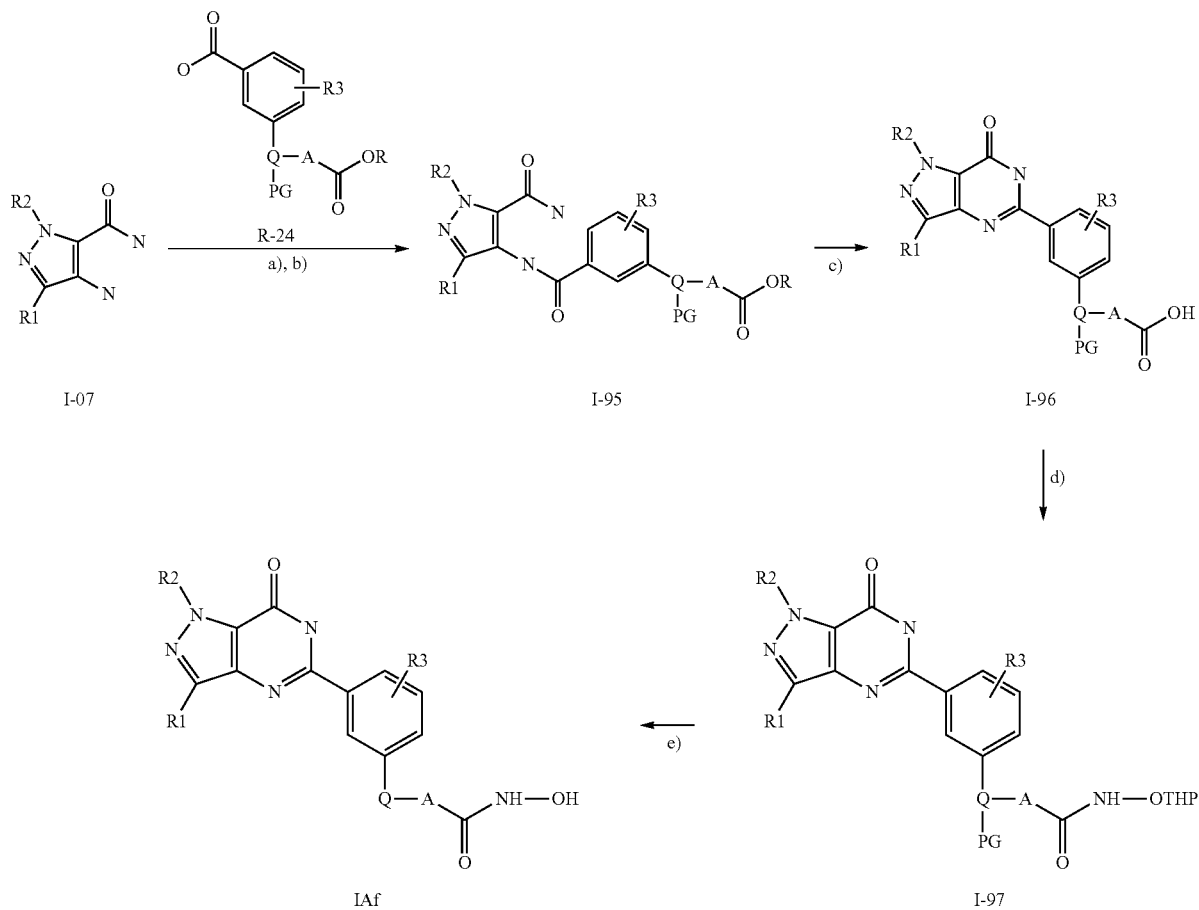

Conditions: a) R-24 in CH2Cl2, (COCl)2 (3 eq), DMF adition at -5° C. then at r.t for 2 hours; b) I-07 in CH2Cl2, Et3N (3 eq) adition at 0° then at r.t. overnight; c) NaOH (9 eq) in ethanol/H₂O/30% H₂O₂ (10:1:1) overnight at 100° C.; d) EDC•HCl (2 eq), HOBt (2 eq),THP—O—NH₂ (2 eq), NMM (3 eq) in DMF, overnight at r.t.; e) HCl/dioxane (4M) at r.t for 4 hours.

In the scheme above R is $(C_1$-$C_6)$alkyl, PG is a protecting group, such as boc, Q is NH or

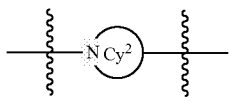

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-95a: methyl 4-[N-tert-butoxycarbonyl-3-[(5-carbamoyl-1-methyl-3-propyl-pyrazol-4-yl)carbamoyl]-4-ethoxy-anilino]benzoate To a solution of reagent R-24a (415 mg, 1 mmol) in CH2Cl2 (30 mL) was added (COCl)2 (381 mg, 3 mmol) and DMF (0.1 mL) at −5° C. under N2. The mixture was stirred at r.t. for 2 hrs. The mixture was concentrated under vacuo to give the crude intermediate used directly in next step. The crude intermediate (~1 mmol) in CH2Cl2 (10 mL) was added to a solution of Et3N (303 mg, 3.0 mmol) and intermediate I-07a (182 mg, 1.0 mmol) dissolved in CH2Cl2 (30 mL) at 0° C. under N2. The resulting mixture was stirred at r.t. overnight until TLC showed the starting material was consumed completely, then water was added and the mixture was extracted with CH2Cl2, the organic layer was washed with brine, dried over anhydrous Na2SO4, concentrated to give the crude intermediate I-95a (350 mg, 60%) which was used directly in next step ESI-MS (M+1): 580.3 calc. for C30H37N5O7: 579.2.

Preparation of intermediate I-96a: 4-[N-tert-butoxy-carbonyl-4-ethoxy-3-(1-methyl-7-oxo-3-propyl-6H-pyrazolo[4,3-d]pyrimidin-5-yl)anilino]benzoic acid To a solution of intermediate I-95a (350 mg, 0.6 mmol) was dissolved in EtOH (10 mL) and water (1 mL), then NaOH (220 mg, 5.5 mmol) and 30% H2O2 (1 mL) was added into the reaction mixture, stirred at 100° C. overnight. The reaction mixture was quenched with Na2SO3 and concentrated under vacuo, washed by water and extracted by EtOAc, dried over anhydrous Na2SO4 and concentrated to give the crude intermediate I-96a (280 mg, 86.7%). ESI-MS (M-55): 492.2 calc. for C29H33N5O6: 547.2.

Preparation of intermediate I-97a: tert-butyl N-[4-ethoxy-3-(1-methyl-7-oxo-3-propyl-6H-pyrazolo[4,3-d]pyrimidin-5-yl)phenyl]-N-[4-(tetrahydropyran-2-yloxycarbamoyl)phenyl]carbamate To a solution of intermediate I-96a (280 mg, 0.51 mmol) in DMF (20 mL) was added EDC.HCl (193 mg, 1 mmol), HOBt (135 mg, 1 mmol), THPO—NH2 (117 mg, 1 mmol), NMM (303 mg, 3 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC to give the pure intermediate I-97a (250 mg, 75% yield) as a white solid. ESI-MS (M+1): 647.4 calc. for C34H42N6O7: 646.3.

Preparation of compound 1-21: 4-[4-ethoxy-3-(1-methyl-7-oxo-3-propyl-6H-pyrazolo[4,3-d]pyrimidin-5-yl)anilino]benzenecarbohydroxamic acid A solution of intermediate I-97a (250 mg, 0.38 mmol) in HCl/dioxane (30 mL, 1 N) was stirred at r.t for 4 hrs, then concentrated to give the crude product which was purified by prep-HPLC (General procedure, Method 1) to obtained pure compound 1-21 (25.4 mg, 14.5% yield) as a yellow solid. ESI-MS (M+1): 463.3 calc. for C24H26N6O4: 646.3; Rt is 2.74.

Synthetic Route 1 h

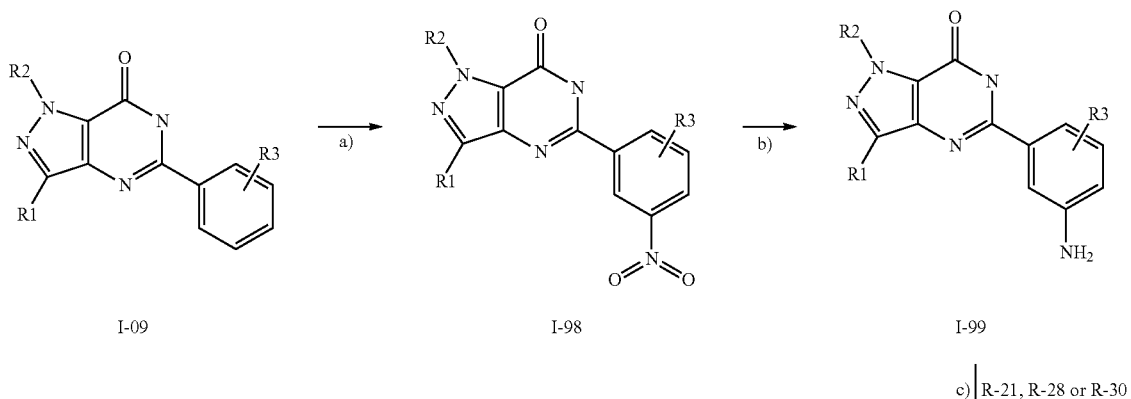

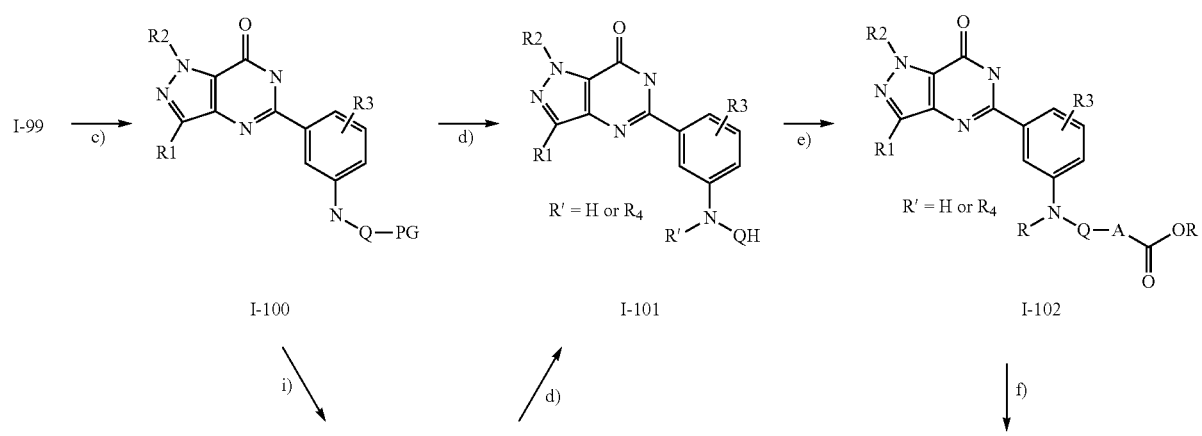

-continued

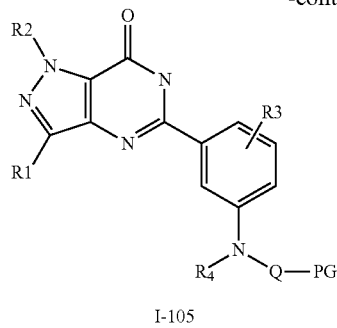

I-105

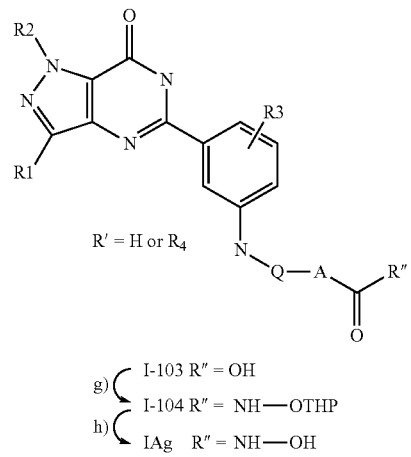

R' = H or R4 g) { I-103 R" = OH
    I-104 R" = NH—OTHP
h) { IAg R" = NH—OH

Conditions: a) concentrated sulfuric acid, KNO3 (1 eq) at 0° C. for 20 min; b) Pd/C, MeOH, overnight at r.t.; c) corresponding ketone R-21/R-28 or aldehyde R-30 (1.2 eq), AcOH (cat), Na(AcO)3BH (2 eq), DCM, overnight at r.t.; d) HCl/AcOEt (4M) at r.t for 1 hour; e) R-11 (1 eq), K2CO3 (2 eq), CH3CN, overnight at 40° C.; f) LiOH•H2O (10 eq) in THF/methanol/H2O, overnight at 40° C.; g) EDC•HCl (2 eq), HOBt (2 eq), THP—O—NH2 (2 eq), NMM (3 eq) in DMF, overnight at r.t.; h) HCl/AcOEt (4M) at r.t for 1 hour; i) corresponding aldehyde (1.5 eq), AcOH (cat), Na(AcO)3BH (2 eq), DCM, overnight at 60° C.

In the scheme above R is $(C_1-C_6)$alkyl, PG is a protecting group, such as boc, Q is NH or

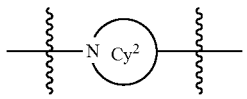

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-98a: 5-(2-ethoxy-5-nitro-phenyl)-1-methyl-3-propyl-6H-pyrazolo[4,3-d]pyrimidin-7-one To a solution of intermediate I-09a (1.0 g, 3.21 mmol) in concentrated sulfuric acid (5 mL) was added KNO3 (324 mg, 3.21 mmol) in portions at 0° C., then the reaction mixture was stirred at 0° C. for 20 min until LC-MS showed the starting material was consumed completely, then the mixture was poured into ice water and extracted with EtOAc three times, the organic layer was washed with aqueous NaHCO3, brine, dried over anhydrous Na2SO4, concentrated to give the crude intermediate I-98a (1.10 g, 95.65%) as a white solid. ESI-MS (M+1): 358 calc. for C17H19N5O4: 357.1.

Preparation of intermediate I-99a: 5-(5-amino-2-ethoxy-phenyl)-1-methyl-3-propyl-6H-pyrazolo[4,3-d]pyrimidin-7-one To a solution of intermediate I-98a (700 mg, 1.961 mmol) in MeOH (20 mL) was added Pd/C (0.5 g) at H2 atmosphere, then the mixture was stirred at room temperature overnight until LC-MS showed the starting material was consumed completely, then filtered, the filtrate was concentrated to give the crude intermediate I-99a (605 mg, 94.38%) as a white solid which was used for the next step directly. ESI-MS (M+1): 328 calc. for C17H21N5O2: 327.1.

Preparation of intermediate I-100a: tert-butyl 4-[4-ethoxy-3-(1-methyl-7-oxo-3-propyl-6H-pyrazolo[4,3-d]pyrimidin-5-yl)anilino]piperidine-1-carboxylate To a solution of intermediate I-99a (200 mg, 0.612 mmol) in anhydrous DCM (20 mL) was added commercially available tert-butyl 4-oxopiperidine-1-carboxylate (R-21) (145 mg, 0.734 mmol), AcOH (cat) and Na(AcO)3BH (259 mg, 1.224 mmol), then the mixture was stirred at room temperature overnight until LC-MS showed the starting material was consumed completely, the mixture was extracted with DCM three times, the organic layer was washed with aqueous NaHCO3, brine, dried over anhydrous Na2SO4, concentrated to give the crude compound which was purified by Prep-TLC (PE/EtOAc=1:1) to give pure intermediate I-100a (300 mg, 96% yield) as a yellow solid. ESI-MS (M+1): 511 calc. for C27H38N6O4: 510.2.

Preparation of intermediate I-101a: 5-[2-ethoxy-5-(4-piperidylamino)phenyl]-1-methyl-3-propyl-6H-pyrazolo[4,3-d]pyrimidin-7-one A solution of intermediate I-100a (300 mg, 0.588 mmol) in HCl/EtOAc (4M, 5 mL) was stirred at room temperature for 1 hr, then concentrated to give the crude intermediate I-101a (240 mg, 99.58%) as a white solid. ESI-MS (M+1): 411 calc. for C22H30N6O2: 410.2.

Preparation of intermediate I-102a: ethyl 2-[4-[4-ethoxy-3-(1-methyl-7-oxo-3-propyl-6H-pyrazolo[4,3-d]pyrimidin-5-yl)anilino]-1-piperidyl]pyrimidine-5-carboxylate To a solution of compound intermediate I-101a (240 mg, 0.585 mmol) in acetonitrile (20 mL) was added K2CO3 (161 mg, 1.17 mmol) and R-11e: ethyl 2-chloropyrimidine-5-carboxylate (109 mg, 0.585 mmol), then the mixture was stirred at 40° C. overnight. After LC-MS showed the starting material was consumed completely, the mixture was extracted with EtOAc and washed with brine, dried over anhydrous Na2SO4, concentrated to give the crude product which was purified by Prep-TLC (PE/EtOAc=1:1) to give the pure intermediate I-102a (263 mg, 80.18%) as a yellow oil. ESI-MS (M+1): 561 calc. for C29H36N8O4: 560.2.

Preparation of intermediate I-103a: 2-[4-[4-ethoxy-3-(1-methyl-7-oxo-3-propyl-6H-pyrazolo[4,3-d]pyrimidin-5-yl)anilino]-1-piperidyl]pyrimidine-5-carboxylic acid To a solution of intermediate I-102a (263 mg, 0.47 mmol) in MeOH/THF/H2O (3/9/3, 15 mL) was added LiOH.H2O (197 mg, 4.70 mmol), the reaction mixture was stirred at 40° C. overnight until LC-MS showed the starting material was consumed completely. Then concentrated, the mixture was diluted with H$_2$O and adjusted pH to 1-2 with 1N HCl, extracted with EtOAc, the organic layer was washed with brine, dried over anhydrous Na2SO4, concentrated to give the crude intermediate I-103a (230 mg, 92.0%) as a yellow solid. ESI-MS (M+1): 533 calc. for C27H32N8O4: 532.2.

Preparation of intermediate I-104a: 2-[4-[4-ethoxy-3-(1-methyl-7-oxo-3-propyl-6H-pyrazolo[4,3-d]pyrimidin-5-yl)anilino]-1-piperidyl]-N-tetrahydropyran-2-yloxy-pyrimidine-5-carboxamide To a solution of intermediate I-103a (230 mg, 0.432 mmol) in DMF (10 mL) was added EDC.HCl (166 mg, 0.864 mmol), HOBt (117 mg, 0.864 mmol), THPO—NH2 (102 mg, 0.864 mmol), NMM (131 mg, 1.296 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-104a (102 mg, 37% yield) as a yellow solid. ESI-MS (M+1): 632 calc. for C32H41N9O5: 631.3.

Preparation of intermediate I-105a: tert-butyl 4-[4-ethoxy-N-methyl-3-(1-methyl-7-oxo-3-propyl-6H-pyrazolo[4,3-d]pyrimidin-5-yl)anilino]piperidine-1-carboxylate To a solution of intermediate I-100a (500 mg, 0.980 mmol) in anhydrous DCM (30 mL) was added paraformaldehyde (132 mg, 1.471 mmol), AcOH (cat) and Na(AcO)3BH (416 mg, 1.960 mmol), then the mixture was stirred at 60° C. overnight until LC-MS showed the starting material was consumed completely, the mixture was extracted with DCM three times, the organic layer was washed with aqueous NaHCO3, brine, dried over anhydrous Na2SO4, concentrated to give the crude compound which was purified by Prep-TLC (PE/EtOAc=1:1) to give pure intermediate I-105a (288 mg, 56% yield) as a yellow oil. ESI-MS (M+1): 525 calc. for C28H40N6O4: 524.3.

Preparation of compound 1-22: 2-[4-[4-ethoxy-3-(1-methyl-7-oxo-3-propyl-6H-pyrazolo[4,3-d]pyrimidin-5-yl)anilino]-1-piperidyl]pyrimidine-5-carbohydroxamic acid A solution of compound intermediate I-104a (102 mg, 0.162 mmol) in HCl/EtOAc (4M, 5 mL) was stirred at room temperature for 1 hr, then concentrated to give the crude compound which was purified by prep-HPLC (General procedure, Method 1) to obtained pure compound 1-22 (50 mg, 56% yield) as a white solid. ESI-MS (M+1): 548 calc. for C27H33N9O4: 547.2; Rt is 2.14.

Following the same synthetic route for compound 1-22 and using the same reagents or intermediates and conditions unless otherwise indicated in the table below, the following compounds were obtained:

| Example | R$_t$ (min) | [M + 1]$^+$ | HPLC Method | Starting Materials or Intermediates/conditions |
|---|---|---|---|---|
| 1-23 | 2.31 | 562 | 1 | tert-butyl 4-formylpiperidine-1-carboxylate (R-30c) |
| 1-25 | 2.13 | 562 | 1 | Intermediate I-105a |
| 1-26 | 2.03 | 469 | 1 | ethyl 4-oxocyclohexane-carboxylate (R-28d) |
| 1-47 | 2.15 | 546.2 | 1 | methyl 4-(4-oxo-1-piperidyl)benzoate (R-28a) |

Synthetic Route 1i

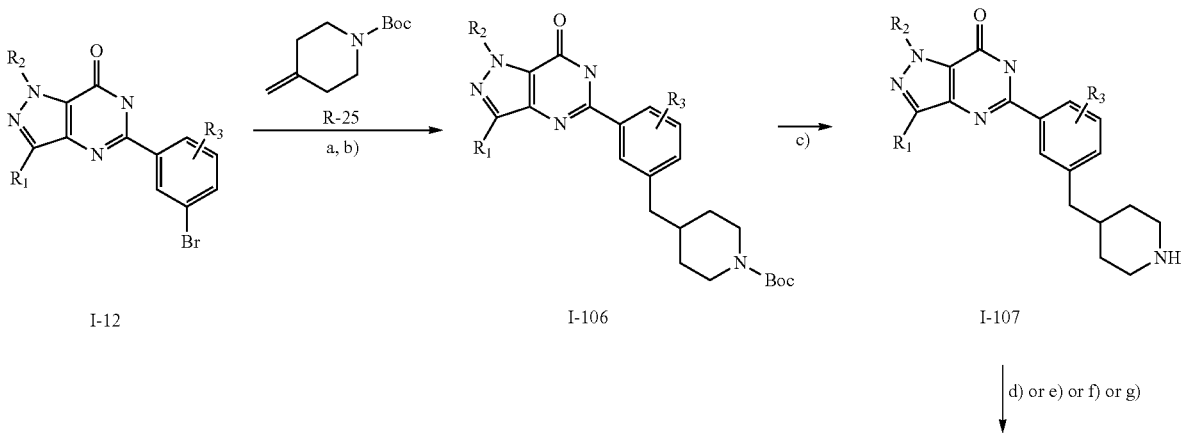

-continued

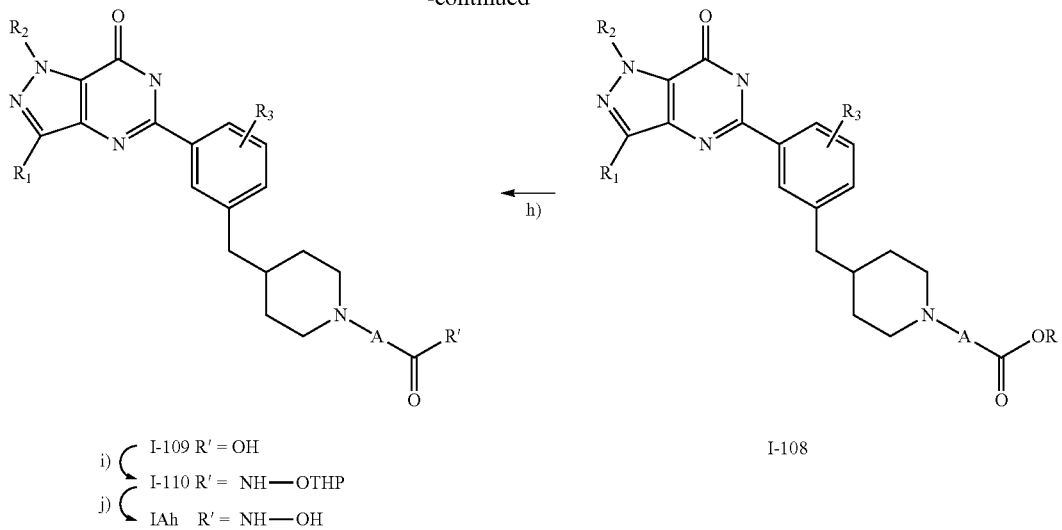

i) { I-109 R' = OH
    I-110 R' = NH—OTHP
j) { IAh  R' = NH—OH

Conditions: a) R-25, 9-BBN (0.5M solution) in THF, reflux for 4 hrs.; b) I-94, Pd2(dba)3 (0.05 eq), X-Phos (0.12 eq), Na2CO3 (2.5 eq), 1,4-dioxane and H2O, reflux overnight; c) HCl/AcOEt (4M) at r.t for 1 hour; d) R-11 (1 eq), K2CO3 (2 eq) in CH3CN, overnight at 40° C.; e) corresponding ketone or aldehyde (1.2 eq), AcOH (cat), Na(AcO)3BH (2 eq), DCM overnight at r.t.; f) corresponding boronic acid (20 eq.), Cu(OAc)2 (10 eq.), Et3N in DCM overnight at r.t.; g) ethyl prop-2-enoate (3 eq), DIEA (3 eq) in CAN, overnight at 80° C.; h) LiOH·H2O (10 eq) in THF/methanol/H2O, overnight at 40° C.; i) EDC·HCl (2 eq), HOBt (2 eq),THP—O—NH2 (2 eq), NMM (3 eq) in DMF, overnight at r.t.; j) HCl/AcOEt (4M) at r.t for 1 hour.

In the scheme above R is ($C_1$-$C_6$)alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-106a: tert-butyl 4-[[4-ethoxy-3-(1-methyl-7-oxo-3-propyl-6H-pyrazolo[4,3-d]pyrimidin-5-yl)phenyl]methyl]piperidine-1-carboxylate Reagent R-25 (6 g, 31 mmol) was treated with a 0.5 M solution of 9-BBN in THF (62 mL), and the mixture was heated at reflux for 4 hrs. The resulting mixture was transferred into a stirred mixture of intermediate I-12a (10.14 g, 26 mmol), Pd(dba2)3 (733 mg, 0.8 mmol), X-Phos (926 mg, 1.6 mmol), and Na2CO3 (6.4 g, 60 mmol) in 1,4-dioxane (60 mL) and H$_2$O (10 mL). The resulting mixture was stirred at reflux overnight until TLC (PE: EtOAc=3:1) showed the starting material was consumed completely, then filtered, the mixture was extracted with EtOAc, the organic layer was washed with brine, dried over anhydrous Na2SO4, concentrated to give the crude compound which was purified by column chromatography (eluting with PE/EtOAc=50:1 to 5:1) to give pure intermediate I-106a (7.1 g, 45% yield) as a pale yellow oil. ESI-MS (M-55): 454.1 calc. for C28H39N5O4: 509.3.

Preparation of intermediate I-107a: 5-[2-ethoxy-5-(4-piperidylmethyl)phenyl]-1-methyl-3-propyl-6H-pyrazolo[4,3-d]pyrimidin-7-one A solution of intermediate I-106a (500 mg, 0.982 mmol) in HCl/EtOAc (4M, 5 mL) was stirred at room temperature for 1 hr, then concentrated to give the crude intermediate I-107a (400 mg, 99%) as a white solid. ESI-MS (M+1): 410 calc. for C23H31 N5O2: 409.2.

Preparation of intermediate I-108a: ethyl 2-[4-[[4-ethoxy-3-(1-methyl-7-oxo-3-propyl-6H-pyrazolo[4,3-d]pyrimidin-5-yl)phenyl]methyl]-1-piperidyl]pyrimidine-5-carboxylate To a solution of crude intermediate I-107a (400 mg, 0.978 mmol) in acetonitrile (20 mL) was added K2CO3 (270 mg, 1.956 mmol) and Rile: ethyl 2-chloropyrimidine-5-carboxylate (182 mg, 0.978 mmol), then the mixture was stirred at 40° C. overnight. After LC-MS showed the starting material was consumed completely, the mixture was extracted with EtOAc and washed with brine, dried over anhydrous Na2SO4, concentrated to give the crude product which was purified by Prep-TLC (PE/EtOAc=1:1) to give the pure intermediate I-108a (450 mg, 82% yield) as a white solid. ESI-MS (M+1): 560 calc. for C30H37N7O4: 559.3.

Preparation of intermediate I-109a: 2-[4-[[4-ethoxy-3-(1-methyl-7-oxo-3-propyl-6H-pyrazolo[4,3-d]pyrimidin-5-yl)phenyl]methyl]-1-piperidyl]pyrimidine-5-carboxylic acid To a solution of intermediate I-108a (450 mg, 0.805 mmol) in MeOH/THF/H2O (3/9/3, 15 mL) was added LiOH.H2O (338 mg, 8.05 mmol), the reaction mixture was stirred at 40° C. overnight until LC-MS showed the starting material was consumed completely. After evaporation, the mixture was diluted with H$_2$O and adjusted pH to 1-2 with 1N HCl, extracted with EtOAc, the organic layer was washed with brine, dried over anhydrous Na2SO4, concentrated to give the crude intermediate I-109a (400 mg, 93%) as a white solid. ESI-MS (M+1): 532 calc. for C28H33N7O4: 531.2.

Preparation of intermediate I-110a: 2-[4-[[4-ethoxy-3-(1-methyl-7-oxo-3-propyl-6H-pyrazolo[4,3-d]pyrimidin-5-yl)phenyl]methyl]-1-piperidyl]-N-tetrahydropyran-2-yloxy-pyrimidine-5-carboxamide To a solution of intermediate I-109a (400 mg, 0.753 mmol) in DMF (10 mL) was added EDC.HCl (289 mg, 1.507 mmol), HOBt (203 mg, 1.507 mmol), THPO—NH2 (176 mg, 1.507 mmol), NMM (228 mg, 2.259 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-110a (400 mg, 84% yield) as a white solid. ESI-MS (M+1): 631 calc. for C33H42N8O5: 630.3.

Preparation of compound 1-24: 2-[4-[[4-ethoxy-3-(1-methyl-7-oxo-3-propyl-6H-pyrazolo[4,3-d]pyrimidin-5-yl)phenyl]methyl]-1-piperidyl]pyrimidine-5-carbohydroxamic acid A solution of intermediate I-110a (400 mg, 0.635 mmol) in HCl/EtOAc (4M, 5 mL) was stirred at room temperature for 1 hr, then concentrated to give the crude compound which was purified by prep-HPLC (General procedure, Method 1) to obtained pure compound 1-24 (150 mg, 43% yield) as a white solid. ESI-MS (M+1): 547 calc. for C28H34N8O4: 546.2; Rt is 3.27.

Following the same synthetic route for compound 1-24 and using the same reagents and conditions unless otherwise indicated in the table below, the following compounds were obtained:

| Example | R$_t$ (min) | [M + 1]$^+$ | HPLC Method | Starting Materials/conditions |
|---|---|---|---|---|
| 1-32 | 2.32 | 483 | 1 | ethyl 2-oxoacetate/e) conditions |
| 1-39 | 2.62 | 546 | 1 | methyl 6-chloropyridine-3-carboxylate (R-11q)/d) conditions |
| 1-45 | 2.84 | 545.2 | 1 | (4-ethoxycarbonylphenyl)boronic acid/f) conditions |
| 1-46 | 2.35 | 497.2 | 1 | ethyl prop-2-enoate/g) conditions |

Synthetic Route 1

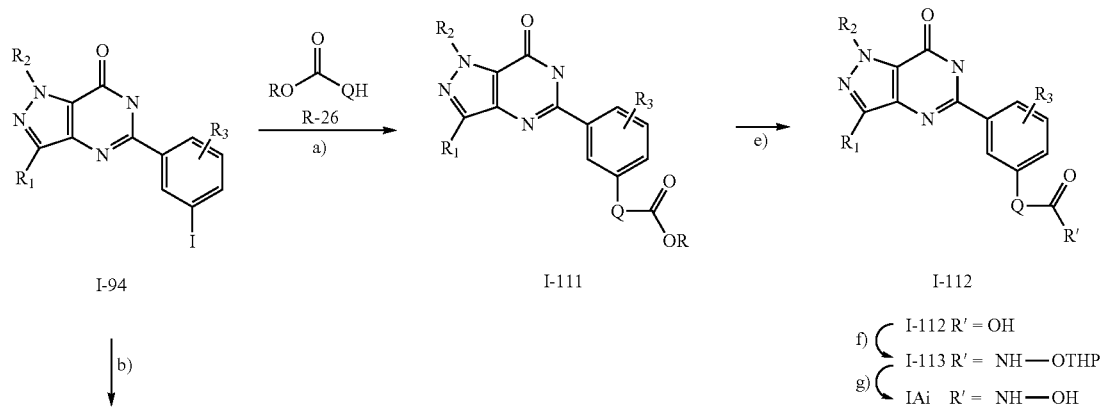

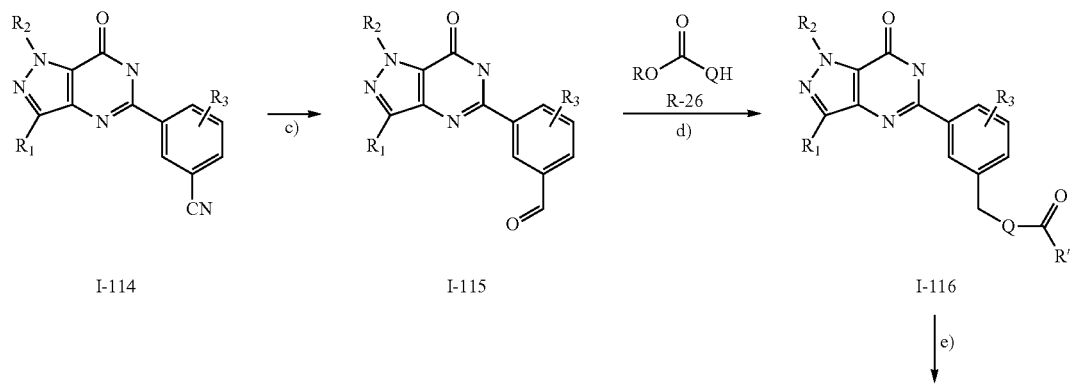

-continued

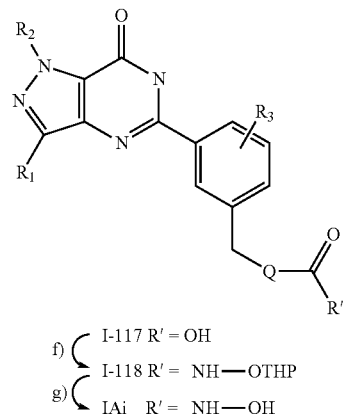

f) ( I-117 R' = OH
   ( I-118 R' = NH—OTHP
g) ( IAi R' = NH—OH

Conditions: a) R-26 (2 eq), Pd2(dba)3 (0.1 eq), X-Phos (0.3 eq), ButOK (2 eq) in toluene at 100° C. for 1 hour under microwave; b) Zn(CN)2 (2 eq), Pd(PPh3)4 (0.1 eq) in DMF overnight at 80° C.; c) DIBAL-H (1.1 eq) in DCM, overnight at r.t.; d) R-26 (0.8 eq), AcOH (cat) and Na(AcO)3BH (1.6 eq) in DCM overnight at r.t; e) LiOH•H₂O (10 eq) in THF/methanol/H₂O, overnight at 40° C.; f) EDC•HCl (2 eq), HOBt (2 eq), THP—O—NH₂ (2 eq), NMM (3 eq) in DMF, overnight at r.t.; g) HCl/AcOEt (4M) at r.t for 1 hour.

In the scheme above R is $(C_1-C_6)$alkyl and Q is NH or

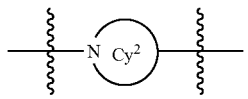

wherein $Cy^2$ is an heterocyclic ring.

Preparation of intermediate I-111a: ethyl 1-[4-ethoxy-3-(1-methyl-7-oxo-3-propyl-6H-pyrazolo[4,3-d]pyrimidin-5-yl)phenyl]piperidine-4-carboxylate To a solution of intermediate I-94a (500 mg, 1.14 mmol) in toluene (5 mL) was added commercially available ethyl piperidine-4-carboxylate (R-26a) (358 mg, 2.28 mmol), x-phos (162 mg, 0.342 mmol), Pd2(dba)3 (104 mg, 0.114 mmol) and ButOK (3 mL, 2.28 mmol). The mixture was heated to 100° C. for 1 h under Microwave. The mixture was quenched with aqueous water and extracted with EtOAc, the organic layer was washed with brine, dried over anhydrous Na2SO4, concentrated to give the crude product which was purified by column to give of intermediate I-111a (200 mg, 36%) as a yellow solid. ESI-MS (M+1): 468.3 calc. for C25H33N5O4: 467.2.

Preparation of intermediate I-112a: 1-[4-ethoxy-3-(1-methyl-7-oxo-3-propyl-6H-pyrazolo[4,3-d]pyrimidin-5-yl)phenyl]piperidine-4-carboxylic acid To a solution of intermediate I-111a (200 mg, 0.43 mmol) in THF/MeOH/H2O (3/3/2, 8 mL) was added LiOH.H2O (184 mg, 10 eq). The resulting mixture was stirred at r.t. for 8 hrs, after TLC showed the starting materials were consumed completely, then the mixture was diluted with water and adjusted pH to 6-7 with 1N HCl and the mixture was extracted with EtOAc, washed with brine, dried over anhydrous Na2SO4, concentrated to give the crude intermediate I-112a (180 mg, 96%). ESI-MS (M+1): 440.2; calc. for C23H29N5O4: 439.2.

Preparation of intermediate I-113a: 1-[4-ethoxy-3-(1-methyl-7-oxo-3-propyl-6H-pyrazolo[4,3-d]pyrimidin-5-yl)phenyl]-N-tetrahydropyran-2-yloxy-piperidine-4-carboxamide To a solution of intermediate I-112a (60 mg, 0.14 mmol) in DMF (10 mL) was added EDC.HCl (54 mg, 0.28 mmol), HOBt (38 mg, 0.28 mmol), THPONH2 (33 mg, 0.28 mmol) and NMM (46 mg, 0.42 mmol) at r.t, then the mixture was stirred at room temperature overnight. The mixture was quenched with aqueous water and extracted with EtOAc, the organic layer was washed with brine, dried over anhydrous Na2SO4, concentrated to give the crude product which was purified by prep-TLC to give the intermediate I-113a (40 mg, 53%) as a pale yellow solid. ESI-MS (M+1): 539.3; calc. for C28H38N6O5: 538.3.

Preparation of compound 1-35: 1-[4-ethoxy-3-(1-methyl-7-oxo-3-propyl-6H-pyrazolo[4,3-d]pyrimidin-5-yl)phenyl]piperidine-4-carbohydroxamic acid A solution of intermediate I-113a (40 mg, 0.074 mmol) in HCl/EtOAc (10 mL) was stirred at r.t for 1 h, then concentrated to give the crude product which was purified by prep-HPLC (General procedure, Method 1) to obtained pure compound 1-35 (6 mg, 19% yield) as a white solid. ESI-MS (M+1): 455.2 calc. for C23H30N6O4: 454.2; Rt is 1.96.

Preparation of intermediate I-114a: 4-ethoxy-3-(1-methyl-7-oxo-3-propyl-6H-pyrazolo[4,3-d]pyrimidin-5-yl)benzonitrile To a solution of intermediate I-94a (4.0 g, 9.13 mmol) in DMF (30 mL) was added Zn(CN)2 (2.21 g, 18.26 mmol), Pd(PPh3)4 (1.06 g, 0.913 mmol), then the mixture was stirred at 80° C. overnight under N2 protection. After LC-MS showed the starting material was consumed completely, the mixture was extracted with EtOAc, the organic layer was washed with brine, dried over anhydrous Na2SO4, concentrated to give the crude compound which was purified by column chromatography to give pure of intermediate I-114a (2.50 g, 81% yield) as a white solid. ESI-MS (M+1): 338 calc. for C18H19N5O2: 337.1.

Preparation of intermediate I-115a: 4-ethoxy-3-(1-methyl-7-oxo-3-propyl-6H-pyrazolo[4,3-d]pyrimidin-5-yl)benzaldehyde To a solution of intermediate I-114a (2.50 g, 7.42 mmol) in anhydrous DCM (30 mL) was added DIBAL-H (8.2 mL, 1.0 M in toluene, 8.16 mmol) slowly at 000, then the mixture was stirred at room temperature overnight under N2 protection until HPLC showed the starting material was consumed completely, the mixture was poured into 2N HCl, extracted with DCM, the organic layer was washed with brine, dried over anhydrous Na2SO4, concentrated to give the crude compound which was purified by column chromatography to give pure intermediate I-115a (1.69 g, 67% yield) as a white solid. ESI-MS (M+1): 341 calc. for C18H20N4O3: 340.1.

Preparation of intermediate I-116a: ethyl 1-[[4-ethoxy-3-(1-methyl-7-oxo-3-propyl-6H-pyrazolo[4,3-d]pyrimidin-5-yl)phenyl]methyl]piperidine-4-carboxylate To a solution of intermediate I-115a (250 mg, 0.736 mmol) in anhydrous DCM (30 mL) was added commercially available ethyl piperidine-4-carboxylate (R-26a) (97 mg, 0.618 mmol), AcOH (cat) and Na(AcO)3BH (260 mg, 1.226 mmol), then the mixture was stirred at room temperature overnight until LC-MS showed the starting material was consumed completely, the mixture was extracted with DCM three times, the organic layer was washed with aqueous NaHCO3, brine, dried over anhydrous Na2SO4, concentrated to give the crude compound which was purified by Prep-TLC (PE/EtOAc=1:1) to give pure intermediate I-116a (150 mg, 50.51%) as a white solid. ESI-MS (M+1): 482 calc. for C26H35N5O4: 481.2.

Preparation of intermediate I-117a: 1-[[4-ethoxy-3-(1-methyl-7-oxo-3-propyl-6H-pyrazolo[4,3-d]pyrimidin-5-yl)phenyl]methyl]piperidine-4-carboxylic acid To a solution of intermediate I-116a (150 mg, 0.312 mmol) in MeOH/THF/H2O (3/9/3, 15 mL) was added LiOH.H2O (131 mg, 3.12 mmol), the reaction mixture was stirred at room temperature overnight until LC-MS showed the starting material was consumed completely. Then concentrated, the mixture was diluted with H2O and adjusted pH to 1-2 with 1N HCl, extracted with EtOAc, the organic layer was washed with brine, dried over anhydrous Na2SO4, concentrated to give the crude intermediate I-117a (130 mg, 92.20%) as a white solid. ESI-MS (M+1): 454 calc. for C24H31 N5O4: 453.2.

Preparation of intermediate I-118a: 1-[[4-ethoxy-3-(1-methyl-7-oxo-3-propyl-6H-pyrazolo[4,3-d]pyrimidin-5-yl)phenyl]methyl]-N-tetrahydropyran-2-yloxy-piperidine-4-carboxamide To a solution of intermediate I-117a (130 mg, 0.287 mmol) in DMF (10 mL) was added EDC.HCl (110 mg, 0.574 mmol), HOBt (77 mg, 0.574 mmol), THPO—NH2 (67 mg, 0.574 mmol), NMM (87 mg, 0.861 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (MeOH/DCM=1:10) to give the pure intermediate I-118a (110 mg, 69% yield) as a yellow solid. ESI-MS (M+1): 553 calc. for C29H40N6O5: 552.3.

Preparation of compound 1-36: 1-[[4-ethoxy-3-(1-methyl-7-oxo-3-propyl-6H-pyrazolo[4,3-d]pyrimidin-5-yl)phenyl]methyl]piperidine-4-carbohydroxamic acid A solution of intermediate I-118a (110 mg, 0.199 mmol) in HCl/EtOAc (4M, 5 mL) was stirred at room temperature for 1 hr, then concentrated to give the crude compound which was purified by prep-HPLC (General procedure, Method 1) to obtained pure compound 1-36 (26.7 mg, 28% yield) as a white solid. ESI-MS (M+1): 469 calc. for C24H32N6O4: 468.2; Rt is 2.00.

Following the same synthetic route for compound 1-36 and using the same reagents unless otherwise indicated in the table below, the following compounds were obtained:

| Example | $R_t$ (min) | $[M + 1]^+$ | HPLC Method | Starting Materials |
|---|---|---|---|---|
| 1-81 | 1.85 | 441.2 | 1 | methyl azetidine-3-carboxylate (R-26b) |

Synthetic Route 1k

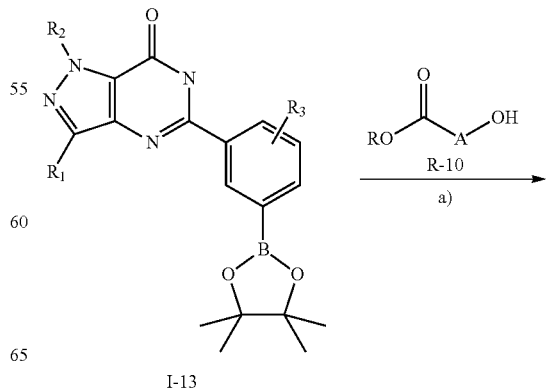

127
-continued

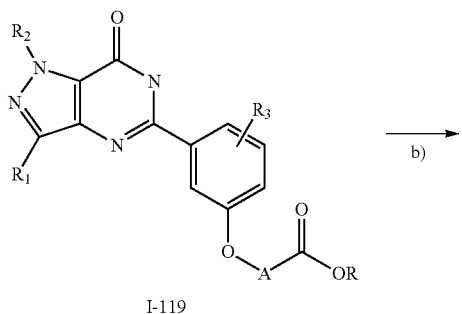

I-119

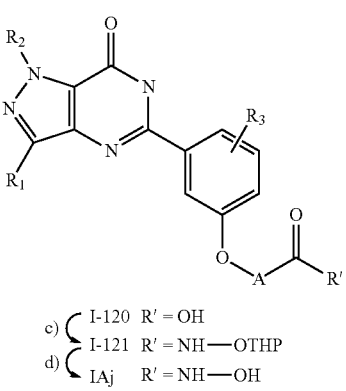

c) ⎧ I-120 R' = OH
d) ⎨ I-121 R' = NH—OTHP
   ⎩ IAj   R' = NH—OH

Conditions: a) R-10 (0.7 eq), Cu(OAc)2 (1 eq), Et3N(3.5 eq) in DCM, overnight at r.t.; b) LiOH·H₂O (10 eq) in THF/methanol/H₂O, overnight at 40° C.; c) EDC·HCl (2 eq), HOBt (2 eq), THP—O—NH₂ (2 eq), NMM (3 eq) in DMF, overnight at r.t.; d) HCl/AcOEt (4M) at r.t for 1 hour.

In the scheme above R is $(C_1-C_6)$alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-119a: ethyl 4-[4-ethoxy-3-(1-methyl-7-oxo-3-propyl-6H-pyrazolo[4,3-d]pyrimidin-5-yl)phenoxy]benzoate To a solution of intermediate I-13a (250 mg, 0.7 mmol) in CH2Cl2 (50 mL) was added commercially available ethyl 4-hydroxybenzoate R-10c (83 mg, 0.5 mmol), Cu(OAc)2 (127 mg, 0.7 mmol), Et3N (253 mg, 2.5 mmol) and 4A molecular sieve (0.5 g), then the mixture was stirred at r.t. overnight under O2 protection until LC-MS showed the starting material was consumed completely, then filtered and the mixture was extracted with CH2Cl2 and washed with brine, dried over anhydrous Na2SO4, concentrated to give the crude product which was purified by Prep-TLC to give the pure intermediate I-119a (115 mg, 48% yield) as yellow solid. ESI-MS (M+1): 477.2 calc. for C26H28N4O5: 476.2.

128
Preparation of intermediate I-120a: 4-[4-ethoxy-3-(1-methyl-7-oxo-3-propyl-6H-pyrazolo[4,3-d]pyrimidin-5-yl)phenoxy]benzoic acid To a solution of intermediate I-119a (115 mg, 0.242 mmol) in MeOH/THF/H2O (3/9/3, 15 mL) was added LiOH.H2O (102 mg, 2.42 mmol), the reaction mixture was stirred at room temperature overnight until LC-MS showed the starting material was consumed completely. Then concentrated, the mixture was diluted with H₂O and adjusted pH to 1-2 with 1N HCl, extracted with EtOAc, the organic layer was washed with brine, dried over anhydrous Na2SO4, concentrated to give the crude pure intermediate I-120a (100 mg, 92%) as a yellow solid. ESI-MS (M+1): 449 calc. for C24H24N4O5: 448.1.

Preparation of intermediate I-121a: 4-[4-ethoxy-3-(1-methyl-7-oxo-3-propyl-6H-pyrazolo[4,3-d]pyrimidin-5-yl)phenoxy]-N-tetrahydropyran-2-yloxybenzamide To a solution of intermediate I-120a (100 mg, 0.223 mmol) in DMF (10 mL) was added EDC.HCl (86 mg, 0.446 mmol), HOBt (60 mg, 0.446 mmol), THPO—NH2 (52 mg, 0.446 mmol), NMM (68 mg, 0.669 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (PE/EtOAc=1:5) to give the pure intermediate I-121a (82 mg, 67% yield) as a yellow solid. ESI-MS (M+1): 548 calc. for C29H33N5O6: 547.2.

Preparation of compound 1-37: 4-[4-ethoxy-3-(1-methyl-7-oxo-3-propyl-6H-pyrazolo[4,3-d]pyrimidin-5-yl)phenoxy]benzenecarbohydroxamic acid A solution of intermediate I-121a (82 mg, 0.150 mmol) in HCl/EtOAc (4M, 5 mL) was stirred at room temperature for 1 hr, then concentrated to give the crude compound which was purified by prep-HPLC (General procedure, Method 1) to obtained pure compound 1-37 (35 mg, 50% yield) as a white solid. ESI-MS (M+1): 464 calc. for C24H25N5O5: 463.1; Rt is 2.95.

Following the same synthetic route for compound 1-37 and using the same reagents unless otherwise indicated in the table below, the following compounds were obtained:

| Example | $R_t$ (min) | $[M + 1]^+$ | HPLC Method | Starting Materials |
|---|---|---|---|---|
| 1-53 | 2.66 | 470 | 1 | ethyl 4-hydroxycyclohexane-carboxylate (R10d) |
| 1-55 | 2.81 | 478.1 | 1 | methyl 4-(hydroxymethyl)benzoate (R-10e) |

Synthetic Route 11

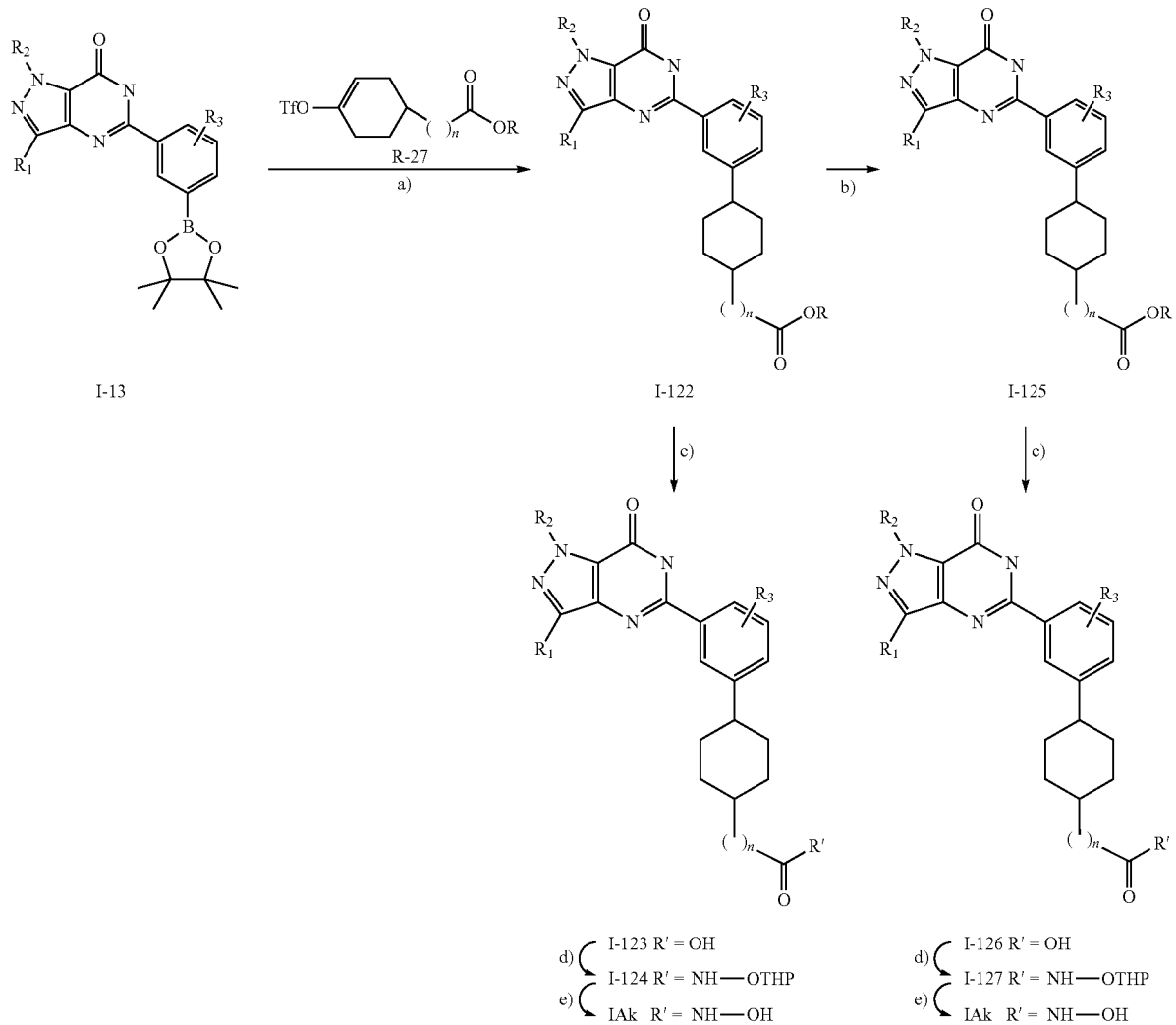

Conditions: a) R-27 (1 eq), Pd(PPh3)4 (0.1 eq) K₂CO₃ (3 eq) in water, in 1,4-dioxane, overnight at 80° C.; b) Pd/C in MeOH at H2 atmosphere, at r.t for 1 hour; c) LiOH•H₂O (10 eq) in THF/methanol/H₂O, overnight at 40° C.; d) EDC•HCl (2 eq), HOBt (2 eq), THP—O—NH₂ (2 eq), NMM (3 eq) in DMF, overnight at r.t.; e) HCl/AcOEt (4M) at r.t for 1 hour.

In the scheme above R is $(C_1-C_6)$alkyl and n is 0 or 1.

Preparation of intermediate I-122a: ethyl 4-[4-ethoxy-3-(1-methyl-7-oxo-3-propyl-6H-pyrazolo[4,3-d]pyrimidin-5-yl)phenyl]cyclohex-3-ene-1-carboxylate To a solution of intermediate I-13a (300 mg, 0.685 mmol) in 1,4-dioxane (20 mL) was added R-27a: ethyl 4-(trifluoromethylsulfonyloxy)cyclohex-3-ene-1-carboxylate (207 mg, 0.685 mmol), K2CO3 (284 mg, 2.06 mmol in 1 mL water), Pd(PPh3)4 (80 mg, 0.0685 mmol), then the mixture was stirred at 80° C. overnight under N2 protection. After LC-MS showed the starting material was consumed completely, the mixture was extracted with EtOAc, the organic layer was washed with brine, dried over anhydrous Na2SO4, concentrated to give the crude compound which was purified by Prep-TLC (PE/EtOAc=1:1) to give pure intermediate I-122a (300 mg, 94% yield) as a white solid. ESI-MS (M+1): 465 calc. for C26H32N4O4: 464.2.

Preparation of intermediate I-123a: 4-[4-ethoxy-3-(1-methyl-7-oxo-3-propyl-6H-pyrazolo[4,3-d]pyrimidin-5-yl)phenyl]cyclohex-3-ene-1-carboxylic acid To a solution of intermediate I-122a (130 mg, 0.280 mmol) in MeOH/THF/H2O (3/9/3, 15 mL) was added LiOH.H2O (118 mg, 2.80 mmol), the reaction mixture was stirred at room temperature overnight until LC-MS showed the starting material was consumed completely. Then concentrated, the mixture was diluted with H₂O and adjusted pH to 1-2 with 1N HCl, extracted with EtOAc, the organic layer was washed with brine, dried over anhydrous Na2SO4, concentrated to give the crude intermediate I-123a (110 mg, 90%) as a yellow solid. ESI-MS (M+1): 437 calc. for C24H28N4O4: 436.2.

Preparation of intermediate I-124a: 4-[4-ethoxy-3-(1-methyl-7-oxo-3-propyl-6H-pyrazolo[4,3-d]pyrimidin-5-yl)phenyl]-N-tetrahydropyran-2-yloxy-cyclohex-3-ene-1-carboxamide To a solution of intermediate I-123a (110 mg, 0.252 mmol) in DMF (10 mL) was added EDC.HCl (97 mg, 0.504 mmol), HOBt (68 mg, 0.504 mmol), THPO—NH2 (59 mg, 0.504 mmol), NMM (77 mg, 0.756 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-124a (90 mg, 66% yield) as a white solid. ESI-MS (M+1): 536 calc. for C29H37N5O5: 535.2.

Preparation of compound 1-38: 4-[4-ethoxy-3-(1-methyl-7-oxo-3-propyl-6H-pyrazolo[4,3-d]pyrimidin-5-yl)phenyl]cyclohex-3-ene-1-carbohydroxamic acid A solution of intermediate I-124a (90 mg, 0.168 mmol) in HCl/EtOAc (4M, 5 mL) was stirred at room temperature for 1 hr, then concentrated to give the crude compound which was purified by prep-HPLC (General procedure, Method 1) to obtained pure compound 1-38 (14.5 mg, 19% yield) as a white solid. ESI-MS (M+1): 452 calc. for C24H29N5O4: 451.2; Rt is 2.85.

Following the same synthetic route for compound 1-38 and using the same reagents unless otherwise indicated in the table below, the following compounds were obtained:

| Example | R$_t$ (min) | [M + 1]$^+$ | HPLC Method | Starting Materials |
| --- | --- | --- | --- | --- |
| 1-42 | 2.98 | 466 | 1 | ethyl 2-[4-(trifluoromethyl-sulfonyloxy)-cyclohex-3-en-1-yl]acetate (R-27b) |

Preparation of intermediate I-125a: ethyl 4-[4-ethoxy-3-(1-methyl-7-oxo-3-propyl-6H-pyrazolo[4,3-d]pyrimidin-5-yl)phenyl]cyclohexanecarboxylate To a solution of intermediate I-122a (170 mg, 0.366 mmol) in MeOH (20 mL) was added Pd/C (50 mg) at H2 atmosphere, then the mixture was stirred at room temperature for 1 hr until LC-MS showed the starting material was consumed completely, then filtered, the filtrate was concentrated to give the crude intermediate I-125a (154 mg, 90%) as a white solid which was used for the next step directly. ESI-MS (M+1): 467 calc. for C26H34N4O4: 466.2.

Preparation of intermediate I-126a: 4-[4-ethoxy-3-(1-methyl-7-oxo-3-propyl-6H-pyrazolo[4,3-d]pyrimidin-5-yl)phenyl]cyclohexanecarboxylic acid To a solution of crude intermediate I-125a (154 mg, 0.330 mmol) in MeOH/THF/H2O (3/9/3, 15 mL) was added LiOH.H2O (139 mg, 3.30 mmol), the reaction mixture was stirred at room temperature overnight until LC-MS showed the starting material was consumed completely. Then concentrated, the mixture was diluted with H2O and adjusted pH to 1-2 with 1N HCl, extracted with EtOAc, the organic layer was washed with brine, dried over anhydrous Na2SO4, concentrated to give the crude intermediate I-126a (110 mg, 75%) as a yellow solid. ESI-MS (M+1): 439 calc. for C24H30N4O4: 438.2.

Preparation of intermediate I-127a: 4-[4-ethoxy-3-(1-methyl-7-oxo-3-propyl-6H-pyrazolo[4,3-d]pyrimidin-5-yl)phenyl]-N-tetrahydropyran-2-yloxy-cyclohexanecarboxamide To a solution of intermediate I-126a (110 mg, 0.251 mmol) in DMF (10 mL) was added EDC.HCl (96 mg, 0.502 mmol), HOBt (68 mg, 0.502 mmol), THPO—NH2 (59 mg, 0.502 mmol), NMM (76 mg, 0.753 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-127a (90 mg, 66% yield) as a yellow oil. ESI-MS (M+1): 538 calc. for C29H39N5O5: 537.3.

Preparation of compounds 1-75, 1-40 & 1-41: racemic, cis & trans 4-[4-ethoxy-3-(1-methyl-7-oxo-3-propyl-6H-pyrazolo[4,3-d]pyrimidin-5-yl)phenyl]cyclohexanecarbohydroxamic acid A solution of intermediate I-127a (98 mg, 0.182 mmol) in HCl/EtOAc (1.0 M, 15 mL) was stirred at room temperature for 1 hr, then concentrated to give a crude which was purified by prep-HPLC (General procedure, Method 1) to obtain racemic compound 1-75 (14.5 mg), ESI-MS (M+1): 454.2 calc. for C24H31N5O4: 453.2 (Rt is 3.05); cis isomers 1-40 (5.8 mg) ESI-MS (M+1): 454.2 calc. for C24H31 N5O4: 453.2 (Rt is 2.95) and trans isomers 1-41 (10 mg) ESI-MS (M+1): 454.2 calc. for C24H31 N5O4: 453.2 (Rt is 3.05).

Following the same synthetic route for compound 1-75 and using the same reagents unless otherwise indicated in the table below, the following compounds were obtained:

| Example | R$_t$ (min) | [M + 1]$^+$ | HPLC Method | Starting Materials |
| --- | --- | --- | --- | --- |
| 1-51 | 3.09 | 468 | 1 | ethyl 2-[4-(trifluoromethyl-sulfonyloxy)cyclohex-3-en-1-yl]acetate (R-27b) |

Synthetic Route 1m

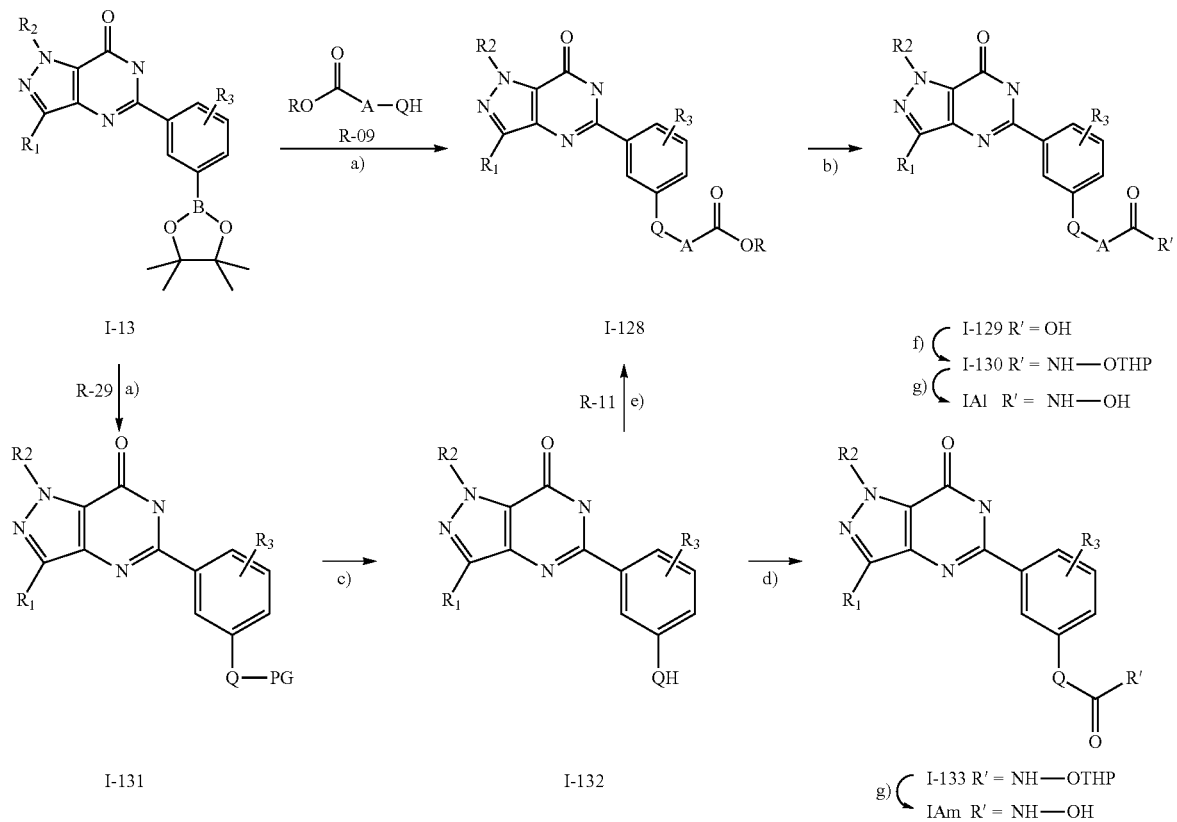

Conditions: a) R-09 or R-29(1.2 eq), Cu(OAc)2 (2 eq), Et3N(3 eq) in anhydrous CH2Cl2 at r.t. for 2 hrs; b) LiOH•H2O (10 eq) in THF/methanol/ H2O, overnight at 40° C.; c) HCl/AcOEt (2M) at r.t for 1 hour; d)THPO—NH2 (2 eq), CDI (2 eq) in anhydrous THF adition at 0° C. then overnight ar r.t.; e) R-11 (1.1 eq) K2CO3 (3 eq) in CH3CN, overnight at 60° C.; f) EDC•HCl (2 eq), HOBt (2 eq), THP—O—NH2 (2 eq), NMM (3 eq) in DMF, overnight at r.t.; g) HCl/AcOEt (4M) at r.t for 1 hour.

In the scheme above R is $(C_1-C_6)$alkyl, Q is NH or

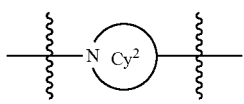

wherein $Cy^2$ is an heterocyclic ring, PG is a protecting group, such as boc, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-128a: ethyl 8-[4-ethoxy-3-(1-methyl-7-oxo-3-propyl-6H-pyrazolo[4,3-d]pyrimidin-5-yl)phenyl]-8-azaspiro[4.5]decane-3-carboxylate To a solution of intermediate I-13a (200 mg, 0.56 mmol), Cu(OAc)2 (217 mg, 1.2 mmol), Et3N (152 mg, 1.5 mmol) and 4A molecular sieve (800 mg) in anhydrous CH2Cl2 (65 mL) was added R-09j: ethyl 8-azaspiro[4.5]decane-3-carboxylate (144 mg, 0.68 mmol) under O2 condition, then the mixture was stirred at r.t. for 3.5 hrs until LC-MS showed the starting material was consumed completely, then the mixture was extracted with CH2Cl2 and washed with brine, dried over anhydrous Na2SO4, concentrated to give the crude product which was purified by Prep-TLC to give pure intermediate I-128a (135 mg, 26% yield). ESI-MS (M+1): 522.1 calc. for C29H39N5O4: 521.3.

Preparation of intermediate I-129a: 8-[4-ethoxy-3-(1-methyl-7-oxo-3-propyl-6H-pyrazolo[4,3-d]pyrimidin-5-yl)phenyl]-8-azaspiro[4.5]decane-3-carboxylic acid To a solution of intermediate I-128a (135 mg, 0.26 mmol) in MeOH/THF/H2O (3/9/3, 30 mL) was added LiOH.H2O (130 mg, 3 mmol), the reaction mixture was stirred at room temperature overnight until LC-MS showed the starting material was consumed completely. Then concentrated, the mixture was diluted with H2O and adjusted pH to 3-4 with 1N HCl, extracted with EtOAc, the organic layer was washed with brine, dried over anhydrous Na2SO4, concentrated to give the crude intermediate I-129a (120 mg, 93%). ESI-MS (M+1): 494.2 calc. for C27H35N5O: 493.2.

Preparation of intermediate I-130a: 8-[4-ethoxy-3-(1-methyl-7-oxo-3-propyl-6H-pyrazolo[4,3-d]pyrimidin-5-yl)phenyl]-N-tetrahydropyran-2-yloxy-8-azaspiro[4.5]decane-3-carboxamide To a solution of intermediate I-129a (120 mg, 0.24 mmol) in DMF (20 mL) was added EDC.HCl (93 mg, 0.48 mmol), HOBt (65 mg, 0.48 mmol), THPO—NH2 (56 mg, 0.48 mmol), NMM (62 mg, 0.6 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude intermediate I-130a (142 mg, ~100%). ESI-MS (M+1): 593.2 calc. for C32H44N6O5: 592.3.

Preparation of compound 1-56: 8-[4-ethoxy-3-(1-methyl-7-oxo-3-propyl-6H-pyrazolo[4,3-d]pyrimidin-5-yl)phenyl]-8-azaspiro[4.5]decane-3-carbohydroxamic acid A solution of intermediate I-130a (142 mg, 0.24 mmol) in HCl/EtOAc (1 N, 25 mL) was stirred at room temperature for 1 hr, then concentrated to give the crude compound which was purified by prep-HPLC (General procedure, Method 1) to obtained pure compound 1-56 (44.8 mg, 37% yield). ESI-MS (M+1): 509.2 calc. for C27H36N6O4: 508.2; Rt is 1.86.

Following the same synthetic route for compound 1-56 and using the same reagents unless otherwise indicated in the table below, the following compounds were obtained:

| Example | R$_t$ (min) | [M + 1]$^+$ | HPLC Method | Starting Materials |
|---|---|---|---|---|
| 1-54 | 1.81 | 483.2 | 1 | ethyl 3-(4-piperidyl)propanoate (R-09k) |
| 1-65 | 2.82 | 523.3 | 1 | methyl 2-azaspiro[5.5]undecane-9-carboxylate;hydrochloride (R-09l) |
| 1-67 | 2.41 | 467.4 | 1 | ethyl 5-azaspiro[2.4]heptane-2-carboxylate (R-09m) |

Preparation of intermediate I-131a: tert-butyl 2-[4-ethoxy-3-(1-methyl-7-oxo-3-propyl-6H-pyrazolo[4,3-d]pyrimidin-5-yl)phenyl]-2,8-diazaspiro[4.5]decane-8-carboxylate To a solution of intermediate I-13a (445 mg, 1.25 mmol) in anhydrous DCM (50 mL) was added R-29a: tert-butyl 2,8-diazaspiro[4.5]decane-8-carboxylate (200 mg, 0.833 mmol), Cu(OAc)2 (181 mg, 1.0 mmol), DMAP (22 mg, 0.167 mmol), Et3N (337 mg, 3.332 mmol) and 4A MS (0.8 g), then the mixture was stirred at room temperature for 3 hrs under O2 atmosphere. After LC-MS showed the starting material was consumed completely, then added water, filtered, the mixture was extracted with DCM, the organic layer was washed with brine, dried over anhydrous Na2SO4, concentrated to give the crude compound which was purified by Prep-TLC (PE/EtOAc=1.5:1) to give the pure intermediate I-131a (60 mg, 13% yield) as a yellow solid. ESI-MS (M+1): 551 calc. for C30H42N6O4: 550.3.

Preparation of intermediate I-132a: 5-[5-(2,8-diazaspiro[4.5]decan-2-yl)-2-ethoxy-phenyl]-1-methyl-3-propyl-6H-pyrazolo[4,3-d]pyrimidin-7-one A solution of intermediate I-131a (60 mg, 0.109 mmol) in HCl/EtOAc (2M, 5 mL) was stirred at room temperature for 1 hr, then concentrated to give the crude pure intermediate I-132a (35 mg, 71%) as a yellow solid. ESI-MS (M+1): 451 calc. for C25H34N6O2: 450.2.

Preparation of intermediate I-133a: 2-[4-ethoxy-3-(1-methyl-7-oxo-3-propyl-6H-pyrazolo[4,3-d]pyrimidin-5-yl)phenyl]-N-tetrahydropyran-2-yloxy-2,8-diazaspiro[4.5]decane-8-carboxamide THPO—NH2 (18 mg, 0.156 mmol) was dissolved in anhydrous THF (5 mL) and added dropwise via cannula to a cooled solution of CU (25 mg, 0.156 mmol) in anhydrous THF (10 mL) under N2 protection at 0° C. After being stirred for 30 min at room temperature, intermediate I-132a (35 mg, 0.078 mmol) dissolved in anhydrous THF (5 mL) was added, then the mixture was stirred at room temperature overnight until LC-MS showed the starting material was consumed completely. The mixture was extracted with EtOAc, the organic layer was washed with brine, dried over anhydrous Na2SO4, concentrated to give the crude product which was purified by Prep-TLC (EtOAc) to give the pure intermediate I-133a (30 mg, 65% yield) as a yellow oil. ESI-MS (M+1): 594 calc. for C31H43N7O5: 593.3.

Preparation of compound 1-57: 2-[4-ethoxy-3-(1-methyl-7-oxo-3-propyl-6H-pyrazolo[4,3-d]pyrimidin-5-yl)phenyl]-2,8-diazaspiro[4.5]decane-8-carbohydroxamic acid A solution of intermediate I-133a (30 mg, 0.051 mmol) in HCl/EtOAc (4M, 5 mL) was stirred at room temperature for 1 hr, then concentrated to give the crude compound which was purified by prep-HPLC (General procedure, Method 1) to obtained pure compound 1-57 (3.8 mg, 14% yield) as a red solid. ESI-MS (M+1): 510 calc. for C26H35N7O4: 509.2; Rt is 2.77.

Following the same synthetic route for compound 1-57 and using the same reagents unless otherwise indicated in the table below, the following compounds were obtained:

| Example | R$_t$ (min) | [M + 1]$^+$ | HPLC Method | Starting Materials |
|---|---|---|---|---|
| 1-58 | 2.90 | 510 | 1 | tert-butyl 2,7-diazaspiro[4.5]-decane-7-carboxylate (R-29b) |

Preparation of intermediate I-128b: ethyl 2-[2-[4-ethoxy-3-(1-methyl-7-oxo-3-propyl-6H-pyrazolo[4,3-d]pyrimidin-5-yl)phenyl]-2,8-diazaspiro[4.5]decan-8-yl]pyrimidine-5-carboxylate To a solution of intermediate I-132a (240 mg, 0.53 mmol) in acetonitrile (60 mL) was added K2CO3 (194 mg, 1.4 mmol) and R-11e: ethyl 2-chloropyrimidine-5-carboxylate (120 mg, 0.64 mmol), then the mixture was stirred at 60° C. overnight. After LC-MS showed the starting material was consumed completely, the mixture was extracted with EtOAc and washed with brine, dried over anhydrous Na2SO4, concentrated to give the crude product which was purified by Prep-TLC to give intermediate I-128b (130 mg, 41% yield) ESI-MS (M+1): 601.2 calc. for C32H40N8O4: 600.3.

Preparation of intermediate I-129b: 2-[2-[4-ethoxy-3-(1-methyl-7-oxo-3-propyl-6H-pyrazolo[4,3-d]pyrimidin-5-yl)phenyl]-2,8-diazaspiro[4.5]decan-8-yl]pyrimidine-5-carboxylic acid To a solution of intermediate I-128b (130 mg, 0.22 mmol) in MeOH/THF/H2O (3/9/3, 15 mL) was added LiOH.H2O (95 mg, 2.2 mmol), the reaction mixture was stirred at room temperature overnight until LC-MS showed the starting material was consumed completely. Then concentrated, the mixture was diluted with H2O and adjusted pH to 3 with 1N HCl, extracted with EtOAc, the organic layer was washed with brine, dried over anhydrous Na2SO4, concentrated to give the crude intermediate I-129b (95 mg, 77%). ESI-MS (M+1): 573.2 calc. for C30H36N8O4: 572.2.

Preparation of intermediate I-130b: 2-[2-[4-ethoxy-3-(1-methyl-7-oxo-3-propyl-6H-pyrazolo[4,3-d]pyrimidin-5-yl)phenyl]-2,8-diazaspiro[4.5]decan-8-yl]-N-tetrahydropyran-2-yloxy-pyrimidine-5-carboxamide To a solution of intermediate I-129b (95 mg, 0.17 mmol) in DMF (30 mL) was added EDC.HCl (68 mg, 0.35 mmol), HOBt (48 mg, 0.35 mmol), THPO—NH2 (41 mg, 0.35 mmol), NMM (61 mg, 0.6 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give intermediate I-130b (100 mg, 87%). ESI-MS (M+1): 672.2 calc. for C35H45N9O5: 671.3.

Preparation of compound 1-69: 2-[2-[4-ethoxy-3-(1-methyl-7-oxo-3-propyl-6H-pyrazolo[4,3-d]pyrimidin-5-yl)phenyl]-2,8-diazaspiro[4.5]decan-8-yl]pyrimidine-5-carbohydroxamic acid A solution of intermediate I-130b (100 mg, 0.15 mmol) in HCl/EtOAc (1.0 N, 20 mL) was stirred at room temperature for 2 hrs, then concentrated to give the crude compound which was purified by prep-HPLC (General procedure, Method 1) to obtained pure compound 1-69 (15.4 mg, 17%) as yellow solid. ESI-MS (M+1): 588.3 calc. for C30H37N9O4: 587.3; Rt is 3.03.

Following the same synthetic route for compound 1-69 and using the same reagents unless otherwise indicated in the table below, the following compounds were obtained:

| Example | R$_t$ (min) | [M + 1]$^+$ | HPLC Method | Starting Materials |
|---|---|---|---|---|
| 1-70 | 3.20 | 588.3 | 1 | tert-butyl 2,7-diazaspiro[4.5]-decane-7-carboxylate (R-29b) |

Synthetic Route 1n

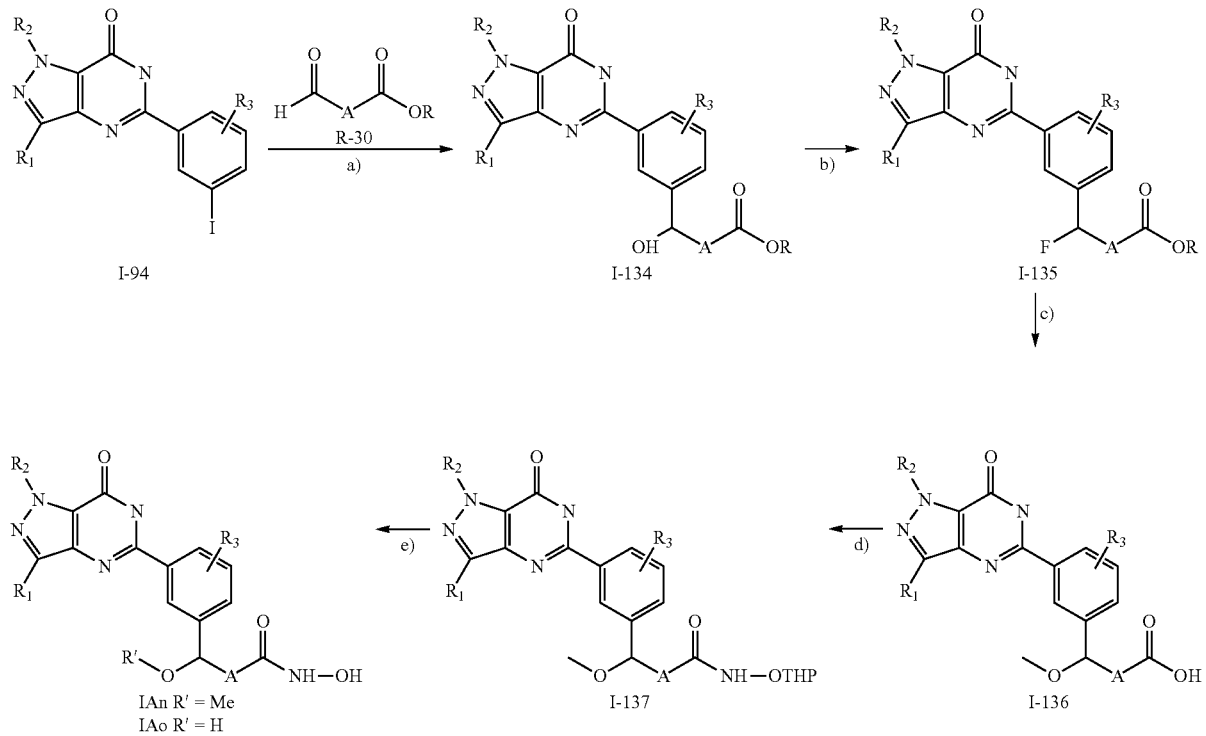

Conditions: a) 1-94, n-BuLi (1.8 eq) in THF at -70° C. for 1 h, then R-30 (1.5 eq) in THF, at r.t. for 15 hrs; b) DAST (1.5 eq) in DCM, at r.t. for 12 hrs; c) LiOH•H$_2$O (12 eq) in THF/methanol/H$_2$O, overnight at r.t.; d) EDC•HCl (2 eq), HOBt (2 eq), THP—O—NH$_2$ (2 eq), NMM (3 eq) in DMF, overnight at r.t.; e) HCl/AcOEt (4M) at r.t for 2 hrs.

In the scheme above R is $(C_1-C_6)$alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-134a: methyl 4-[[4-ethoxy-3-(1-methyl-7-oxo-3-propyl-6H-pyrazolo[4,3-d]pyrimidin-5-yl)phenyl]-hydroxy-methyl]benzoate n-BuLi (1.4 mL, 3.5 mmol) was added to a stirred suspension of intermediate I-94a (850 mg, 1.95 mmol) in THF (60 mL) at −70° C. over a period of 10 min under nitrogen. The resulting solution was stirred at −40° C. for 1 hr, and then commercially available R-30a: methyl 4-formylbenzoate (534 mg, 3.0 mmol) in THF (10 mL) was added over a period of 5 min under nitrogen. The resulting solution was stirred at room temperature for 15 hrs. The reaction was quenched aq. NH4Cl and then extracted with EtOAc. The combined organic phase was washed with saturated brine, dried over anhydrous Na2SO4, filtered and concentrated in vacuo. The residue was purified by column to give the pure intermediate I-134a (400 mg, 43% yield). ESI-MS (M+1): 477.1 calc. for C26H28N4O5: 476.2.

Preparation of intermediate I-135a: methyl 4-[[4-ethoxy-3-(1-methyl-7-oxo-3-propyl-6H-pyrazolo[4,3-d]pyrimidin-5-yl)phenyl]-fluoro-methyl]benzoate To a solution of intermediate I-134a (400 mg, 0.84 mmol) in DCM (40 mL) was added DAST (215 mg, 1.34 mmol) under N2 at 0° C. Then the reaction mixture was stirred at r.t. for 12 hrs. TLC or LCMS showed the starting material was consumed completely. The reaction was quenched by aq. NaHCO3 and then extracted with DCM. The combined organic phase was washed with saturated brine, dried over anhydrous Na2SO4, filtered and concentrated in vacuo. The residue was purified by column to give the pure intermediate I-135a (295 mg, 73% yield). ESI-MS (M+1): 479.1 calc. for C26H27FN4O4: 478.2.

Preparation of intermediate I-136a: 4-[[4-ethoxy-3-(1-methyl-7-oxo-3-propyl-6H-pyrazolo[4,3-d]pyrimidin-5-yl)phenyl]-methoxy-methyl]benzoic acid To a solution of intermediate I-135a (120 mg, 0.25 mmol) in THF/H2O (9/6, 15 mL) was added LiOH.H2O (130 mg, 3 mmol), the reaction mixture was stirred at r.t. overnight until LC-MS showed the starting material was consumed completely. Then concentrated, the mixture was diluted with H2O and adjusted pH to 3-4 with 1N HCl, extracted with EtOAc, the organic layer was washed with brine, dried over anhydrous Na2SO4, concentrated to give intermediate I-136a (110 mg, 92%). ESI-MS (M+1): 477.2 calc. for C26H28N4O5: 476.2.

Preparation of intermediate I-137a: 4-[[4-ethoxy-3-(1-methyl-7-oxo-3-propyl-6H-pyrazolo[4,3-d]pyrimidin-5-yl)phenyl]-methoxy-methyl]-N-tetrahydropyran-2-yloxy-benzamide To a solution of intermediate I-136a (110 mg, 0.23 mmol) in DMF (30 mL) was added EDC.HCl (97 mg, 0.5 mmol), HOBt (68 mg, 0.5 mmol), THPO—NH2 (59 mg, 0.5 mmol), NMM (101 mg, 1.0 mmol). The mixture was stirred at room temperature overnight until LC-MS showed starting material was consumed completely, then quenched with water and extracted with EtOAc, the organic layer was washed with brine, dried over anhydrous Na2SO4, concentrated to give the crude intermediate I-137a (123 mg, 93%). ESI-MS (M+1): 576.2 calc. for C31H37N5O6: 575.2.

Preparation of compounds 1-77: 4-[[4-ethoxy-3-(1-methyl-7-oxo-3-propyl-6H-pyrazolo[4,3-d]pyrimidin-5-yl)phenyl]-methoxy-methyl]benzenecarbohydroxamic acid & 1-78: 4-[[4-ethoxy-3-(1-methyl-7-oxo-3-propyl-6H-pyrazolo[4,3-d]pyrimidin-5-yl)phenyl]-hydroxy-methyl]benzenecarbohydroxamic acid A solution of intermediate I-137a (123 mg, 0.21 mmol) in HCl/EtOAc (1.0 M, 25 mL) was stirred at room temperature for 2 hrs, then concentrated to give a crude mixture of two compounds which was purified by prep-HPLC (General procedure, Method 1) to obtained pure compound 1-77 (22.4 mg). ESI-MS (M+1): 492.2 calc. for C26H29N5O5: 491.2; Rt is 2.88. and pure compound 1-78 (9.9 mg) ESI-MS (M+1): 478.2 calc. for C25H27N5O5: 477.2; Rt is 2.40.

Synthesis of Singletons from Previous Intermediates

Preparation of intermediate I-138a: ethyl 4-ethoxy-3-(1-methyl-7-oxo-3-propyl-6H-pyrazolo[4,3-d]pyrimidin-5-yl)benzoate To a solution of intermediate I-12a (350 mg, 0.897 mmol) in EtOH (30 mL) was added Et3N (227 mg, 2.243 mmol) and Pd(dppf)Cl2 (146 mg, 0.179 mmol) at CO atmosphere, then the mixture was stirred at 80° C. overnight under CO protection until LC-MS showed the starting material was consumed completely, then filtered, concentrated, the mixture was extracted with EtOAc and washed with brine, dried over anhydrous Na2SO4, concentrated to give the crude product which was purified by Prep-TLC (PE/EtOAc=1:1) to give the pure intermediate I-138a (254 mg, 73% yield) as a white solid. ESI-MS (M+1): 385 calc. for C20H24N4O4: 384.2.

Preparation of intermediate I-139a: 4-ethoxy-3-(1-methyl-7-oxo-3-propyl-6H-pyrazolo[4,3-d]pyrimidin-5-yl)benzoic acid To a solution of intermediate I-138a (254 mg, 0.661 mmol) in MeOH/THF/H2O (3/9/3, 15 mL) was added LiOH.H2O (278 mg, 6.61 mmol), the reaction mixture was stirred at 40° C. overnight until LC-MS showed the starting material was consumed completely. Then concentrated, the mixture was diluted with H2O and adjusted pH to 1-2 with 1N HCl, extracted with EtOAc, the organic layer was washed with brine, dried over anhydrous Na2SO4, concentrated to give the crude intermediate I-139a (220 mg, 93%) as a white solid. ESI-MS (M+1): 357 calc. for C18H20N4O4: 356.1.

Preparation of intermediate I-140a: 4-ethoxy-3-(1-methyl-7-oxo-3-propyl-6H-pyrazolo[4,3-d]pyrimidin-5-yl)-N-tetrahydropyran-2-yloxy-benzamide To a solution of intermediate I-139a (220 mg, 0.618 mmol) in DMF (10 mL) was added EDC.HCl (237 mg, 1.236 mmol), HOBt (167 mg, 1.236 mmol), THPO—NH2 (145 mg, 1.236 mmol), NMM (187 mg, 1.854 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-140a (140 mg, 49% yield) as a yellow solid. ESI-MS (M+1): 456 calc. for C23H29N5O5: 455.21.

Preparation of compound 1-27: 4-ethoxy-3-(1-methyl-7-oxo-3-propyl-6H-pyrazolo[4,3-d]pyrimidin-5-yl)benzenecarbohydroxamic acid A solution of intermediate I-140a (140 mg, 0.308 mmol) in HCl/EtOAc (4M, 5 mL) was stirred at room temperature for 1 hr, then concentrated to give the crude compound which was purified by prep-HPLC (General procedure, Method 1) to obtained pure compound 1-27 (85 mg, 74% yield) as a white solid. ESI-MS (M+1): 372 calc. for C18H21 N5O4: 371.1; Rt is 2.25.

Preparation of intermediate I-141a: ethyl (E)-3-[4-ethoxy-3-(1-methyl-7-oxo-3-propyl-6H-pyrazolo[4,3-d]pyrimidin-5-yl)phenyl]prop-2-enoate A mixture of intermediate I-94a (100 mg, 0.228 mmol), ethyl acrylate (71 mg, 0.71 mmol), POT (28 mg, 0.091 mmol) and Et3N (81 mg, 0.798 mmol) was heated in a heavy-walled Pyrex tube at 100° C. overnight under N2 protection. After LC-MS showed the starting material was consumed completely, the mixture was extracted with EtOAc, the organic layer was washed with brine, dried over anhydrous Na2SO4, concentrated to give the crude compound which was purified by Prep-TLC (PE/EtOAc=1:1) to give pure of intermediate I-141a (85 mg, 90% yield) as a yellow solid. ESI-MS (M+1): 411 calc. for C22H26N4O4: 410.2.

Preparation of intermediate I-142a: ethyl 3-[4-ethoxy-3-(1-methyl-7-oxo-3-propyl-6H-pyrazolo[4,3-d]pyrimidin-5-yl)phenyl]propanoate To a solution of intermediate I-141a (85 mg, 0.207 mmol) in MeOH (10 mL) was added Pd/C (30 mg) at H2 atmosphere, then the mixture was stirred at room temperature overnight until LC-MS showed the starting material was consumed completely, then filtered, the filtrate was concentrated to give the crude intermediate I-142a (81 mg, 95%) as a yellow solid which was used in the next step directly. ESI-MS (M+1): 413 calc. for C22H28N4O4: 412.2.

Preparation of intermediate I-143a: 3-[4-ethoxy-3-(1-methyl-7-oxo-3-propyl-6H-pyrazolo[4,3-d]pyrimidin-5-yl)phenyl]propanoic acid To a solution of intermediate I-142a (81 mg, 0.197 mmol) in MeOH/THF/H2O (3/9/3, 15 mL) was added LiOH.H2O (83 mg, 1.97 mmol), the reaction mixture was stirred at 40° C. overnight until LC-MS showed the starting material was consumed completely. Then concentrated, the mixture was diluted with H₂O and adjusted pH to 1-2 with 1N HCl, extracted with EtOAc, the organic layer was washed with brine, dried over anhydrous Na2SO4, concentrated to give the crude of intermediate I-143a (60 mg, 79%) as a yellow solid. ESI-MS (M+1): 385 calc. for C20H24N4O4: 384.1.

Preparation of intermediate I-144a: 3-[4-ethoxy-3-(1-methyl-7-oxo-3-propyl-6H-pyrazolo[4,3-d]pyrimidin-5-yl)phenyl]-N-tetrahydropyran-2-yloxypropanamide To a solution of intermediate I-143a (60 mg, 0.156 mmol) in DMF (10 mL) was added EDC.HCl (60 mg, 0.312 mmol), HOBt (42 mg, 0.312 mmol), THPO—NH2 (36 mg, 0.312 mmol), NMM (48 mg, 0.468 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-144a (60 mg, 80% yield) as a white solid. ESI-MS (M+1): 484 calc. for C25H33N5O5: 483.2.

Preparation of compound 1-31: 3-[4-ethoxy-3-(1-methyl-7-oxo-3-propyl-6H-pyrazolo[4,3-d]pyrimidin-5-yl)phenyl]propanehydroxamic acid A solution of intermediate I-144a (60 mg, 0.124 mmol) in HCl/EtOAc (4M, 5 mL) was stirred at room temperature for 1 hr, then concentrated to give the crude compound which was purified by prep-HPLC (General procedure, Method 1) to obtained pure compound 1-31 (20 mg, 40% yield) as a red solid. ESI-MS (M+1): 400 calc. for C20H25N5O4: 399.2; Rt is 2.44.

Preparation of intermediate I-145a: methyl 3-[4-ethoxy-3-(1-methyl-7-oxo-3-propyl-6H-pyrazolo[4,3-d]pyrimidin-5-yl)anilino]propanoate To a solution of intermediate I-99a (500 mg, 1.53 mmol) and methyl 3,3-dimethoxypropanoate (274 mg, 1.85 mmol) in CH2Cl2 (16 mL) under nitrogen were TFA (8 mL) and triethylsilane (TES, 534 mg, 4.6 mmol) and the reaction mixture was stirred at room temperature overnight until LC-MS showed the starting material was consumed completely. Then concentrated, the mixture was diluted with H₂O and adjusted pH to 7 with aq. NaHCO3, extracted with CH2Cl2, the organic layer was washed with brine, dried over anhydrous Na2SO4, concentrated to give intermediate I-145a (620 mg, 98%). ESI-MS (M+1): 414.2 calc. for C21H27N5O4: 413.2.

Preparation of intermediate I-146a: 3-[4-ethoxy-3-(1-methyl-7-oxo-3-propyl-6H-pyrazolo[4,3-d]pyrimidin-5-yl)anilino]propanoic acid To a solution of intermediate I-145a (620 mg, 1.5 mmol) in THF/MeOH/H2O (3/3/2, 32 mL) was added LiOH.H2O (645 mg, 10 eq). The resulting mixture was stirred at r.t. for 8 hrs, after TLC (PE/EA 5:1) showed the starting materials were consumed completely, then the mixture was diluted with water and adjusted pH to 3-4 with 1N HCl and the mixture was extracted with EtOAc, washed with brine, dried over anhydrous Na2SO4, concentrated to give the crude intermediate I-146a (580 mg, 96%) as a pale yellow oil which was used directly in the next step. ESI-MS (M+1): 400.2; calc. for C20H25N5O4: 399.2.

Preparation of intermediate I-147a: 3-[4-ethoxy-3-(1-methyl-7-oxo-3-propyl-6H-pyrazolo[4,3-d]pyrimidin-5-yl)anilino]-N-tetrahydropyran-2-yloxypropanamide To a solution of intermediate I-146a (580 mg, 1.45 mmol) in DMF (40 mL) was added EDC.HCl (560 mg, 2.9 mmol), HOBt (392 mg, 2.9 mmol), THPO—NH2 (340 mg, 2.9 mmol), NMM (505 mg, 5.0 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by column to give the pure intermediate I-147a (630 mg, 87% yield) as pale yellow oil. ESI-MS (M+1): 499.3 calc. for C25H34N6O5: 498.2.

Preparation of compound 1-33: 3-[4-ethoxy-3-(1-methyl-7-oxo-3-propyl-6H-pyrazolo[4,3-d]pyrimidin-5-yl)anilino]propanehydroxamic acid A solution of intermediate I-147a (300 mg, 0.6 mmol) in HCl/EtOAc (1.0 M, 40 mL) was stirred at room temperature for 4 hrs, then concentrated to give the crude compound which was purified by prep-HPLC (General procedure, Method 1) to obtained pure compound 1-33 (41.2 mg, 16% yield) as white solid. ESI-MS (M+1): 415.1 calc. for C20H26N6O4: 414.2; Rt is 1.88.

Preparation of intermediate I-148a: 5-[5-(1,4-dioxa-8-azaspiro[4.5]decan-8-yl)-2-ethoxy-phenyl]-1-methyl-3-propyl-6H-pyrazolo[4,3-d]pyrimidin-7-one To a solution of intermediate I-94a (1.7 g, 3.87 mmol) in toluene (10 mL) was added Butok (7.74 mL, 1M, 7.74 mmol), Pd2(dab)3 (355 mg, 0.387 mmol), 1,4-dioxa-8-azaspiro[4.5]decane (1.1 g, 7.74 mmol) and x-phos (553 mg, 1.16 mmol). The solution was heated to 120° C. for 1 h under Microwave. The mixture was quenched with aqueous water and extracted with EtOAc, the organic layer was washed with brine, dried over anhydrous Na2SO4, concentrated to give the crude product which was purified by column to give intermediate I-148a (1.4 g, 80%) as a yellow solid. ESI-MS (M+1): 454.2 calc. for C24H31N5O4: 453.2.

Preparation of intermediate I-149a: 5-[2-ethoxy-5-(4-oxo-1-piperidyl)phenyl]-1-methyl-3-propyl-6H-pyrazolo[4,3-d]pyrimidin-7-one A solution of intermediate I-148a (1.4 g, 3.1 mmol) in HCl (6N, 10 mL) was stirred at 70° C. overnight, then concentrated to give the crude product which was purified by the column to obtained pure intermediate I-149a (1.1 g, 85% yield) as white solid. ESI-MS (M+1): 410.2 calc. for C22H27N5O3: 409.2.

Preparation of intermediate I-150a: ethyl 2-[1-[4-ethoxy-3-(1-methyl-7-oxo-3-propyl-6H-pyrazolo[4,3-d]pyrimidin-5-yl)phenyl]-4-piperidylidene]acetate To a solution of methyl 2-diethoxyphosphorylacetate (279 mg, 1.34 mmol) in THF (20 mL) was added NaH (54 mg, 1.34 mmol) at 0° C. The mixture solution was stirred at 0° C. for 1 h. Then, a solution of intermediate I-149a (500 mg, 1.22 mmol) in THF (5 mL) was added at 0° C. The solution was stirred at r.t overnight. The mixture was quenched with aqueous NH4Cl and extracted with EtOAc, the organic layer was washed with brine, dried over anhydrous Na2SO4, concentrated to give the crude product which was purified by the column to give intermediate I-150a (260 mg, 45% yield) as a white solid. ESI-MS (M+1): 480.2; calc. for C26H33N5O4: 479.2.

Preparation of intermediate I-151a: ethyl 2-[1-[4-ethoxy-3-(1-methyl-7-oxo-3-propyl-6H-pyrazolo[4,3-d]pyrimidin-5-yl)phenyl]-4-piperidyl]acetate To a solution of intermediate I-150a (140 mg, 0.29 mmol) in MeOH (40 mL) was added Pd/C (0.3 g) The solution was stirred at r.t for 3 hrs under H2 atmosphere. The solution was filtered and the filtrate was concentrated to give intermediate I-151a (100 mg, 71%) as a white solid. ESI-MS (M+1): 482.2 calc. for C26H35N5O4: 481.2.

Preparation of intermediate I-152a: 2-[1-[4-ethoxy-3-(1-methyl-7-oxo-3-propyl-6H-pyrazolo[4,3-d]pyrimidin-5-yl)phenyl]-4-piperidyl]acetic acid To a solution of intermediate I-151a (100 mg, 0.21 mmol) in THF/MeOH/H2O (3/3/2, 8 mL) was added LiOH.H2O (88 mg, 10 eq). The resulting mixture was stirred at r.t. for 8 hrs, after TLC showed the starting materials were consumed completely, then the mixture was diluted with water and adjusted pH to 6-7 with 1N HCl and the mixture was extracted with EtOAc, washed with brine, dried over anhydrous Na2SO4, concentrated to afford the desired intermediate I-152a (90 mg, 95%). ESI-MS (M+1): 454.2; calc. for C24H31N5O4: 453.2.

Preparation of intermediate I-153a: 2-[1-[4-ethoxy-3-(1-methyl-7-oxo-3-propyl-6H-pyrazolo[4,3-d]pyrimidin-5-yl)phenyl]-4-piperidyl]-N-tetrahydropyran-2-yloxy-acetamide To a solution of intermediate I-152a (90 mg, 0.2 mmol) in DMF (10 mL) was added EDC.HCl (77 mg, 0.4 mmol), HOBt (54 mg, 0.4 mmol), THPONH2 (47 mg, 0.4 mmol) and NMM (62 mg, 0.6 mmol) at r.t, then the mixture was stirred at room temperature overnight. The mixture was quenched with aqueous water and extracted with EtOAc, the organic layer was washed with brine, dried over anhydrous Na2SO4, concentrated to give the crude product which was purified by prep-TLC to give intermediate I-153a (70 mg, 64% yield) as a pale yellow solid. ESI-MS (M+1): 553.3; calc. for C29H40N6O5: 552.3.

Preparation of compound 1-44: 2-[1-[4-ethoxy-3-(1-methyl-7-oxo-3-propyl-6H-pyrazolo[4,3-d]pyrimidin-5-yl)phenyl]-4-piperidyl]ethanehydroxamic acid A solution of intermediate I-153a (70 mg, 0.13 mmol) in HCl/EtOAc (10 mL) was stirred at r.t for 1 h, then concentrated to give the crude product which was purified by prep-HPLC (General procedure, Method 1) to obtained pure compound 1-44 (22.9 mg, 35% yield) as a white solid. ESI-MS (M+1): 469.2 calc. for C24H32N6O4: 468.2; Rt is 2.01.

Preparation of intermediate I-154a: tert-butyl 4-[[4-ethoxy-3-(1-methyl-7-oxo-3-propyl-6H-pyrazolo[4,3-d]pyrimidin-5-yl)phenyl]methyl]piperazine-1-carboxylate To a solution of intermediate I-115a (400 mg, 1.176 mmol) in anhydrous toluene (20 mL) was added tert-butyl piperazine-1-carboxylate (325 mg, 1.764 mmol), Ti(Oi-Pr)4 (413 mg, 1.764 mmol), then the mixture was stirred at room temperature for 1.5 hrs under N2 protection, and Na(AcO)3BH (499 mg, 2.352 mmol) was added, the mixture was stirred at room temperature overnight, the mixture was extracted with EtOAc three times, the organic layer was washed with aqueous brine, dried over anhydrous Na2SO4, concentrated to give the crude compound which was purified by Prep-TLC (PE/EtOAc=1:1.5) to give pure intermediate I-154a (450 mg, 75% yield) as a white solid. ESI-MS (M+1): 511 calc. for C27H38N6O4: 510.2.

Preparation of intermediate I-155a: 5-[2-ethoxy-5-(piperazin-1-ylmethyl)phenyl]-1-methyl-3-propyl-6H-pyrazolo[4,3-d]pyrimidin-7-one A solution of intermediate I-154a (450 mg, 0.882 mmol) in HCl/EtOAc (4M, 10 mL) was stirred at room temperature for 1 hr, then concentrated to give the crude intermediate I-155a (340 mg, 93%) as a white solid. ESI-MS (M+1): 411 calc. for C22H30N6O2: 410.2.

Preparation of intermediate I-156a: ethyl 2-[4-[[4-ethoxy-3-(1-methyl-7-oxo-3-propyl-6H-pyrazolo[4,3-d]pyrimidin-5-yl)phenyl]methyl]piperazin-1-yl]pyrimidine-5-carboxylate To a solution of intermediate I-155a (170 mg, 0.307 mmol) in acetonitrile (20 mL) was added K2CO3 (85 mg, 0.614 mmol) and R-11e: ethyl 2-chloropyrimidine-5-carboxylate (57 mg, 0.307 mmol), then the mixture was stirred at 60° C. overnight. The mixture was extracted with EtOAc and washed with brine, dried over anhydrous Na2SO4, concentrated to give the crude product which was purified by Prep-TLC (PE/EtOAc=1:1.5) to give the pure intermediate I-156a (150 mg, 87%) as a yellow solid. ESI-MS (M+1): 561 calc. for C29H36N8O4: 560.2.

Preparation of intermediate I-157a: 2-[4-[[4-ethoxy-3-(1-methyl-7-oxo-3-propyl-6H-pyrazolo[4,3-d]pyrimidin-5-yl)phenyl]methyl]piperazin-1-yl]pyrimidine-5-carboxylic acid To a solution of intermediate I-156a (150 mg, 0.268 mmol) in MeOH/THF/H2O (3/9/3, 15 mL) was added LiOH.H2O (112 mg, 2.68 mmol), the reaction mixture was stirred at room temperature overnight until LC-MS showed the starting material was consumed completely. Then concentrated, the mixture was diluted with $H_2O$ and adjusted pH to 1-2 with 1N HCl, extracted with EtOAc, the organic layer was washed with brine, dried over anhydrous Na2SO4, concentrated to give the crude intermediate I-157a (130 mg, 90.91%) as a white solid. ESI-MS (M+1): 533 calc. for C27H32N8O4: 532.2.

Preparation of intermediate I-158a: 2-[4-[[4-ethoxy-3-(1-methyl-7-oxo-3-propyl-6H-pyrazolo[4,3-d]pyrimidin-5-yl)phenyl]methyl]piperazin-1-yl]-N-tetrahydropyran-2-yloxy-pyrimidine-5-carboxamide To a solution of intermediate I-157a (130 mg, 0.244 mmol) in DMF (10 mL) was added EDC.HCl (94 mg, 0.488 mmol), HOBt (66 mg, 0.488 mmol), THPO—NH2 (57 mg, 0.488 mmol), NMM (74 mg, 0.732 mmol). The mixture was stirred at room temperature overnight, then quenched with water and extracted with EtOAc, the organic layer was washed with brine, dried over anhydrous Na2SO4, concentrated to give the crude product which was purified by Prep-TLC (EtOAc) to give the pure intermediate I-158a (120 mg, 78% yield) as a white solid. ESI-MS (M+1): 632 calc. for C32H41N9O5: 631.3.

Preparation of compound 1-48: 2-[4-[[4-ethoxy-(1-methyl-7-oxo-3-propyl-6H-pyrazolo[4,3-d]pyrimidin-5-yl)phenyl]methyl]piperazin-1-yl]pyrimidine-5-carbohydroxamic acid A solution of intermediate I-158a (120 mg, 0.190 mmol) in HCl/EtOAc (4M, 5 mL) was stirred at room temperature for 1 hr, then concentrated to give the crude compound which was purified by prep-HPLC (General procedure, Method 1) to obtained pure compound 1-48 (26.2 mg, 25%) as a white solid. ESI-MS (M+1): 548 calc. for C27H33N9O4: 547.2; Rt is 1.88.

Preparation of intermediate I-159a: 4-[[4-ethoxy-3-(1-methyl-7-oxo-3-propyl-6H-pyrazolo[4,3-d]pyrimidin-5-yl)phenyl]methyl]-N-tetrahydropyran-2-yloxy-piperazine-1-carboxamide THPO—NH2 (146 mg, 1.248 mmol) was dissolved in anhydrous THF (10 mL) and added dropwise via cannula to a cooled solution of CDI (202 mg, 1.248 mmol) in anhydrous THF (20 mL) under N2 protection at 0° C. After being stirred for 30 min at room temperature, intermediate I-155a (170 mg, 0.415 mmol) dissolved in anhydrous THF (10 mL) was added, then the reaction mixture was stirred at room temperature overnight. The mixture was extracted with EtOAc, the organic layer was washed with brine, dried over anhydrous Na2SO4, concentrated to give the crude product which was purified by Prep-TLC (EtOAc) to give the pure intermediate I-159a (150 mg, 65% yield) as a yellow oil. ESI-MS (M+1): 554 calc. for C28H39N7O5: 553.3.

Preparation of compound 1-50: 4-[[4-ethoxy-3-(1-methyl-7-oxo-3-propyl-6H-pyrazolo[4,3-d]pyrimidin-5-yl)phenyl]methyl]piperazine-1-carbohydroxamic acid A solution of intermediate I-159a (150 mg, 0.271 mmol) in HCl/EtOAc (4M, 5 mL) was stirred at room temperature for 1 hr, then concentrated to give the crude compound which was purified by prep-HPLC (General procedure, Method 1) to obtained pure compound 1-50 (43.4 mg, 34% yield) as a white solid. ESI-MS (M+1): 470 calc. for C23H31N7O4: 469.2; Rt is 1.97.

Preparation of intermediate I-160a: 4-[[4-ethoxy-3-(1-methyl-7-oxo-3-propyl-6H-pyrazolo[4,3-d]pyrimidin-5-yl)phenyl]methyl]-N-tetrahydropyran-2-yloxy-piperidine-1-carboxamide THPO—NH2 (57 mg, 0.487 mmol) was dissolved in anhydrous THF (10 mL) and added dropwise via cannula to a cooled solution of CDI (79 mg, 0.487 mmol) in anhydrous THF (20 mL) under N2 protection at 0° C. After being stirred for 30 min at room temperature, intermediate I-107a (100 mg, 0.244 mmol) dissolved in anhydrous THF (10 mL) was added, then the mixture was stirred at room temperature. The mixture was extracted with EtOAc, the organic layer was washed with brine, dried over anhydrous Na2SO4, concentrated to give the crude product which was purified by Prep-TLC (EtOAc) to give the pure intermediate I-160a (105 mg, 77% yield) as a white solid. ESI-MS (M+1): 553 calc. for C29H40N6O5: 552.3.

Preparation of compound 1-49: 4-[[4-ethoxy-3-(1-methyl-7-oxo-3-propyl-6H-pyrazolo[4,3-d]pyrimidin-5-yl)phenyl]methyl]piperidine-1-carbohydroxamic acid A solution of intermediate I-160a (105 mg, 0.190 mmol) in HCl/EtOAc (4M, 5 mL) was stirred at room temperature for 1 hr, then concentrated to give the crude compound which was purified by prep-HPLC (General procedure, Method 1) to obtained pure compound 1-49 (19.1 mg, 21%)

Preparation of intermediate I-161a: ethyl 2-[4-ethoxy-3-(1-methyl-7-oxo-3-propyl-6H-pyrazolo[4,3-d]pyrimidin-5-yl)phenyl]acetate To a solution of intermediate I-12a (500 mg, 1.282 mmol), Pd2(dba)3 (118 mg, 0.128 mmol), X-Phos (147 mg, 0.256 mmol) in anhydrous THF (30 mL) was added R-31a: bromo-(2-ethoxy-2-oxo-ethyl)zinc (20 mL, excess) under N2 protection, then the mixture was stirred at 80° C. overnight under N2 protection until LC-MS showed the starting material was consumed completely, then the mixture was extracted with EtOAc and washed with brine, dried over anhydrous Na2SO4, concentrated to give the crude product which was purified by Prep-TLC (PE/EtOAc=1:1) to give pure intermediate I-161a (270 mg, 52% yield) as a white solid. ESI-MS (M+1): 399 calc. for C21H26N4O4: 398.2.

Preparation of intermediate I-162a: 2-[4-ethoxy-3-(1-methyl-7-oxo-3-propyl-6H-pyrazolo[4,3-d]pyrimidin-5-yl)phenyl]acetic acid To a solution of intermediate I-161a (270 mg, 0.678 mmol) in MeOH/THF/H2O (3/9/3, 15 mL) was added LiOH.H2O (285 mg, 6.78 mmol), the reaction mixture was stirred at room temperature overnight. Then concentrated, the mixture was diluted with H$_2$O and adjusted pH to 1-2 with 1N HCl, extracted with EtOAc, the organic layer was washed with brine, dried over anhydrous Na2SO4, concentrated to give the crude intermediate I-162a (230 mg, 91%) as a white solid. ESI-MS (M+1): 371 calc. for C19H22N4O4: 370.1.

Preparation of intermediate I-163a: 2-[4-ethoxy-3-(1-methyl-7-oxo-3-propyl-6H-pyrazolo[4,3-d]pyrimidin-5-yl)phenyl]-N-tetrahydropyran-2-yloxy-acetamide To a solution of intermediate I-162a (115 mg, 0.311 mmol) in DMF (10 mL) was added EDC.HCl (119 mg, 0.622 mmol), HOBt (84 mg, 0.622 mmol), THPO—NH2 (73 mg, 0.622 mmol), NMM (94 mg, 0.933 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude product which was purified by Prep-TLC (EtOAc) to give the pure intermediate I-163a (116 mg, 79% yield) as a white solid. ESI-MS (M+1): 470 calc. for C24H31 N5O5: 469.2.

Preparation of compound 1-52: 2-[4-ethoxy-3-(1-methyl-7-oxo-3-propyl-6H-pyrazolo[4,3-d]pyrimidin-5-yl)phenyl]ethanehydroxamic acid A solution of intermediate I-163a (116 mg, 0.247 mmol) in HCl/EtOAc (4M, 5 mL) was stirred at room temperature for 1 hr, then concentrated to give the crude compound which was purified by prep-HPLC (General procedure, Method 1) to obtained pure compound 1-52 (12.2 mg, 13%) as a white solid. ESI-MS (M+1): 386 calc. for C19H23N5O4: 385.2; Rt is 2.32.

Preparation of intermediate I-164a: methyl 5-[4-ethoxy-3-(1-methyl-7-oxo-3-propyl-6H-pyrazolo[4,3-d]pyrimidin-5-yl)benzoyl]thiophene-2-carboxylate To a solution of intermediate I-13a (1.25 g, 3.5 mmol) in anisole (40 mL) was added methyl 5-bromothiophene-2-carboxylate (R-11z) (655 mg, 4.2 mmol), Pd(dppf)Cl2 (146 mg, 0.2 mmol), K2CO3 (1.52 g, 11 mmol) and KI (1.83 g, 11 mmol). The solution was carried out at 85° C. under CO (1 atm) for 3 days. Then the reaction mixture was cooled to room temperature, water was added and extracted with EtOAc, washed with brine and dried over anhydrous Na2SO4, concentrated to give the crude product which was purified by column to the pure intermediate I-164a (260 mg, 15% yield). ESI-MS (M+1): 481.1 calc. for C24H24N4O5S: 480.1.

Preparation of intermediate I-165a: 5-[4-ethoxy-3-(1-methyl-7-oxo-3-propyl-6H-pyrazolo[4,3-d]pyrimidin-5-yl)benzoyl]thiophene-2-carboxylic acid To a solution of intermediate I-164a (100 mg, 0.21 mmol) in MeOH/THF/H2O (3/9/3, 15 mL) was added LiOH.H2O (130 mg, 3 mmol), the reaction mixture was stirred at r.t. overnight. Then concentrated, the mixture was diluted with H$_2$O and adjusted pH to 3-4 with 1N HCl, extracted with EtOAc, the organic layer was washed with brine, dried over anhydrous Na2SO4, concentrated to give the crude intermediate I-165a (83 mg, 85%). ESI-MS (M+1): 467.1 calc. for C23H22N4O5S: 466.1.

Preparation of intermediate I-166a: 5-[4-ethoxy-3-(1-methyl-7-oxo-3-propyl-6H-pyrazolo[4,3-d]pyrimidin-5-yl)benzoyl]-N-tetrahydropyran-2-yloxy-thiophene-2-carboxamide To a solution of intermediate I-165a (83 mg, 0.18 mmol) in DMF (30 mL) was added EDC.HCl (78 mg, 0.4 mmol), HOBt (55 mg, 0.4 mmol), THPO—NH2 (47 mg, 0.4 mmol), NMM (101 mg, 1.0 mmol). The mixture was stirred at room temperature overnight until LC-MS showed the starting material was consumed completely, then quenched with water and extracted with EtOAc, the organic layer was washed with brine, dried over anhydrous Na2SO4, concentrated to give the crude intermediate I-166a (95 mg, 93%). ESI-MS (M+1): 566.2 calc. for C28H31N5O6S: 565.2.

Preparation of compound 1-79: 5-[4-ethoxy-3-(1-methyl-7-oxo-3-propyl-6H-pyrazolo[4,3-d]pyrimidin-5-yl)benzoyl]thiophene-2-carbohydroxamic acid A solution of intermediate I-166a (95 mg, 0.168 mmol) in HCl/EtOAc (1.0 M, 20 mL) was stirred at room temperature for 2 hrs, then concentrated to give the crude compound which was purified by prep-HPLC (General procedure, Method 1) to obtained pure compound 1-79 (48.9 mg, 60% yield). ESI-MS (M+1): 482.1 calc. for C23H23N5O5S: 481.1; Rt is 2.52.

Preparation of intermediate I-167a: tert-butyl 3-[4-ethoxy-3-(1-methyl-7-oxo-3-propyl-6H-pyrazolo[4,3-d]pyrimidin-5-yl)phenyl]-3-hydroxy-cyclobutanecarboxylate n-BuLi (2.6 mL, 6.5 mmol) was added to a stirred suspension of intermediate I-94a (2.63 g, 6.0 mmol) in THF (60 mL) at −70° C. over a period of 5 mins under nitrogen.

(as a white solid. ESI-MS (M+1): 469 calc. for C24H32N6O4: 468.2; Rt is 2.99.)

The resulting solution was stirred at −40° C. for 1 hr, and then then R-28b: tert-butyl 3-oxocyclobutanecarboxylate (1.1 g, 6.5 mmol) in THF (10 mL) was added over a period of 5 mins under nitrogen. The resulting solution was stirred at room temperature for 15 hrs. The reaction was quenched aq. NH4Cl and then extracted with EtOAc. The combined organic phase was washed with saturated brine, dried over anhydrous Na2SO4, filtered and concentrated in vacuo. The residue was purified by column to give the pure intermediate I-167a (830 mg, 26% yield). ESI-MS (M+1): 483.2 calc. for C26H34N4O5: 482.2.

Preparation of intermediate I-168a: 3-[4-ethoxy-3-(1-methyl-7-oxo-3-propyl-6H-pyrazolo[4,3-d]pyrimidin-5-yl)phenyl]cyclobutanecarboxylic acid To a solution of intermediate I-167a (700 mg, 1.45 mmol) in TFA (8 mL) was added a solution of TESH (8 mL) in DCM (8 mL) dropwise at 0° C. The reaction mixture was stirred at room temperature for another 10 hrs. LCMS showed the starting material was consumed completely. The reaction was quenched by aq. NaHCO3 slowly and then extracted with DCM (50 mL). The combined organic phase was washed with saturated brine (60 mL), dried over anhydrous Na2SO4, filtered and concentrated to give the crude intermediate I-168a (512 mg, 86%). ESI-MS (M+1): 411.1 calc. for C22H26N4O4: 410.2.

Preparation of compound 1-82: (racemic) 3-[4-ethoxy-3-(1-methyl-7-oxo-3-propyl-6H-pyrazolo[4,3-d]pyrimidin-5-yl)phenyl]cyclobutanecarbohydroxamic acid To a solution of intermediate I-168a (512 mg, 1.25 mmol) in DMF (40 mL) was added BOP (995 mg, 2.25 mmol), DIEA (413 mg, 3.2 mmol) and NH2OH HCl (152 mg, 2.2 mmol). The mixture was stirred at 80° C. overnight until LC-MS showed the starting material was consumed completely, then quenched with water and extracted with EtOAc, the organic layer was washed with brine, dried over anhydrous Na2SO4, concentrated to give the crude product which was purified by prep-HPLC (General procedure, Method 1) to obtained compound 1-82 as a racemic mixture (320 mg, 60% yield) as a yellow solid. ESI-MS (M+1): 426.2 calc. for C22H27N5O4: 425.2. Rt is 2.61.

Preparation of compound 1-84 & 1-85: cis & trans 3-[4-ethoxy-3-(1-methyl-7-oxo-3-propyl-6H-pyrazolo[4,3-d]pyrimidin-5-yl)phenyl]cyclobutanecarbohydroxamic acid The cis and trans corresponding isomers were separated from the racemic mixture 1-82 by SFC to obtain cis isomers 1-84 (57.6 mg): ESI-MS (M+1): 426.2 calc. for C22H27N5O4: 425.2 (Rt is 2.48) and trans isomers 1-85 (49.7 mg): ESI-MS (M+1): 426.2 calc. for C22H27N5O4: 425.2 (Rt is 2.43).

Preparation of intermediate I-183a: ethyl 2-[[4-ethoxy-3-(1-methyl-7-oxo-3-propyl-6H-pyrazolo[4,3-d]pyrimidin-5-yl)phenyl]-hydroxy-methyl]cyclopropanecarboxylate n-BuLi (1.1 mL, 2.7 mmol) was added to a stirred suspension of intermediate I-94a (1.1 g, 2.5 mmol) in THF (40 mL) at −70° C. over a period of 10 min under nitrogen. The resulting solution was stirred at −40° C. for 1 hr, and then reagent ethyl (1S,2S)-2-formylcyclopropanecarboxylate (R-30d) (375 mg, 2.64 mmol, CAS:20417-61-2, predominantly trans, purchased from Aldrich) in THF (10 mL) was added over a period of 5 min under nitrogen. The resulting solution was stirred at room temperature for 15 hrs. The reaction was quenched aq. NH4Cl and then extracted with EtOAc. The combined organic phase was washed with saturated brine, dried over anhydrous Na2SO4, filtered and concentrated in vacuo. The residue was purified by column to give the pure intermediate I-183a (210 mg, 18% yield). ESI-MS (M+1): 455.1 calc. for C24H30N4O5: 454.2.

Preparation of intermediate I-184a: ethyl 2-[[4-ethoxy-3-(1-methyl-7-oxo-3-propyl-6H-pyrazolo[4,3-d]pyrimidin-5-yl)phenyl]methyl]cyclopropanecarboxylate To a solution of intermediate I-183a (210 mg, 0.46 mmol) in TFA (8 mL) was added a solution of TESH (8 mL) in DCM (8 mL) dropwise at −0° C. The reaction mixture was stirred at room temperature for another 10 hrs. The reaction was quenched by aq. NaHCO3 slowly and then extracted with DCM (50 mL). The combined organic phase was washed with saturated brine (60 mL), dried over anhydrous Na2SO4, filtered and concentrated to give the crude intermediate I-184a (135 mg, 67%). ESI-MS (M+1): 439.1 calc. for C24H30N4O4: 438.2.

Preparation of intermediate I-185a: 2-[[4-ethoxy-3-(1-methyl-7-oxo-3-propyl-6H-pyrazolo[4,3-d]pyrimidin-5-yl)phenyl]methyl]cyclopropanecarboxylic acid To a solution of intermediate I-184a (135 mg, 0.31 mmol) in MeOH/THF/H2O (3/9/3, 15 mL) was added LiOH.H2O (130 mg, 3 mmol), the reaction mixture was stirred at r.t. overnight. Then concentrated, the mixture was diluted with H2O and adjusted pH to 3-4 with 1N HCl, extracted with EtOAc, the organic layer was washed with brine, dried over anhydrous Na2SO4, concentrated to give intermediate I-185a (125 mg, 98%). ESI-MS (M+1): 411.1 calc. for C22H26N4O4: 410.2.

Preparation of intermediate I-186a: 2-[[4-ethoxy-3-(1-methyl-7-oxo-3-propyl-6H-pyrazolo[4,3-d]pyrimidin-5-yl)phenyl]methyl]-N-tetrahydropyran-2-yloxy-cyclopropanecarboxamide To a solution of intermediate I-185a (125 mg, 0.3 mmol) in DMF (20 mL) was added EDC.HCl (97 mg, 0.5 mmol), HOBt (68 mg, 0.5 mmol), THPO—NH2 (59 mg, 0.5 mmol), NMM (101 mg, 1.0 mmol). The mixture was stirred at room temperature overnight, then quenched with water and extracted with EtOAc, the organic layer was washed with brine, dried over anhydrous Na2SO4, concentrated to give the crude intermediate I-186a (93 mg, 61%). ESI-MS (M+1): 510.2 calc. for C27H35N5O5: 509.2.

Preparation of compound 1-86: 2-[[4-ethoxy-3-(1-methyl-7-oxo-3-propyl-6H-pyrazolo[4,3-d]pyrimidin-5-yl)phenyl]methyl]cyclopropanecarbohydroxamic acid A solution of intermediate I-186a (93 mg, 0.183 mmol) in HCl/EtOAc (1.0 M, 20 mL) was stirred at room temperature for 2 hrs, then concentrated to give the crude compound which was purified by prep-HPLC (General procedure, Method 1) to obtained pure compound 1-86 (32.2 mg, 41% yield). ESI-MS (M+1): 426.2. calc. for C22H27N5O4: 425.2; Rt is 2.71.

Preparation of intermediate I-187a: 4-[4-ethoxy-3-(1-methyl-7-oxo-3-propyl-6H-pyrazolo[4,3-d]pyrimidin-5-yl)anilino]-N-tetrahydropyran-2-yloxypiperidine-1-carboxamide THPO—NH2 (34.2 mg, 0.293 mmol) was dissolved in anhydrous THF (5 mL) and added dropwise via cannula to a cooled solution of CU (47.7 mg, 0.293 mmol) in anhydrous THF (10 mL) under N2 protection at 0° C. After being stirred for 30 min at room temperature, intermediate I-101a (100 mg, 0.244 mmol) dissolved in anhydrous THF (5 mL) was added, then the mixture was stirred at room temperature overnight. The mixture was extracted with EtOAc, the organic layer was washed with brine, dried over anhydrous Na2SO4, concentrated to give the crude product which was purified by Prep-TLC (EtOAc) to give the pure intermediate I-187a (100 mg, 73% yield) as a yellow oil. ESI-MS (M+1): 554 calc. for C28H39N7O5: 553.3.

Preparation of compound 1-64: 4-[4-ethoxy-3-(1-methyl-7-oxo-3-propyl-6H-pyrazolo[4,3-d]pyrimidin-5-yl)anilino]piperidine-1-carbohydroxamic acid A solution of intermediate I-187a (100 mg, 0.18 mmol) in HCl/EtOAc (4M, 5 mL) was stirred at room temperature for 1 hr, then concentrated to give the crude compound which was purified by prep-HPLC (General procedure, Method 1) to obtained pure compound 1-64 (28 mg, 33% yield) as a yellow solid. ESI-MS (M+1): 470.2 calc. for C23H31N7O4: 469.2; Rt is 1.96.

Synthetic Route 2a

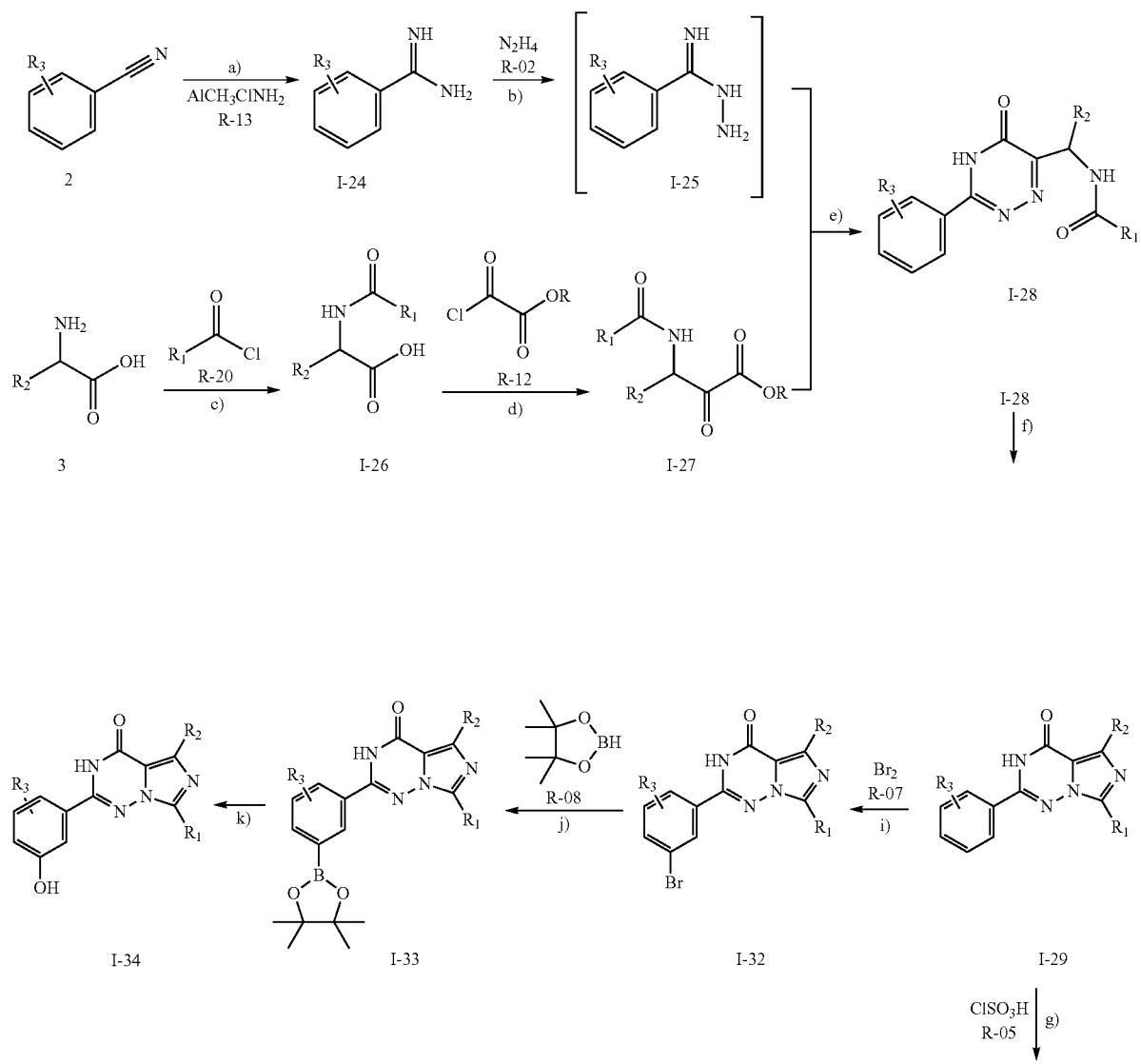

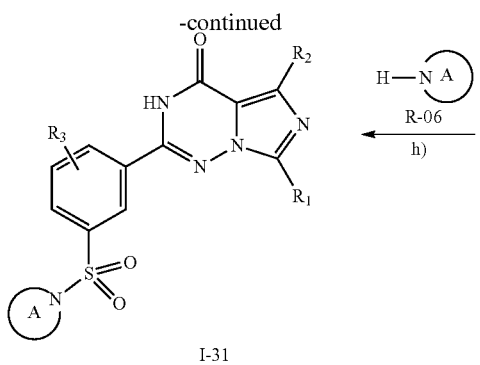
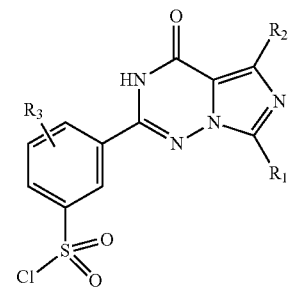

Conditions: a) R-13 obtained in-situ (NH₄Cl and Al(CH₃)₃ 2 N in toluene at 0° C.); then, 2 added and refluxed for 9 hours; b) N₂H₄·H₂O in methanol at r.t.; c) R-20 (1.1 eq) added to 3 in NaOH 4 N (3 eq) solution at 0° C.; d) DMAP (cat.) and pyridine, in THF, at 55° C.; then, R-12 is added and refluxed for 2 hours; e) refluxed in methanol for 4 hours; f) POCl₃ and AcOH, at 110° C. for 2 hours; g) ClSO₃H, r.t. for 2 hours; h) R-06 (2 eq) in methanol, MW at 100° C. for 1 hour; i) Br₂ (1.2 eq) in AcOH overnight at r.t.; j) AcOK (2 eq), R-08 (1.2 eq) and (dppf)₂Cl₂Pd (0.1 eq), in dioxane, overnight at 90° C.; k) NaOH/H₂O (4M) and H₂O₂ (1.3 eq) in water overnight at r.t.

In the scheme above R is $(C_1-C_6)$alkyl, X is halogen, A is an optionally substituted 3- to 7-membered heterocyclic monocyclic ring.

Preparation of intermediate I-24a: 2-Ethoxybenzamidine

To a solution of 2-ethoxybenzonitrile (2, 10 g, 68 mmol) in toluene (150 mL) was added AlCH₃ClNH₂ (1 eq). The methylchloroaluminum amide was freshly prepared, in-situ; NH₄Cl (0.535 g, 10 mmol) was dissolved in dry toluene (10 mL) at 0° C. and trimethylaluminum (2 M in toluene, 5.0 mL, 10 mmol) was added and the reaction was warmed to r.t. and stirred for 1 hour to give the AlCH₃ClNH₂, which was used directly. The mixture was stirred at 80° C. for 6 hours. The reaction mixture was concentrated under vacuo to give crude I-24a (8.42 g, 75.4% yield). ESI-MS (M+1): 165 calc. for $C_9H_{12}N_2O$: 164.2.

Preparation of intermediate I-26a: 2-Acetamidopentanoic acid

Butyryl chloride (R-20a, 9.6 g, 90 mmol) was added dropwise to a solution of D,L-alanine (3, 6.68 g, 75 mmol) in aqueous sodium hydroxide (7.2 g, 180 mmol) at about 5° C. to 10° C. The mixture was stirred overnight at r.t. The reaction mixture was extracted with DCM which was recovered to obtain crude I-26a as an oily residue (7.65 g, 64% yield). ESI-MS (M+1): 160 calc. for $C_7H_{13}NO_3$: 159.2.

Preparation of intermediate I-27a: Ethyl 3-acetamido-2-oxohexanoate

Ethoxalyl chloride (R-12, 8.6 g, 63.0 mmol, 2 eq) was added dropwise with stirring to a solution of I-26a (5 g, 31.4 mmol), pyridine (5.15 g, 66 mmol, 2.1 eq), and DMAP (0.125 g, 1 mmol) in THF (200 mL). The reaction mixture was refluxed for 4 hours, cooled, diluted with water (100 mL) and extracted with EA. Ethyl acetate was recovered to obtain oily material. This crude was dissolved in ethanol (100 mL) and sodium bicarbonate (1.58 g, 18.8 mmol) was added. The contents were refluxed for 4 hours, cooled and sodium bicarbonate was removed by filtration. The mixture was concentrated to give the crude product which was purified by column chromatography with hexane:EA (3:1) to obtain I-27a (2.1 g, 31% yield). ESI-MS (M+1): 216 calc. for $C_{10}H_{17}NO_4$: 215.2.

Preparation of intermediate I-28a: N-(1-(3-(2-ethoxyphenyl)-4,5-dihydro-5-oxo-1,2,4-triazin-6-yl)ethyl)butanamide To a solution of I-24a (1.11 g, 6.8 mmol) in ethanol (15 mL) was added a solution of hydrazine hydrate (0.345 g, 6.8 mmol) in ethanol (5 mL) over about 10 to 15 minutes. The reaction mixture was stirred at r.t. for 10 minutes. MgSO₄ (1 g) was added and the reaction mixture, where intermediate I-25 was generated and reacted without isolation, was heated to reflux. Then, a solution of I-27a (1.48 g, 6.8 mmol) in ethanol (10 mL) was added in about 15 minutes. The reaction mixture was refluxed for 3 hours. The mixture was concentrated to give the crude product which was purified by column chromatography to obtain the compound I-28a (638 mg, 28.4% yield). ESI-MS (M+1): 331 calc. for $C_{17}H_{22}N_4O_3$: 330.4.

Preparation of intermediate I-29a: 2-(2-Ethoxyphenyl)-5-methyl-7-propyl-3H-imidazo[5,1-f][1,2,4]triazin-4-one To a solution of I-28a (456 mg, 1.38 mmol) in 1,2-dichloroethane (10 mL) was added POCl₃ (1.67 g, 11 mmol, 8 eq). The reaction was refluxed for 2 hours. The reaction mixture was cooled at r.t., diluted in DCM (20 mL) and neutralized by adding aqueous sodium hydroxide solution. The reaction mixture was extracted and concentrated under vacuo to give the crude product compound I-29a (169 mg, 39.2% yield). ESI-MS (M+1): 313 calc. for $C_{17}H_{20}N_4O_2$: 312.4.

Preparation of intermediate I-30a: 4-Ethoxy-3-(5-methyl-4-oxo-7-propyl-3H-imidazo[5,1-f][1,2,4]triazin-2-yl)benzenesulfonyl chloride I-30a was obtained starting from I-29a in an analogous manner to I-10a. 80% yield. ESI-MS (M+1): 411 calc. for $C_{17}H_{19}ClN_4O_4S$: 410.08.

Preparation of intermediate I-31a: 2-(2-Ethoxy-5-piperazin-1-ylsulfonylphenyl)-5-methyl-7-propyl-3H-imidazo[5,1-f][1,2,4]triazin-4-one I-31a was obtained starting from I-30a in an analogous manner to I-11a 82.6% yield. ESI-MS (M+1): 461 calc. for $C_{21}H_{28}N_6O_4S$: 460.2.

Synthetic Route 2b

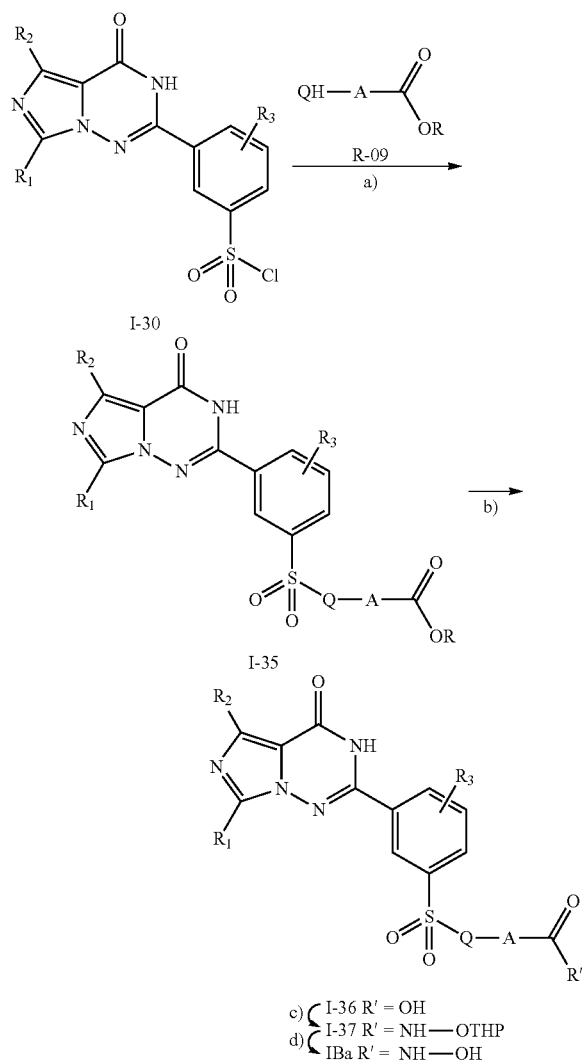

Conditions: a) Et₃N and R-09 in ethanol, MW at 100° C. for 2 hours;
b) LiOH·H₂O (5 eq) in THF/methanol/H₂O, overnight at r.t.; c) EDC·HCl (1.2 eq), HOBt (1.2 eq), THP—O—NH₂ (1.5 eq), NMM (3 eq) in DMF, overnight at r.t.;
d) HCl/dioxane (4M) at r.t for 3 hours.

In the scheme above R is (C₁-C₆)alkyl, Q is NH or

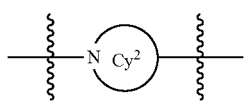

wherein Cy² is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-35a: Ethyl (E)-3-[4-[[4-[4-Ethoxy-3-(5-methyl-4-oxo-7-propyl-3H-imidazo[5,1-f][1,2,4]triazin-2-yl)phenyl]sulfonylpiperazin-1-yl]methyl]phenyl]prop-2-enoate I-35a was obtained starting from I-30a in an analogous manner to I-15a, but using (E)-ethyl 3-(4-((piperazin-1-yl)methyl)phenyl)-prop-2-enoate (R-09c) instead of ethyl 2-(piperazin-1-yl)pyrimidine-5-carboxylate (R-09a). 87% yield. ESI-MS (M+1): 649 calc. for $C_{33}H_{40}N_6O_6S$: 648.3.

Preparation of intermediate I-36a: (E)-3-[4-[[4-[4-Ethoxy-3-(5-methyl-4-oxo-7-propyl-3H-imidazo[5,1-f][1,2,4]triazin-2-yl)phenyl]sulfonylpiperazin-1-yl]methyl]phenyl]prop-2-enoic acid I-36a was obtained starting from I-35a in an analogous manner to I-16a. 60.1% yield. ESI-MS (M+1): 621 calc. for $C_{31}H_{36}N_6O_6S$: 620.2.

Preparation of intermediate I-37a: (E)-3-[4-[[4-[4-ethoxy-3-(5-methyl-4-oxo-7-propyl-3H-imidazo[5,1-f][1,2,4]triazin-2-yl)phenyl]sulfonylpiperazin-1-yl]methyl]phenyl]-N-tetrahydropyran-2-yloxy-prop-2-enamide I-37a was obtained starting from I-36a in an analogous manner to I-17a. 45% yield. ESI-MS (M+1): 720 calc. for $C_{36}H_{45}N_7O_7S$: 719.3.

Preparation of compound 2-01: (E)-3-[4-[[4-[4-Ethoxy-3-(5-methyl-4-oxo-7-propyl-3H-imidazo[5,1-f][1,2,4]triazin-2-yl)phenyl]sulfonylpiperazin-1-yl]methyl]phenyl]prop-2-enehydroxamic acid Compound 2-01 was obtained starting from I-37a in an analogous manner to compound 1-06. 24% yield. ESI-MS (M+1): 636 calc. for $C_{31}H_{37}N_7O_6S$: 635.2

Following the same synthetic route for compound 2-01 and using the same reagents unless otherwise indicated in the table below, the following compounds were obtained:

| Example | $R_t$ (min) | $[M + 1]^+$ | HPLC Method | Starting Materials |
|---|---|---|---|---|
| 2-03 | 2.04 | 553.1 | 1 | (E)-Ethyl 3-(4-aminophenyl)prop-2-enoate (R-09d) |
| 2-05 | 1.92 | 598.1 | 1 | Ethyl 2-(piperazin-1-yl)pyrimidine-5-carboxylate (R-09a) |
| 2-09 | 2.10 | 463.1 | 1 | ethyl 2-(methylamino)acetate (R-09n) |

Synthetic Route 2c

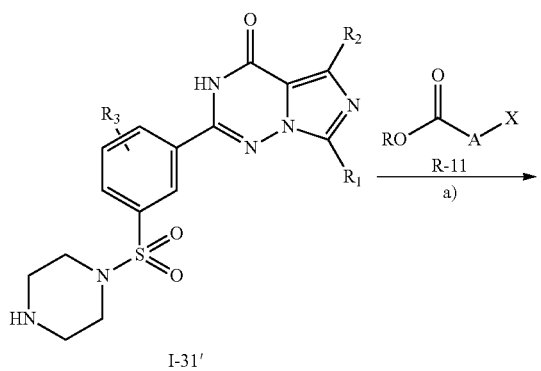

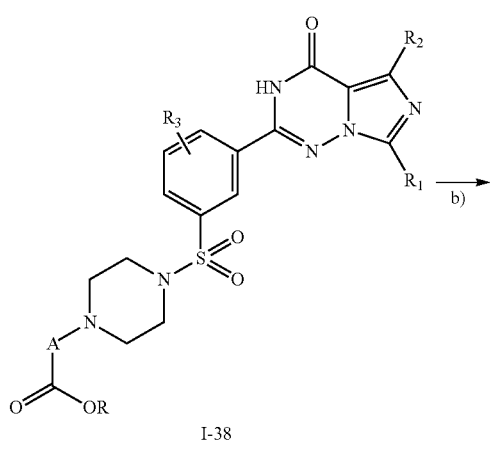

c) ⎧ I-39 R' = OH
d) ⎨ I-40 R' = NH—OTHP
   ⎩ IBb R' = NH—OH

Conditions: a) K₂CO₃ (3 eq) and R-11 (1.5 eq) in CH₃CN, MW at 100° C. for 2 hours;
b) LiOH·H₂O (5 eq) in THF/methanol/H₂O, overnight at r.t.; c) EDC·HCl (1.2 eq),
HOBt (1.2 eq), THP—O—NH₂ (1.5 eq), NMM (3 eq) in DMF, overnight at r.t.;
d) HCl/dioxane (4M) at r.t for 3 hours.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-38a: Ethyl 4-[4-[4-ethoxy-3-(5-methyl-4-oxo-7-propyl-3H-imidazo[5,1-f][1,2,4]triazin-2-yl)phenyl]sulfonylpiperazin-1-yl]butanoate I-38a was obtained starting from I-31a in an analogous manner to I-18a, but using ethyl 4-bromobutanoate (R-11 b) instead of ethyl 3-bromopropionate (R-11a). 62.89% yield, ESI-MS (M+1): 575 calc. for $C_{27}H_{38}N_6O_6S$: 574.26

Preparation of intermediate I-39a: 4-[4-[4-ethoxy-3-(5-methyl-4-oxo-7-propyl-3H-imidazo[5,1-f][1,2,4]triazin-2-yl)phenyl]sulfonylpiperazin-1-yl]butanoic acid I-39a was obtained starting from I-38a in an analogous manner to I-19a. 70.2% yield. ESI-MS (M+1): 547 calc. for $C_{25}H_{34}N_6O_6S$: 546.23.

Preparation of intermediate I-40a: 4-[4-[4-ethoxy-3-(5-methyl-4-oxo-7-propyl-3H-imidazo[5,1-f][1,2,4]triazin-2-yl)phenyl]sulfonylpiperazin-1-yl]-N-tetra-hydropyran-2-yloxy-butanamide I-40a was obtained starting from I-39a in an analogous manner to I-20a. 83.3% yield. ESI-MS (M+1): 646 calc. for $C_{30}H_{43}N_7O_7S$: 645.29.

Preparation of compound 2-02: 4-[4-[4-ethoxy-3-(5-methyl-4-oxo-7-propyl-3H-imidazo[5,1-f][1,2,4]triazin-2-yl)phenyl]sulfonylpiperazin-1-yl]butanehy-droxamic acid Compound 2-02 was obtained starting from I-40a in an analogous manner to compound 1-04. 35% yield. ESI-MS (M+1): 562.1 (HPLC Method: 1) calc. for $C_{25}H_{35}N_7O_6S$: 561.24.

Synthetic Route 2d

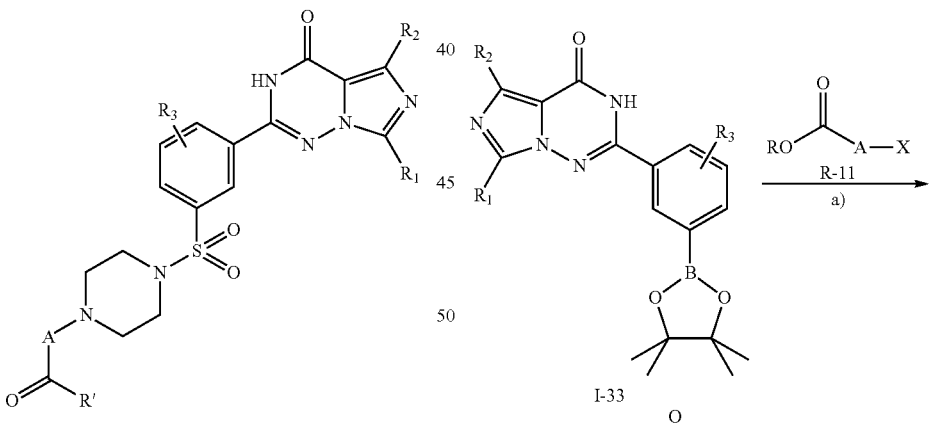

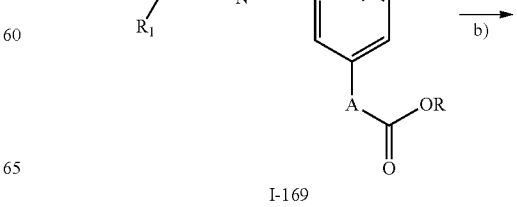

-continued

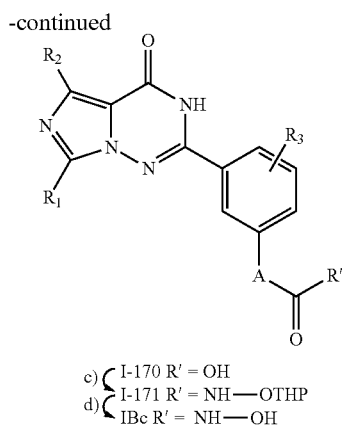

c) { I-170 R' = OH
d) { I-171 R' = NH—OTHP
     IBc R' = NH—OH

Conditions: a) R-11 (1.1 eq), K₂CO₃ (3 eq) in water, Pd(PPh3)4 (0.1 eq) in 1,4-dioxane, at 85° C. for 1 h in mw; b) LiOH·H₂O (10 eq) in THF/methanol/H₂O, overnight at r.t.; c) EDC·HCl (2 eq), HOBt (2 eq), THP—O—NH₂ (2 eq), NMM (3 eq) in DMF, overnight at r.t.; d) HCl/dioxane (4M) at r.t for 1 hour In the scheme above R is (C₁-C₆)alkyl, X is an halogen and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-33a: 2-[2-ethoxy-5-(4,4,5,5-tetramethyl-1,3,2-dioxaborolan-2-yl)phenyl]-5-methyl-7-propyl-3H-imidazo[5,1-f][1,2,4]triazin-4-one To a solution of intermediate I-172a (5.5 g, 12.56 mmol), 101-3 (3.84 g, 15.12 mmol), Pd(dppf)Cl2 (2.6 g, 3.77 mmol) and KOAc (3.69 g, 37.7 mmol) in dioxane (30 mL) was stirred at 90° C. overnight. The mixture was quenched with aqueous water and extracted with EtOAc, the organic layer was washed with brine, dried over anhydrous Na2SO4, concentrated to give the crude product which was purified by the column to give intermediate I-33a (3.5 g, 64° A) yield) as a white solid. ESI-MS (M+1): 439.1; calc. for C23H31 BN4O4: 438.2.

Preparation of intermediate I-169a: methyl 4-[[4-ethoxy-3-(5-methyl-4-oxo-7-propyl-3H-imidazo[5,1-f][1,2,4]triazin-2-yl)phenyl]methyl]benzoate To a solution of intermediate I-33a (300 mg, 0.685 mmol), R-11j: methyl 4-(bromomethyl)benzoate (172 mg, 0.75 mmol), Pd(PPh3)4 (79 mg, 0.0685 mmol) and K2CO3 (284 mg, 2.06 mmol) in dioxane/H2O (5/2 mL) was stirred at 85° C. for 1 h under MW. The mixture was quenched with aqueous water and extracted with EtOAc, the organic layer was washed with brine, dried over anhydrous Na2SO4, concentrated to give the crude product which was purified by the column to give intermediate I-169a (100 mg, 32% yield) as a white solid. ESI-MS (M+1): 461.2; calc. for C26H28N4O4: 460.2.

Preparation of intermediate I-170a: 4-[[4-ethoxy-3-(5-methyl-4-oxo-7-propyl-3H-imidazo[5,1-f][1,2,4]triazin-2-yl)phenyl]methyl]benzoic acid To a solution of intermediate I-169a (100 mg, 0.22 mmol) in THF/MeOH/H2O (3/3/2, 8 mL) was added LiOH.H2O (84 mg, 10 eq). The resulting mixture was stirred at r.t. for 8 hrs. Then, the mixture was diluted with water and adjusted pH to 6-7 with 1N HCl and the mixture was extracted with EtOAc, washed with brine, dried over anhydrous Na2SO4, concentrated to afford the desired intermediate I-170a (80 mg, 82%). ESI-MS (M+1): 447.2; calc. for C25H26N4O4: 446.2.

Preparation of intermediate I-171a: 4-[[4-ethoxy-3-(5-methyl-4-oxo-7-propyl-3H-imidazo[5,1-f][1,2,4]triazin-2-yl)phenyl]methyl]-N-tetrahydropyran-2-yloxy-benzamide To a solution of intermediate I-170a (80 mg, 0.18 mmol) in DMF (10 mL) was added EDC.HCl (69 mg, 0.36 mmol), HOBt (49 mg, 0.36 mmol), THPONH2 (39 mg, 0.36 mmol) and NMM (55 mg, 0.54 mmol) at r.t, then the mixture was stirred at room temperature overnight. The mixture was quenched with aqueous water and extracted with EtOAc, the organic layer was washed with brine, dried over anhydrous Na2SO4, concentrated to give the crude product which was purified by prep-TLC to give intermediate I-171a (50 mg, 50% yield) as a pale yellow solid. ESI-MS (M+1): 546.2; calc. for C30H35N5O5: 545.2.

Preparation of compound 2-06: 4-[[4-ethoxy-3-(5-methyl-4-oxo-7-propyl-3H-imidazo[5,1-f][1,2,4]triazin-2-yl)phenyl]methyl]benzenecarbohydroxamic acid A solution of intermediate I-171a (50 mg, 0.09 mmol) in HCl/EtOAc (10 mL) was stirred at r.t for 1 h, then concentrated to give the crude product which was purified by prep-HPLC (General procedure, Method 1) to obtained pure compound 2-06 (2.1 mg, 5% yield) as a white solid. ESI-MS (M+1): 462.2 calc. for C25H27N5O4: 461.2; Rt is 2.31.

Following the same synthetic route for compound 2-06 and using the same reagents unless otherwise indicated in the table below, the following compounds were obtained:

| Example | R$_t$ (min) | [M + 1]$^+$ | HPLC Method | Starting Materials |
|---|---|---|---|---|
| 2-08 | 2.49 | 488.2 | 1 | methyl (E)-3-[4-(bromomethyl)phenyl]prop-2-enoate (R-11r) |
| 2-10 | 2.34 | 468.1 | 1 | ethyl 5-(bromomethyl)thiophene-2-carboxylate (R-11k) |
| 2-11 | 2.25 | 448.1 | 1 | ethyl 4-iodobenzoate (R-11o) |

Synthetic Route 2e

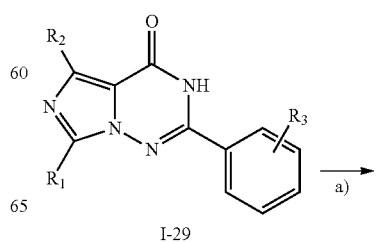

I-29

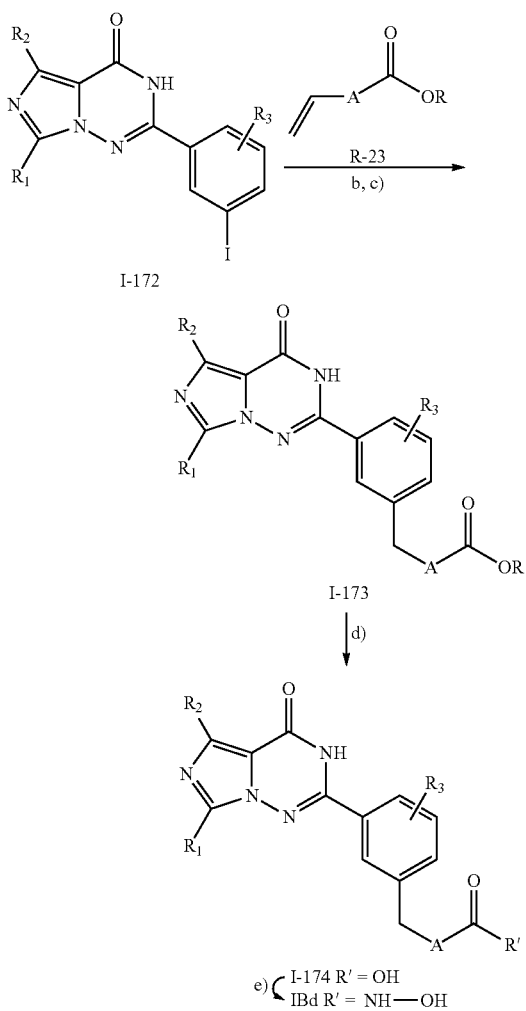

Conditions: a) NIS (1.2 eq) in TFA, overnight at r.t; b) R-23, 9-BBN (0.5M solution) in THF, reflux for 4 hrs.; c) I-172, Pd2(dba)3 (0.05 eq), X-Phos (0.12 eq), Na2CO3 (2.5 eq), 1,4-dioxane and H2O, reflux overnight; d) LiOH•H₂O (10 eq) in THF/methanol/H₂O, overnight at r.t.; e) NH2OH HCl (20 eq), BOP (2.5 eq), DIEA (10 eq), DMF, overnight at r.t.

In the scheme above R is ($C_1$-$C_6$)alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-172a: 2-(2-ethoxy-5-iodo-phenyl)-5-methyl-7-propyl-3H-imidazo[5,1-f][1,2,4]triazin-4-one To a solution of intermediate I-29a (5 g, 16 mmol) in TFA (50 mL) was added NIS (4.3 g, 19.2 mmol) at 0° C. The mixture solution was stirred at r.t overnight. The mixture was quenched with aqueous water and extracted with EtOAc, the organic layer was washed with brine, dried over anhydrous Na2SO4, concentrated to give the crude product which was purified by the column to give intermediate I-172a (5 g, 79%) as a white solid. ESI-MS (M+1): 439.1; calc. for C17H19IN4O2: 438.0.

Preparation of intermediate I-173a: ethyl 3-[[4-ethoxy-3-(5-methyl-4-oxo-7-propyl-3H-imidazo[5,1-f][1,2,4]triazin-2-yl)phenyl]methyl]cyclobutanecarboxylate Reagent ethyl 3-methylenecyclobutanecarboxylate R-23a (200 mg, 1.43 mmol) was treated with a 0.5 M solution of 9-BBN in THF (10 mL), and the mixture was heated at reflux for 4 hrs. The resulting mixture was transferred into a stirred mixture of intermediate I-172a (0.6 g, 1.37 mmol), Pd2(dba)3 (120 mg, 0.14 mmol), X-Phos (66 mg, 0.14 mmol), and Na2CO3 (454 mg, 4.2 mmol) in 1,4-dioxane (20 mL) and H₂O (4 mL). The resulting mixture was stirred at reflux overnight. Then filtered, the mixture was extracted with EtOAc, the organic layer was washed with brine, dried over anhydrous Na2SO4, concentrated to give the crude compound which was purified by column chromatography (eluting with PE/EtOAc=50:1 to 5:1) to give pure intermediate I-173a (200 mg, 33% yield) as a pale yellow oil. ESI-MS (M+1): 453.2 calc. for C25H32N4O4: 452.2.

Preparation of intermediate I-174a: 3-[[4-ethoxy-3-(5-methyl-4-oxo-7-propyl-3H-imidazo[5,1-f][1,2,4]triazin-2-yl)phenyl]methyl]cyclobutanecarboxylic acid To a solution of intermediate I-173a (200 mg, 0.44 mmol) in THF/MeOH/H2O (3/3/2, 16 mL) was added LiOH.H2O (168 mg, 10 eq). The resulting mixture was stirred at r.t. for 8 hrs, after TLC showed the starting materials were consumed completely, then the mixture was diluted with water and adjusted pH to 6~7 with 1N HCl and the mixture was extracted with EtOAc, washed with brine, dried over anhydrous Na2SO4, concentrated to afford the desired intermediate I-174a (160 mg, 82%). ESI-MS (M+1): 425.2; calc. for C23H28N4O4.

Preparation of compound 2-07: 3-[[4-ethoxy-3-(5-methyl-4-oxo-7-propyl-3H-imidazo[5,1-f][1,2,4]triazin-2-yl)phenyl]methyl]cyclobutanecarbohydroxamic acid To a solution of intermediate I-174a (160 mg, 0.38 mmol) in DMF (10 mL) was added NH2OH.HCl (590 mg, 7.6 mmol), DIEA (900 mg, 3.8 mmol) and BOP (300 mg, 0.76 mmol) at r.t, then the mixture was stirred at room temperature overnight. The mixture was quenched with aqueous water and extracted with EtOAc, the organic layer was washed with brine, dried over anhydrous Na2SO4, concentrated to give the crude product which was purified by prep-HPLC to give compound 2-07 (58.4 mg, 50%) as a pale yellow solid. ESI-MS (M+1): 440.2; calc. for C23H29N5O4: 439.2; Rt is 2.15.

Synthetic Route 2f

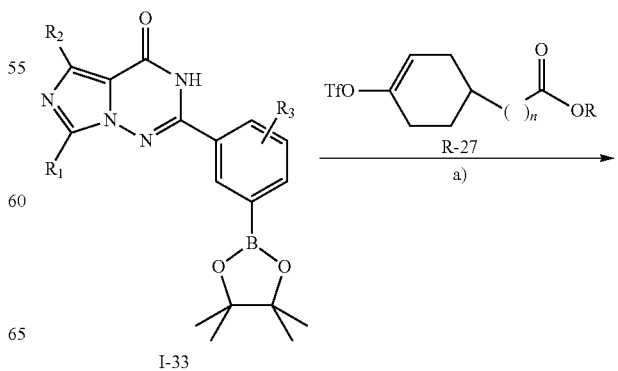

-continued

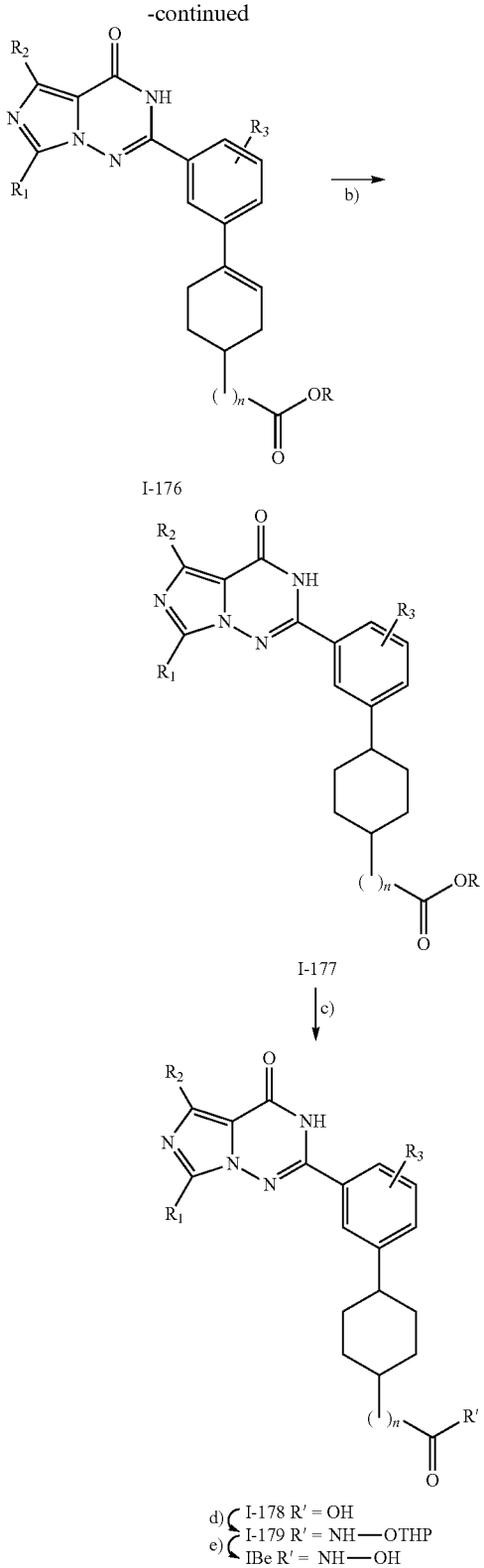

Conditions: a) R-27 (1.4 eq), Pd(PPh3)4 (0.1 eq) K₂CO₃ (3 eq) in water, in 1,4-dioxane, overnight at 80° C.; b) Pd/C in MeOH at H₂ atmosphere, at r.t for 2 hour; c) LiOH•H₂O (10 eq) in THF/methanol/H₂O, overnight at r.t.; d) EDC•HCl (2 eq), HOBt (2 eq), THP—O—NH₂ (2 eq), NMM (3 eq) in DMF, overnight at r.t.; e) HCl/AcOEt (4M) at r.t for 1 hour.

In the scheme above R is $(C_1-C_6)$alkyl.

Preparation of intermediate I-176a: ethyl 4-[4-ethoxy-3-(5-methyl-4-oxo-7-propyl-3H-imidazo[5,1-f][1,2,4]triazin-2-yl)phenyl]cyclohex-3-ene-1-carboxylate To a solution of intermediate I-33a (1.1 g, 2.5 mmol) in 1,4-dioxane (60 mL)/H2O (10 mL) was added R-27a: ethyl 4-(trifluoromethylsulfonyloxy)cyclohex-3-ene-1-carboxylate (1.06 g, 3.5 mmol), K2CO3 (1.1 g, 8.0 mmol), Pd(PPh3)4 (230 mg, 0.2 mmol), then the mixture was stirred at 80° C. overnight under N2 protection. After LC-MS showed the starting material was consumed completely, the mixture was extracted with EtOAc, the organic layer was washed with brine, dried over anhydrous Na2SO4, concentrated to give the crude compound which was purified by column to give pure intermediate I-176a (680 mg, 58% yield) as a white solid. ESI-MS (M+1): 465 calc. for C26H32N4O4: 464.2.

Preparation of intermediate I-177a: ethyl 4-[4-ethoxy-3-(5-methyl-4-oxo-7-propyl-3H-imidazo[5,1-f][1,2,4]triazin-2-yl)phenyl]cyclohexanecarboxylate To a solution of intermediate I-176a (680 mg, 1.46 mmol) in EtOAc (40 mL) was added Pd/C (0.2 g) at H2 atmosphere, then the mixture was stirred at room temperature for 2 hrs until LC-MS showed the starting material was consumed completely, then filtered, the filtrate was concentrated to give the crude intermediate I-177a (667 mg, 98%) as a white solid which was used for the next step directly.

ESI-MS (M+1): 467 calc. for C26H34N4O4: 466.2.

Preparation of intermediate I-178a: 4-[4-ethoxy-3-(5-methyl-4-oxo-7-propyl-3H-imidazo[5,1-f][1,2,4]triazin-2-yl)phenyl]cyclohexanecarboxylic acid To a solution of intermediate I-177a (667 mg, 1.43 mmol) in MeOH/THF/H2O (3/9/3, 30 mL) was added LiOH.H2O (645 mg, 15 mmol), the reaction mixture was stirred at room temperature overnight until LC-MS showed the starting material was consumed completely. Then concentrated, the mixture was diluted with H₂O and adjusted pH to 1-2 with 1N HCl, extracted with EtOAc, the organic layer was washed with brine, dried over anhydrous Na2SO4, concentrated to give the crude intermediate I-178a (613 mg, 98%) as a yellow solid. ESI-MS (M+1): 439 calc. for C24H30N4O4: 438.2.

Preparation of intermediate I-179a: 4-[4-ethoxy-3-(5-methyl-4-oxo-7-propyl-3H-imidazo[5,1-f][1,2,4]triazin-2-yl)phenyl]-N-tetrahydropyran-2-yloxy-cyclohexanecarboxamide To a solution of intermediate I-178a (93 mg, 0.21 mmol) in DMF (30 mL) was added EDC.HCl (78 mg, 0.4 mmol), HOBt (54 mg, 0.4 mmol), THPO—NH2 (47 mg, 0.4 mmol), NMM (56 mg, 0.55 mmol). The mixture was stirred at room temperature overnight. The mixture was quenched with water and extracted with EtOAc, the organic layer was washed with brine, dried over anhydrous Na2SO4, concentrated to give the crude product which was purified by Prep-TLC to give the pure intermediate I-179a (98 mg, 87% yield) as a yellow solid. ESI-MS (M+1): 538 calc. for C29H39N5O5: 537.2.

Preparation of compounds 2-12 (racemic), 2-13 (cis) & 2-14 (trans): 4-[4-ethoxy-3-(5-methyl-4-oxo-7-propyl-3H-imidazo[5,1-f][1,2,4]triazin-2-yl)phenyl]cyclohexanecarbohydroxamic acid A solution of intermediate I-179a (98 mg, 0.182 mmol) in HCl/EtOAc (1.0 M, 15 mL) was stirred at room temperature for 1 hr, then concentrated to give a reaction crude which was purified by prep-HPLC (General procedure, Method 1) to obtain compound 2-12 as a racemic mixture (14.5 mg), ESI-MS (M+1): 454.2 calc. for C24H31 N5O4: 453.2; cis isomers: 2-13 (5.8 mg), ESI-MS (M+1): 454.2 calc. for C24H31 N5O4: 453.2 (Rt is 2.62) and trans isomers: 2-14 (10 mg). ESI-MS (M+1): 454.2 calc. for C24H31 N5O4 (Rt is 2.78).

Synthetic Route 3a (300 mL) was slowly added sodium ethoxide (32.6 g, 479 mmol, 2.1 eq), and the resulting mixture was stirred for 1 hour at r.t. The reaction mixture was then transferred into a solution of the commercially available reagent (ethoxymethylene)malononitrile (4, 27.8 g, 228 mmol) in ethanol (300 mL). After 30 minutes at r.t., the mixture was heated at reflux for 2 hours. It was then cooled to r.t. and concentrated in vacuo to afford I-44a as a solid which was used in the next step without purification.

Preparation of intermediate I-44b:
5-amino-1-cyclopentyl-pyrazole-4-carbonitrile To a mixture of commercially available cyclopentylhydrazine hydrochloride (R-14b) (1.82 g, 18.18 mmol) and commercially available compound 4: (ethoxymethylene)

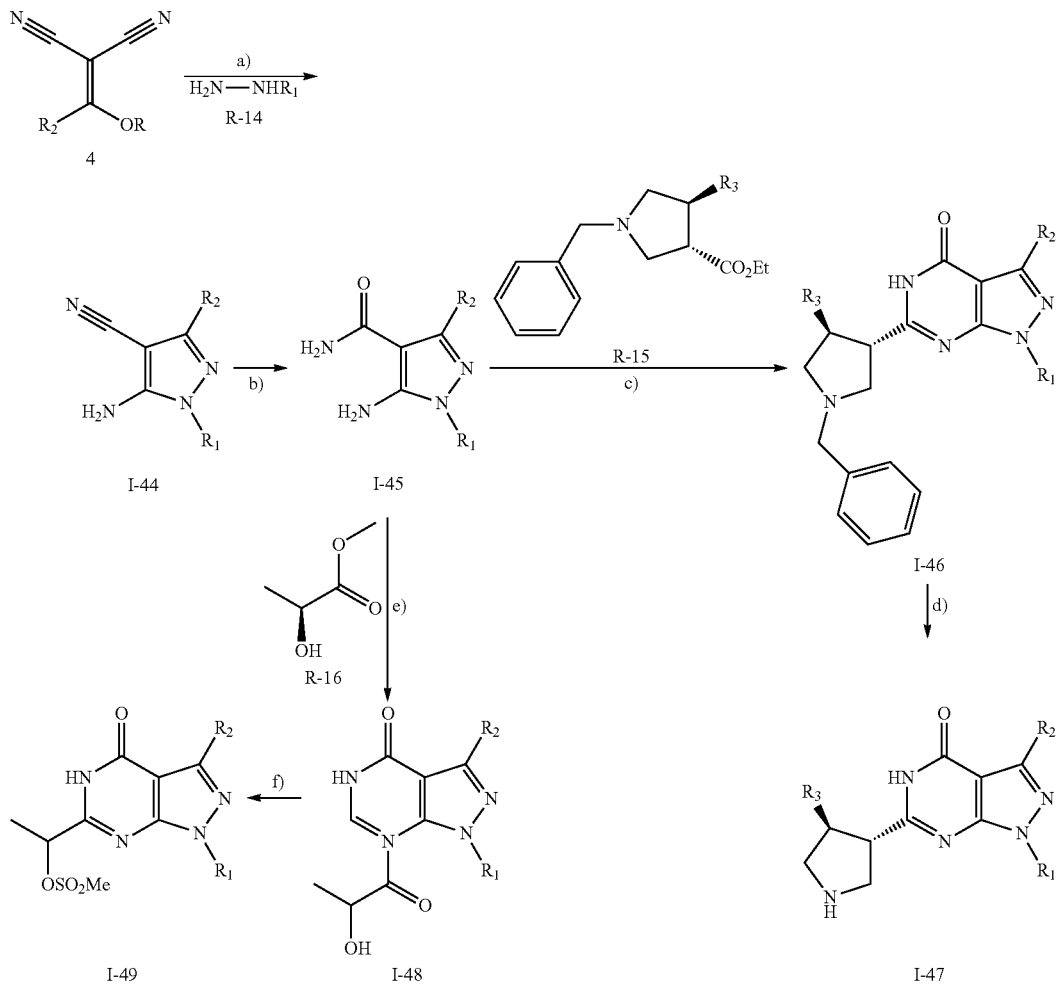

Conditions: a) R-14 in ethanol and refluxed for 18 hours; b) 30% H₂O₂ solution added to I-44 in NH₄OH (sat.), 18 hours at r.t.; c) ᵗBuOK in THF, refluxed for 16 hours; d) AcOH and Pd(OH)₂ in ethanol at r.t. under 40 Psi of H₂ atmosphere during 16 hours; e) R-16 (enantiomerically pure, S; 3 eq) in ethanol and EtONa (2.7M), at 80° C. overnight; f) Et₃N (1.5 eq) and CH₃SO₂Cl (15 eq) in DCM, at 0° C. for 30 minutes., In the scheme above R is $(C_1-C_6)$alkyl. Any racemic mixture and pure enantiomer is considered.

Preparation of intermediate I-44a: 5-Amino-1-(tetrahydro-2H-pyran-4-yl)-1H-pyrazole-4-carbonitrile To a solution of the commercially available tetrahydro-2H-pyran-4-ylhidrazine (R-14, 43 g, 228 mmol) in ethanol malononitrile (1.34 g, 10.97 mmol) in EtOH (20 mL), was added Et3N (3.03 g, 29.93 mmol) in one portion at r.t. under N2. The mixture was stirred at r.t. for 10 min. Then heated to 50° C. and stirred for 2 hrs. The mixture was cooled to r.t. and concentrated in reduced pressure. The residue was poured into water and the aqueous phase was extracted with EA (50 mL). The combined organic phase was washed with saturated brine (20 mL), dried with anhydrous Na2SO4, filtered and concentrated in vacuum. The residue was purified by silica gel chromatography to afford intermediate I-44b (1.22 g, 69% yield) as yellow solid. ESI-MS (M+1): 177.1 calc. for C9H12N4: 176.1.

Preparation of intermediate I-45a: 5-Amino-1-(tetrahydro-2H-pyran-4-yl)-1H-pyrazole-4-carboxamide A solution of I-44a (<228 mmol, crude from previous reaction) in ethanol (300 mL) was treated with 35% aqueous hydrogen peroxide (100 mL) followed by concentrated aqueous ammonia solution (300 mL) The reaction mixture was stirred for 48 hours at r.t., then quenched with saturated aqueous sodium thiosulfate solution (800 mL). Removal of ethanol in vacuo provided a solid that was isolated by filtration and washed with water (2×200 mL) and diethyl ether (2×150 mL) to provide I-45a (31 g, 147 mmol). Yield for these two steps, from reagent 4 to I-45a, was 64%. ESI-MS (M+1): 211 calc. for $C_9H_{14}N_4O_2$: 210.1

Preparation of intermediate I-45b: 5-amino-1-cyclopentyl-pyrazole-4-carboxamide

To a mixture of intermediate I-44b (2.20 g, 12.48 mmol) in CH3CH2OH (20 mL), was added H2O2 (4.24 g, 124.80 mmol) in one portion at r.t. under N2. Then NH3.H2O (4.37 g, 124.80 mmol) was added dropwise. The mixture was stirred at r.t. for 2 hrs. HPLC (TLC) showed the reaction was completed. The residue was added Na2SO3 aq. (150 mL) and stirred for 2 hrs. The aqueous phase was extracted with EA (50 mL). The combined organic phase was washed with saturated brine (20 mL), dried with anhydrous Na2SO4, filtered and concentrated in vacuum. The residue was purified by silica gel chromatography to afford intermediate I-45b (1.54 g, 63% yield) as yellow solid. ESI-MS (M+1): 195.1 calc. For C9H14N4O: 194.1.

Preparation of intermediate I-46a: 6-(1-Benzyl-4-methylpyrrolidin-3-yl)-1-(tetrahydro-2H-pyran-4-yl)-1H-pyrazolo[3,4-d]pyrimidin-4(5H)-one (trans racemic To I-45a (0.4 g, 1.9 mmol) and ethyl 1-benzyl-4-methyl-pyrrolidine-3-carboxylate, trans racemic, R-15a (0.564 g, 2.28 mmol) was added a solution of potassium t-butoxide in (1M) in THF (10 mL, 5 eq.). The reaction mixture was refluxed for 16 h and then the reaction mixture was poured into saturated sodium bicarbonate solution. The aqueous layer was extracted with ethyl acetate, dried over anhydrous $Na_2SO_4$, filtered and concentrated to give crude I-46a (0.55 g, 73.5%) as a pale yellow solid which was used for the next step without further purification. ESI-MS (M+1): 394 calc. for $C_{22}H_{27}N_5O_2$: 393.1.

Preparation of intermediate I-46b: 6-(1-benzyl-4-methyl-pyrrolidin-3-yl)-1-cyclopentyl-5H-pyrazolo[3,4-d]pyrimidin-4-one (trans racemic)

To a solution of I-45b (1.3 g, 5.26 mmol) in EtOH (10 mL) was added ethyl 1-benzyl-4-methylpyrroli-dine-3-carboxylate, trans racemic, R-15a (510 mg, 2.63 mmol) and NaH (631 mg, 26.3 mmol), then the reaction mixture was stirred at 120° C. for 1 h by MW. The mixture was quenched with water and extracted with EtOAc, the organic layer was washed with brine, dried over anhydrous Na2SO4, concentrated to give a reaction crude which was purified by column chromatography to give pure intermediate I-46b (685 mg, 69.0% yield) as a yellow solid. ESI-MS (M+1): 378.2 calc. for C22H27N5O: 377.2.

Preparation of intermediate I-47a: 1-(Tetrahydro-2H-pyran-4-yl)-6-(3S,4S)-4-methylpyrrolidin-3-yl)-1H-pyrazolo[3,4-d]pyrimidin-4(5H)-one (trans racemic)

To a solution of I-46a (1 g, 2.5 mmol) in methanol (30 mL) was added Pd/C (1.5 g). The reaction mixture was stirred at r.t. for 5 h at hydrogen atmosphere. After TLC (PE/EA 5:1) showed the starting material was consumed, the mixture was filtered and the filtrate was concentrated under vacuo. The residue was extracted with EA, the organic layer was washed with brine, dried over anhydrous $Na_2SO_4$, The mixture was concentrated to give the product which was purified by column chromatography to give I-47a (0.65 g, 84.41% yield) as a yellow solid; (trans) racemic. ESI-MS (M+1): 304 calc. for $C_{15}H_{21}N_5O_2$: 303.2.

Preparation of intermediate I-47b: 1-cyclopentyl-6-(4-methylpyrrolidin-3-yl)-5H-pyrazolo[3,4-d]pyrimidin-4-one (trans racemic)

To a solution of intermediate I-46b (2 g, 5.3 mmol) in MeOH (10 mL) was added Pd/C (1 g), then the reaction mixture was stirred at r.t 5 hrs at H2 (40 psi) atmospheres. The mixture was filtrated and concentrated under vacuo, and extracted with EtOAc, the organic layer was washed with brine, dried over anhydrous Na2SO4, The mixture was concentrated to give intermediate I-47b (687 mg, 45.11% yield) as a yellow solid. ESI-MS (M+1): 288.2 calc. for C15H21N5O: 287.2.

Preparation of intermediate I-48a: 6-(1-Hydroxy-ethyl)-1-tetrahydropyran-4-yl-5H-pyrazolo[3,4-d]pyrimidin-4-one To a solution of intermediate I-45a (5.0 g, 23.86 mmol) in anhydrous EtOH (100 mL) was added R-16, (S)-methyl 2-hydroxypropanoate, (7.28 g, 70 mmol) and EtONa (25 mL, 2.7M), the reaction mixture was stirred at 80° C. for overnight. Then the reaction mixture was concentrated under vacuo and purified by column (PE: EA=10:1 to 0:1) to give intermediate I-48a as a racemic mixture (3.0 g, 47.7%). ESI-MS (M+1): 265 calc. for $C_{12}H_{16}N_4O_3$: 264.1.

Preparation of intermediate I-49a: 1-(4-oxo-1-tetra-hydropyran-4-yl-5H-pyrazolo[3,4-d]pyrimidin-6-yl) ethyl methanesulfonate To a solution of intermediate I-48a (0.792 g, 3 mmol) in DCM (30 mL) was added $Et_3N$ (454.5 mg, 4.5 mmol) and methanesulfonyl chloride (9.25 g, 50 mmol) slowly at 0° C. The reaction mixture was stirred 30 mins at 0° C. Then the reaction mixture was extracted by DCM and washed by water, dried by $Na_2SO_4$ and concentrated under vacuo and purified by column to give the desired intermediate I-49a as a racemic mixture (0.3 g, 32.5%). ESI-MS (M+1): 343 calc. for $C_{13}H_{19}N_4O_5S$: 342.1.

Synthetic Route 3b

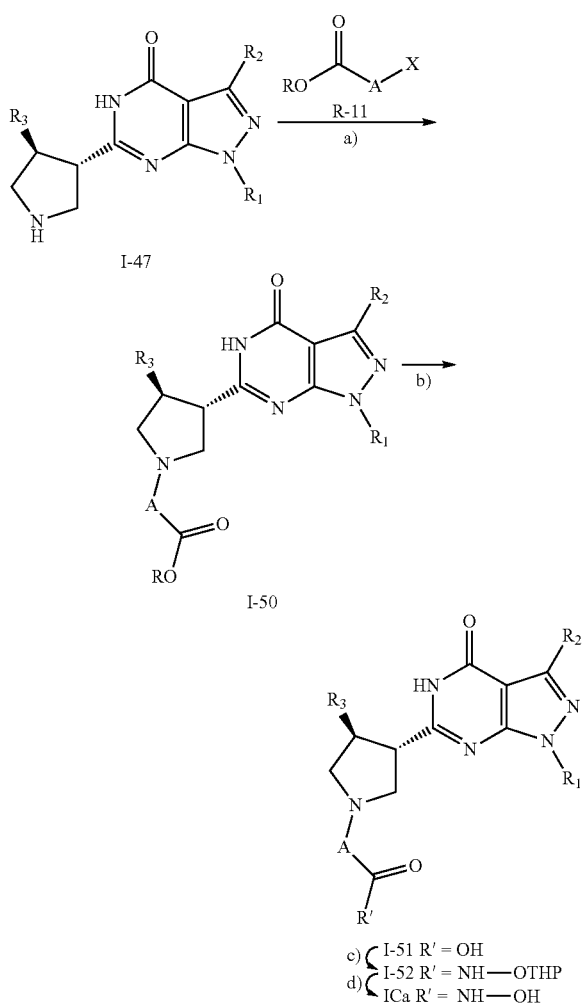

Conditions: a) K₂CO₃ (3 eq) and R-11 (1.5 eq) in CH₃CN, at 80° C. for 2-48 hours; b) LiOH·H₂O (5 eq) in THF/methanol/H₂O, overnight at r.t.; c) EDC·HCl (1.2 eq), HOBt (1.2 eq), THP—O—NH₂ (1.5 eq), NMM (3 eq) in DMF, overnight at r.t.; d) HCl/dioxane (4M) at r.t for 1-3 hours.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings. Any racemic mixture and pure enantiomer is considered.

Preparation of intermediate I-50a: Ethyl 2-(4-((3-(4,5-dihydro-1-(tetrahydro-2H-pyran-4-yl)-4-oxo-1H-pyrazolo[3,4-d]pyrimidin-6-yl)-4-methylpyrrolidin-1-yl)methyl)piperidin-1-yl)pyrimidine-5-carboxylate (trans racemic)

To a solution of I-47a (200 mg, 0.66 mmol) in CH₃CN (10 mL) was added the reagent (1-(5-(ethoxycarbonyl)pyrimidin-2-yl)piperidin-4-yl)methyl methanesulfonate (R-11c, 272 mg, 0.79 mmol) and K₂CO₃ (364 mg, 2.64 mmol). The reaction was stirred at 80° C. for 48 h. After TLC (PE/AE 3:1) showed the starting material was consumed, the mixture was filtrated and concentrated under vacuo, and extracted with DCM, the organic layer was washed with brine, and dried over anhydrous Na₂SO₄. The mixture was concentrated to give I-50a (210 mg, 51.59% yield) which was purified by preparative TLC as a yellow solid. ESI-MS (M+1): 551 calc. for $C_{28}H_{38}N_8O_4$: 550.1

Preparation of intermediate I-51a: 2-(4-((3-(4,5-Dihydro-1-(tetrahydro-2H-pyran-4-yl)-4-oxo-1H-pyrazolo[3,4-d]pyrimidin-6-yl)-4-methylpyrrolidin-1-yl)methyl)piperidin-1-yl)pyrimidine-5-carboxylic acid (trans racemic)

I-51a was obtained starting from I-50a in an analogous manner to I-19a. 95.81% yield. ESI-MS (M+1): 523 calc. for $C_{26}H_{34}N_8O_4$: 522.1.

Preparation of intermediate I-52a: 2-(4-((3-(4,5-Dihydro-1-(tetrahydro-2H-pyran-4-yl)-4-oxo-1H-pyrazolo[3,4-d]pyrimidin-6-yl)-4-methylpyrrolidin-1-yl)methyl)piperidin-1-yl)-N-(tetrahydro-2H-pyran-2-yloxy)pyrimidine-5-carboxamide (trans racemic)

I-52a was obtained starting from I-51a in an analogous manner to I-20a. 38.89% yield, ESI-MS (M+1): 622 calc. for $C_{31}H_{43}N_9O_5$: 621.1.

Preparation of compound 3-02: 2-(4-((3-(4,5-Dihydro-1-(tetrahydro-2H-pyran-4-yl)-4-oxo-1H-pyrazolo[3,4-d]pyrimidin-6-yl)-4-methylpyrrolidin-1-yl) methyl)piperidin-1-yl)-N-hydroxypyrimidine-5-carboxamide (trans racemic)

Compound 3-02 was obtained starting from I-52a in an analogous manner to compound 1-04. 46.67% yield. ESI-MS (M+1): 538.3 (HPLC Method: 2; $R_t$ is 2.96) calc. for $C_{26}H_{35}N_9O_4$: 537.1; Rt is 2.59.

Following the same synthetic route for compound 3-02 and using the same reagents unless otherwise indicated in the table below, the following compounds were obtained:

| Example | $R_t$ (min) | $[M + 1]^+$ | HPLC Method | Starting Materials |
|---|---|---|---|---|
| 3-01 (trans racemic) | 2.96 | 479.3 | 2 | 4-((E)-2-(Ethoxycarbonyl)vinyl)benzyl methanesulfonate (R-11d) |
| 3-04 (trans racemic) | 2.64 | 531.2 | 2 | Methyl 4-[2-(methylsulfonyloxymethyl)pyrimidin-5-yl]benzoate (R-11h) |
| 3-08 (trans racemic) | 1.42 | 538.3 | 2 | Methyl 1-[5-(methylsulfonyloxymethyl)pyrimidin-2-yl]piperidine-4-carboxylate (R-11i) |

Synthetic Route 3c

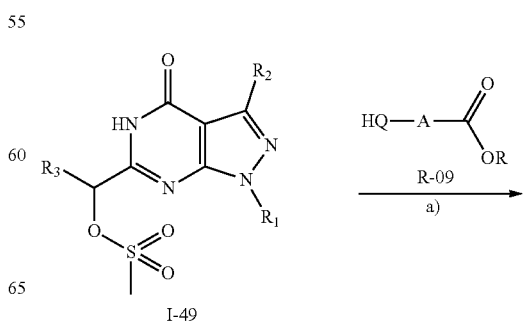

-continued

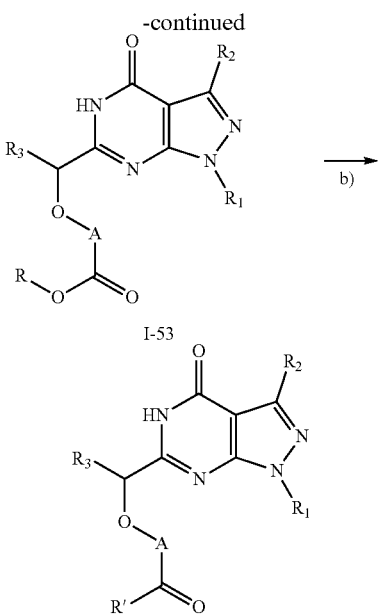

c) { I-54 R' = OH
   { I-55 R' = NH-OTHP d) ↘ ICb R' = NH-OH

Conditions: a) Et₃N and R-09 in CH₃CN/toluene, at 110° C. for 2 hours; b) LiOH•H₂O (5 eq) in THF/methanol/H₂O, overnight at r.t.; c) EDC•HCl (1.2 eq), HOBt (1.2 eq), THP—O—NH₂ (1.5 eq), NMM (3 eq) in DMF, overnight at r.t.; d) HCl/dioxane (4 M) at r.t. for 3 hours.

In the scheme above R is $(C_1\text{-}C_6)$alkyl, Q is oxygen, NH or

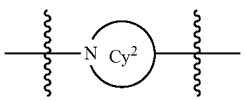

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings. Any racemic mixture and pure enantiomer is considered.

Preparation of intermediate I-53a: Methyl 4-[4-[1-[1-(4-oxo-1-tetrahydropyran-4-yl-5H-pyrazolo[3,4-d]pyrimidin-6-yl)ethyl]azetidin-3-yl]oxyphenyl]benzoate To a solution of reagent R-09f (204 mg, 0.877 mmol) in CH₃CN (10 mL) was added K₂CO₃ (276 mg, 2 mmol) and I-49a (250 mg, 0.731 mmol). The reaction mixture was stirred at 110° C. under MW for 2 hours. Then concentrated under vacuo and purified by column (DCM:MeOH=1:0 to 10:1) to give the desired product compound I-53a (72 mg, 18.7%). ESI-MS (M+1): 530.1 calc. for $C_{29}H_{31}N_5O_5$: 529.2.

Preparation of intermediate I-54a: 4-[4-[1-[1-(4-Oxo-1-tetrahydropyran-4-yl-5H-pyrazolo[3,4-d]pyrimidin-6-yl)ethyl]azetidin-3-yl]oxyphenyl]benzoic acid To a solution of compound I-53a (72 mg, 0.137 mmol) in THF/MeOH/H₂O (10/1/3 mL) was added LiOH.H₂O (29.3 mg, 0.681 mmol). The resulting mixture was stirred at r.t. overnight. After TLC showed that most of the starting materials were consumed completely, the mixture was diluted with water and adjusted pH to 2-3. The mixture was concentrated to give the product I-54a (42 mg, 71.7%). ESI-MS (M+1): 516.1 calc. for $C_{28}H_{29}N_5O_5$: 515.2.

Preparation of intermediate I-55a: 4-[4-[1-[1-(4-Oxo-1-tetrahydropyran-4-yl-5H-pyrazolo[3,4-d]pyrimidin-6-yl)ethyl]azetidin-3-yl]oxyphenyl]-N-tetrahydropyran-2-yloxy-benzamide To a solution of I-54a (93 mg, 0.2 mmol) in DMF (15 mL) was added EDC.HCl (68.8 mg, 0.4 mmol), HOBt (54 mg, 0.4 mmol), THP-O—NH₂ (34.4 mg, 0.3 mmol), NMM (40.4 mg, 0.4 mmol). The mixture was stirred at room temperature overnight. The mixture was diluted with EA and washed with brine, dried over anhydrous Na2SO4 and concentrated to give the crude product which was purified by pre-hplc to give the compound I-55a (50 mg, 40.9%). ESI-MS (M+1): 615.1 calc. for $C_{33}H_{38}N_6O_6$: 614.3.

Preparation of compound 3-03: 4-[4-[1-[1-(4-Oxo-1-tetrahydropyran-4-yl-5H-pyrazolo[3,4-d]pyrimidin-6-yl)ethyl]azetidin-3-yl]oxyphenyl]benzene carbohydroxamic acid A solution of compound I-55a (56.4 mg, 0.1 mmol) in HCl/dioxane (4M, 5 mL) was stirred at r.t. for 1 h, the reaction mixture was concentrated to give the desired compound 3-03 (7 mg, 13.2%). ESI-MS (M+1): 531.3 (HPLC Method: 2; $R_t$ is 2.89) calc. for $C_{28}H_{30}N_6O_5$: 530.2.

Following the same synthetic route for compound 3-03 and using the same reagents unless otherwise indicated in the table below, the following compounds were obtained:

| Example | $R_t$ (min) | [M + 1]⁺ | HPLC Method | Starting Materials |
|---|---|---|---|---|
| 3-05 | 2.43 | 538.3 | 2 | ethyl 1-[4-(azetidin-3-yloxy)phenyl]piperidine-4-carboxylate (R-09g) |
| 3-06 | 3.51 | 480.1 | 2 | methyl (E)-3-[4-(azetidin-3-yloxy)phenyl]prop-2-enoate (R-09h) |
| 3-07 | 2.69 | 540.3 | 2 | ethyl 5-[4-(azetidin-3-yloxy)-1-piperidyl] pyrimidine-2-carboxylate (R-09i) |
| 3-13 | 2.29 | 455.2 | 2 | ethyl 4-(azetidin-3-yloxy)benzoate (R-09o) |
| 3-15 | 2.25 | 453.2 | 2 | ethyl 4-(azetidin-3-ylmethyl)-benzoate (R-09p) |
| 3-16 | 2.23 | 459.2 | 2 | ethyl 5-(azetidin-3-ylmethyl)thiophene-2-carboxylate (R-09q) |

Synthetic Route 3d

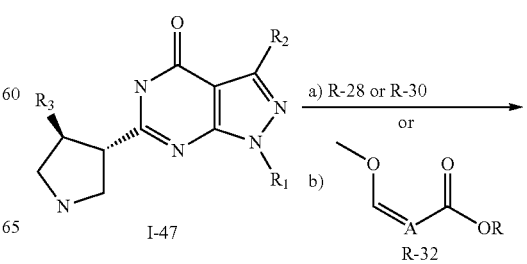

173
-continued

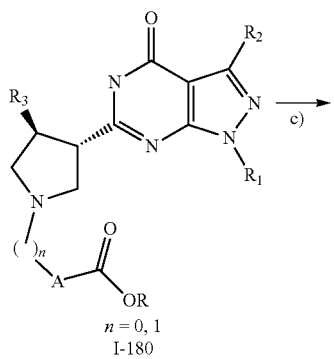

n = 0, 1
I-180

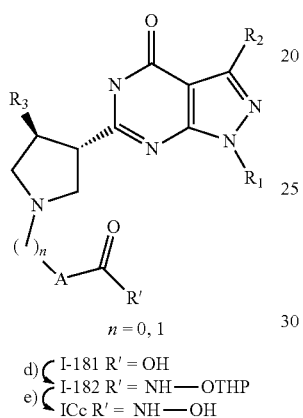

n = 0, 1 d) ⎧ I-181 R' = OH
   ⎨ I-182 R' = NH—OTHP
e) ⎩ ICc R' = NH—OH

Conditions: a) ketone R-28 (1 eq) or aldehyde R-30 (1.2 eq), AcOH (cat), Na(AcO)3BH (2 eq), DCM, overnight at r.t.; b) R-32 (1.5 eq), CH3COOH (2 eq) in DCM at 0° C. for 3 h, Na(AcO)3BH (2 eq), at r.t for 15 h; c) LiOH·H2O (12 eq) in THF/methanol/H2O, r.t. for 4 h; d) EDC·HCl (2 eq), HOBt (2 eq), THP—O—NH2 (2 eq), NMM (3 eq) in DMF, overnight at r.t.; e) HCl/AcOEt (4M) at r.t for 1 h.

In the scheme above R is $(C_1-C_6)$alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-180a: methyl 4-[[(3R, 4R)-3-methyl-4-(4-oxo-1-tetrahydropyran-4-yl-5H-pyrazolo[3,4-d]pyrimidin-6-yl)pyrrolidin-1-yl] methyl]benzoate (trans racemic)

To a solution of intermediate I-147a (130 mg, 0.43 mmol) in DCM (10 mL) was added R-30a: methyl 4-formylbenzoate (84.4 mg, 0.515 mmol), and the mixture was added CH3COOH (0.1 mL) Then the mixture was stirred at r.t for 1 h. Then the mixture was added NaBH(OAc)3 (182.3 mg, 0.86 mmol), and stirred at r.t overnight. After TLC (DCM/MeOH 10:1) showed the starting material was consumed, the mixture was filtrated and concentrated to give the crude product which was purified by prep-TLC to obtained pure intermediate I-180a (130 mg, 67% yield) as a yellow solid. ESI-MS (M+1): 452.2 calc. for C24H29N5O4: 451.2.

174

Preparation of intermediate I-181a: 4-[[(3R,4R)-3-methyl-4-(4-oxo-1-tetrahydropyran-4-yl-5H-pyrazolo[3,4-d]pyrimidin-6-yl)pyrrolidin-1-yl]methyl] benzoic acid (trans racemic)

To a solution of intermediate I-180a (130 mg, 0.29 mmol) in THF/MeOH/H2O (3/3/2, 10 mL) was added LiOH.H2O (122 mg, 29 mmol). The resulting mixture was stirred at r.t for 4 hrs. Then, the mixture was diluted with water and adjusted pH to 2-3 with 1N HCl and the mixture was extracted with EtOAc, washed with brine, dried over anhydrous Na2SO4, concentrated to give the crude intermediate I-181a (125 mg, 98%) as a pale yellow solid which was used in the next step without purification. ESI-MS (M+1): 438.2 calc. for C23H27N5O4: 437.2.

Preparation of intermediate I-182a: 4-[[(3R,4R)-3-methyl-4-(4-oxo-1-tetrahydropyran-4-yl-5H-pyrazolo[3,4-d]pyrimidin-6-yl)pyrrolidin-1-yl]methyl]-N-tetrahydropyran-2-yloxy-benzamide (trans racemic)

To a solution of intermediate I-181a (125 mg, 0.286 mmol) in DMF (10 mL) was added EDC.HCl (110 mg, 0.572 mmol), HOBt (77.2 mg, 0.572 mmol), THP-O—NH2 (67 mg, 0.572 mmol), NMM (86.6 mg, 0.858 mmol), then the mixture was stirred at r.t overnight. The mixture was quenched with water and extracted with EtOAc, the organic layer was washed with brine, dried over anhydrous Na2SO4, concentrated to give the crude intermediate I-182a (40 mg, 26%) as a pale yellow solid. ESI-MS (M+1): 537.3 calc. for C28H36N6O5: 536.2.

Preparation of compound 3-09: 4-[[(3R,4R)-3-methyl-4-(4-oxo-1-tetrahydropyran-4-yl-5H-pyrazolo[3,4-d]pyrimidin-6-yl)pyrrolidin-1-yl]methyl] benzenecarbohydroxamic acid (trans racemic)

A solution of intermediate I-182a (40 mg, 0.074 mmol) in HCl/EA (4M, 5 mL) was stirred at room temperature for 1 hr, then concentrated to give the crude compound which was purified by prep-HPLC (General procedure, Method 1) to obtained pure compound 3-09 (24 mg, 72.7%) as a yellow solid. ESI-MS (M+1): 453.2 calc. for C23H28N6O4: 452.2; Rt is 2.33.

Following the same synthetic route for compound 3-09 and using the same reagents or intermediates unless otherwise indicated in the table below, the following compounds were obtained:

| Example | $R_t$ (min) | $[M + 1]^+$ | HPLC Method | Starting Materials |
|---|---|---|---|---|
| 3-10 (trans racemic) | 2.19 | 459.1 | 2 | methyl 5-formylthiophene-2-carboxylate (R-30b) |
| 3-11 (trans racemic) | 2.91 | 437.2 | 2 | Intermediate I-47b |
| 3-12 (trans racemic) | 3.08 | 431.2 | 2 | benzyl 3-(methoxymethylene)cyclobutanecarboxylate (R-32a) |
| 3-14 (trans racemic) | 2.45 | 417.2 | 2 | methyl 3-oxocyclobutanecarboxylate (R-28c) |
| 3-17 (trans racemic) | 2.87 | 443.1 | 2 | Intermediate I-47b & methyl 5-formylthiophene-2-carboxylate (R-30b) |

Synthetic Route 4a

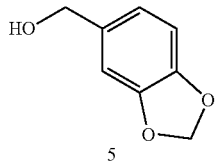

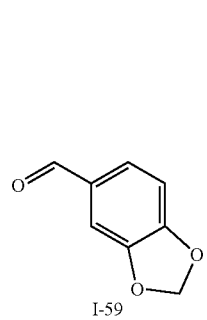

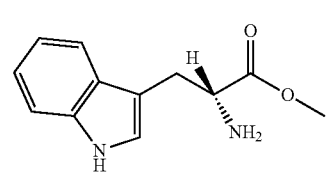

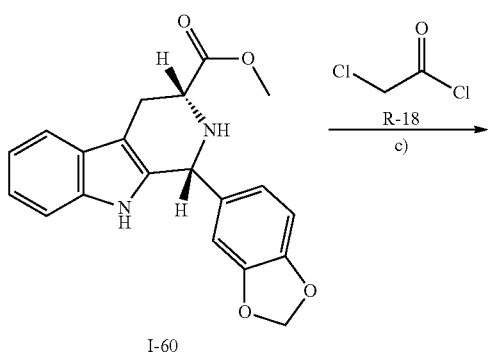

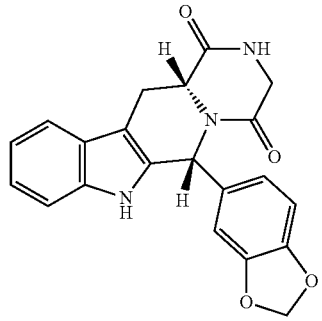

I-62

Conditions: a) MnO$_2$ (10 eq) in DCM, overnight at r.t.; b) R-17 in $^i$PrOH, refluxed overnight; c) Et$_3$N (2 eq) in THF, R-18 (1 eq) is added at 0° C.; then, 3 hours at r.t.; d) NH$_3$/methanol (30%) at 40° C. for 3 days.

Any racemic mixture and pure enantiomer is considered.

Preparation of intermediate I-59a: Benzo[d][1,3]dioxole-5-carbaldehyde

A solution of the commercially available piperonol (5, 100 g, 0.66 mmol) and active MnO$_2$ (572 g, 6.6 mmol) in DCM (1000 ml) was stirred at r.t overnight. The reaction mixture was filtrated and the filtrate were washed with brine, dried over anhydrous Na$_2$SO$_4$ and concentrated to give crude I-59a (80 g, 80% yield) as white solid. ESI-MS (M+1): 151 calc. for C$_8$H$_6$O$_3$: 150.1

Preparation of intermediate I-60a: Methyl 1-(benzo[d][1,3]dioxol-5-yl)-2,3,4,9-tetrahydro-1H-pyrido[3,4-b]indole-3-carboxylate The solution of I-59a (30 g, 0.2 mol) and the reagent (R)-methyl 2-amino-3-(1H-indol-3 yl)propanoate (R-17, 43.6 g, 0.2 mol) in propan-2-ol (500 mL) was refluxed overnight. The reaction mixture was concentrated and the solid was dissolved in aq. NaHCO$_3$ and DCM. The organic phase was separated and dried over Na$_2$SO$_4$, concentrated and the residue was dissolve in 50 mL DCM and hexane (600 mL) was added with stirring. The solid was filtered off and the filtration was concentrated to give crude compound I-60a as racemic mixture (90% cis isomer) (50 g, 70% yield). ESI-MS (M+1): 351 calc. for C$_{20}$H$_{18}$N$_2$O$_4$: 350.

Preparation of intermediate I-61a: Methyl 1-(benzo[d][1,3]dioxol-5-yl)-2-(2-chloroacetyl)-2,3,4,9-tetrahydro-1H-pyrido[3,4-b]indole-3-carboxylate To a solution of I-60a (50 g, 0.14 mol) and Et$_3$N (29 g, 0.28 mol) in anhydrous THF (500 mL) was added chloroacetyl chloride (R-18, 17.7 mg, 0.15 mol) at 0° C. The reaction mixture was stirred at r.t. for 3 h. Diluted with 300 mL of DCM and washed by aqueous NaHCO$_3$, dried and concentrated to give I-61a, racemic mixture (mainly as cis isomer), (20 g, 2.57 mmol, 27% yield) as a yellow solid. ESI-MS (M+1): 427 calc. for C$_{22}$H$_{19}$ClN$_2$O$_5$: 426.1

Preparation of intermediate I-62a: 6-(1,3-Benzodioxol-5-yl)-2,3,6,7,12,12a-hexahydropyrazino[1',2':1,6]pyrido[3,4-b]indole-1,4-dione The solution of compound I-61a (5 g, 9.5 mmol) in NH$_3$/methanol (30 mL, 30%) was stirred at 40° C. for 3 days. Concentrated and dissolved in 50 mL of DCM. Washed with water (50 mL×3) and dried. The organic phase was concentrated to give product I-62a, racemic mixture (mainly as cis isomer), (3 g, 84.2% yield) as white solid. ESI-MS (M+1): 376 calc. for C$_{21}$H$_{17}$N$_3$O$_4$: 375.1

Synthetic Route 4b
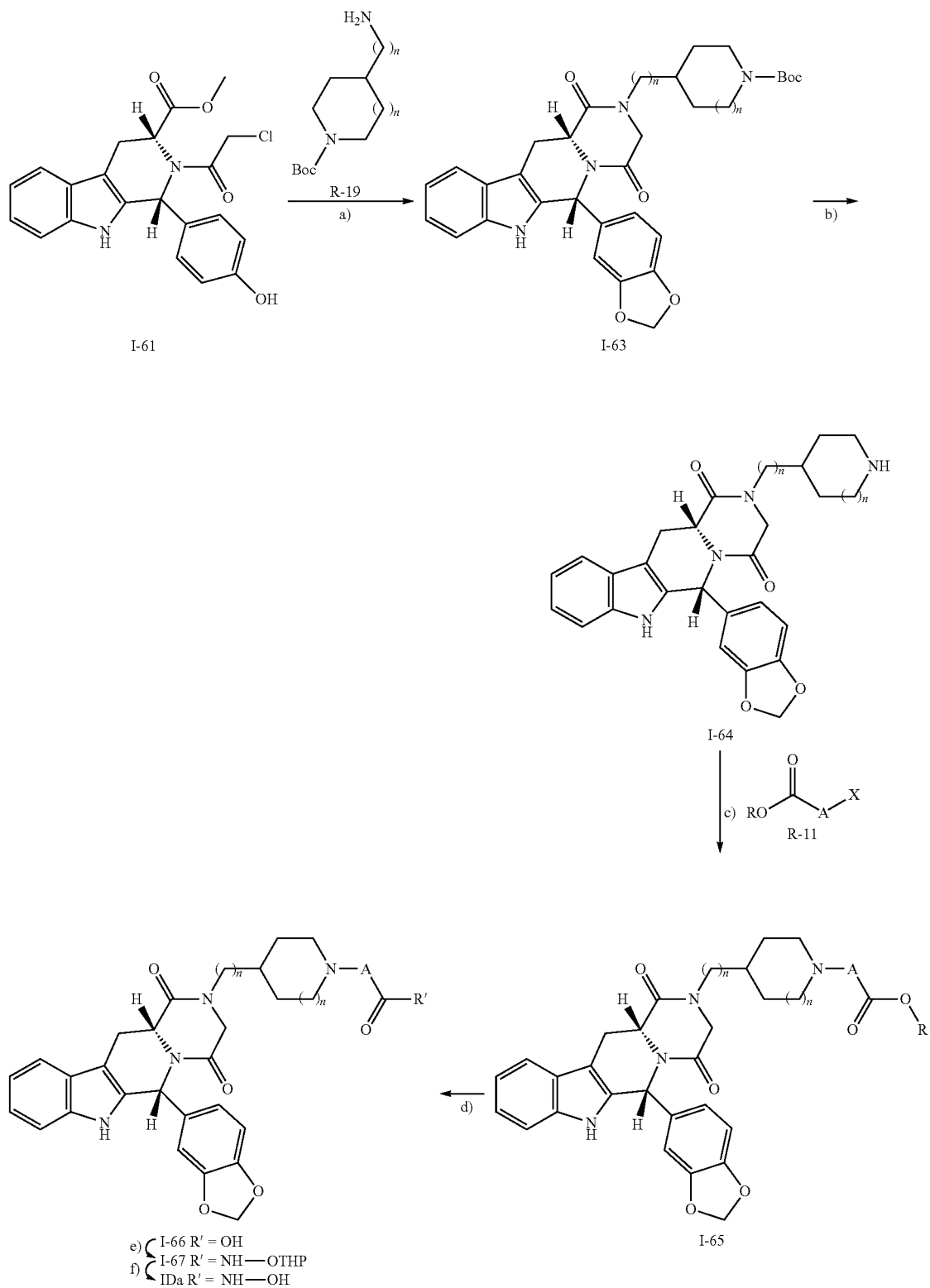
Conditions: a) R-19 (1 eq) in methanol at 90° C. for 3 days; b) TFA/DCM at r.t. for 2 hours; c) K$_2$CO$_3$ (3 eq), R-11 (2 eq) and KI (0.2 eq) in CH$_3$CN, at r.t. for 5 hours;
d) LiOH·H$_2$O (7 eq) in THF/H$_2$O, overnight at r.t.; e) EDC·HCl (2 eq), HOBt (2 eq), THP—O—NH$_2$ (1.2 eq), NMM (3 eq) in DMF, overnight at r.t.;
f) HCl/dioxane (4M) at r.t for 3 hours.

In the scheme above R is $(C_1\text{-}C_6)$alkyl, n is 0 or 1, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-63a: 4-[6-(1,3-Benzodioxol-5-yl)-2,3,6,7,12,12a-hexahydropyrazino[1',2':1,6]pyrido[3,4-b]indole-1,4-dion-2-yl]1-(tert-butoxycarbonyl)piperidine To a solution of I-61a (10.8 g, 0.025 mol) in methanol (300 mL) was added the commercially available reagent tert-butyl 4-aminopiperidine-1-carboxylate (R-19a, 5.1 g, 0.025 mol), the reaction was stirred at 90° C. for 3 days. Then mixture was concentrated and extracted with EA. The combined organic layers were washed with brine, dried over anhydrous $Na_2SO_4$ and concentrated to give the crude product which was purified by column chromatography (EA:PE=1:100-1:3) to give I-63a, racemic mixture (mainly as cis isomer), (2.5 g, 17.6% yield) as a pale white solid. ESI-MS (M+1): 559 calc. for $C_{31}H_{34}N_4O_6$: 558.1.

Preparation of intermediate I-64a: 4-[6-(1,3-Benzodioxol-5-yl)-2,3,6,7,12,12a-hexahydropyrazino[1',2':1,6]pyrido[3,4-b]indole-1,4-dion-2-yl]piperidine To a solution of I-63a (2.5 g, 4.4 mol) in DCM (50 mL) was added TFA (1 mL), the reaction was stirred at r.t for 2 hours. Then mixture was concentrated to give crude I-64a, racemic mixture (mainly as cis isomer), (2.4 g, 100% yield) as a yellow solid. ESI-MS (M+1): 459 calc. for $C_{26}H_{26}N_4O_4$: 458.0.

Preparation of intermediate I-65a: Ethyl 2-(4-[6-(1,3-benzodioxol-5-yl)-2,3,6,7,12,12a-hexahydropyrazino[1',2':1,6]pyrido[3,4-b]indole-1,4-dion-2-yl]piperidin-1-yl)pyrimidine-5-carboxylate To a solution of I-64a (0.5 g, 1.09 mmol) in $CH_3CN$ (10 mL) was added commercially available ethyl 2-chloropyrimidine-5-carboxylate (R-11e, 0.41 g, 2.18 mmol), $K_2CO_3$ (0.45 g, 3.27 mmol), KI (0.036 g, 0.22 mmol), the reaction was stirred at r.t for 5 h. Then the mixture was concentrated and extracted with EA. The combined organic layers were washed with brine, dried over anhydrous $Na_2SO_4$ and concentrated to give the crude product which was purified by column chromatography (EA:PE=1:50-1:3) to give I-65a, racemic mixture (mainly as cis isomer), (0.6 g, 90% yield) as a yellow solid. ESI-MS (M+1): 609 calc. for $C_{33}H_{32}N_6O_6$: 608.1.

Preparation of intermediate I-66a: 2-(4-[6-(1,3-Benzodioxol-5-yl)-2,3,6,7,12,12a-hexahydropyrazino[1',2':1,6]pyrido[3,4-b]indole-1,4-dion-2-yl]piperidin-1-yl)pyrimidine-5-carboxylic acid To a solution of I-65a (0.4 g, 0.66 mmol) in $THF/H_2O$ (20/10 mL) was added $LiOH.H_2O$ (0.22 g, 5 mol), the reaction mixture was stirred at r.t for overnight. The mixture was diluted with EA and washed with 2M HCl solution, dried over anhydrous $Na_2SO_4$ and concentrated to give crude I-66a, racemic mixture (mainly as cis isomer), (0.2 g, 51% yield) as a yellow solid. ESI-MS (M+1): 581 calc. for: $O_{31}H_{28}N_6O_6$: 580.1.

Preparation of intermediate I-67a: N-(Tetrahydro-2H-pyran-2-yloxy)-2-(4-[6-1,3-benzodioxol-5-yl)-2,3,6,7,12,12a-hexahydropyrazino[1',2':1,6]pyrido[3,4-b]indole-1,4-dion-2-yl]piperidin-1-yl)pyrimidine-5-carboxamide To a solution of I-66a (260 mg, 0.45 mmol) in DMF (10 mL) was added EDC.HCl (173 mg, 0.9 mmol), HOBt (122 mg, 0.9 mmol), THP-O—$NH_2$ (63 mg, 0.54 mmol), NMM (136 mg, 1.35 mmol). The mixture was stirred at 30° C. overnight. The mixture was diluted with EA and washed with brine, dried over anhydrous $Na_2SO_4$ and purified by column (EA:PE=1:50-1:5) to give I-67a, racemic mixture (mainly as cis isomer), (250 mg, 82% yield) as a pale yellow solid. ESI-MS (M+1): 680 calc. for: $C_{36}H_{37}N_7O_7$: 679.1

Preparation of compound 4-03: N-Hydroxy-2-(4-[6-(1,3-benzodioxol-5-yl)-2,3,6,7,12,12a-hexahydropyrazino[1',2':1,6]pyrido[3,4-b]indole-1,4-dion-2-yl]piperidin-1-yl)pyrimidine-5-carboxamide A solution of I-67a (125 mg, 0.18 mmol) in HCl/dioxane (3M, 10 mL) was stirred at r.t. overnight. The reaction mixture was concentrated and purificated by preparative HPLC to give pure 4-03, racemic mixture (mainly as cis isomer), (22.6 mg, 21% yield) as a pale yellow solid. ESI-MS (M+1): 596.3 (HPLC Method: 1) calc. for $O_{31}H_{29}N_7O_6$: 595.1

Following the same synthetic route for compound 4-03 and using the same reagents unless otherwise indicated in the table below, the following compounds were obtained:

| Example | $R_t$ (min) | [M + 1]$^+$ | HPLC Method | Starting Materials |
|---|---|---|---|---|
| 4-02 (mainly as cis isomer) | 2.03 | 560.1 | 1 | tert-Butyl 4-aminopiperidine-1-carboxylate (R-19a) and ethyl 4-bromobutanoate (R-11b) |
| 4-04 (mainly as cis isomer) | 2.42 | 634.3 | 1 | tert-Butyl 4-aminopiperidine-1-carboxylate (R-19a) and 4-((E)-2-(ethoxycarbonyl)-vinyl)benzyl methanesulfonate (R-11d) |
| 4-05 (mainly as cis isomer) | 2.50 | 610.3 | 1 | tert-Butyl 4-(aminomethyl)-piperidine-1-carboxylate (R-19b) and ethyl 2-chloro-pyrimidine-5-carboxylate (R-11e) |

Synthetic Route 4c

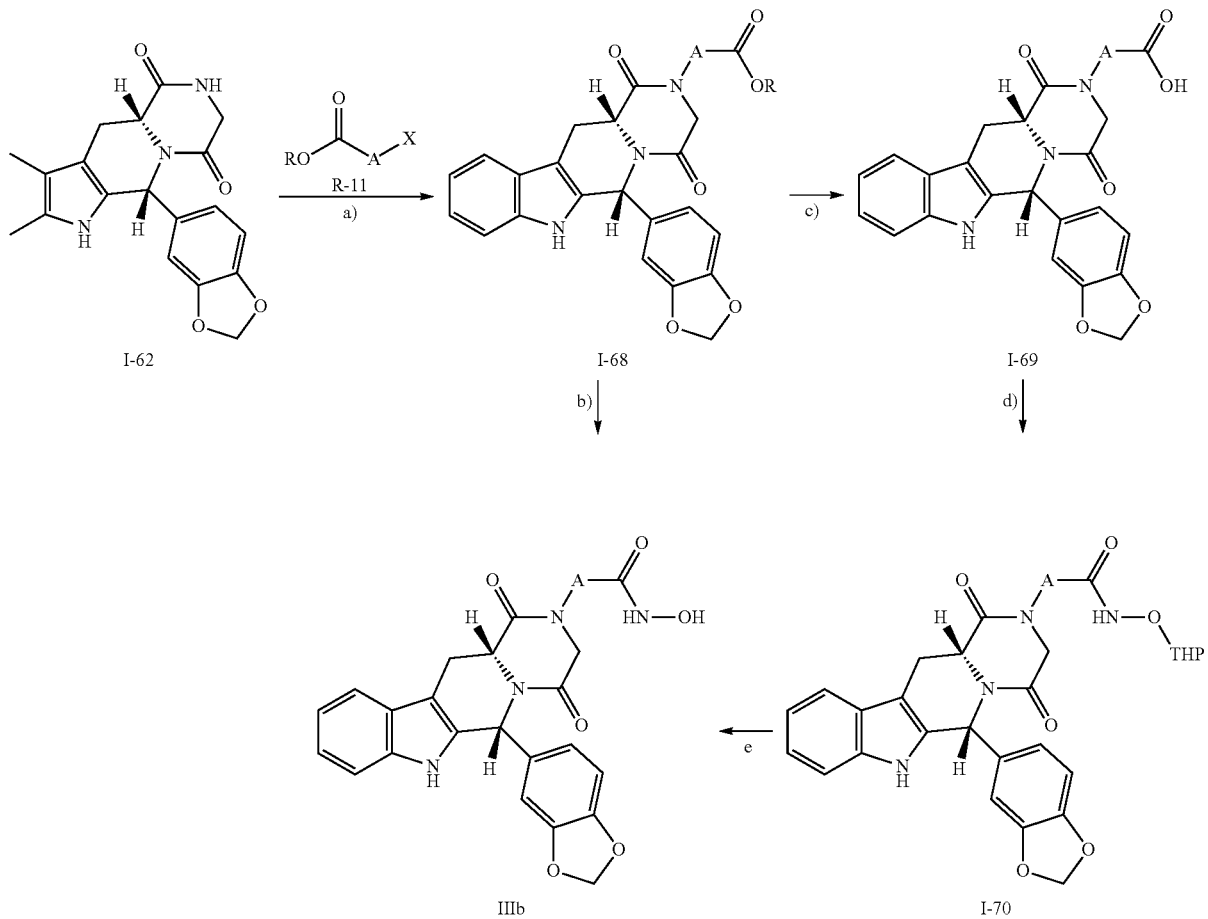

Conditions: a) CuI (2 eq), K₃PO₄ (2 eq), (±)-trans-1,2 diaminocyclohexane (4 eq) and R-11 (1 eq) in dioxane, at r.t. for 8 days; b) NaCN (0.2 eq) in NH₂•OH/methanol, at 50° C. for 3 hours; c) LiOH•H₂O (7 eq) in THF/H₂O, overnight at r.t.; d) EDC•HCl (2 eq), HOBt (2 eq), THP—O—NH₂ (1.2 eq), NMM (3 eq) in DMF, overnight at r.t.; e) HCl/dioxane (4M) at r.t for 3 hours.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings. Any racemic mixture and pure enantiomer is considered Preparation of intermediate I-68a: (E)-Ethyl 4-[6-(1,3-benzodioxol-5-yl)-2,3,6,7,12,12a-hexahydropyrazino[1',2':1,6]pyrido[3,4-b]indole-1,4-dion-2-yl] phenylprop-2-enoate To a solution of I-62a (0.6 g, 1.6 mmol) in dioxane (15 mL) was added CuI (0.6 g, 3.2 mmol, 2 eq), K₃PO₄ (0.68 g, 3.2 mmol, 2 eq), (±)-trans-1,2-diaminocyclohexane (0.72 g, 6.4 mmol, 4 eq), (E)-ethyl 3-(4-iodophenyl)prop-2-enoate (R-11f, 0.48 g, 1.6 mmol, 1 eq) in dioxane, at r.t for 8 days. Then mixture was concentrated and extracted with EA. The combined organic layers were washed with brine, dried over anhydrous Na₂SO₄ and concentrated to give the crude product which was purified by column chromatography (EA:PE=1:10-1:3) to give I-68a, racemic mixture (mainly as cis isomer), (0.3 g, 34% yield) as a pale yellow solid. ESI-MS (M+1): 550 calc. for $C_{32}H_{27}N_3O_6$: 549.1

Preparation of compound 4-01: (E)-N-Hydroxy-4-[6-(1,3-benzodioxol-5-yl)-2,3,6,7,12,12a-hexahydro-pyrazino[1',2':1,6]pyrido[3,4-b]indole-1,4-dion-2-yl] phenylprop-2-enamide To a solution of I-68a (100 mg, 0.18 mmol) in NH₂.OH/methanol (2 M/L, 3 mL) was added NaCN (1.7 mg, 0.036 mmol), the reaction was stirred at 50° C. for 3 h. Then mixture was concentrated and extracted with EA. The combined organic layers were washed with brine, dried over anhydrous Na₂SO₄ and concentrated to directly give the crude product which was purified by preparative HPLC to obtain pure 4-01, racemic mixture (mainly as cis isomer), (5.6 mg, 5.7% yield) as a pale yellow solid. ESI-MS (M+1): 537.2 (HPLC Method: 1) calc. for $C_{30}H_{24}N_4O_6$: 536.1

Synthetic Route 5a

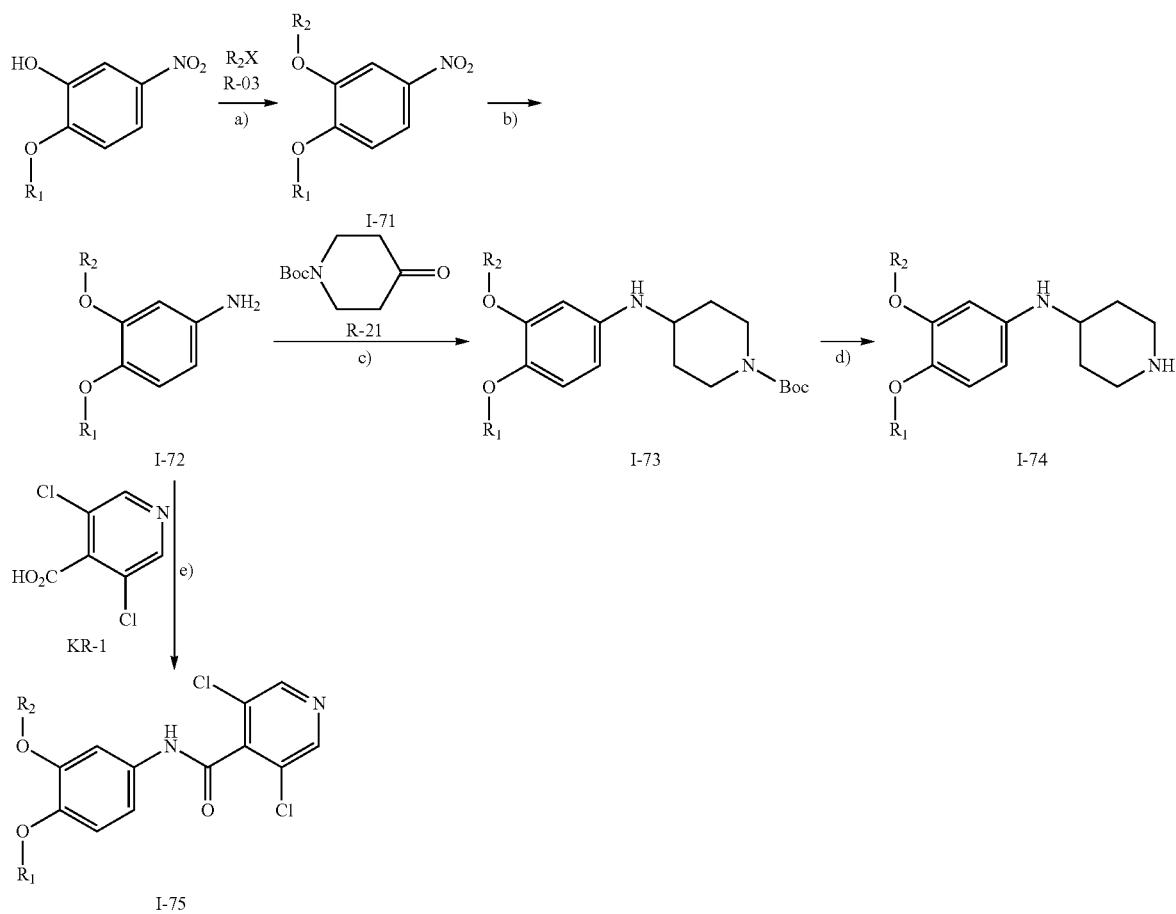

Conditions: a) R-03 (1.2 eq), K₂CO₃ (2 eq) in CH₃CN, overnight at 90° C.; b) Pd/C in methanol, at r.t. for 5 hours; c) R-21 (1.5 eq), NaBH₃CN (2 eq), AcOH (2 eq) in methanol, overnight at 60° C.; d) TFA/DCM at r.t. for 2 hours; e) EDC•HCl (2 eq), HOBt (2 eq), KR-1 (1 eq), NMM (3 eq) in DMF at r.t. overnight.

In the scheme above, X is a leaving group, such halogen.

Preparation of intermediate I-71a: 2-(Cyclopentyloxy)-1-methoxy-4-nitrobenzene

To a solution of the commercially available reagent 2-methoxy-5-nitrophenol (19.4 g, 111 mmol) in anhydrous CH₃CN (300 mL) was added bromocyclopentane (20.34 g, 140 mmol), K₂CO₃ (30 g, 222 mmol), the reaction mixture was stirred at 90° C. overnight. The mixture was diluted with EA and washed with brine, dried over anhydrous Na₂SO₄ and concentrated to give the crude product which was purified by column chromatography to give I-71a (20 g, 76.9% yield) as a yellow solid. ESI-M (M+1): 238 calc. for $C_{12}H_{15}NO_4$: 237.1.

Preparation of intermediate I-72a: 3-(Cyclopentyloxy)-4-methoxybenzenamine

To a solution of compound I-71a (20 g, 84 mmol) in methanol (300 mL) was added Pd/C (6 g). The reaction mixture was stirred at r.t for 5 h. The resulting mixture was filtered, the filtrate was concentrated to give crude I-72a (16 g, 92.0% yield) as a pale yellow solid. ESI-MS (M+1): 208 calc. for $C_{12}H_{17}NO_2$: 207.0.

Preparation of intermediate I-73a: N-(3-(Cyclopentyloxy)-4-methoxyphenyl)-1-(tert-butoxycarbonyl) piperidin-4-amine To a solution of I-72a (5 g, 240 mmol) in methanol (100 mL) was added tert-butyl 4-oxopiperidine-1-carboxylate (R-21, 7.1 g, 360 mmol), NaBH₃CN (3 g, 480 mmol), AcOH (3 g, 480 mmol). The reaction mixture was stirred at 60° C. overnight. The mixture was diluted with EA and washed with brine, dried over anhydrous Na₂SO₄ and concentrated to give the crude product which was purified by column chromatography (EA:PE=1:20-1:5) to give I-73a (4 g, 42% yield) as a yellow solid. ESI-MS (M+1): 391 calc. for $C_{22}H_{34}N_2O_4$: 390.1.

Preparation of intermediate I-75a (5-01): 3,5-Dichloro-N-(3-(cyclopentyloxy)-4-methoxyphenyl) pyridine-4-carboxamide To a solution of compound I-72a (600 mg, 2.88 mmol) in DMF (30 mL) was added EDC.HCl (1.1 g, 5.76 mmol), HOBt (780 mg, 5.76 mmol), KR-1 (550 mg, 2.88 mmol), NMM (870 mg, 8.64 mmol). The mixture was stirred at r.t. overnight. The mixture was diluted with EA and washed with brine, dried over anhydrous Na₂SO₄ and concentrated to give the crude compound which was purified by column chromatography (EA:PE=1:30-1:3) and recrystallization (EA) to give I-75a (5-01, 85 mg, 8.5% yield) as a pale solid.

ESI-MS (M+1): 382.0 (HPLC Method: 3) calc. for $C_{18}H_{18}Cl_2N_2O_3$: 381.2.

Synthetic Route 5b

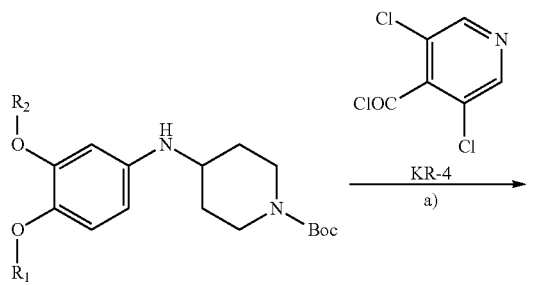

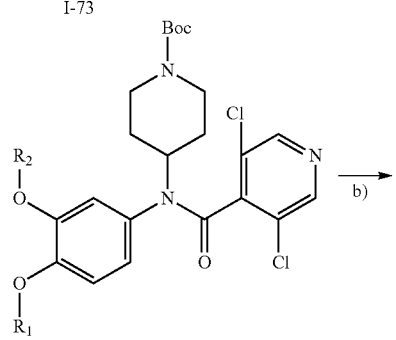

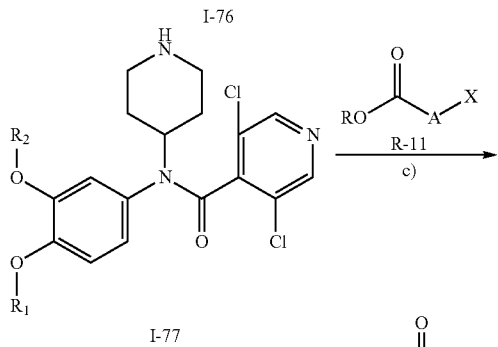

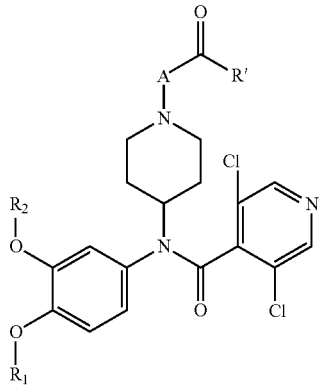

d) ⎰ I-78 R' = OR
e) ⎱ I-79 R' = OH
f) ⎰ I-80 R' = NH—OTHP
    ⎱ Va R' = NH—OH

Conditions: a) Et$_3$N (2 eq) and KR-4 (1 eq) in DCM, at r.t. overnight; b) HCl/dioxane (4M) at r.t. for 2 hours; c) R-11 (1.2 eq), K$_2$CO$_3$ (3 eq) in CH$_3$CN, MW at 120° C. for 2 hours; d) LiOH·H$_2$O (5 eq) in THF/H$_2$O, overnight at 60° C.; e) EDC·HCl (2 eq), HOBt (2 eq), THP—O—NH$_2$ (1.2 eq), NMM (3 eq) in DMF, overnight at r.t.; f) HCl/dioxane (4M) at r.t for 3 hours.

In the scheme above R is (C$_1$-C$_6$)alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-76a: 4-(N-[3,5-Dichloropyridin-4-ylcarbonyl]-N-[(3-(cyclopentyloxy)-4-methoxyphenyl)]amino)-1-(tert-butoxycarbonyl)-piperidine To a solution of I-73a (7 g, 17.9 mmol) in DCM (100 mL) was added 3,5-dichloroisonicotinoyl chloride, KR-4, (3.7 g, 17.9 mmol, 1 eq), Et$_3$N (3.6 g, 36 mmol, 2 eq). The reaction mixture was stirred at r.t overnight. The mixture was diluted with EA and washed with brine, dried over anhydrous Na$_2$SO$_4$ and concentrated to give the crude product which was purified by column chromatography (EA:PE=1:50-1:30) to give the compound I-76a (1.1 g, 11% yield) as a yellow solid. ESI-MS (M+1): 564 calc. for $C_{28}H_{35}Cl_2N_3O_5$: 563.1.

Preparation of intermediate I-77a: 4-(N-[3,5-Dichloropyridin-4-ylcarbonyl]-N-[(3-(cyclopentyloxy)-4-methoxyphenyl)]amino)piperidine A solution of I-76a (1.1 g, 1.95 mmol) in HCl/Dioxane (4 M/L, 10 mL) was stirred at r.t. for 2 h. The mixture was concentrated to give I-77a (1 g, 100% yield) as a yellow solid. ESI-MS (M+1): 464 calc. for $C_{23}H_{27}Cl_2N_3O_3$: 463.0.

Preparation of intermediate I-78a: Ethyl 4-[4-(N-[3,5-dichloropyridin-4-ylcarbonyl]-N-[(3-(cyclopentyloxy)-4-methoxyphenyl)]amino)piperidin-1-yl]butanoate I-78a was obtained starting from I-77a in an analogous manner to I-18a, but using ethyl 4-bromobutanoate (R-11 b) instead of ethyl 3-bromopropionate (R-11a). 81% yield as a yellow solid. ESI-MS (M+1): 578 calc. for $C_{29}H_{37}Cl_2N_3O_5$: 577.1.

Preparation of intermediate I-79a: 4-[4-(N-[3,5-Dichloropyridin-4-ylcarbonyl]-N-[(3-(cyclopentyloxy)-4-methoxyphenyl)]amino)piperidin-1-yl]butanoic acid I-79a was obtained starting from I-78a in an analogous manner to I-19a. 79% yield as a yellow solid. ESI-MS (M+1): 550 calc. for $C_{27}H_{33}Cl_2N_3O_5$: 549.1.

Preparation of intermediate I-80a: N-(Tetrahydro-2H-pyran-2-yloxy)-4-[4-(N-[3,5-dichloropyridin-4-ylcarbonyl]-N-[(3-(cyclopentyloxy)-4-methoxyphenyl)]amino)piperidin-1-yl]butanamide I-80a was obtained starting from I-79a in an analogous manner to I-20a. 64% yield) as a yellow solid. ESI-MS (M+1): 649 calc. for $C_{32}H_{42}Cl_2N_4O_6$: 648.1.

Preparation of compound 5-03: N-Hydroxy-4-[4-(N-[3,5-dichloropyridin-4-ylcarbonyl]-N-[(3-(cyclopentyloxy)-4-methoxyphenyl)]amino)piperidin-1-yl]butanamide Compound 5-03 was obtained starting from I-80a in an analogous manner to compound 1-04. 9.4% yield as a white solid. ESI-MS (M+1): 565 (HPLC Method: 1) calc. for $C_{27}H_{34}Cl_2N_4O_5$: 564.2.

Following the same synthetic route for compound 5-03 and using the same reagents unless otherwise indicated in the table below, the following compounds were obtained:

| Example | $R_t$ (min) | $[M + 1]^+$ | HPLC Method | Starting Materials |
|---|---|---|---|---|
| 5-02 | 2.31 | 640.2 | 1 | 4-((E)-2-(Ethoxycarbonyl)vinyl)-benzyl methanesulfonate (R-11d) |
| 5-04 | 2.66 | 602.2 | 1 | Ethyl 2-chloropyrimidine-5-carboxylate (R-11e) |

Synthetic Route 5c

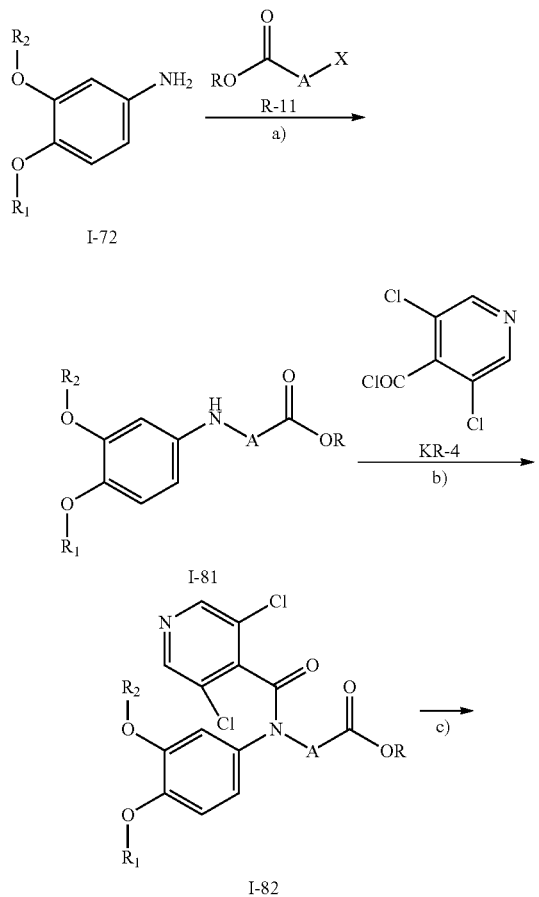

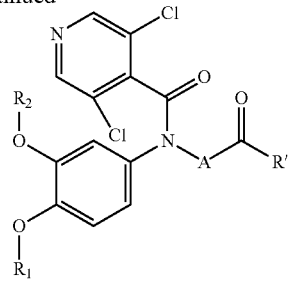

d) I-83 R' = OH
e) I-84 R' = NH—OTHP
   IIa R' = NH—OH

Conditions: a) $K_2CO_3$ (2.5 eq), R-11 (1 eq) and KI (0.5 eq) in DMF, at r.t. overnight; b) $Et_3N$ (3 eq) and KR-4 (1 eq) in DCM, at r.t. overnight; c) LiOH•$H_2O$ (10 eq) in THF/methanol/$H_2O$, for 4 hours at r.t.; d) EDC•HCl (2 eq), HOBt (2 eq), THP—O—$NH_2$ (1.2 eq), NMM (3 eq) in DMF, overnigth at r.t.; e) HCl/dioxane (4M) at 0° C. for 20 minutes.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of intermediate I-81a: Ethyl 7-[(3-(cyclopentyloxy)-4-methoxyphenyl)amino]heptanoate To a solution of I-72a (2.5 g, 12.1 mmol) in DMF (50 mL) was added the commercially available reagent ethyl 7-bromoheptanoate (R-11g, 2.86 g, 12.1 mmol), $K_2CO_3$ (4.2 g, 30.3 mmol) and KI (1 g, 6.1 mmol). The reaction mixture was stirred at r.t. overnight. The mixture was diluted with EA and washed with brine, dried over anhydrous $Na_2SO_4$ and concentrated to give the crude product. Which was purified by column chromatography (EA:PE=1:20-1:5) to give I-81a (1.5 g, 34% yield) as an oil. ESI-MS (M+1): 364.2 calc. for $O_{21}H_{33}NO_4$: 363.1.

Preparation of intermediate I-82a: Ethyl 7-(N-[3,5-dichloropyridin-4-ylcarbonyl]-N-[(3-(cyclopentyloxy)-4-methoxyphenyl)]amino)heptanoate To a solution of I-81a (727 mg, 2 mmol) in DCM (50 mL) was added 3,5-dichloroisonicotinoyl chloride (KR-4, 421 mg, 2 mmol) and $Et_3N$ (606 mg, 6 mmol) at −20° C. The reaction mixture was stirred at r.t. overnight. The mixture was extracted with EA and washed with brine, dried over anhydrous $Na_2SO_4$ and concentrated to give the crude product which was purified by column chromatography (EA:PE=1:50-1:30) to give the compound I-82a (640 mg, 60% yield) as an oil. ESI-MS (M+1): 537.1 calc. for $C_{27}H_{34}Cl_2N_2O_5$: 536.1.

Preparation of intermediate I-83a: 7-(N-[3,5-dichloropyridin-4-ylcarbonyl]-N-[(3-(cyclopentyloxy)-4-methoxyphenyl)]amino)heptanoic acid I-83a was obtained starting from I-82a in an analogous manner to I-19a. 75% yield. ESI-MS (M+1): 509.1; calc. for $C_{25}H_{30}Cl_2N_2O_5$: 508.1.

Preparation of intermediate I-84a: 7-(N-[3,5-dichloropyridin-4-ylcarbonyl]-N-[(3-(cyclopentyloxy)-4-methoxyphenyl)]amino)-N-(tetrahydro-2H-pyran-2-yloxy)heptanamide I-84a was obtained starting from I-83a in an analogous manner to I-20a. 41% yield. ESI-MS (M-55): 609; calc. for $C_{30}H_{39}Cl_2N_3O_6$: 608.2

Preparation of compound 5-05: 7-(N-[3,5-Dichloropyridin-4-ylcarbonyl]-N-[(3-(cyclopentyloxy)-4-methoxyphenyl)]amino)-N-hydroxyheptanamide Compound 5-05 was obtained starting from I-84a in an analogous manner to compound 1-04. 12% yield. ESI-MS (M+1): 525.2 (HPLC Method: 2) calc. for $C_{25}H_{31}Cl_2N_3O_5$: 524.4.

COMPARATIVE EXAMPLES

Comparative Example 2-01

2-[[4-ethoxy-3-(5-methyl-4-oxo-7-propyl-3H-imidazo[5,1-f][1,2,4]triazin-2-yl)phenyl]sulfonyl-methyl-amino]-N-methoxy-N-methyl-acetamide (Compound 14 of WO 2008/024494)

Its synthesis was performed according to procedure described in the mentioned patent application, and characterized by ESI-MS (M+1): 507.1 calc. for C22H30N6O6S (as reported in WO 2008/024494).

Comparative Example 2-02

3-[[4-ethoxy-3-(5-methyl-4-oxo-7-propyl-3H-imidazo[5,1-f][1,2,4]triazin-2-yl)phenyl]methyl]-N-methoxy-N-methylcyclobutanecarboxamide Its synthesis was performed from intermediate I-174a:

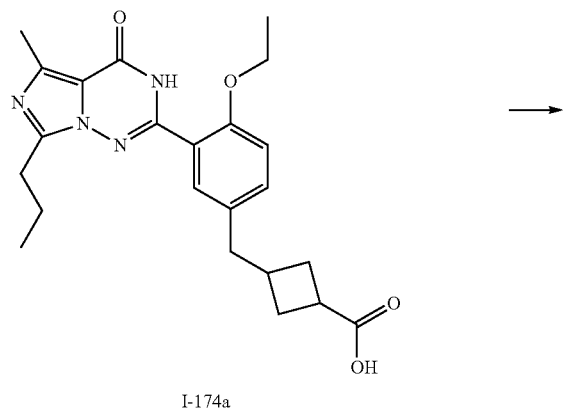

I-174a

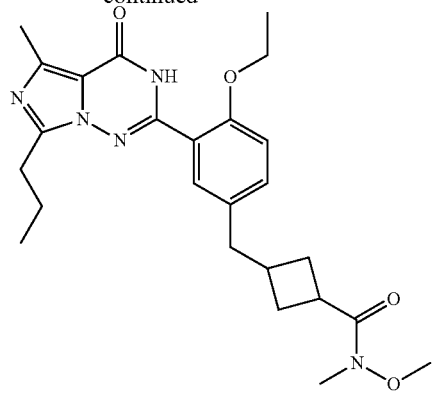

Comparative example 2-02

To a solution of intermediate I-174a (500 mg, 1.17 mmol) in DMF (10 mL) was added EDC.HCl (461 mg, 2.4 mmol), HOBt (324 mg, 2.4 mmol), N, O dimethylhydroxylamine (146 mg, 2.4 mmol) and NMM (363 mg, 3.6 mmol) at r.t, then the mixture was stirred at room temperature overnight. The mixture was quenched with aqueous water and extracted with EtOAc, the organic layer was washed with brine, dried over anhydrous Na2SO4, concentrated to give the crude product which was purified by prep-TLC to give comparative example 2-02 (17 mg, 3% yield) as a pale yellow solid. ESI-MS (M+1): 468.2; calc. for C25H33N5O4: 467.2; Rt is 2.74.

Comparative Example 3-01

(1R,2R)-2-(1-(4,4-difluorocyclohexyl)-3a,4,5,7a-tetrahydro-4-oxo-1H-pyrazolo[3,4-d]pyrimidin-6-yl)-N-methoxy-N-methylcyclobutanecarboxamide (trans racemic) (Example 8B of WO2012/020022)

Its synthesis was performed according to procedure described in the mentioned patent application, and characterized by ESI-MS (M+1): 396.1 calc. for C18H23F2N5O3 (as reported in WO2012/020022).

Biological Tests

PDE Enzyme Activity Assay

The biochemical assay to measure PDE5A, PDE9A isoform b, PDE4D7, and PDE4A1 enzyme activities relies on the HTRF cGMP assay kit from CisBio (CisBio, Cat. #62GM2PEB), that determines the amount of cGMP present in the reaction. The enzymes were obtained from BPS Biosciences (GenBank Accession number for PDE5A: NM_001083, Cat. #60050; PDE9A: NM_001001567, Cat. #60090; PDE4D7: NM_001165899, Cat. #60047; and PDE4A1: U97584, Cat. #60040) and they are full-length with N-terminal GST tag. They were expressed in a baculovirus infected Sf9 cell expression system.

For each enzyme, enzyme activity assay was carried out in a 384-well plate in a final volume of 20 μL, as follows:
2.5 μL of vehicle or studied compound 4× concentrated prepared in assay buffer containing 50 mM Tris-HCl, 6 mM $MgCl_2$, pH 7.4 (PDE5A, PDE4D7, PDE4A1) and additionally 0.03% Tween-20 (PDE9A). Final percentage of DMSO was 0.5%.
2.5 μL of PDE5A (7 μg/mL) or 2.5 μL PDE9A (0.2 μg/mL) or 2.5 μL PDE4D7 (1.25 μg/mL) or 2.5 μL PDE4A1 (1.5 μg/mL) diluted in assay buffer. Final concentration was 1.75 µg/mL (PDE5A) or 0.05 µg/mL (PDE9A) or 0.31 µg/mL (PDE4D7) or 0.375 µg/mL (PDE4A1).

5 µL of substrate cGMP 4× concentrated to reach a final concentration of cyclic nucleotide of 100 nM (PDE5A and PDE9A) or 250 nM (PDE4D7 and PDE4A1).

After plate sealing, mixture was incubated for 30 minutes at 37° C.

Reaction was stopped by adding 5 µL of labelled cGMP labelled with the dye D2 (cGMP-D2) and 5 µL of Mab anti-cGMP labelled with cryptate (cGMP-cryptate) as recommended by the assay kit of CisBio.

Plate was sealed and incubated 1 hour at room temperature.

Fluorescence of each well was determined at 665 nm excitation and 620 nm emission using the plate reader EnVision (Perkin-Elmer). Results were calculated from the 665 nm/620 nm ratio. Positive control was obtained in the presence of the vehicle of the compounds. Negative control was obtained in the absence of cGMP and labelled cGMP-D2 cyclic nucleotide.

HDAC Enzyme Activity Assay

The biochemical assay to measure HDAC1, HDAC2, HDAC3, and HDAC6 enzyme activities relies on the fluorescence signal produced by a specific labelled substrate (BPS Biosciences, Cat #50037) after its deacetylation by HDACs. Fluorogenic substrate, containing a acetylated lysine side chain, can be deacetylated and then sensitized to subsequent treatment with the lysine developer (BPS Biosciences, Cat #50030), which produced a fluorophore that can be measured with a fluorescence plate reader.

The enzymes were obtained from BPS Biosciences. The enzyme HDAC1 (GenBank Accession number No. NM_004964; Cat. #50051) is full-length with C-terminal his tag and C-terminal Flag tag. The enzyme HDAC2 (GenBank Accession number No. NM_001527; Cat. #50002) is full-length with C-terminal his tag. The enzyme HDAC3 (GenBank Accession number No. NM_003883; Cat. #50003) is full-length with C-terminal his tag and human NCOR2, N-terminal GST tag. The enzyme HDAC6 (GenBank Accession number No. BC069243; Cat. #50006) is full-length with N-terminal GST tag. The enzymes were expressed in a baculovirus infected Sf9 cell expression system.

Enzyme activity assay was carried out in a black 96-well plate in a final volume of 100 µL, as follows:

5 µL of vehicle or studied compound 10× concentrated prepared in assay buffer (BPS Biosciences, Cat #50031). Final percentage of DMSO was 1%.

5 µL of HDAC1 (4 µg/mL HDAC1) or 5 µL of HDAC2 (15 µg/mL) or 5 µL of HDAC3 (10 µg/mL) or 5 µL of HDAC6 (36 µg/mL) diluted in assay buffer. Final concentration was 0.4 µg/mL (HDAC1), 1.5 µg/mL (HDAC2) or 1 µg/mL (HDAC3) or 3.6 µg/mL (HDAC6).

Start the reaction by adding 40 µL of reaction mixture containing 0.125 mg/mL BSA and 12.5 µM of fluorogenic HDACs substrate. Final concentrations of BSA and substrate were 0.1 mg/mL and 10 µM, respectively.

After plate sealing, mixture was incubated for 30 minutes at 37° C.

Reaction was stopped by adding 50 µL of lysine assay developer.

Plate was incubated 20 minutes at room temperature.

Fluorescence of each at 355 nm excitation and 460 nm emission was determined using the plate reader Mithras (Berthold). Positive control was obtained in the presence of the vehicle of the compounds. Negative control was obtained in the absence of HDAC1 enzyme activity.

Table 1 shows the inhibition values for recombinant enzymes ($IC_{50}$); where, $IC_{50} \geq 10$ µM (+), 1 µM≤$IC_{50}$<10 µM (++), 10 nM≤$IC_{50}$<1 µM (+++) and $IC_{50}$<10 nM (++++). Known PDE inhibitors (Sildenafil, Vardenafil, Tadalafil, Piclamilast and PF-4447943 (6-[(3S,4S)-4-methyl-1-(pyrimidin-2-ylmethyl)pyrrolidin-3-yl]-1-(tetrahydro-2H-pyran-4-yl)-1H-pyrazolo[3,4-d]pyrimidin-4(5H)-one)) as well as HDAC inhibitors (Vorinostat and Panobinostat) were also included as references.

TABLE 1

| Example | PDE4A1 | PDE4D7 | PDE5A1 | PDE9A | HDAC1 | HDAC2 | HDAC3 | HDAC6 |
|---|---|---|---|---|---|---|---|---|
| Sildenafil | ++ | | ++++ | ++ | + | | | |
| Vardenafil | ++ | | ++++ | +++ | | | | |
| Tadalafil | + | | ++++ | + | + | | | |
| Piclamilast | ++++ | | ++ | + | | | | |
| PF-4447943 | ++ | | ++ | +++ | | | | |
| Vorinostat | | | + | + | +++ | +++ | +++ | +++ |
| Panobinostat | | | | | ++++ | ++++ | ++++ | +++ |
| 1-01 | | | +++ | | + | + | | |
| 1-02 | | | ++++ | | +++ | ++ | | |
| 1-03 | | | ++++ | ++ | +++ | +++ | | |
| 1-04 | | | ++++ | | ++ | + | | |
| 1-05 | | | ++++ | | ++ | ++ | | |
| 1-06 | | | ++++ | + | ++++ | +++ | +++ | +++ |
| 1-07 | | | ++++ | ++ | +++ | +++ | +++ | +++ |
| 1-11 | | | ++ | | +++ | | | |
| 1-12 | | | +++ | ++ | +++ | | | |
| 1-14 | | | ++ | | +++ | | | +++ |
| 1-15 | | | +++ | | +++ | ++ | ++ | +++ |
| 1-16 | | | +++ | | +++ | ++ | ++ | +++ |
| 1-17 | | | ++++ | | ++ | + | + | +++ |
| 1-18 | | | +++ | | + | + | + | +++ |
| 1-19 | | | +++ | | +++ | +++ | +++ | +++ |
| 1-21 | | | ++++ | | +++ | + | | +++ |
| 1-22 | | | ++++ | | +++ | +++ | +++ | +++ |
| 1-23 | | | +++ | | +++ | +++ | | +++ |
| 1-24 | | | ++++ | | +++ | +++ | +++ | ++ |
| 1-25 | | | ++++ | | +++ | +++ | +++ | +++ |
| 1-26 | | | +++ | | ++ | + | | + |
| 1-27 | | | ++++ | | ++ | + | | + |

TABLE 1-continued

| Example | PDE4A1 | PDE4D7 | PDE5A1 | PDE9A | HDAC1 | HDAC2 | HDAC3 | HDAC6 |
|---|---|---|---|---|---|---|---|---|
| 1-28 | | | +++ | | +++ | + | | +++ |
| 1-29 | | | +++ | | +++ | + | | +++ |
| 1-30 | | | ++++ | | +++ | ++ | | +++ |
| 1-31 | | | +++ | | ++ | + | | ++ |
| 1-32 | | | ++++ | | | + | | ++ |
| 1-33 | | | +++ | | ++ | + | | + |
| 1-34 | | | +++ | | + | + | | +++ |
| 1-35 | | | +++ | | ++ | + | | ++ |
| 1-36 | | | +++ | | ++ | + | | ++ |
| 1-37 | | | +++ | | +++ | ++ | | +++ |
| 1-38 | | | +++ | | ++ | + | | +++ |
| 1-39 | | | +++ | | ++ | ++ | | +++ |
| 1-40 | | | +++ | | ++ | + | | +++ |
| 1-41 | | | +++ | | + | + | | ++ |
| 1-42 | | | +++ | | ++ | + | | +++ |
| 1-43 | | | +++ | | ++ | + | | +++ |
| 1-47 | | | +++ | | ++ | | | ++ |
| 1-48 | | | ++++ | | +++ | +++ | | +++ |
| 1-49 | | | +++ | | + | + | | ++ |
| 1-51 | | | +++ | | ++ | + | | ++ |
| 1-53 | | | +++ | | ++ | ++ | | ++ |
| 1-54 | | | +++ | | +++ | ++ | | ++ |
| 1-55 | | | +++ | | ++ | + | | +++ |
| 1-56 | | | +++ | | + | + | | ++ |
| 1-59 | | | +++ | | ++ | + | | ++ |
| 1-60 | | | +++ | | + | + | | + |
| 1-62 | | | +++ | | +++ | +++ | | +++ |
| 1-63 | | | +++ | | +++ | ++ | | +++ |
| 1-65 | | | +++ | | ++ | + | | + |
| 1-66 | | | +++ | | ++ | + | | +++ |
| 1-67 | | | +++ | | + | + | | + |
| 1-68 | | | +++ | | ++ | + | | +++ |
| 1-69 | | | +++ | | +++ | ++ | | ++ |
| 1-70 | | | +++ | | +++ | ++ | | ++ |
| 1-71 | | | ++++ | | | | | +++ |
| 1-72 | | | ++++ | | | | | +++ |
| 1-73 | | | ++++ | | | | | +++ |
| 1-74 | | | ++++ | | | | | ++ |
| 1-75 | | | +++ | | | | | ++ |
| 1-76 | | | +++ | | | | | +++ |
| 1-77 | | | +++ | | | | | +++ |
| 1-78 | | | ++++ | | | | | +++ |
| 1-79 | | | ++++ | | | | | +++ |
| 1-80 | | | +++ | | | | | +++ |
| 1-82 | | | +++ | | | | | +++ |
| 1-83 | | | +++ | | | | | +++ |
| 1-84 | | | +++ | | +++ | ++ | | +++ |
| 1-85 | | | +++ | | ++ | ++ | | +++ |
| 1-86 | | | +++ | | ++ | + | | ++ |
| 2-01 | | | ++++ | | ++ | | | |
| 2-02 | | | ++++ | +++ | +++ | | | |
| 2-03 | | | ++++ | ++ | +++ | | | |
| 2-05 | | | ++++ | + | ++++ | | | |
| 2-07 | | | ++++ | | +++ | ++ | | +++ |
| 2-08 | | | ++++ | | ++ | ++ | | +++ |
| 2-10 | | | ++++ | | | | | +++ |
| 2-11 | | | ++++ | | | | | +++ |
| 2-12 | | | ++++ | | | | | ++ |
| 2-13 | | | ++++ | | | | | +++ |
| 3-01 | | | + | ++++ | +++ | | | |
| 3-02 | | | ++ | +++ | +++ | | | |
| 3-03 | | | + | +++ | ++ | | | |
| 3-04 | | | | ++++ | +++ | | | |
| 3-05 | | | | +++ | + | | | |
| 3-06 | | | | ++++ | +++ | | | |
| 3-07 | | | | +++ | +++ | | | |
| 3-08 | | | | +++ | ++ | | | |
| 3-09 | | | | +++ | | | | +++ |
| 3-10 | | | | +++ | | | | +++ |
| 3-11 | | | | +++ | | | | +++ |
| 3-12 | | | | +++ | ++ | + | | ++ |
| 3-13 | | | | +++ | +++ | ++ | | +++ |
| 3-14 | | | | +++ | ++ | + | | ++ |
| 3-15 | | | | +++ | ++ | ++ | | +++ |
| 3-16 | | | | +++ | ++ | ++ | | ++ |
| 3-17 | | | | ++++ | +++ | ++ | | +++ |
| 4-01 | | +++ | | | + | | | |
| 4-02 | | +++ | | | + | | | |

TABLE 1-continued

| Example | PDE4A1 | PDE4D7 | PDE5A1 | PDE9A | HDAC1 | HDAC2 | HDAC3 | HDAC6 |
|---|---|---|---|---|---|---|---|---|
| 4-03 | | | +++ | | +++ | | | |
| 4-04 | | | +++ | | +++ | | | |
| 4-05 | | | +++ | + | +++ | +++ | | +++ |
| 5-02 | + | + | | | +++ | | | |
| 5-03 | + | + | | | ++ | | | |
| 5-04 | + | + | | | +++ | | | |
| 5-05 | ++ | + | | | +++ | | | |

As can be seen in the above table, tested compounds of the invention show a dual inhibition of PDEs and HDACs.

Comparative Example 2-02 bears an imidazo[5,1-f][1,2,4]triazin-4-one core and a hydroxamic acid ester; in fact, this molecule provided a direct pairwise comparison with compound 2-07 where hydroxamic acid was replaced by hydroxamic acid ester. This compound, comparative example 2-02, kept primary activity against PDE5A1, IC50<10 nM; however, it was inactive against HDAC1, HDAC2 and HDAC6; IC50>20 μM.

Comparative Example 2-01 and comparative example 3-01 were inactive against HDAC1, HDAC2 and HDAC6; IC50>20 μM under the tested conditions.

In-Vitro Assay Using Primary Neuronal Cultures
PDE and HDAC Activity Wild Type Neurons The cellular assay to determine PDE and HDAC activity was assessed by Western blot analysis using specific antibodies against pCREB-Ser129 and acetylated histone 3 at Lys9 (AcH3K9), respectively. In this case the reported $EC_{50}$, Table 2 (below), means a 50% increase in pCREB or in AcH3K9 levels over basal (saline, no treatment).

Primary neuronal cultures derived from the hippocampus and cortex of embryonic day 16 (E16) of wild type mice were used. Tissue was triturated using glass pipettes until neurons were dissociated. Neurons were plated in serum-free neurobasal media with B27 supplement (Invitrogen, Gaithersburg, Md.) and 2 mM L-glutamine on poly-L-lysine-treated (0.1 mg/ml; Sigma) 60 mm dishes.

To determine the concentration-response curve effect of the compounds, cell cultures of 15 days in vitro (DIV) were treated at different concentrations (1, 10, 50, 100 and 500 nM, 1 and 2 μM) during 30 min. Cells were collected in a buffer containing a cold lysis buffer with protease inhibitors (0.2 M NaCl, 0.1 M HEPES (4-(2-hydroxyethyl)-1-piperazineethanesulfonic acid), 10% glycerol, 200 mM NaF, 2 mM $Na_4P_2O_7$, 5 mM EDTA (ethylenediaminetetraacetic acid), 1 mM EGTA (ethylene glycol tetraacetic acid), 2 mM DTT (dithiothreitol), 0.5 mM PMSF (phenylmethylsulfonyl fluoride), 1 mM $Na_3VO_4$ and Complete Protease Inhibitor Cocktail, Roche Diagnostics), centrifuged at 14,000×g 4° C. for 20 min and the supernatant was aliquoted and stored at −80° C. Total protein concentrations were determined using the BioRad Bradford protein assay (BioRad Laboratories).

Protein samples were mixed with Laemmli sample buffer, resolved onto SDS-polyacrylamide gels and transferred to nitrocellulose membrane. The membranes were blocked with 5% milk, 0.05% Tween-20 in PBS (Phosphate-Buffered Saline) or TBS (Tris-Buffered Saline) followed by overnight incubation with the following primary antibodies: rabbit polyclonal anti-acetylated Histone 3 (acetyl K9), rabbit polyclonal anti-pCREB-Ser129 (Cell Signalling), mouse monoclonal anti-actin (Sigma) in the corresponding buffer. All the antibodies were used at 1:1000 dilution except the mouse monoclonal anti-β-actin which was used at 1:50.000. Following two washes in TBS/Tween20 and one wash in TBS alone, immunolabeled protein bands were detected by using HRP-conjugated anti-rabbit or anti-mouse antibody (Santa Cruz; dilution 1:5.000) following an enhanced chemiluminescence system (ECL, GE Healthcare Bioscience, Buckinghamshire, UK), and autoradiographic exposure to HyperfilmtECL (GE Healthcare Bioscience). Quantity One™ software v.4.6.3 (Bio-Rad) was used for quantification.

AD-Related Markers (APP Processing, pTau and Acetylated-Tubulin) in Tg2576 Neurons The effects of the compounds on amyloid pathology were analysed in primary cultures (15 DIV) of neurons derived from the hippocampus and cortex of Tg2576 mouse embryos. Tg2576 mice express the human 695-aa isoform of APP (hAPP) containing the Swedish double mutation, which favours Aβ production. Neurons were treated for two days and collected at day 3, 24 h after the last treatment. First it was analysed the effect of the compounds on hAPP processing by the amyloidogenic pathway by measuring the carboxyl terminal fragment AβPP (C99), which is the precursor of Aβ42. In this case the reported $EC_{50}$, Table 2 (below), means a 50% decrease in C99 levels over basal (saline, no treatment).

It was next analyzed the effect of the compounds on levels of phosphorylated tau (p-tau) in the same samples, another marker of AD, using a phospho-specific antibody (AT8) that recognizes hyperphosphorylated epitopes on Ser202/Thr205. In this case the reported $EC_{50}$, Table 2 (below), means a 50% decrease in pTau levels over basal (saline, no treatment).

Moreover, recently it has been described that HDAC6 might be a suitable molecular target for the development of novel therapeutic strategies against AD. The inhibition of HDAC6 levels ameliorated the impairment of acetylated-α-tubulin and associative and spatial memory formation in AD. Thus, next it was measured the levels of acetylated-α-tubulin in Tg2576 neurons after the treatment. In this case the reported $EC_{50}$, Table 2 (below), means a 50% increase in acetylated-α-tubulin levels over basal (saline, no treatment).

To analyze APP-derived fragments and p-tau levels in primary neuronal cultures, cells were collected in a buffer containing SDS (2%), Tris-HCl (10 mM, pH 7.4), protease inhibitors (1 mM PMSF and Complete Protease Inhibitor Cocktail: Roche Diagnostics) and phosphatase inhibitors (0.1 mM $Na_3VO_4$ and 1 mM NaF). The homogenates were sonicated for 2 min and centrifuged at 100,000×g for 1 h. Aliquots of the supernatant were frozen at −80° C. and their protein concentrations determined by the Bradford method using the Bio-Rad protein assay (Bio-Rad, Hercules, Calif., USA). Aliquots of the protein extracts were mixed with XT sample buffer plus XT reducing agent (Bio-Rad, Hercules, Calif., USA) and boiled for 5 min. Proteins were separated in a Criterion precast Bis-Tris 4-12% gradient precast gel (Bio-Rad, Hercules, Calif., USA) and transferred to a PVDF membrane with a removal rating of 0.2 mm (Hybond LFP, Amersham Biosciences, Little Chalfont, UK). The membranes were blocked with 5% milk, 0.05% Tween-20 in PBS or TBS, and incubated overnight with the following primary antibodies in the corresponding buffers: mouse monoclonal anti-phosphotau AT8 (Pierce Biotechnology Inc., Rockford), mouse monoclonal anti-tau (clone Tau46, Sigma-Aldrich, St Louis, Mo.), 6E10 mouse monoclonal antibody (amino acids 1-17 of Aβ peptide; Millipore), mouse monoclonal anti-β-actin, mouse monoclonal anti-α-tubulin and mouse monoclonal anti-Acetylated-tubulin (Sigma). All antibodies were used at dilutions of 1:1,000 except for the mouse monoclonal anti-β-actin, anti-Acetylated-tubulin and anti-tubulin (1:50,000). Following two washes in TBS/Tween20 and one wash in TBS alone, immunolabelled protein bands were detected using HRP-conjugated anti-rabbit or anti-mouse antibodies (diluted 1:5,000: Santa Cruz). Binding was visualised by enhanced chemiluminescence (ECL, GE Healthcare Bioscience, Buckinghamshire, UK) and autoradiographic exposure to Hyperfilm ECL (GE Healthcare Bioscience), using Quantity One™ software v.4.6.3 (Bio-Rad) for quantification.

Table 2 shows the functional response on primary cultures ($EC_{50}$); where, N.E. means No Effect, $EC_{50} \geq 10$ μM (+), 1 μM $\leq EC_{50} < 10$ μM (++), 10 nM $\leq EC_{50} < 1$ μM (+++) and $EC_{50} < 10$ nM (++++). Known PDE5 inhibitor (Tadalafil) as well as HDAC inhibitor (Vorinostat) were also included as references.

TABLE 2

| Example | pCREB[a] | AcH3[a] | pTau[b] | AcTub[b] | C99[b] |
|---|---|---|---|---|---|
| Tadalafil | +++ | N.E. | +++ | | |
| Vorinostat | N.E. | +++ | +++ | +++ | |
| 1-06 | +++ | +++ | | +++ | +++ |
| 1-12 | +++ | +++ | | | |
| 1-15 | +++ | +++ | | +++ | +++ |
| 1-16 | +++ | +++ | +++ | +++ | +++ |
| 1-19 | +++ | +++ | +++ | +++ | +++ |
| 1-25 | ++ | +++ | | | |
| 1-29 | ++ | ++ | | | |
| 1-30 | +++ | +++ | | | |
| 1-40 | ++ | +++ | | | |
| 1-48 | +++ | +++ | | | |
| 2-07 | +++ | +++ | | | |

[a]data obtained from wild type neurons,
[b]data obtained from Tg2576 neurons.

As can be seen in the above table, tested compounds of the invention show a functional dual activity in primary neurons, from wild type and Tg2576 mice, that may play a critical role for AD treatment and is not achieved by reference compounds (Tadalafil and Vorinostat).

In-Vivo Activity

To determine the ability of the compounds to inhibit HDAC and PDE in the brain, the compound was administered to wild type mice by i.p. at a dose of 40 mg/kg (n=3). Another group of animals received the vehicle (1/1/8, v:v:v, DMSO/Tween 20/saline). One hour later, mice were sacrificed by cervical dislocation and their hippocampus was quickly dissected from the brains.

Total tissue homogenates were obtained by homogenizing the hippocampus in a cold lysis buffer with protease inhibitors (0.2 M NaCl, 0.1 M HEPES, 10% glycerol, 200 mM NaF, 2 mM $Na_4P_2O_7$, 5 mM EDTA, 1 mM EGTA, 2 mM DTT, 0.5 mM PMSF, 1 mM $Na_3VO_4$ and Complete Protease Inhibitor Cocktail, Roche Diagnostics). The homogenate was then centrifuged at 14,000×g at 4° C. for 20 min and the supernatant aliquoted and stored at −80° C. Total protein concentrations were determined using the BioRad Bradford protein assay (BioRad Laboratories). Protein samples were analyzed as described in the "in vitro" section.

AD-related markers (APP processing, pTau and acetylated-tubulin) in Tg2576 mice. The effects of the compounds were also analysed in Tg2576 mice after chronic treatment (3-5 weeks) using hippocampal homogenates obtained in a buffer containing SDS (2%) and following the same protocol as described in the in vitro studies.

Table 3 shows increment in biological response vs basal (no treatment); thus, basal×1 means no increment (+), basal× 1 ≤ (++) < basal×2, basal×2 ≤ (+++) < basal×3, basal×3 ≤ (++++) < basal×4 and basal×4 ≤ (+++++). N.E. means No Effect. Known PDE5 inhibitor (Tadalafil) as well as HDAC inhibitor (Vorinostat) were also included as references.

TABLE 3

| Example | pCREB[a] | AcH3[a] | pTau[b] | AcTub[b] | C99[b] |
|---|---|---|---|---|---|
| Tadalafil | +++ | N.E. | +++ | | |
| Vorinostat | N.E. | +++ | | | |
| 1-06 | +++ | +++ | | | |
| 1-12 | +++ | ++ | | | |
| 1-15 | + | + | | | |
| 1-16 | + | ++ | | | |
| 1-19 | +++ | +++ | | | |

[a]data obtained from wild type mice
[b]data obtained from Tg2576 mice

As can be seen in the above table, tested compounds of the invention show a functional dual activity in-vivo that may play a critical role for AD treatment and is not achieved by reference compounds (Tadalafil and Vorinostat).

Pharmacokinetics

Plasma and brain samples for measuring compounds concentrations were collected at predetermined times from four wild type mice per point. Three time points were measured: 0.25, 0.5 and 1.0 hour. Compounds concentration was measured using a Xevo-TQ MS triple quadropole mass spectrometer with an electrospray ionization (ESI) source and an Acquity UPLC (Waters, Manchester, UK).

Dose Preparation and Dose Administration:

Compounds solutions were prepared by dissolving the samples in DMSO and this solution was made up to a final volume by addition of a mixture of Tween 20 and 0.9% NaCl (1/1/8, v:v:v, DMSO/Tween 20/saline). Compounds were injected as a single intraperitoneal injection. Animals were killed by decapitation.

Sample Collection:

Plasma. Blood was collected into tubes containing EDTA and plasma was collected via centrifugation (4° C., 13200 rpm, 5 min) and stored at −80° C. until analysis.

Brain. Brains were collected immediately after mice death. The brains were excised, weighed and frozen at −80° C. until further process for analysis.

Chromatography:

Chromatographic separation was performed by gradient elution at 0.4 mL/min using an Acquity UPLC BEH C18 column (100×2.1 mm, 1.7 μm particle size; Waters). The mobile phase consisted of A: water with 0.1% formic acid, B: methanol with 0.1% formic acid. After 1.5 min at the initial condition of 95% A, solvent B was increased from 5% to 100% over 2 min, maintained at 100% for 1.5 min, then a linear gradient to initial conditions was applied for 0.1 min and maintained for 3.4 minutes to re-equilibrate the column, giving a cycle time of 8.5 min. The autosampler temperature was set at 10° C. and column temperature at 45° C.

Mass Spectrometry:

Compounds were monitored using a triple quadrupole mass spectrometer equipped with an electrospray ionization interface. For detection and quantification, a capillary voltage of 3.5 kV and a cone voltage of 38 V were used. Source and desolvation temperatures were 150° C. and 650° C., respectively. Ultra-high purity nitrogen was used for cone gas (75 L h$^{-1}$) and desolvation gas (1000 L h$^{-1}$). The electrospray ionization operated in the positive mode, and the collision gas used was ultra-pure argon at a flow rate of 0.15 mL min$^{-1}$.

Quantification and Sample Preparation:

Quantification was achieved by external calibration using matrix-matched standards. Concentrations were calculated using a weighted least-squares linear regression (W=1/x). Calibration standards were prepared by adding the appropriate volume of diluted solutions of the compound (made in a mixture of methanol and water, 50:50, v:v) to aliquots of 50 uL of blank plasma or to 75 mg of homogenized blank brain. 2% formic acid in acetonitrile was added to precipitate the proteins. The mixture was then agitated for 10 min and centrifuged at 13200 rpm for 5 min at 4° C. The resulting supernatants were transferred to a Ostro plate (Waters, Manchester, UK), designed to remove phospholipids. The resulting eluents were evaporated at 37° C. under a stream of nitrogen. Residues were dissolved in 75 μL of a mixture of methanol and water (50:50, v:v). A 10-uL aliquot of the resulting solution was injected onto the LC-MS/MS system for analysis. Frozen plasma samples were thawed at room temperature, vortexed thoroughly and subjected to the above described extraction procedure. Brain samples were thawed unassisted at room temperature and homogenized using a Branson 250 ultrasonic sonifier (Branson, Danbury, Conn., USA). When homogenized, 75 mg were weighted and extracted as described previously.

Results

Concentration values obtained from the LC-MS/MS analyses are described in Table 4. Table 4 shows the time at which maximum concentration in brain occurs, plasma and brain concentration at that time and brain/plasma ratio for the compounds. $^a$dosage was 20 mg/Kg, $^b$dosage was 40 mg/Kg.

TABLE 4

| Compound | $t_{Max}$ (h) | $C_{Max}$ (plasma; nM) | $C_{Max}$ (brain; nmol/Kg) | Brain/Plasma ratio (%) | Crosses BBB? |
|---|---|---|---|---|---|
| 1-06$^a$ | 0.25 | 283 (37)$^c$ | 5.8 (1.8)$^c$ | 2.0 | Yes |
| 1-12$^b$ | 0.25 | 1881 (168)$^c$ | 71.3 (19.5)$^c$ | 3.8 | Yes |
| 1-15$^a$ | 0.25 | 653 (83)$^c$ | 29 (8)$^c$ | 4.4 | Yes |
| 1-16$^a$ | 0.50 | 11810 (1042)$^c$ | 102 (7)$^c$ | 0.9 | Yes |
| 1-19$^b$ | 0.25 | 15782 (3898)$^c$ | 609 (178)$^c$ | 3.9 | Yes |

$^c$Standard Deviation value

As can be seen in the above table, tested compounds of the invention crosses the blood-brain barrier and reach the brain with effective concentration—as it is confirmed above in Table 3 (functional response).

REFERENCES CITED IN THE APPLICATION

Green and P. G. M. Wuts, Protective Groups in Organic Chemistry, Wiley, 3rd ed. 1999, Chapter 2, pp. 17-200 and Chapter 5, pp. 369-451.
WO 2008/024494
WO2012/020022

The invention claimed is:

1. A compound of formula (I), or a pharmaceutically acceptable salt thereof, or any stereoisomer or mixtures thereof, either of the compound of formula (I) or of any of its pharmaceutically acceptable salts,

(I)

wherein $B_1$ is a radical selected from the group consisting of formula (A") and formula (C"):

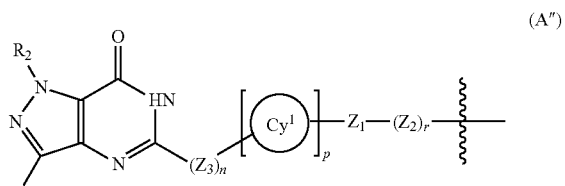

(A")

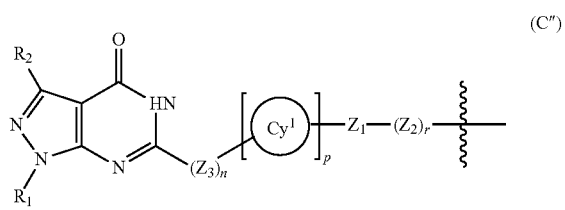

(C")

with the condition that the moiety ($L_1$) of the formula (A") and formula (C")

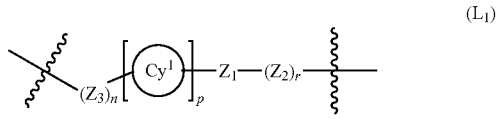

($L_1$)

has a chain length comprised of from 1 to 20 atoms;

wherein the radical of formula (A") has the formula:

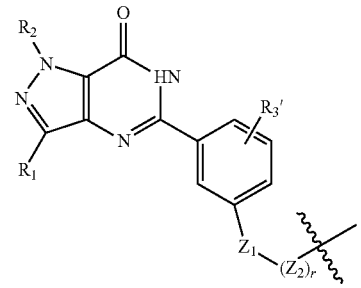

whereby the compound of formula (I) is a compound of formula (IA):

(IA)

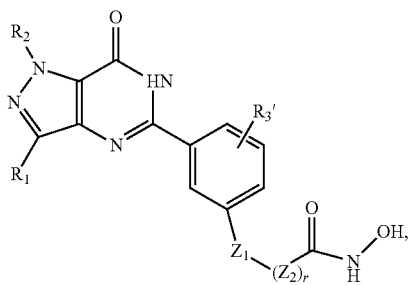

and wherein the radical of formula (C") has the formula:

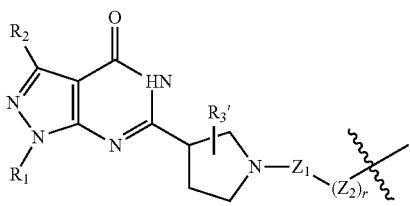

whereby the compound of formula (I) is a compound of formula (IC$^{III}$):

(IC''')

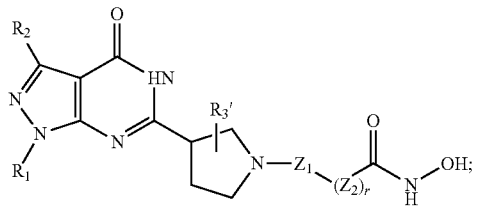

or alternatively, wherein the radical of formula (C") has the formula:

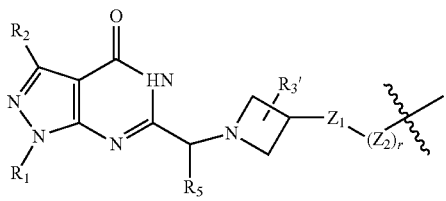

whereby the compound of formula (I) is a compound of formula (IC$^{IV}$):

(IC$^{IV}$)

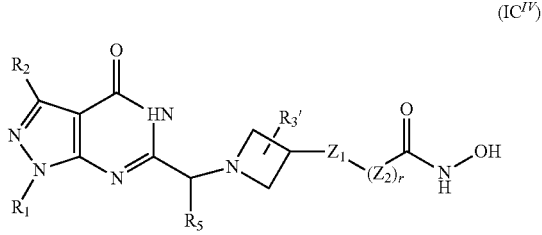

wherein
p, n and r are independently 0 or 1;
$R_1$ and $R_2$ are independently selected from the group consisting of H; saturated or unsaturated ($C_1$-$C_7$)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from halogen and ($C_1$-$C_3$)alkyl;
$R_5$ is selected from the group consisting of: H, halogen, and ($C_1$-$C_4$)alkyl optionally substituted with one or more halogen atoms;
$Z_1$ is a biradical selected from the group consisting of a formula (E), formula (F"'), formula (G'), formula (H'), formula (J'), and formula (K):

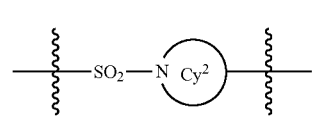
(E)

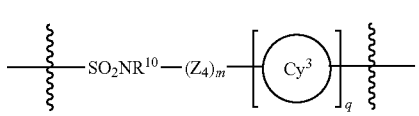
(F''')

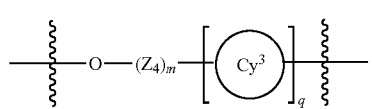
(G')

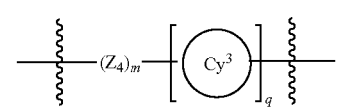
(H')

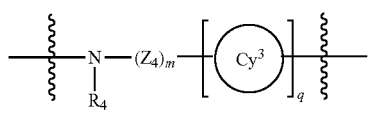
(J')

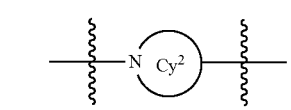
(K)

$Z_2$ is selected from the group consisting of —$Z_5$—; —$Z_5$-Cy$^4$-; —$Z_5$-Cy$^4$-$Z_5$—; and -Cy$^4$-;
each $Z_5$ is independently a biradical of a saturated or unsaturated ($C_1$-$C_6$)alkyl optionally substituted with one or more halogen atoms;
$Z_4$ is a biradical of a saturated or unsaturated ($C_1$-$C_6$)alkyl optionally substituted with one or more substituents selected from halogen, OH, and —O($C_1$-$C_3$)alkyl optionally substituted with one or more halogen atoms; or alternatively $Z_4$ is —CR$^{11}$R$^{12}$—, wherein R$^{11}$ and R$^{12}$ taken together with the carbon they are attached to form C=O or a 3- to 7-membered carbocyclic or heterocyclic monocyclic ring, which is saturated or partially unsaturated, and which is optionally substituted with one or more halogen atoms or ($C_1$-$C_3$)alkyl optionally substituted with one or more halogen atoms;
q and m are independently 0 or 1;
Cy$^3$ and Cy$^4$ are independently phenyl or a 3- to 7-membered carbocyclic or heterocyclic monocyclic ring, which is saturated or partially unsaturated or aromatic, and which is optionally substituted with one or more $R_3$ groups;

$Cy^2$ is a N-attached 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein $Cy^2$ is optionally substituted with one or more $R_3$ groups;

$R_3'$ is H or $R_3$;

$R_3$ is selected from halogen; saturated or unsaturated $(C_1-C_7)$alkyl optionally substituted with one or more halogen atoms; saturated or unsaturated $—O(C_1-C_7)$alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and $(C_1-C_6)$alkyl optionally substituted with one or more halogen atoms;

$R^4$ and $R^{10}$ are independently H or $(C_1-C_6)$alkyl optionally substituted with one or more halogen atoms; and wherein in any heterocyclic ring one or more of the ring members are selected from NH, N, O, and S;

wherein in all saturated or partially unsaturated rings one or two members of the rings are optionally $C(=O)$ and/or $C(=NH)$ and/or $C[=N(C_1-C_4)alkyl]$, wherein saturated alkyl refers to a linear or branched hydrocarbon chain which contains only single bonds; and unsaturated alkyl refers to a linear or branched hydrocarbon chain which contains one or two double bonds and/or one or two triple bonds;

wherein in any alkyl group one or two chain members selected from $CH_2$ or CH are optionally replaced by chain members independently selected from N, $NR_4$, O, $C(=O)$, $C(=O)NR_4$, $NR_4C(=O)$, and S.

2. The compound of formula (I) according to claim 1, wherein $R_1$ is selected from the group consisting of saturated or unsaturated $(C_1-C_4)$alkyl optionally substituted with one or more halogen atoms, 5- to 6-membered saturated carbocyclic ring optionally substituted with one or more substituents selected from halogen and $(C_1-C_3)$alkyl, and 5- to 6-membered saturated heterocyclic ring optionally substituted with one or more substituents selected from halogen and $(C_1-C_3)$alkyl.

3. The compound of formula (I) according to claim 1, wherein $R_2$ is H or saturated or unsaturated $(C_1-C_4)$alkyl optionally substituted with one or more halogen atoms.

4. The compound of formula (I) according to claim 1, wherein $Z_1$ is a biradical selected from the group consisting of a formula (E), formula (G'), and formula (H').

5. The compound of formula (I) according to claim 2, wherein $R_2$ is H or saturated or unsaturated $(C_1-C_4)$alkyl optionally substituted with one or more halogen atoms; and $Z_1$ is a biradical selected from the group consisting of a formula (E), formula (G'), and formula (H').

6. The compound of formula (I) according to claim 1, which is a compound of formula (IA), wherein $R_1$ is optionally substituted $(C_1-C_7)$alkyl.

7. The compound of formula (I) according to claim 1, which is a compound of formula ($IC^{III}$) or a compound of formula ($IC^{IV}$), wherein $R_1$ is a saturated 3- to 7-membered carbocyclic or heterocyclic ring.

8. The compound of formula (I) according to claim 1, which is a compound of formula (IA), wherein $R_2$ is optionally substituted $(C_1-C_4)$alkyl.

9. The compound of formula (I) according to claim 1, which is a compound of formula ($IC^{III}$) or a compound of formula ($IC^{IV}$), wherein $R_2$ is H.

10. The compound of formula (I) according to claim 1, which is a compound of formula (IA), wherein $R_3'$ is selected from H, halogen, saturated or unsaturated $(C_1-C_4)$alkyl optionally substituted with one or more halogen atoms; and saturated or unsaturated $—O(C_1-C_4)$alkyl optionally substituted with one or more halogen atoms.

11. The compound of formula (I) according to claim 10, wherein $R_3'$ is optionally substituted $—O(C_1-C_4)$alkyl.

12. The compound of formula (I) according to claim 1, which is a compound of formula ($IC^{III}$) or a compound of formula ($IC^{IV}$), wherein $R_3'$ is selected from H and saturated or unsaturated $(C_1-C_4)$alkyl optionally substituted with one or more halogen atoms.

13. The compound of formula (I) according to claim 1, wherein $Z_1$ is a biradical of formula (H'), wherein m is 0 and q is 0.

14. The compound of formula (I) according to claim 1, wherein $Z_1$ is selected from the group consisting of:

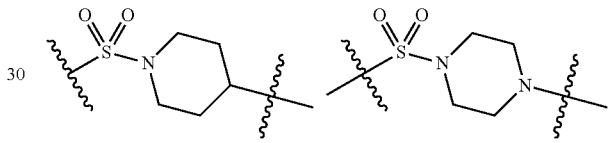

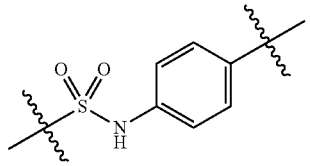

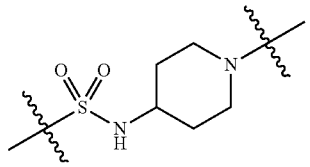

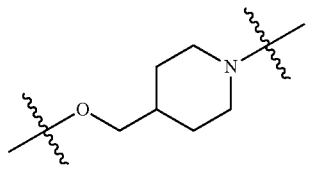

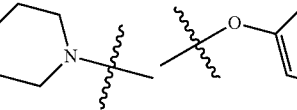

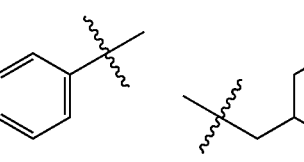

-continued

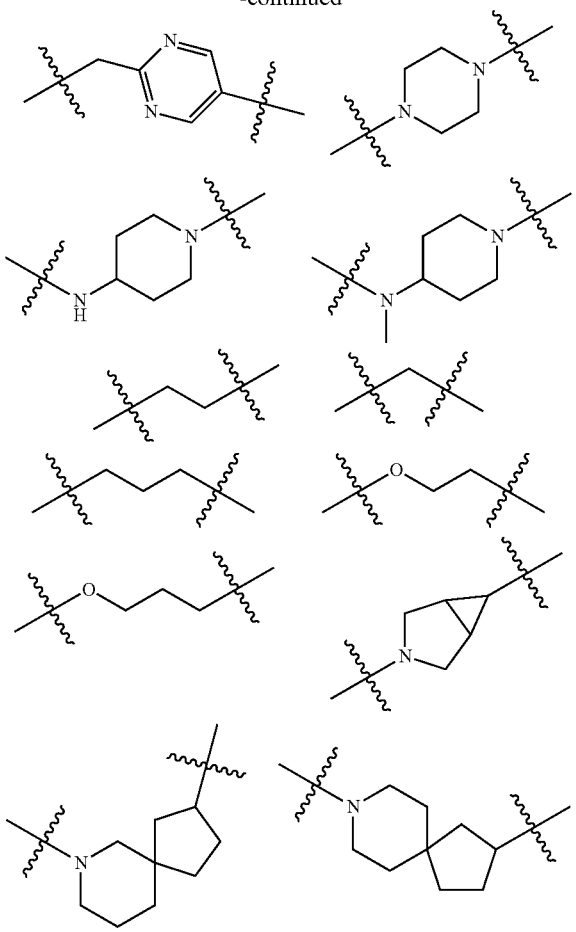

-continued

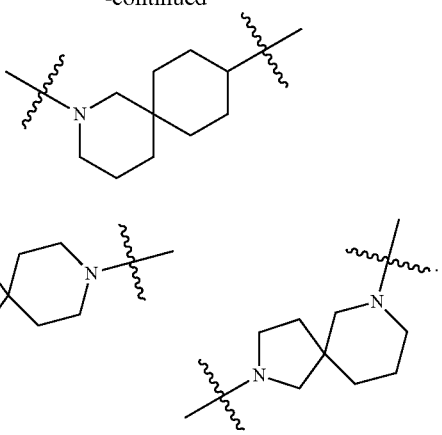

15. A pharmaceutical composition which comprises a therapeutically effective amount of a compound of formula (I) as defined in claim 1, together with one or more pharmaceutically acceptable excipients or carriers.

16. A method for the treatment of a neurological disorder coursing with a cognition deficit or impairment selected from mild cognitive impairment and age-associated cognition impairment, or a neurodegenerative disease associated to hyperphosphorylation of the cytoskeletal protein tau, comprising administering a therapeutically effective amount of a compound of formula (I) as defined in claim 1, and one or more pharmaceutical acceptable excipients or carriers, in a subject in need thereof, including a human.

17. The method according to claim 16, wherein the disease is Alzheimer's disease.

* * * * *